(12) United States Patent
Carroll et al.

(10) Patent No.: US 8,835,475 B2
(45) Date of Patent: *Sep. 16, 2014

(54) COMPOUNDS AS CANNABINOID RECEPTOR LIGANDS

(75) Inventors: William A. Carroll, Evanston, IL (US); Michael J. Dart, Highland Park, IL (US); Teodozyj Kolasa, Lake Villa, IL (US); Tongmei Li, Lake Bluff, IL (US); Derek W. Nelson, Highland Park, IL (US); Meena Patel, Green Oaks, IL (US); Sridhar Peddi, Grayslake, IL (US); Arturo Perez-Medrano, Grayslake, IL (US); Xueqing Wang, Northbrook, IL (US)

(73) Assignee: AbbVie Inc., North Chicago, IL (US)

( * ) Notice: Subject to any disclaimer, the term of this patent is extended or adjusted under 35 U.S.C. 154(b) by 857 days.

This patent is subject to a terminal disclaimer.

(21) Appl. No.: 12/967,282

(22) Filed: Dec. 14, 2010

(65) Prior Publication Data

US 2011/0082116 A1 Apr. 7, 2011

Related U.S. Application Data

(62) Division of application No. 12/100,731, filed on Apr. 10, 2008, now Pat. No. 7,872,033.

(60) Provisional application No. 60/923,951, filed on Apr. 17, 2007.

(51) Int. Cl.
| | | |
|---|---|---|
| A61K 31/425 | (2006.01) | |
| A61K 31/5377 | (2006.01) | |
| A61K 31/4725 | (2006.01) | |
| A61K 31/4436 | (2006.01) | |
| A61K 31/429 | (2006.01) | |
| A61K 31/427 | (2006.01) | |

(52) U.S. Cl.
CPC ........... *A61K 31/425* (2013.01); *A61K 31/5377* (2013.01); *A61K 31/4725* (2013.01); *A61K 31/4436* (2013.01); *A61K 31/429* (2013.01); *A61K 31/427* (2013.01)
USPC ...... 514/372; 514/373; 514/326; 514/255.05; 514/342; 514/228.8; 514/236.8; 514/365

(58) Field of Classification Search
CPC ........... A61K 31/5377; A61K 31/4725; A61K 31/4436; A61K 31/429; A61K 31/425; A61K 31/427
USPC ......... 514/372, 373, 326, 255.05, 342, 228.8, 514/236.8, 365
See application file for complete search history.

(56) References Cited

U.S. PATENT DOCUMENTS

| | | |
|---|---|---|
| 3,843,683 A | 10/1974 | Bell |
| 3,928,327 A | 12/1975 | Takamizawa et al. |
| 4,885,295 A | 12/1989 | Bell |
| 4,966,828 A | 10/1990 | Doenges et al. |
| 4,973,587 A | 11/1990 | Ward et al. |
| 4,978,664 A | 12/1990 | Bell |
| 5,013,837 A | 5/1991 | Ward et al. |
| 5,055,579 A | 10/1991 | Pawlowski et al. |
| 5,250,498 A | 10/1993 | Andree et al. |
| 5,468,722 A | 11/1995 | Shibata et al. |
| 5,530,019 A | 6/1996 | Okada et al. |
| 5,654,322 A | 8/1997 | Hirata et al. |
| 6,323,214 B1 | 11/2001 | Baraldi |
| 6,358,992 B1 | 3/2002 | Pamukcu et al. |
| 6,369,052 B1 | 4/2002 | Kellar et al. |
| 6,559,186 B1 | 5/2003 | Campbell |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,560,456 B2 | 7/2009 | Araki et al. |

(Continued)

FOREIGN PATENT DOCUMENTS

| | | |
|---|---|---|
| CA | 2587667 A1 | 5/2006 |
| DE | 1522361 A1 | 7/1969 |

(Continued)

OTHER PUBLICATIONS

Atwood et al. "CB2: Therapeutic target-in-waiting" Progress in Neuro-Psychopharmacology & Biological Psychiatry 2012, 38, 16-20.*
Arevalo-Martin, et al., "Therapeutic Action of Cannabinoids in a Murine Model of Multiple Sclerosis," Journal of Neuroscience, 2003, vol. 23 (7), pp. 2511-2516.
Benito, et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.
Berge, et al., "Pharmaceutical Salts," Journal of Pharmaceutical Sciences, 1977, vol. 66 (1), pp. 1-19.
Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle, et al., "Osteoclast Differentiation and Activation," Nature, 2003, vol. 423 (6937), pp. 337-342.

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The present application relates to isothiazolylidene containing compounds of Formula (I)

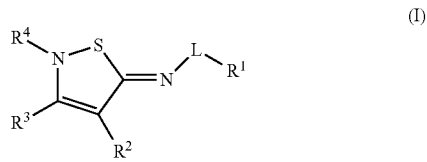

(I)

wherein $R^1$, $R^2$, $R^3$, $R^4$, and L are as defined in the specification, compositions comprising such compounds, and methods of treating conditions and disorders using such compounds and compositions.

2 Claims, No Drawings

(56) References Cited

U.S. PATENT DOCUMENTS

| | | | |
|---|---|---|---|
| 7,560,481 B2 | 7/2009 | Frost et al. | |
| 7,674,912 B2 | 3/2010 | Sams et al. | |
| 7,683,084 B2 | 3/2010 | Faghih et al. | |
| 7,750,039 B2 | 7/2010 | Frost et al. | |
| 7,868,038 B2 | 1/2011 | Nelson et al. | |
| 7,872,006 B2 | 1/2011 | Moritani et al. | |
| 7,872,033 B2 * | 1/2011 | Carroll et al. | 514/372 |
| 7,875,639 B2 | 1/2011 | Florjancic et al. | |
| 7,875,640 B2 | 1/2011 | Kolasa et al. | |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |
| 8,236,822 B2 | 8/2012 | Wang et al. | |
| 8,288,428 B2 | 10/2012 | Wang et al. | |
| 8,338,467 B2 | 12/2012 | Kolasa et al. | |
| 8,481,574 B2 | 7/2013 | Meyer et al. | |
| 8,492,371 B2 | 7/2013 | Carroll et al. | |
| 8,501,794 B2 * | 8/2013 | Carroll et al. | 514/372 |
| 8,586,596 B2 | 11/2013 | Dart et al. | |
| 2004/0023862 A1 | 2/2004 | Smart et al. | |
| 2004/0029040 A1 | 2/2004 | Watanabe et al. | |
| 2004/0034090 A1 | 2/2004 | Barth et al. | |
| 2004/0077617 A1 | 4/2004 | Bennani et al. | |
| 2004/0166539 A1 | 8/2004 | Akhavan-Tafti et al. | |
| 2004/0259912 A1 | 12/2004 | Matsumoto et al. | |
| 2005/0176713 A1 | 8/2005 | Freyne et al. | |
| 2006/0199817 A1 | 9/2006 | Tasker et al. | |
| 2007/0061360 A1 | 3/2007 | Holcombe et al. | |
| 2007/0155738 A1 | 7/2007 | Steeneck et al. | |
| 2008/0058335 A1 | 3/2008 | Florjancic et al. | |
| 2008/0058355 A1 | 3/2008 | Westheim et al. | |
| 2008/0139635 A1 | 6/2008 | Martin et al. | |
| 2008/0242654 A1 | 10/2008 | Kolasa et al. | |
| 2008/0287510 A1 | 11/2008 | Carroll et al. | |
| 2008/0312435 A1 | 12/2008 | Saito et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105305 A1 | 4/2009 | Butlin et al. | |
| 2009/0105306 A1 | 4/2009 | Carroll et al. | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0041720 A1 | 2/2010 | Carroll et al. | |
| 2010/0063022 A1 | 3/2010 | Carroll et al. | |
| 2010/0069348 A1 | 3/2010 | Carroll et al. | |
| 2010/0069349 A1 | 3/2010 | Carroll et al. | |
| 2010/0216760 A1 | 8/2010 | Frost et al. | |
| 2011/0065685 A1 | 3/2011 | Frost et al. | |
| 2011/0086832 A1 | 4/2011 | Kolasa et al. | |
| 2011/0086838 A1 | 4/2011 | Nelson et al. | |

FOREIGN PATENT DOCUMENTS

| | | |
|---|---|---|
| DE | 1772867 A1 | 6/1971 |
| DE | 2458933 A1 | 6/1975 |
| DE | 3533331 A1 | 3/1987 |
| EP | 412404 A2 | 2/1991 |
| EP | 568096 A1 | 11/1993 |
| EP | 0619316 A1 | 10/1994 |
| EP | 0639569 A1 | 2/1995 |
| EP | 1060734 A2 | 12/2000 |
| EP | 1219612 A1 | 7/2002 |
| EP | 1300401 A1 | 4/2003 |
| EP | 1640369 A1 | 3/2006 |
| EP | 1820504 A1 | 8/2007 |
| FR | 2796643 A1 | 1/2001 |
| JP | S57171986 A | 10/1982 |
| JP | 6345736 A | 12/1994 |
| WO | WO-9507271 A1 | 3/1995 |
| WO | WO9531448 A1 | 11/1995 |
| WO | WO-9601591 A1 | 1/1996 |
| WO | WO-9700860 A1 | 1/1997 |
| WO | WO-9710223 A1 | 3/1997 |
| WO | WO0063207 A1 | 10/2000 |
| WO | WO-0116138 A1 | 3/2001 |
| WO | WO-0128557 A1 | 4/2001 |
| WO | WO0155139 A1 | 8/2001 |
| WO | WO0155140 A1 | 8/2001 |
| WO | WO-0183422 A1 | 11/2001 |
| WO | WO-0242269 A1 | 5/2002 |
| WO | WO-02060447 A1 | 8/2002 |
| WO | WO-02102232 A2 | 12/2002 |
| WO | WO-03049741 A1 | 6/2003 |
| WO | WO-03097605 A1 | 11/2003 |
| WO | WO-2004050086 A1 | 6/2004 |
| WO | WO2004110453 A1 | 12/2004 |
| WO | WO-2005023818 A2 | 3/2005 |
| WO | WO-2005058887 A1 | 6/2005 |
| WO | WO-2005075464 A1 | 8/2005 |
| WO | WO-2005099353 A2 | 10/2005 |
| WO | WO-2005099353 A3 | 10/2005 |
| WO | WO-2005115972 A1 | 12/2005 |
| WO | WO-2005115986 A1 | 12/2005 |
| WO | WO-2006008754 A1 | 1/2006 |
| WO | WO2006051704 A1 | 5/2006 |
| WO | WO-2006051704 A1 | 5/2006 |
| WO | WO-2006070106 A1 | 7/2006 |
| WO | WO-2006100208 A1 | 9/2006 |
| WO | WO-2007061360 A2 | 5/2007 |
| WO | WO-2007140385 A2 | 12/2007 |
| WO | WO-2007140439 A2 | 12/2007 |
| WO | WO-2007140439 A3 | 1/2008 |
| WO | WO-2007140385 A3 | 2/2008 |
| WO | WO-2008063781 A2 | 5/2008 |
| WO | WO-2008079687 A1 | 7/2008 |
| WO | WO-2008121558 A1 | 10/2008 |
| WO | WO-2008130953 A2 | 10/2008 |
| WO | WO-2008144360 A1 | 11/2008 |
| WO | WO-2009009550 A1 | 1/2009 |
| WO | WO-2009048936 A1 | 4/2009 |
| WO | WO-2009067613 A1 | 5/2009 |
| WO | WO-2009114566 A1 | 9/2009 |
| WO | WO-2010019547 A1 | 2/2010 |
| WO | WO-2010033543 A2 | 3/2010 |
| WO | WO-2010054024 A2 | 5/2010 |
| WO | WO-2010071783 A1 | 6/2010 |
| WO | WO-2010111573 A1 | 9/2010 |
| WO | WO-2010111574 A1 | 9/2010 |

OTHER PUBLICATIONS

Brennan, et al., "Characterization of a Rat Model of Incisional Pain," Pain, 1996, vol. 64, pp. 493-450.

Buckley, et al., "Immunomodulation by Cannabinoids is Absent in Mice Deficient for the Cannabinoid CB2 Receptor," European Journal of Pharmacology, 2000, vol. 396, pp. 141-149.

Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.

Carrier, et al., "Endocannabinoids in Neuroimmunology and Stress," Current Drug Targets CNS and Neurological Disorders, 2005, vol. 4, pp. 657-665.

Casanova, et al., "Inhibition of Skin Tumor Growth and Angiogenesis in vivo by Activation of Cannabinoid Receptors," Journal of Clinical Investigation, 2003, vol. 111 (1), pp. 43-50.

Chaplan, et al., "Quantitative Assessment of Tactile Allodynia in the Rat Paw," Journal of Neuroscience Methods, 1994, vol. 53, pp. 55-63.

Cichewicz, D., "Synergistic Interactions Between Cannabinoid and Opioid Analgesics," Life Sciences, 2004, vol. 74 (11), pp. 1317-1324.

Clayton, et al., "CB1 and CB2 Cannabinoid Receptors are Implicated in Inflammatory Pain," Pain, 2002, vol. 96 (3), pp. 253-260.

(56) References Cited

OTHER PUBLICATIONS

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Dixon, W., "Efficient Analysis of Experimental Observations," Annual Review of Pharmacology and Toxicology, 1980, vol. 20, pp. 441-462.
Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.
Galiégue, et al., "Expression of Central and Peripheral Cannabinoid Receptors in Human Immune Tissues and Leukocyte Subpopulations," European Journal of Biochemistry, 1995, vol. 232 (1), pp. 54-61.
Goerdeler, et al., "Uber Isothiazole, VIII. Synthese von Sulfonylamino-isothiazolen und Sulfonyliminoisothiazolinen aus Sulfonylsenfolen," Chemische Berichte, 1969, vol. 102 (7), pp. 2273-2284.
Greene, et al., Protective Groups in Organic Synthesis, 3rd Edition, John Wiley and Sons, Inc., 1999, Table of Contents.
Grotenhermen, et al., "IACM 2nd Conference on Cannabinoids in Medicine," Expert Opinion in Pharmacotherapy, 1976, vol. 4 (12), pp. 2367-2371.
Hanus, et al., "HU-308: A Specific Agonist for CB 2, a Peripheral Cannabinoid Receptor," Proceedings of the National Academy of Science, 1999, vol. 96, pp. 14228-14233.
Hohmann, et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Ibrahim, et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.
Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.
Ihenetu, et al., "Inhibition of Interleukin-8 Release in the Human Colonic Epithelial Cell Line HT-29 by Cannabinoids," European Journal of Pharmacology, 2003, vol. 458 (1-2), pp. 207-215.
International Search Report for Application No. PCT/US08/060400, mailed on Oct. 17, 2008, 3 pages.
Joshi, et al., "Comparison of Antinociceptive Actoins of Standard Analgesics in Attenuating Capsaicin and Nerve-Injury-Induced Mechanical Hypersensitivity," Neuroscience, 2006, vol. 143, pp. 587-596.
Julien, et al., "Antifibrogenic Role of the Cannabinoid Receptor CB2 in the Liver," Gastroenterology, 2005, vol. 128, pp. 742-755.
Karsak, et al., "Cannabinoid Receptor Type 2 Gene is Associated with Human Osteoporosis," Human Molecular Genetics, 2005, vol. 14 (22), pp. 3389-3396.
Kim, et al., "An Experimental Model for Peripheral Neuropathy Produced by Segmental Spinal Nerve Ligation in the Rat," Pain, 1992, vol. 50 (3), pp. 355-363.
Lepicier, et al., "Endocannabinoids Protect the Rat Isolated Heart Against Ischaemia," British Journal of Pharmacology, 2003, vol. 139, pp. 805-815.
Linn, et al., Journal of American Chemistry Society, 1963, 2032, vol. 85.
Lotersztajn, et al., "Hepatic Fibrosis: Molecular Mechanisms and Drug Targets," Annual Review of Pharmacology and Toxicology, 2005, vol. 45, pp. 605-628.
Malan, et al., "CB2 Cannabinoid Receptor-Mediated Peripheral Antinociception," Pain, 2001, vol. 93, pp. 239-245.
Maresz, et al., "Modulation of the Cannabinoid CB2 Receptor in Microglial Cells in Response to Inflammatory Stimuli," Journal of Neurochemistry, 2005, vol. 95, pp. 437-445.

Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.
McKallip, et al., "Targeting CB2 Cannabinoid Receptors as a Novel Therapy to Treat Malignant Lymphoblastic Disease," Blood, 2002, vol. 15 (2), pp. 627-634.
Nackley, et al., "Selective Activation of Cannabinoid CB2 Receptors Suppresses Spinal for Protein Expression and Pain Behavior in a Rat Model of Inflammation," Neuroscience, 2003, vol. 119, pp. 747-757.
Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.
Patel, et al., "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.
Pertwee, R., "Cannabinoids and Multiple Sclerosis," Pharmacology & Therapeutics, 2002, vol. 95, pp. 165-174.
Poste, et al., "Lipid Vesicles as Carriers for Introducing Biologically Active Materials into Cells," Methods in Cell Biology, 1976, vol. 14, pp. 33-71.
Quartilho, et al., "Inhibition of Inflammatory Hyperalgesia by Activation of Peripheral CB2 Cannabinoid Receptors," Anesthesiology, 2003, vol. 99, pp. 955-960.
Ralston, "Regulation of Bone Mass, Bone Loss and Osteoclast Activity by Cannabinoid Receptors," Nature Medicine, 2005, vol. 11 (7), pp. 774-779.
Ramirez, et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.
Rautio, et al, "Prodrugs: Design and Clinical Applications," Nature Reviews Drug Discovery, 2008, vol. 7 (3), pp. 255-270.
Sanchez, et al., "Inhibition of Glioma Growth in Vivo by Selective Activation of the CB2 Cannabinoid Receptor1," Cancer Research, 2001, vol. 61, pp. 5784-5789.
Smith, D., "Do Prodrugs Deliver?" Current Opinion in Drug Discovery and Development, 2007, vol. 10 (5), 550-559.
Steffens, et al., "Low Dose Oral Cannabinoid Therapy Reduces Progression of Atherosclerosis in Mice," Nature, 2005, vol. 434, pp. 782-786.
Testa, B., "Prodrugs: Bridging Pharmacodynamic/Pharmacokinetic Gaps," Current Opinion in Chemical Biology, 2009, vol. 13 (3), pp. 338-344.
Valenzano, et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.
Wang B., et al., Drug Delivery: Principles and Applications, John Wiley & Sons, Inc., 2005, pp. 136-137.
Warhurst, et al., "Interferon Gamma Induces Differential Upregulation of Alpha and Beta Chemokine Secretion in Colonic Epithelial Cell Lines," Gut, 1998, vol. 42 (2), pp. 208-213.
Wright, et al., "Differential Expression of Cannabinoid Receptors in the Human Colon: Cannabinoids Promote Epithelial Wound Healing," Gastroenterology, 2005, vol. 129 (2), pp. 437-453.
Yoshihara, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.
Yoshihara, et al., "Endogenous Cannabinoid Receptor Agonists Inhibit Neurogenic Inflammations in Guinea Pig Airways," Allergy and Immunology, 2005, vol. 138, pp. 80-87.
Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.
Abreo M.A., et al., "Novel 3-Pyridyl Ethers with Subnanomolar Affinity for Central Neuronal Nicotinic Acetylcholine Receptors," Journal of Medicinal Chemistry, 1996, vol. 39 (4), pp. 817-825.
Alfaro I., et al., "Dihydroaromatic Compounds in the Diels-Alder Reaction—III :In Situ Generation and Diels-Alder Reaction of Cyclohexa-1,3-Dienes," Tetrahedron, 1970, vol. 26, pp. 201-218.

(56) References Cited

OTHER PUBLICATIONS

Ambartsumova R.F., et al., "Effect of Various Factors on the Reaction of 2-Aminobenzothiazoles with Propylene Oxide," Chemistry of Heterocyclic Compounds, 2002, vol. 38 (8), pp. 994-999.
Andreani, et al., "Ring-opened, etc," Collection of Czechoslovak Chemical Communications, 1999, vol. 64, pp. 299-312.
Ansell M.F., et al., "The Synthesis of (+/−)-10a-Homo-11a-Carbathromboxane A1, a Stable Thromboxane A Analogue," Journal of Chemical Society Perkin Trans, 1984, pp. 1061-1068.
Araki, et al., (2003): STN International HCAPLUS database, (Columbus, OH). Accession No. 2003-931334.
Atwood B.K., et al., "CB : Therapeutic Target-in-Waiting," Progress in Neuro-Psychopharmacology & Biological Psychiatry, 2012, vol. 38 (1), pp. 16-20.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Baker T.J., et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Bartlett P.A., et al., "Chorismate Mutase Inhibitors: Synthesis and Evaluation of Some Potential Transition-State Analogues," Journal of Organic Chemistry, 1988, vol. 53, pp. 3195-3210.
Benito C., et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Bennett G.J., et al., "A Peripheral Mononeuropathy in Rat that Produces Disorders of Pain Sensation like those Seen in Man," Pain, 1988, vol. 33 (1), pp. 87-107.
Bermudez-Silva, et al., "Role of Cannabinoid CB2 Receptors in Glucose Homeostasis in Rats," European Journal of Pharmacology, 2007, vol. 565 (1-3), pp. 207-211.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Bozidar K., et al., "Transformations of 1,2,4-Thiadiazolo/2,3-X/ Azines," Heterocycles, 1987, vol. 26 (3), pp. 689-697.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Bruson H.A., et al., "Action of Sulfuric Acid upon Unsaturated Isothiocyanates: Mercaptothiazolines ," Journal of American Chemical Society, 2011, vol. 59 (10), pp. 2011-2013.
Cai, et al., Ex Parte Appeal No. 2011005302, decided Jul. 12, 2011.
Campbell V.A., et al., "Alzheimer's Disease; Taking the Edge off with Cannabinoids?," British Journal of Pharmacology, 2007, vol. 152 (5), pp. 655-662.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
"Caplus Record of U.S. Patent Application Publication No. 2008/0058335 by Westheim et al., 2007,".
"Caplus Record of U.S. Patent Application Publication No. 2008/0242654 by Kolasa et al., 2008,".
CAS Registry No. 1061668-81-2, which entered STN on Oct. 15, 2008.
Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chauhan M.S., "The Reaction of Some Heterocyclic Thiones with Ethyl Azidoformate," Canadian Journal of Chemistry, 1976, vol. 54 (24), pp. 3879-3883.
Chemical Abstracts Accession No. 1030770638, Jun. 26, 2008.
Cotarca L., et al., "Bis (trichloromethyl) Carbonate in Organic Synthesis," 1996, vol. 6, pp. 553-576.
Cross., et al., "Rules for the Nomenclature of Organic Chemistry, Section E: Stereochemistry," International Union of Pure and Applied Chemistry, 1976, vol. 45, pp. 11-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Dart et al (2007): STN International HCAPLUS database, Columbus (OH), Accession No. 2007:1396538.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.
Dauben W.G., et al., "Organic Reactions at High Pressure Cycloadditions with Furans," Journal of the American Chemical Society, 1976, vol. 98 (7), pp. 1992-1993.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Ebata et al., "Synthesis of Both Enantiomers of 4-Hexanolide and 4-Dodecanolide," Agriculture Biochemical, 1991, vol. 55 (6), pp. 1685-1686.
Eckert H., et al., "Triphosgene, a Crystalline Phosgene Substitute," Angewandte Chemie International Edition in English, 1987, vol. 26 (9), pp. 894-895.
European Search Report for Application No. EP12187944, mailed on Nov. 20, 2012, 7 pages.
Ex Parte Quayle Action mailed Oct. 12, 2012 for U.S. Appl. No. 13/160,952, filed Jun. 15, 2011.
Fattori D., et al.,, "The Demjanov and Tiffeneau-Demjanov One-Carbon Ring Enlargements of 2-Aminomethyl-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Oct. 3, 2013 for U.S. Appl. No. 12/246,808, filed Oct. 7, 2008.
Final Office Action mailed Mar. 10, 2010 for U.S. Appl. No. 11/755,434, filed May 30, 2007.
Final Office Action mailed Jul. 14, 2011 for U.S. Appl. No. 12/246,808, filed Oct. 7, 2008.
Final Office Action mailed Sep. 14, 2011 for U.S. Appl. No. 12/274,105, filed Nov. 19, 2008.

(56) References Cited

OTHER PUBLICATIONS

Final Office Action mailed Feb. 15, 2011 for U.S. Appl. No. 12/120,969, filed May 15, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Apr. 16, 2011 for U.S. Appl. No. 12/539,120, filed Aug. 11, 2009.
Final Office Action mailed Oct. 19, 2011 for U.S. Appl. No. 12/560,893, filed Sep. 16, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Final Office Action mailed Mar. 24, 2011 for U.S. Appl. No. 11/755,434, filed May 30, 2007.
Final Office Action mailed Dec. 28, 2011 for U.S. Appl. No. 12/639,173, filed Dec. 16, 2009.
Florjancic A., et al (2009): Caplus Entry for WO2009067613, Accession No. 2009:649814.
Florjancic et al (2010): STN International HCAPLUS database, Columbus (OH), Accession No. 2010:478868.
Foster, A. B. et al., "Deuterium Isotope Effects in the Metabolism of Drugs and Xenobiotics: Implications for Drug Design," Advances in Drug Research, 1985, vol. 14, pp. 2-36.
Giron D., "Applications of Thermal Analysis and Coupled Techniques in Pharmaceutical Industry," Journal of Thermal Analysis and Calorimetry, 2002, vol. 68, pp. 335-357.
Giron D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Golech S.A., et al., "Human Brain Endothelium: Coexpression and Function of Vannilloid and Endocannabinoid Receptors," Molecular Brain Research, 2004, vol. 132 (1), pp. 87-92.
Golub T.R., et al., "Molecular Classification of Cancer: Class Discovery and Class Prediction by Gene Expression Monitoring," Science, 1999, vol. 286 (5439), pp. 531-537.
Goodman A.J., et al., "CB2 Selective Sulfamoyl Benzamides; Optimization of the Amide Functionality," Bioorganic & Medicinal Chemistry Letters , 2009, vol. 19 (2), pp. 309-313.
Gouldson P., et al., "Mutational Analysis and Molecular Modelling of the Antagonist SR144528 Binding Site on the Human Cannabinoid CB2 Receptor," European Journal of Pharmacology, 2000, vol. 401 (1), pp. 17-25.
Greene T.W., et al., "Protection for the Amino group," Protective Groups in Organic Synthesis, 1999, Third Edition, pp. 494-653.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Hargreaves K., et al., "A New and Sensitive Method for Measuring Thermal Nociception in Cutaneous Hyperalgesia," Pain, 1988, . 32 (1), pp. 77-88.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability and Written Opinion for Application No. PCT/US2010/028790, mailed on Sep. 27, 2008, 5 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report, European Patent Office (Nov. 20, 2007).
International Search Report for Application No. PCT/US07/069921, mailed on Nov. 27, 2007, 4 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/063648, mailed on Aug. 13, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US08/080253, mailed on Mar. 3, 2009, 3 pages.

(56) References Cited

OTHER PUBLICATIONS

International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/063318, mailed on May 6, 2010, 3 pages.
International Search Report for Application No. PCT/US2009/068173, mailed on Feb. 5, 2010, 3 pages.
International Search Report for Application No. PCT/US2010/028790, mailed Jul. 19, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Izdebski J., et al., "A New Convenient Method for the Synthesis of Symmetrical and Unsymmetrical N,N'-Disubstituted Ureas," Synthesis, 1989, pp. 423-425.
Jain S., et al., "The Synthesis and Antimicrobial Screening of Some Novel Aza—Imidoxy Compounds as Potential Chemotherapeutic Agents," Phosphorus Sulfur and Silicon, 2006, vol. 181 (7), pp. 1665-1673.
Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Kato, S. et al., "Synthesis of Deuterated Mosapride Citrate," Journal of Labelled Compounds and Radiopharmaceuticals, 1995, vol. 36 (10), pp. 927-932.
Katritzky A.R., et al., "A General Synthesis of Unsymmetrical Tetrasubstituted Ureas," Journal of Organic Chemistry, 1997, vol. 62 (11), pp. 4155-4158.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.
Knolker H.J., et al., "A Novel Method for the Synthesis of Isocyanates Under Mild Conditions," Angewandte Chemie International Edition in English, 1995, vol. 34 (22), pp. 2497-2500.
Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.
Kolasa., "Thiazolylidene Derivatives as Cannabinoid Receptor Ligands and Their Preparation" Accession No. 2008:1184581, Mar. 22, 2011.
Koren B., et al., "Transformations of 1-(2-Chloropyridy1-3)-4-ethoxycarbonyl and 1-(2-Chloropyridy1-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Kreutzberg G.W., et al., "Microglia: A Sensor for Pathological Events in the CNS," Trends in Neuroscience, 1996, vol. 19, pp. 312-318.
Kruijtzer J., et al., "Approaches to the Synthesis of Ureapeptoid Peptidomimetics," Tetrahedron Letters, 1997, vol. 38 (30), pp. 5335-5338.
Kubinyi, "3D QSAR in Drug Design: Ligand Protein Interactions & Molecular Similarity, 800 pages," Springer, 1998, vol. 2-3, pp. 243-244.
Kushner, et al., "Pharmacological uses and perspectives of heavy water and deuterated compounds," Canadian Journal of Physiology and Pharmacology, 1999, vol. 77 (2), pp. 79-88.
Lamothe M., et al., "A Simple One-Pot Preparation of N,N'-unsymmetrical ureas from N-Boc Protected Primary Anilines and Amines," Synlett, 1996, vol. 6, pp. 507-508.
Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.
Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.
Li, W., et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Lizondo, J. et al., "Linezolid: Oxazolidinone antibacterial," Drugs of the Future, 1996, vol. 21 (11), pp. 1116-1123.
MacLennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Majer P., et al., "A Safe and Efficient Method for Preparation of N,"-Unsymmetrically Disubstituted Ureas Utilizing Triphosgene," Journal of Organic Chemistry, 1994, vol. 59, pp. 1937-1938.
Malan T.P., et al., "Inhibition of Pain Responses by Activation of CB(2) Cannabinoid Receptors," Chemistry and Physics of Lipids, 2002, vol. 121 (1-2), pp. 191-200.
Maligres, P.E., et al., "Stereocontrolled Preparation of a Nonpeptidal (−)-Spirobicyclic NK-1 Receptor Antagonist," Journal of Organic Chemistry, 2002, vol. 67 (4), pp. 1093-1101.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.
Mallesham, B. et al., "Highly Efficient CuI-Catalyzed Coupling of Aryl Bromides with Oxazolidinones Using Buchwald's Protocol: A Short Route to Linezolid and Toloxatone," Organic Letters, 2003, vol. 5 (7), pp. 963-965.
Manaka A., et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.
Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Mayo clinic, Alzheimer's disease, [retrieved on Mar. 11, 2013]. Retrieved from the Internet:<URL:http://www.mayoclinic.com/health/alzheimers-disease/DS00161/DSECTION=prevention>.
Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.
Miyaura N., et al., ed., Topics in Current Chemistry: Cross-Coupling Reactions, Springer, 2002, Table of Contents.
Molina-Holgado F., et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Morii T., et al., "A General Strategy to Determine a Target DNA Sequence of a Short Peptide: Application to a [D]-Peptide," Journal American Chemical Society, 2002, vol. 124 (2), pp. 180-181.

(56) References Cited

OTHER PUBLICATIONS

Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.
Mucke L., "Neuroscience: Alzheimer's Disease," Nature, 2009, vol. 461 (7266), pp. 895-897.
Negishi E., et al., eds., Handbook of Organopalladium Chemistry for Organic Synthesis, vol. 1, John Wiley & Sons, 2002, Table of Contents.
Nieuwenhuijzen J.W., et al., "Solid and Solution Phase Combinatorial Synthesis of Ureas," Tetrahedron Letters, 1998, vol. 39, pp. 7811-7814.
Non-Final Office Action mailed Jun. 1, 2011 for U.S. Appl. No. 12/554,445, filed Sep. 4, 2009.
Non-Final Office Action mailed Jun. 1, 2011 for U.S. Appl. No. 12/560,897, filed Sep. 16, 2009.
Non-Final Office Action mailed Jun. 2, 2009 for U.S. Appl. No. 11/755,434, filed May 30, 2007.
Non-Final Office Action mailed Sep. 7, 2010 for U.S. Appl. No. 12/120,969, filed May 15, 2008.
Non-Final Office Action mailed Mar. 9, 2012 for U.S. Appl. No. 12/732,428, filed Mar. 26, 2010.
Non-Final Office Action mailed Jan. 12, 2010 for U.S. Appl. No. 12/120,969, filed May 15, 2008.
Non-Final Office Action mailed May 17, 2011 for U.S. Appl. No. 12/560,893, filed Sep. 16, 2009.
Non-Final Office Action mailed Aug. 23, 2011 for U.S. Appl. No. 12/639,173, filed Dec. 16, 2009.
Non-Final Office Action mailed Jan. 27, 2011 for U.S. Appl. No. 12/274,105, filed Nov. 19, 2008.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Nunez E., et al,. "Cannabinoid CB2 Receptors Are Expressed by Perivascular Microglial Cells in the Human Brain: An Immunohistochemical Study," Synapse, 2004, vol. 53, pp. 208-213.
Office Action mailed Nov. 15, 2013 for European Application No. 05855099.7 filed Dec. 21, 2005.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Ohta H., et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Opposition filed by "Asociacion de Industries Farmaceuticas Dominicanas Inc" for the Dominican Patent application Nr P2008-0060, received on Apr. 1, 2009, 8 pages.
Ozaki S., et al., "Recent Advances in Isocyanate Chemistry," Chemical Reviews, 1972, vol. 72 (5), pp. 457-496.
Padgett L.W., et al., "Recent Developments in Cannabinoid Ligands," Life Sciences, 2005, vol. 77 (14), pp. 1767-1798.
Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.
Radulescu C., et al., "Actes Du Colloque Franco-Roumain De Chimie Appliquee, 3Rd, Bacau, Romania," 2004, pp. 117-120.
Radulescu C., et al., "The Comparative Study on the Synthesis Methods of a Heterocyclic System 2-Aminothiazolo[4,5-13]Pyricline," Revista de Chimie, 2005, vol. 56 (6), pp. 659-662.
Radulescu C., et al., "Synthesis and Characterics of Compact Condensed Heterocyclic System 2-Aminothiazolo[5,4-c]Pyridine," Revista de Chimie, 2004, vol. 55 (11), pp. 889-893.
Ralston S.H., "Genetic Determinants of Susceptibility to Osteoporosis," Current Opinion in Pharmacology, 2003, vol. 3, pp. 286-290.

Rezoni G.E., et al., "Synthesis of 7-Carboxytricyclo[33103,7]nonan-3-ol," Journal of Organic Chemistry, 1983, vol. 48, pp. 5231-5236.
Rodriquez-Spong B., et al., "General Principles of Pharmaceutical Solid Polymorphism: A Supramolecular Perspective," Advanced Drug Delivery Reviews, 2004, vol. 56 (3), pp. 241-274.
Ross W.J., et al., "Antianaphylactic agents. 1. 2-(Acylamino)oxazoles," Journal of Medicinal Chemistry, 1979, vol. 22(4), pp. 412-417.
Sabnis R.W., et al., "2-Aminothiophenes by the Gewald Reaction," Journal of Heterocyclic Chemistry, 1999, vol. 36, pp. 333-345.
Schafer S.,et al., "Failure is an Option: Learning from Unsuccessful Proof-of-concept Trials," Drug Discovery Today, 2008, vol. 13 (21-22), pp. 913-916.
Schuart J., et al., "2-aminooxazoles and 2-iminooxazolines. 3. Selected Examples of a Homolog Series of 3 Substituted 2-imino-4-methyl-5-phenyloxazolines," Die Pharmazie, 1974, vol. 29 (3), pp. 170-172.
Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.
Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.
Souillac P., et al, "Characterization of Delivery Systems, Differential Scanning Calorimetry," Encyclopedia of Controlled Drug Delivery, 1999, pp. 217-218.
STN International HCAPLUS database Accession No. 2008:1184581, Columbus, Ohio, Lolasa et al, 2008.
Supplementary European Search Report for Application No. EP08837396, mailed on Jan. 16, 2012, 2 pages.
Supplementary European Search Report for Application No. EP08852528, mailed on Nov. 8, 2010, 2 pages.
Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.
Thomson, J.F., "Physiological Effects of D20 in Mammals," Annals of the New York Academy of Sciences, 1960, vol. 84, pp. 736-744.
Vasil'eva V.F., et al., "Synthesis and Properties of 2-imino-3-benzyl-5-phenyl-1,3,4-oxadiazoline," Caplus, 1970.
Viallet, et al., "2-Aminothiazoline, etc," 1980, CA 93:8074.
Vippagunta S.R., et al., "Crystalline Solids," Advanced Drug Delivery Reviews, 2001, vol. 48 (1), pp. 3-26.
Walter L., et al., "Cannabinoids and Neuroinflammation," British Journal of Pharmacology, 2004, vol. 141 (5), pp. 775-785.
Watkins L.R., et al., "Glial Activation: A Driving Force for Pathological Pain," Trends in Neuroscience, 2001, vol. 24 (8), pp. 450-455.
Werbel L.M., et al., "1-Alkyl-3-(3-alkyl-5-nitro-4-thiazolin-2-ylidene)ureas nd Related Compounds as Schistosomicides," Journal of Medicinal Chemistry, 1972, vol. 15 (9), pp. 955-963.
Wermuth, "The practice of Medicinal chemistry," 2003, Chapters 9-10, 2nd edition,768 pages.
Weyer V.R., et al., "Blutzuckersenkende Chinolin-8-Carboxamidoalkyl-Benzol Sulfonamid Derivate ," Arzneimittel-Forschung, 1974, vol. 24 (3), pp. 269-275.
Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.
Widdowson D.A., et al., "Palladium Catalysed Suzuki Reactions of Fluoroarenes," Chemical Communication (Camb), 2003, vol. 5, pp. 578-579.
Williams K., et al., "Central Nervous System Perivascular Cells Are Immunoregulatory Cells that Connect the CNS tith the Peripheral mune System," Journal of Glia, 2001, vol. 36 (2), pp. 156-164.
Williams P.D., et al., "Renin Inhibitors Containing Conformationally Restricted P1-P1 Dipeptide Mimetics," Journal of Medicinal Chemistry, 1991, vol. 34 (3), pp. 887-900.
Wu K.M., et al., "Regulatory Perspectives of Type II Prodrug Development and Time-Dependent Toxicity Management: Nonclinical

(56) References Cited

OTHER PUBLICATIONS

Pharm/Tox Analysis and the Role of Comparative Toxicology,"Toxicology, 2007, vol. 236 (1-2), pp. 1-6.

Yao B.B., et al., "In Vitro Pharmacological Characterization of Am1241: A Protean Agonist at the Cannabinoid Cb2 Receptor," British Journal of Pharmacology, 2006, vol. 149 (2), pp. 145-154.

Zimmer A., et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.

Notice of Allowance mailed Jan. 17, 2014 for U.S. Appl. No. 12/120,969, filed May 15, 2008.

Final Office Action mailed Mar. 14, 2014 for U.S. Appl. No. 12/970,480, filed Dec. 16, 2010.

* cited by examiner

COMPOUNDS AS CANNABINOID RECEPTOR LIGANDS

This application is a divisional of U.S. patent application Ser. No. 12/100,731 filed on Apr. 10, 2008, which claims priority to U.S. patent application Ser. No. 60/923,951, filed Apr. 17, 2007, and are incorporated herein by reference in their entirety.

TECHNICAL FIELD

The present application relates to isothiazolylidene containing compounds, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of therapeutic effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic side effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

The present invention generally provides compounds that are $CB_2$ receptor ligands and pharmaceutical compositions and methods for the treatment of disorders using these compounds and pharmaceutical compositions.

One embodiment of the present invention generally provides compounds of Formula (I)

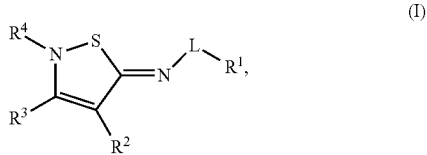

or pharmaceutically acceptable salts, prodrugs, salts of prodrugs, or combinations thereof, wherein L is C=O, C=S, S(O)$_2$, or C=NCN;

$R^1$ is alkyl, alkenyl, alkynyl, —(CR$^a$R$^b$)$_m$—OH, —(CR$^a$R$^b$)$_m$—O(alkyl), —(CR$^a$R$^b$)$_m$—CN, haloalkyl, or G$^1$;

$R^2$ is alkyl, alkenyl, alkynyl, G$^1$, —C(R$^{Zb}$)=NO(R$^{Z1}$), —O(R$^{Za}$), —N(R$^{Z1}$)(R$^{Z2b}$), —(CR$^a$R$^b$)$_m$—N$_3$, —(CR$^a$R$^b$)$_m$—CN, haloalkyl, —(CR$^a$R$^b$)$_m$—O(R$^{Za}$), —(CR$^a$R$^b$)$_m$—S(R$^{Zb}$), —(CR$^a$R$^b$)$_m$—C(O)O(R$^{Zb}$), —(CR$^a$R$^b$)$_m$—C(O)N(R$^{Z1}$)(R$^{Z2a}$), —(CR$^a$R$^b$)$_m$—SO$_2$N(R$^{Z1}$)(R$^{Z2a}$), —(CR$^a$R$^b$)$_m$—C(O)(R$^{Zb}$), —(CR$^a$R$^b$)$_m$—SO$_2$(R$^{Zd}$), —SO$_2$(R$^{Zd}$), —(CR$^a$R$^b$)$_m$—C(R$^{Zb}$)=NO(R$^{Z1}$), —(CR$^a$R$^b$)$_m$—N(R$^{Z1}$)(R$^{Z2b}$), or —(CR$^a$R$^b$)$_m$-G$^1$;

$R^3$ is hydrogen, alkyl, halogen, —CN, -G$^2$, haloalkyl, or —(CR$^a$R$^b$)$_m$-G$^2$;

$R^4$ is alkyl, alkenyl, alkynyl, —(CR$^a$R$^b$)$_n$—CN, —(CR$^a$R$^b$)$_n$—OH, —(CR$^a$R$^b$)$_n$—O(alkyl), haloalkyl, G$^2$, or —(CR$^a$R$^b$)$_m$-G$^2$; or $R^2$ and $R^3$, or $R^3$ and $R^4$, together with the atoms to which they are attached, form a five-, six-, or seven-membered monocyclic ring containing zero or one additional double bond, zero or one additional heteroatom selected from O, S, N, or N(H), each said ring is independently unsubstituted or substituted with 1, 2, 3, 4, or 5 substituents (R$^{21}$) selected from the group consisting of oxo, alkyl, alkenyl, alkynyl, halogen, —CN, —O(R$^{1a}$), —C(O)OH, —C(O)O(alkyl), —C(O)(R$^{1a}$), —N(R$^{Z3}$)(R$^{3a}$), —N(R$^{3a}$)C(O)R$^{1a}$, —N(R$^{3a}$)C(O)O(R$^{1a}$), —N(R$^{3a}$)C(O)N(R$^{Z3}$)(R$^{3a}$), —N(R$^{3a}$)S(O)$_2$(R$^{2a}$), —N(R$^{3a}$)S(O)$_2$N(R$^{Z3}$)(R$^{3a}$), —SO$_2$(R$^{2a}$), —C(O)N(R$^{Z3}$)(R$^{3a}$), —S(O)$_2$N(R$^{Z3}$)(R$^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O(R$^{1a}$), and haloalkyl, two adjacent or non-adjacent atoms of each said rings are optionally linked by an alkylene bridge of one, two, three, or four carbon atoms; and two substituents (R$^{21}$) on the same carbon atom, together with said carbon atom, optionally form a 3-6 membered monocyclic ring containing 0, 1, or 2 heteroatoms selected from O, S, or N(H);

R$^{Za}$, at each occurrence, is independently hydrogen, alkyl, haloalkyl, —(CR$^c$R$^d$)$_p$—O(alkyl), G$^1$, —(CR$^c$R$^d$)$_q$—CN, or —(CR$^c$R$^d$)$_q$-G$^1$;

R$^{Zb}$, at each occurrence, is independently hydrogen, alkyl, haloalkyl, G$^1$, or —(CR$^c$R$^d$)$_q$-G$^1$;

R$^{Z1}$, at each occurrence, is independently hydrogen, alkyl, or haloalkyl;

R$^{Z2a}$, at each occurrence, is independently hydrogen, alkyl, haloalkyl, G$^1$, or —(CR$^c$R$^d$)$_q$-G$^1$, or R$^{Z2b}$, at each occurrence, is independently hydrogen, alkyl, haloalkyl, G$^1$, —C(O)R$^{Zc}$, —C(O)OR$^{Zc}$, —C(O)N(R$^{Z1}$)(R$^{Zc}$), —S(O)$_2$R$^{Zd}$, —S(O)$_2$N(R$^{Z1}$)(R$^{Zc}$), or —(CR$^c$R$^d$)$_q$-G$^1$, R$^{Zc}$, at each occurrence, is independently hydrogen, alkyl, haloalkyl, G$^1$, or —(CR$^e$R$^f$)$_t$-G$^1$;

R$^{Zd}$, at each occurrence, is independently alkyl, haloalkyl, G$^1$, or —(CR$^e$R$^f$)$_t$-G$^1$;

G$^1$, at each occurrence, is aryl, heteroaryl, cycloalkyl, cycloalkenyl, or heterocycle, wherein each G$^1$ is independently unsubstituted or substituted with 1, 2, 3, 4, or 5 substituents selected from the group consisting of alkyl, alkenyl, alkynyl, halogen, —CN, oxo, -G$^2$, —NO$_2$, —C(R$^{Z3}$)=N—O(R$^{1a}$), —OR$^{1a}$, —O—(CR$^{1g}$R$^{1h}$)$_u$—CN, —OC(O)R$^{1a}$, —OC(O)N(R$^{Z3}$)(R$^{3a}$), —O—(CR$^{1g}$R$^{1h}$)$_u$—CON(R$^{Z3}$)(R$^{3a}$), —O—(CR$^{1g}$R$^{1h}$)$_u$SO$_2$N(R$^{Z3}$)(R$^{3a}$), —SR$^{1a}$, —S(O)$_2$R$^{2a}$, —S(O)$_2$N(R$^{Z3}$)(R$^{3a}$), —C(O)R$^{1a}$, —C(O)OR$^{1a}$, —C(O)N(R$^{Z3}$)(R$^{3a}$), —N(R$^{Z3}$)(R$^{3a}$), —N(R$^{Z3}$)C(O)R$^{1a}$, —N(R$^{Z3}$)S(O)$_2$R$^{2a}$, —N(R$^{Z3}$)C(O)O(R$^{1a}$), —N(R$^{Z3}$)C(O)N(R$^{Z3}$)(R$^{3a}$), —(CR$^{1g}$R$^{1h}$)$_u$NO$_2$, —(CR$^{1g}$R$^{1h}$)$_u$—OR$^{1a}$, —(CR$^{1g}$R$^{1h}$)$_u$—OC(O)R$^{1a}$, —(CR$^{1g}$R$^{1h}$)$_u$—OC(O)N(R$^{Z3}$)(R$^{3a}$), —(CR$^{1g}$R$^{1h}$)$_u$—SR$^{1a}$, —(CR$^{1g}$R$^{1h}$)$_u$—S(O)$_2$R$^{2a}$, —(CR$^{1g}$R$^{1h}$)$_u$—S(O)$_2$N(R$^{Z3}$)(R$^{3a}$), —(CR$^{1g}$R$^{1h}$)$_u$—C(O)R$^{1a}$, —(CR$^{1g}$R$^{1h}$)$_u$—C(O)OR$^{1a}$, —(CR$^{1g}$R$^{1h}$)$_u$—C(O)N(R$^{Z3}$)(R$^{3a}$), —(CR$^{1g}$R$^{1h}$)$_u$—N(R$^{Z3}$)(R$^{3a}$), —(CR$^{1g}$R$^{1h}$)$_u$—N(R$^{Z3}$)C(O)R$^{1a}$, —(CR$^{1g}$R$^{1h}$)$_u$—N(R$^{Z3}$)S(O)$_2$R$^{2a}$, —(CR$^{1g}$R$^{1h}$)$_u$—N(R$^{Z3}$)C(O)O(R$^{1a}$), —(CR$^{1g}$R$^{1h}$)$_u$—N(R$^{Z3}$)C(O)N(R$^{Z3}$)(R$^{3a}$), —(CR$^{1g}$R$^{1h}$)$_u$-G$^2$, —(CR$^{1g}$R$^{1h}$)$_u$—CN, and haloalkyl;

R$^{1a}$ and R$^{3a}$, at each occurrence, is independently hydrogen, alkyl, haloalkyl, G$^2$, or —(CR$^k$R$^x$)$_v$-G$^2$;

R$^{2a}$, at each occurrence, is independently alkyl, haloalkyl, G$^2$, or —(CR$^k$R$^x$)$_v$-G$^2$;

G$^2$, at each occurrence, is aryl, heteroaryl, cycloalkyl, cycloalkenyl, or heterocycle, wherein each G$^2$ is independently unsubstituted or substituted with 1, 2, 3, 4, or 5 substituents selected from the group consisting of alkyl, alkenyl, alkynyl, halogen, —CN, oxo, —NO$_2$, —OR$^{1b}$, —OC(O)R$^{1b}$, —OC(O)N(R$^{Z4}$)(R$^{3b}$), —SR$^{1b}$, —S(O)$_2$R$^{2b}$, —S(O)$_2$N(R$^{Z4}$)(R$^{3b}$), —C(O)R$^{1b}$, —C(O)OR$^{1b}$, —C(O)N(R$^{Z4}$)(R$^{3b}$), —N(R$^{Z4}$)(R$^{3b}$), —N(R$^{Z4}$)C(O)R$^{1b}$—N(R$^{Z4}$)C(O)O(R$^{1b}$), —N(R$^{Z4}$)C(O)N(R$^{Z4}$)(R$^{3b}$), —(CR$^{2g}$R$^{2h}$)$_w$—NO$_2$, —(CR$^{2g}$R$^{2h}$)$_w$—OR$^{1b}$, —(CR$^{2g}$R$^{2h}$)$_w$—OC(O)R$^{1b}$, —(CR$^{2g}$R$^{2h}$)$_w$—OC(O)N(R$^{Z4}$)(R$^{3b}$), —(CR$^{2g}$R$^{2h}$)$_w$—SR$^{1b}$, —(CR$^{2g}$R$^{2h}$)$_w$—S(O)$_2$R$^{2b}$, —(CR$^{2g}$R$^{2h}$)$_w$S(O)$_2$N(R$^{Z4}$)(R$^{3b}$), —(CR$^{2g}$R$^{2h}$)$_w$—C(O)R$^{1b}$, —(CR$^{2g}$R$^{2h}$)$_w$—C(O)OR$^{1b}$, —(CR$^{2g}$R$^{2h}$)$_w$—C(O)N(R$^{Z4}$)(R$^{3b}$), —(CR$^{2g}$R$^{2h}$)$_w$—N(R$^{Z4}$)(R$^{3b}$), —(CR$^{2g}$R$^{2h}$)$_w$—N(R$^{Z4}$)C(O)R$^{1b}$, —(CR$^{2g}$R$^{2h}$)$_w$—N(R$^{Z4}$)C(O)O(R$^{1b}$), —(CR$^{2g}$R$^{2h}$)$_w$—N(R$^{Z4}$)C(O)N(R$^{Z4}$)(R$^{3b}$), —(CR$^{2g}$R$^{2h}$)$_w$—CN, and haloalkyl;

m, q, t, u, v, and w, at each occurrence, are each independently 1, 2, 3, 4, or 5;

n and p, at each occurrence, are each independently 2, 3, 4, or 5;

R$^{1b}$ and R$^{3b}$, at each occurrence, is independently hydrogen, alkyl, or haloalkyl;

R$^{2b}$, at each occurrence, is independently alkyl or haloalkyl;

R$^a$, R$^c$, R$^d$, R$^e$, R$^f$, R$^{1g}$, R$^{1h}$, R$^{2g}$, R$^{2h}$, R$^k$, and R$^x$, at each occurrence, are each independently hydrogen, halogen, alkyl, or haloalkyl;

each occurrence of R$^b$ is independently hydrogen, halogen, alkyl, haloalky, or OH; and R$^{Z3}$ and R$^{Z4}$, at each occurrence, are each independently hydrogen, alkyl, or haloalkyl; with the proviso that the compound is other than 4-methyl-N-[(3Z)-1-phenyl-1,4,5,6-tetrahydro-3H-cyclopenta[c]isothiazol-3-ylidene]benzenesulfonamide;

N-[(3 Z)-1-cyclohexyl-4,5,6,7-tetrahydro-2,1-benzisothiazol-3(1H)-ylidene]-4-methylbenzenesulfonamide; or 4-methyl-N-[(3Z)-1-phenyl-4,5,6,7-tetrahydro-2,1-benzisothiazol-3(1H)-ylidene]benzenesulfonamide.

In another embodiment, the present invention provides a method for treating pain (for example, neuropathic pain or nociceptive pain) in a mammal in need of such treatment. The method comprises administering to the mammal a therapeutically effective amount of a compound of Formula (I) or a pharmaceutically acceptable salt thereof.

In yet another embodiment, the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of Formula (I) or a pharmaceutically acceptable salt thereof.

In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of compounds of the present invention or a pharmaceutically acceptable salt thereof, in the manufacture of a medicament for the treatment of the disease conditions described above.

These and other objects of the invention are described in the following paragraphs. These objects should not be deemed to narrow the scope of the invention.

DETAILED DESCRIPTION

Compounds of Formula (I) are disclosed in this invention,

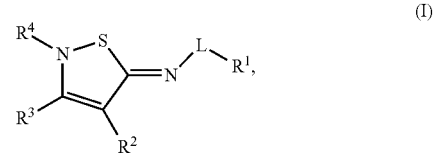

(I)

wherein $R^1$, $R^2$, $R^3$, $R^4$, and L are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition of Terms

All patents, patent applications, and literature references cited in the specification are herein incorporated by reference in their entirety. In the case of inconsistencies, the present disclosure, including definitions, will prevail.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl (allyl), 2-methyl-2-propenyl, 3-butenyl, but-1-enyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl (1-methylpropyl), iso-butyl, tert-butyl, n-pentyl, 1,1-dimethylpropyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl (ethynyl), 1-propynyl, 2-propynyl, 3-butynyl, 2-pentynyl, and 1-butynyl.

The term "aryl" as used herein, means phenyl or a bicyclic aryl. The bicyclic aryl is naphthyl (including naphth-1-yl), or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The term "$C_{3-6}$ cycloalkyl" as used herein, means a monocyclic cycloalkyl containing three to six carbon atoms, zero heteroatoms and zero double bonds. Examples of $C_{3-6}$ cycloalkyl include cyclopropyl, cyclobutyl, cyclopentyl, and cyclohexyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic cycloalkyls include, but are not limited to, bicyclo[3.1.1]heptyl, bicyclo[2.2.1]heptyl, bicyclo[2.2.2]octyl (including bicyclo[2.2.2]oct-1-yl), bicyclo[3.2.2]nonyl, bicyclo[3.3.1]nonyl, and bicyclo[4.2.1]nonyl. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of between one and four carbon atoms of the bicyclic cycloalkyl ring. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, fluoromethyl, 2-fluoroethyl, 1,1-difluoroethyl, 2,2,2-trifluoroethyl, 2,2,2-trifluoro-1,1-dimethylethyl, 2-fluoro-1,1-dimethylethyl, trifluoromethyl, difluoromethyl, 4-fluoro-4-methylpentyl, 4,4-difluoropentyl, 4-fluorobutyl, 3-fluoro-3-methylbutyl, 4,4,4-trifluorobutyl, pentafluoroethyl, and 2-chloro-3-fluoropentyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven-membered ring contains zero, one, two, or three double bonds and one, two, or three heteroatoms selected from the group consisting of O, N, and S. Representative examples of monocyclic heterocycles include, but are not limited to, azetidinyl (including azetidin-1-yl), azepanyl, aziridinyl, diazepanyl, 1,3-dioxanyl (including 1,3-dioxan-2-yl), 1,3-dioxolanyl (including 1,3-dioxolan-2-yl), dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl (including morpholin-4-yl), 4,5-dihydroisoxazolyl (including 4,5-dihydroisoxazol-5-yl), oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl (including pyrrolidin-3-yl, pyrrolidin-5-yl), tetrahydrofuranyl (including tetrahydrofuran-2-yl), tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, oxabicyclo[2.2.1]heptyl (including oxabicyclo[2.2.1]hept-1-yl), and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge consisting of one, two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, azaadmantane such as 1-azatricyclo[3.3.1.1$^{3,7}$]decane, and oxaadamantane such as 2-oxatricyclo[3.3.1.1$^{3,7}$]decane. The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl (including furan-2-yl), imidazolyl, isoxazolyl, isothiazolyl, oxadiazolyl, 1,3-oxazolyl, pyridinyl (including pyridin-2-yl), pyridazinyl, pyrimidinyl, pyrazinyl, pyrazolyl, pyrrolyl, tetrazolyl, thiadiazolyl, 1,3-thiazolyl (including 1,3-thiazol-4-yl, 1,3-thiazol-2-yl), thienyl (including thien-2-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl (including quinolin-8-yl), thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "oxo" as used herein, means a =O group.

b. Compounds

Compounds of the invention have the Formula (I) as described above.

Particular values of variable groups in compounds of Formula (I) are as follows. Such values may be used where appropriate with any of the other values, definitions, claims or embodiments defined hereinbefore or hereinafter.

As described generally in the Summary section for compounds of Formula (I), $R^2$ is alkyl, alkenyl, alkynyl, $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl, —(CR$^a$R$^b$)$_m$—O($R^{Za}$), —(CR$^a$R$^b$)$_m$—S($R^{Zb}$), —(CR$^a$R$^b$)$_m$—C(O)O($R^{Zb}$), —(CR$^a$R$^b$)$_m$—C(O)N($R^{Z1}$)($R^{Z2a}$), —(CR$^a$R$^b$)$_m$—SO$_2$N($R^{Z1}$)($R^{Z2a}$), —(CR$^a$R$^b$)$_m$—C(O)($R^{Zb}$), —(CR$^a$R$^b$)$_m$—SO$_2$($R^{Zd}$), —SO$_2$($R^{Zd}$), —(CR$^a$R$^b$)$_m$—C($R^{Zb}$)=NO($R^{Z1}$), —(CR$^a$R$^b$)$_m$—N($R^{Z1}$)($R^{Z2b}$), or —(CR$^a$R$^b$)$_m$-$G^1$.

In certain embodiments of compounds of Formula (I), $R^2$ is alkyl (e.g., methyl, ethyl, isobutyl, n-butyl, n-pentyl, and the like), alkenyl (for example, allyl, but-1-enyl, and the like), alkynyl, $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —(CR$^a$R$^b$)$_m$—O($R^{Za}$), —(CR$^a$R$^b$)$_m$—C(O)O($R^{Zb}$), —(CR$^a$R$^b$)$_m$—C(O)($R^{Zb}$), —(CR$^a$R$^b$)$_m$—C($R^{Zb}$)=NO($R^{Z1}$), —(CR$^a$R$^b$)$_m$—N($R^{Z1}$)($R^{Z2b}$), or —(CR$^a$R$^b$)$_m$-$G^1$.

In certain embodiments of compounds of Formula (I), $R^2$ is alkyl (e.g., methyl, ethyl, isobutyl, n-butyl, n-pentyl, and the like), alkenyl (for example, allyl, but-1-enyl, and the like), alkynyl, or $C_{1-6}$ haloalkyl (e.g., 4-fluoro-4-methylpentyl, 4,4-difluoropentyl, 3-fluoro-3-methylbutyl, 4,4,4-trifluorobutyl, 4-fluorobutyl).

In certain embodiments, $R^2$ is $G^1$ wherein $G^1$ is as described in the Summary. Examples of $G^1$ include, but are not limited to, cycloalkyl (e.g. cyclopropyl) and heterocycle (e.g. tetrahydropyranyl), each of which is optionally substituted as described generally in the Summary section. Examples of the optional substituents, when present, include, but are not limited to, alkyl (e.g. methyl, ethyl), oxo, and haloalkyl.

In certain embodiments, $R^2$ is —$(CR^aR^b)_m$-$G^1$ wherein $G^1$, $R^a$, and $R^b$ are as described in the Summary. Examples of $G^1$ include, but are not limited to, aryl (e.g. phenyl), cycloalkyl (e.g. cyclopropyl, cyclobutyl, cyclopentyl, cyclohexyl), heterocycle (e.g. 4,5-dihydroisoxazolyl, morpholinyl, 1,3-dioxanyl, 1,3-dioxolanyl, tetrahydrofuranyl), heteroaryl (e.g. furanyl, 1,3-thiazolyl, thienyl), each of which is optionally substituted as described generally in the Summary section. Examples of the optional substituents, when present, include, but are not limited to, alkyl, haloalkyl, and oxo. $R^a$ and $R^b$ are as described generally in the Summary section. Examples of $R^a$ include, but are not limited to, hydrogen and $C_{1-6}$ alkyl (e.g. methyl, ethyl, isopropyl). Examples of $R^b$ include, but are not limited to, hydrogen, $C_{1-6}$ alkyl (e.g. methyl, ethyl, isopropyl), and OH.

In certain embodiments, $R^2$ is —$C(R^{Zb})$=$NO(R^{Z1})$, —$(CR^aR^b)_m$—$N_3$, —$(CR^aR^b)_m$—CN, —$(CR^aR^b)_m$—C(O)O($R^{Zb}$), —$(CR^aR^b)_m$—C(O)($R^{Zb}$), —$(CR^aR^b)_m$—C($R^{Zb}$)=$NO(R^{Z1})$, or —$(CR^aR^b)_m$—$N(R^{Z1})(R^{Z2b})$, wherein $R^a$, $R^b$, $R^{Z1}$, $R^{Zb}$, m, $R^{Z2b}$ re as described in the Summary. Each occurrence of $R^a$, $R^b$, $R^{Zb}$, $R^{Z1}$, and $R^{Z2b}$, are, for example, independently, hydrogen and $C_{1-6}$ alkyl (e.g. methyl, ethyl, isopropyl).

In certain embodiments, $R^2$ is —$O(R^{Za})$ or —$N(R^{Z1})(R^{Z2b})$. Examples of $R^{Za}$ include, but are not limited to, alkyl (e.g., isopropyl, sec-butyl), haloalkyl (e.g., 4-fluorobutyl), —$(CR^cR^d)_q$—CN and —$(CR^cR^d)_q$-$G^1$. $G^1$, for example, is unsubstituted phenyl or pyrrolidinyl, unsubstituted or substituted with 1 or 2 substituents selected from the group consisting of oxo and $C_{1-6}$ alkyl (e.g. methyl). Each occurrence of $R^c$ and $R^d$, are independently hydrogen or $C_{1-6}$ alkyl (e.g. methyl, ethyl). q is 1 or 2. In certain embodiments, q is 1. $R^{Z1}$, for example, is hydrogen. $R^{Z2b}$, for example, is —C(O)O($R^{Zc}$) wherein $R^{Zc}$ is as described in the Summary. $R^{Zc}$, for example, is $C_{1-6}$ alkyl (e.g. tert-butyl).

In certain embodiments, $R^2$ is —$(CR^aR^b)_m$—$O(R^{Za})$ or —$(CR^aR^b)_m$—$N(R^{Z1})(R^{Z2b})$ wherein m, $R^a$, $R^b$, $R^{Za}$, $R^{Z1}$, and $R^{Z2b}$ are as described in the Summary. In certain embodiments, $R^{Za}$ is hydrogen, alkyl (e.g. methyl, ethyl, isopropyl), haloalkyl (e.g. 2,2,2-trifluoroethyl, 2-fluoroethyl, 2,2-difluoroethyl), or —$(CR^cR^d)_q$-$G^1$ wherein q, $R^c$, $R^d$, and $G^1$ are as described in the Summary. $G^1$, for example, is optionally substituted tetrahydrofuran. In certain embodiments, each occurrence of $R^a$, $R^b$, $R^c$, and $R^d$, are, for example, independently, hydrogen or $C_{1-6}$ alkyl (e.g. methyl, ethyl, isopropyl). q, for example, is 1. $R^{Z1}$ and $R^{Z2b}$ are, for example, independently hydrogen or $C_{1-6}$ alkyl (e.g. methyl, ethyl, isopropyl).

In certain embodiments, m is 1, 2, 3, or 4. In other embodiments, m is 1, 2, or 3. In yet other embodiments, m is 1 or 2.

As described generally above in the Summary, $R^3$ is hydrogen, alkyl, halogen, —CN, -$G^2$, haloalkyl, or —$(CR^aR^b)_m$-$G^2$. In certain embodiments, $R^3$ is hydrogen, $C_{1-6}$ alkyl (e.g. methyl), haloalkyl or cycloalkyl. In certain embodiments, $R^3$ is hydrogen or $C_{1-6}$ alkyl (e.g. methyl).

As generally described in the Summary, L is C=O, C=S, $S(O)_2$, or C=NCN.

In certain embodiments, L is C=O.
In certain embodiments, L is C=S.
In certain embodiments, L is $S(O)_2$.
In certain embodiments, L is C=NCN.

As described generally in the Summary, $R^1$ is alkyl, alkenyl, alkynyl, —$(CR^aR^b)_m$—OH, —$(CR^aR^b)_m$—O(alkyl), —$(CR^aR^b)_m$—CN, haloalkyl, or $G^1$.

In certain embodiments, $R^1$ is $G^1$ wherein $G^1$ is as described generally in the Summary. In yet other embodiments, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein below.

In certain embodiments, $R^1$ is phenyl or naphthyl, each of which is optionally substituted as described generally in the Summary and embodiments herein below.

In certain embodiments, $R^1$ is heteroaryl, optionally substituted as described in the Summary and embodiments herein below. In certain embodiments, $R^1$ is optionally substituted quinolin-8-yl.

In certain embodiments, $R^1$ is cycloalkyl (e.g., e.g., cyclopropyl, cyclobutyl, cyclopentyl, cyclohexyl, bicyclo[2.2.2]octyl, adamantyl, noradamantyl), each of which is optionally substituted as described in the Summary and embodiments herein below.

In certain embodiments, $R^1$ is heterocycle, optionally substituted as described in the Summary. In certain embodiments, $R^1$ is pyrrolidinyl, dihydropyranyl, oxa-adamantyl, or oxabicyclo[2.2.1]heptyl, each of which is optionally substituted as described in the Summary and in embodiments herein below.

In certain embodiments, the optional substituents of the aryl and the heteroaryl of $R^1$ include, but are not limited to alkyl (e.g. methyl, ethyl, isopropyl), alkynyl (e.g. ethynyl), halogen (e.g. F, Cl, I), —CN, —$C(R^{Z3})$=N—$O(R^{1a})$ wherein $R^{Z3}$ and $R^{1a}$ are independently hydrogen or $C_{1-6}$ alkyl (e.g. methyl), —$OR^{1a}$ wherein $R^{1a}$ is hydrogen, $C_{1-6}$ alkyl (e.g. methyl, ethyl), or haloalkyl (e.g. trifluoromethyl, 2-fluoroethyl, 2,2,2-trifluoroethyl), —O—$(CR^{1g}R^{1h})_u$—CN (e.g. —O—$CH_2CN$), —O—$(CR^{1g}R^{1h})_u$—$CON(R^{Z3})(R^{3a})$ wherein $R^{1g}$ and $R^{1h}$ are hydrogen, u is 1, and $R^{Z3}$ and $R^{3a}$ are independently hydrogen or $C_{1-6}$ alkyl (e.g., methyl), —$S(O)_2R^{2a}$ wherein $R^{2a}$ is $C_{1-6}$ alkyl (e.g., methyl), —$C(O)R^{1a}$ wherein $R^{1a}$ is hydrogen or $C_{1-6}$ alkyl (e.g. methyl, ethyl), —$C(O)OR^{1a}$ wherein $R^{1a}$ is hydrogen or $C_{1-6}$ alkyl (e.g. methyl, ethyl), —$C(O)N(R^{Z3})(R^{3a})$ wherein $R^{Z3}$ and $R^{3a}$ are independently hydrogen or $C_{1-6}$ alkyl (e.g., methyl), —$N(R^{Z3})(R^{3a})$ wherein $R^{Z3}$ and $R^{3a}$ are independently hydrogen or $C_{1-6}$ alkyl (e.g., methyl), —$N(R^{Z3})C(O)R^{1a}$ wherein $R^{Z3}$ and $R^{1a}$ are independently hydrogen or $C_{1-6}$ alkyl (e.g., methyl), and haloalkyl (e.g. difluoromethyl, fluoromethyl, trifluoromethyl).

In certain embodiments, the optional substituents of the heterocycle and the cycloalkyl of $R^1$ include, but are not limited to, oxo, alkyl (e.g. methyl), C(O)OH, $C(O)O(C_{1-6}$ alkyl) (e.g. C(O)O(methyl), C(O)O(ethyl), C(O)O(tert-butyl)), CN, $G^2$ (e.g. phenyl, pyridinyl, each of which is unsubstituted or substituted with 1 or 2 substituents selected from halogen or CN), —$C(O)R^{1a}$, and —$C(O)N(R^{Z3})(R^{3a})$, wherein $R^{1a}$, $R^{Z3}$, $R^{3a}$ are as described generally in the Summary. $R^{1a}$, for example, is $C_{1-6}$ alkyl (e.g. methyl) or optionally substituted heterocycle. $R^{Z3}$ and $R^{3a}$ are each independently hydrogen or $C_{1-6}$ alkyl (e.g. methyl).

As generally described in the Summary, $R^4$ is alkyl, alkenyl, alkynyl, —$(CR^aR^b)_n$—CN, —$(CR^aR^b)_n$OH, —$(CR^aR^b)_n$—O(alkyl), haloalkyl, $G^2$, or —$(CR^aR^b)_m$-$G^2$. In certain embodiments, $R^4$ is alkyl (e.g. methyl, tert-butyl, 1,1-dimethylpropyl), haloalkyl (e.g. 2-fluoro-1,1-dimethylethyl, 2,2,2-trifluoro-1,1-dimethylethyl), or $G^2$ (e.g. optionally substituted $C_{3-6}$ cycloalkyl such as, but not limited to, optionally substituted cyclopropyl or optionally substituted cyclobutyl, or optionally substituted monocyclic heterocycle such as, but not limited to, optionally substituted oxetanyl or optionally substituted tetrahydrofuranyl).

It is appreciated that the present invention contemplates compounds of Formula (I) with combinations of the above embodiments, including particular, more particular and preferred embodiments.

Accordingly, one aspect of the invention is directed to a group of compounds of Formula (I) wherein $R^3$ is hydrogen or $C_{1-6}$ alkyl (e.g. methyl), and $R^2$ is alkyl (e.g., methyl, ethyl, isobutyl, n-butyl, n-pentyl, and the like), alkenyl (for example, allyl, but-1-enyl, and the like), $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —(CR$^a$R$^b$)$_m$—O(R$^{Za}$), —(CR$^a$R$^b$)$_m$—C(O)O(R$^{Zb}$), —(CR$^a$R$^b$)$_m$—C(O)(R$^{Zb}$), —(CR$^a$R$^b$)$_m$—C(R$^{Zb}$)=NO(R$^{Z1}$), —(CR$^a$R$^b$)$_m$—N(R$^{Z1}$)(R$^{Z2b}$), or —(CR$^a$R$^b$)$_m$-G$^1$ wherein G$^1$, R$^{Zb}$, R$^{Z1}$, R$^{Za}$, R$^{Z2b}$, R$^a$, R$^b$, and m are as described generally in the Summary and the embodiments herein.

Another aspect of the invention is directed to a group of compounds of Formula (I) wherein $R^3$ is hydrogen or $C_{1-6}$ alkyl (e.g. methyl), and $R^2$ is alkyl (e.g., methyl, ethyl, isobutyl, n-butyl, n-pentyl, and the like), alkenyl (for example, allyl, but-1-enyl, and the like) or $C_{1-6}$ haloalkyl (e.g., 4-fluoro-4-methylpentyl, 4,4-difluoropentyl, 3-fluoro-3-methylbutyl, 4,4,4-trifluorobutyl, 4-fluorobutyl).

Yet another aspect of the invention is directed to a group of compounds of Formula (I) wherein $R^3$ is hydrogen or $C_{1-6}$ alkyl (e.g. methyl), and $R^2$ is G$^1$ wherein G$^1$ is as described in the Summary. Examples of G$^1$ include, but are not limited to, cycloalkyl (e.g. cyclopropyl) and heterocycle (e.g. tetrahydropyranyl), each of which is optionally substituted as described generally in the Summary section. Examples of the optional substituents, when present, include, but are not limited to, alkyl (e.g. methyl, ethyl), oxo, and haloalkyl.

Still another aspect of the invention is directed to a group of compounds of Formula (I) wherein $R^3$ is hydrogen or $C_{1-6}$ alkyl (e.g. methyl), and $R^2$ is —(CR$^a$R$^b$)$_m$-G$^1$ wherein G$^1$, R$^a$, and R$^b$ are as described in the Summary. Examples of G$^1$ include, but are not limited to, aryl (e.g. phenyl), cycloalkyl (e.g. cyclopropyl, cyclobutyl, cyclopentyl, cyclohexyl), heterocycle (e.g. 4,5-dihydroisoxazolyl, morpholinyl, 1,3-dioxanyl, 1,3-dioxolanyl, tetrahydrofuranyl), heteroaryl (e.g. furanyl, 1,3-thiazolyl, thienyl), each of which is optionally substituted as described generally in the Summary section. Examples of the optional substituents, when present, include, but are not limited to, alkyl, haloalkyl, and oxo. R$^a$ and R$^b$ are as described generally in the Summary section. Examples of R$^a$ include, but are not limited to, hydrogen and $C_{1-6}$ alkyl (e.g. methyl, ethyl, isopropyl). Examples of R$^b$ include, but are not limited to, hydrogen, $C_{1-6}$ alkyl (e.g. methyl, ethyl, isopropyl), and OH.

A further aspect of the invention is directed to a group of compounds of Formula (I) wherein $R^3$ is hydrogen or $C_{1-6}$ alkyl (e.g. methyl), and $R^2$ is —C(R$^{Zb}$)=NO(R$^{Z1}$), —(CR$^a$R$^b$)$_m$—N$_3$, —(CR$^a$R$^b$)$_m$—CN, —(CR$^a$R$^b$)$_m$—C(O)O(R$^{Zb}$), —(CR$^a$R$^b$)$_m$—C(O)(R$^{Zb}$), —(CR$^a$R$^b$)$_m$—C(R$^{Zb}$)=NO(R$^{Z1}$), or —(CR$^a$R$^b$)$_m$—N(R$^{Z1}$)(R$^{Z2b}$), wherein R$^{Zb}$, R$^a$, R$^b$, R$^{Z1}$, m, and R$^{Z2b}$ are as described in the Summary. Each occurrence of R$^{Zb}$, R$^a$, R$^b$, R$^{Z1}$, and R$^{Z2b}$, are, for example, independently, hydrogen and $C_{1-6}$ alkyl (e.g. methyl, ethyl, isopropyl).

A still further aspect of the invention is directed to a group of compounds of Formula (I) wherein $R^3$ is hydrogen or $C_{1-6}$ alkyl (e.g. methyl), and $R^2$ is -O(R$^{Za}$) or —N(R$^{Z1}$)(R$^{Z2b}$). Examples of R$^{Za}$ include, but are not limited to, alkyl (e.g., isopropyl, sec-butyl), haloalkyl (e.g., 4-fluorobutyl), —(CR$^c$R$^d$)$_q$—CN and —(CR$^c$R$^d$)$_q$-G$^1$. G$^1$, for example, is unsubstituted phenyl or pyrrolidinyl, unsubstituted or substituted with 1 or 2 substituents selected from the group consisting of oxo and $C_{1-6}$ alkyl (e.g. methyl). Each occurrence of R$^c$ and R$^d$, are independently hydrogen or $C_{1-6}$ alkyl (e.g. methyl, ethyl). q is 1 or 2. In certain embodiments, q is 1. R$^{Z1}$, for example, is hydrogen. R$^{Z2b}$, for example, is —C(O)O(R$^{Zc}$) wherein R$^{Zc}$ is as described in the Summary. R$^{Zc}$, for example, is $C_{1-6}$ alkyl (e.g. tert-butyl).

Still yet another aspect of the invention is directed to a group of compounds of Formula (I) wherein $R^3$ is hydrogen or $C_{1-6}$ alkyl (e.g. methyl), and $R^2$ is —(CR$^a$R$^b$)$_m$—O(R$^{Za}$) or —(CR$^a$R$^b$)$_m$—N(R$^{Z1}$)(R$^{Z2b}$) wherein R$^a$, R$^b$, R$^{Za}$, R$^{Z1}$, and R$^{Z2b}$ are as described in the Summary. In certain embodiments, R$^{Za}$ is hydrogen, alkyl (e.g. methyl, ethyl, isopropyl), haloalkyl (e.g. 2,2,2-trifluoroethyl, 2-fluoroethyl, 2,2-difluoroethyl), or —(CR$^c$R$^d$)$_q$-G$^1$ wherein q, R$^c$, R$^d$, and G$^1$ is as described in the Summary. G$^1$, for example, is optionally substituted tetrahydrofuran. In certain embodiments, each occurrence of R$^a$, R$^b$, R$^c$, and R$^d$, are, for example, independently, hydrogen or $C_{1-6}$ alkyl (e.g. methyl, ethyl, isopropyl). q, for example, is 1. R$^{Z1}$ and R$^{Z2b}$ are, for example, independently hydrogen or $C_{1-6}$ alkyl (e.g. methyl, ethyl, isopropyl).

For each of the groups of compounds of Formula (I) described in the preceding paragraphs, m, if present, is 1, 2, 3, 4, or 5. In certain embodiments, m is 1, 2, 3, or 4. In other embodiments, m is 1, 2, or 3. In yet other embodiments, m is 1 or 2.

Still another group of compounds of Formula (I) include, but are not limited to, those wherein $R^2$ and $R^3$, together with the atoms to which they are attached, form a five-, six-, or seven-membered monocyclic ring containing zero or one additional double bond, zero or one heteroatom selected from O, S, N, or N(H), each said ring is independently unsubstituted or substituted with 1, 2, 3, 4, or 5 substituents (R$^{21}$) selected from the group consisting of oxo, alkyl, alkenyl, alkynyl, halogen, —CN, —O(R$^{1a}$), —C(O)OH, —C(O)O(alkyl), —C(O)(R$^{1a}$), —N(R$^{Z3}$)(R$^{3a}$), —N(R$^{3a}$)C(O)R$^{1a}$, —N(R$^{3a}$)C(O)O(R$^{1a}$), —N(R$^{3a}$)C(O)N(R$^{Z3}$)(R$^{3a}$), —N(R$^{3a}$)S(O)$_2$(R$^{2a}$), —N(R$^{3a}$)S(O)$_2$N(R$^{Z3}$)(R$^{3a}$), —SO$_2$(R$^{2a}$), —C(O)N(R$^{Z3}$)(R$^{3a}$), —S(O)$_2$N(R$^{Z3}$)(R$^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O(R$^{1a}$), and haloalkyl, two adjacent or non-adjacent atoms of each said rings are optionally linked by an alkylene bridge of one, two, three, or four carbon atoms; and two substituents (R$^{21}$) on the same carbon atom, together with said carbon atom, optionally form a 3-6 membered monocyclic ring containing 0, 1, or 2 heteroatoms selected from O, S, or N(H).

Yet another groups of compounds of formula (I) include those wherein $R^2$ and $R^3$, together with the atoms to which they are attached, form a six-membered monocyclic ring containing zero additional double bond, zero or one N(H) in the ring, each said ring is independently unsubstituted or substituted with 1, 2, 3, 4, or 5 substituents (R$^{21}$) selected from the group consisting of oxo, alkyl, alkenyl, alkynyl, halogen, —CN, —O(R$^{1a}$), —C(O)OH, —C(O)O(alkyl), —C(O)(R$^{1a}$), —N(R$^{Z3}$)(R$^{3a}$), —N(R$^{3a}$)C(O)R$^{1a}$, —N(R$^{3a}$)C(O)O(R$^{1a}$), —N(R$^{3a}$)C(O)N(R$^{Z3}$)(R$^{3a}$), —N(R$^{3a}$)S(O)$_2$(R$^{2a}$), —N(R$^{3a}$)S(O)$_2$N(R$^{Z3}$)(R$^{3a}$), —SO$_2$(R$^{2a}$), —C(O)N(R$^{Z3}$)(R$^{3a}$), —S(O)$_2$N(R$^{Z3}$)(R$^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O(R$^{1a}$), and haloalkyl; and two substituents (R$^{21}$) on the same carbon atom, together with said carbon atom, optionally form a 3-6 membered monocyclic ring containing 0, 1, or 2 heteroatoms selected from O, S, or N(H).

Yet other examples of a group of compounds of Formula (I) include, but are not limited to, those wherein $R^2$ and $R^3$, together with the atoms to which they are attached, form a six-membered monocyclic ring as described herein above, having formula (II)

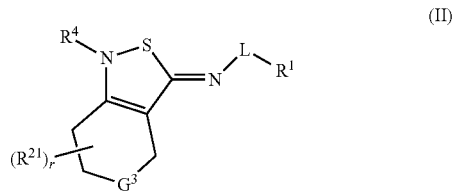

(II)

wherein $G^3$ is $CH_2$ or N(H), $R^{21}$ is an optional substituent on any substitutable atom of the six-membered ring, and has values as described herein above, r is 0, 1, 2, 3, 4, or 5, and $R^1$, $R^4$, and L are as described generally above and in embodiments herein. In certain embodiments, $G^3$ is N(H). In yet other embodiments $G^3$ is $CH_2$. Examples of $R^{21}$ include, but are not limited to, alkyl (e.g. methyl, ethyl, isopropyl, n-butyl, n-propyl), haloalkyl (e.g. trifluoromethyl), —C(O)O($C_{1-6}$ alkyl), —C(O)OH, and oxo; and two $R^{21}$ on the same carbon atoms, together with said carbon atom, optionally form a monocyclic ring as described generally in the Summary. In certain embodiments, r is 0, 1, 2, or 3. In other embodiments, r is 0, 1 or 2.

Within each of the groups of compounds of Formula (I) and (II) as described in the preceding paragraphs, $R^1$, $R^4$, L, and the optional substituents, when present, are as described generally in the Summary section and in embodiments described above and herein.

For each group of compounds of Formula (I) and (II) as described herein above, examples of a subgroup include those wherein $R^1$ is $G^1$. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein above.

Yet examples of another subgroup of compounds of Formula (I) and (II) include those wherein L is C=O and $R^1$ is $G^1$ wherein $G^1$ is as described generally in the Summary and in embodiments herein above. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein above.

Yet other examples of another subgroup of compounds of Formula (I) and (II) include those wherein L is C=O and $R^1$ is phenyl or naphthyl, each of which is optionally substituted as described generally in the Summary and in embodiments herein above.

Yet other examples of a subgroup of compounds of Formula (I) and (II) include, but are not limited to, those wherein L is C=O and $R^1$ is heteroaryl, optionally substituted as described generally in the Summary and in embodiments herein above.

Yet other examples of a subgroup of compounds of Formula (I) and (II) include, but are not limited to, those wherein L is C=O and $R^1$ is heterocycle, optionally substituted as described generally in the Summary and in embodiments herein above.

Yet other examples of a subgroup of compounds of Formula (I) and (II) include, but are not limited to, those wherein L is C=O and $R^1$ is cycloalkyl, optionally substituted as described generally in the Summary and in embodiments herein above.

Yet other examples of a subgroup of compounds of Formula (I) and (II) include, but are not limited to, those wherein L is C=S and $R^1$ is $G^1$; wherein $G^1$ is as described generally in the Summary and in embodiments herein above. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein above.

Yet other examples of a subgroup of compounds of Formula (I) and (II) include, but are not limited to, those wherein L is C=S and $R^1$ is phenyl or naphthyl, each of which is optionally substituted as described generally in the Summary and in embodiments herein above.

Yet other examples of a subgroup of compounds of Formula (I) and (II) include, but are not limited to, those wherein L is C=S and $R^1$ is heteroaryl, optionally substituted as described generally in the Summary and in embodiments herein above.

Yet other examples of a subgroup of compounds of Formula (I) and (II) include, but are not limited to, those wherein L is C=S and $R^1$ is heterocycle, optionally substituted as described generally in the Summary and in embodiments herein above.

Yet other examples of a subgroup of compounds of Formula (I) and (II) include, but are not limited to, those wherein L is C=S and $R^1$ is cycloalkyl, optionally substituted as described generally in the Summary and in embodiments herein above.

Yet other examples of a subgroup of compounds of Formula (I) and (II) include, but are not limited to, those wherein L is $S(O)_2$ and $R^1$ is G'; wherein $G^1$ is as described generally in the Summary and in embodiments herein above. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein above.

Yet other examples of a subgroup of compounds of Formula (I) and (II) include, but are not limited to, those wherein L is $S(O)_2$ and $R^1$ is phenyl or naphthyl, each of which is optionally substituted as described generally in the Summary and in embodiments herein above.

Yet other examples of a subgroup of compounds of Formula (I) and (II) include, but are not limited to, those wherein L is $S(O)_2$ and $R^1$ is heteroaryl, optionally substituted as described generally in the Summary and in embodiments herein above.

Yet other examples of a subgroup of compounds of Formula (I) and (II) include, but are not limited to, those wherein L is $S(O)_2$ and $R^1$ is heterocycle, optionally substituted as described generally in the Summary and in embodiments herein above.

Yet other examples of a subgroup of compounds of Formula (I) and (II) include, but are not limited to, those wherein $S(O)_2$ and $R^1$ is cycloalkyl, optionally substituted as described generally in the Summary and in embodiments herein above.

Yet another aspect of the invention is directed to groups of compounds of Formula (I) and (II) wherein L is C=NCN and $R^1$ is $G^1$; wherein $G^1$ is as described generally in the Summary and in embodiments herein above. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein above.

Yet other examples of a subgroup of compounds of Formula (I) and (II) include, but are not limited to, those wherein L is C=NCN and $R^1$ is phenyl or naphthyl, each of which is optionally substituted as described generally in the Summary and in embodiments herein above.

Yet other examples of a subgroup of compounds of Formula (I) and (II) include, but are not limited to, those wherein L is C=NCN and $R^1$ is heteroaryl, optionally substituted as described generally in the Summary and in embodiments herein above.

Yet other examples of a subgroup of compounds of Formula (I) and (II) include, but are not limited to, those wherein L is C=NCN and $R^1$ is heterocycle, optionally substituted as described generally in the Summary and in embodiments herein above.

Yet other examples of a subgroup of compounds of Formula (I) and (II) include, but are not limited to, those wherein L is C=NCN and $R^1$ is cycloalkyl, optionally substituted as described generally in the Summary and in embodiments herein above. Within each of the groups and subgroups of compounds of Formula (I)-(II) as described in the preceding paragraphs, $R^4$ is as described generally in the Summary section and in embodiments described above and herein. In certain embodiments, $R^4$ is alkyl (e.g. methyl, tert-butyl, 1,1-dimethylpropyl), haloalkyl (e.g. 2-fluoro-1,1-dimethylethyl, 2,2,2-trifluoro-1,1-dimethylethyl), or $G^2$ (e.g. optionally substituted $C_{3-6}$ cycloalkyl such as, but not limited to, optionally substituted cyclopropyl or optionally substituted cyclobutyl, or optionally substituted monocyclic heterocycle such as, but not limited to, optionally substituted oxetanyl or optionally substituted tetrahydrofuranyl).

Compounds included in the present application are also those in which $R^3$ is hydrogen or $C_{1-6}$ alkyl, and $R^4$ is alkyl, haloalkyl, or $G^2$.

It is intended that the present application also includes those compounds wherein $R^3$ is hydrogen, $C_{1-6}$ alkyl, haloalkyl, or cycloalkyl; $R^2$ is alkyl, alkenyl, alkynyl, $G^1$, —$C(R^{Zb})$=NO($R^{Z1}$), —O($R^{Za}$), —N($R^{Z1}$)($R^{Z2b}$), —$(CR^aR^b)_m$—$N_3$, —$(CR^aR^b)_m$—CN, haloalkyl, —$(CR^aR^b)_m$—O($R^{Za}$), —$(CR^aR^b)_m$—C(O)O($R^{Zb}$), —$(CR^aR^b)_m$—C(O)($R^{Zb}$), —$(CR^aR^b)_m$—C($R^{Zb}$)=NO($R^{Z1}$), —$(CR^aR^b)_m$—N($R^{Z1}$)($R^{Z2b}$), or —$(CR^aR^b)_m$-$G^1$; $R^1$ is $G^1$; and $R^4$ is alkyl, haloalkyl, or $G^2$, and any combination of L as described above. For example, L is C=O.

Other compounds that are contemplated include those wherein $R^3$ is hydrogen or $C_{1-6}$ alkyl; $R^2$ is alkyl, alkenyl, alkynyl, —$(CR^aR^b)_m$—CN, haloalkyl, —$(CR^aR^b)_m$—O($R^{Za}$) or —$(CR^aR^b)_m$-$G^1$; $R^4$ is $C_{1-6}$ alkyl, haloalkyl, or $C_{3-6}$ cycloalkyl; and $R^1$ is optionally substituted phenyl or optionally substituted naphthyl, and any combination of L as described above. For example, L is C=O. In certain embodiments, L is C=NCN.

Yet other compounds that are contemplated include those wherein $R^3$ is hydrogen or $C_{1-6}$ alkyl; $R^2$ is alkyl, alkenyl, alkynyl, —$(CR^aR^b)_m$—CN, haloalkyl, —$(CR^aR^b)_m$—O($R^{Za}$) or —$(CR^aR^b)_m$-$G^1$; $R^4$ is $C_{1-6}$ alkyl, haloalkyl, or $C_{3-6}$ cycloalkyl; and $R^1$ is optionally substituted cycloalkyl, and any combination of L as described above. For example, L is C=O. In certain embodiments, L is C=NCN.

Still other compounds that are intended include those wherein $R^2$ and $R^3$, together with the carbon atoms to which they are attached, form a monocyclic ring as generally described in the Summary and in embodiments herein above, $R^1$ is $G^1$, and $R^4$ is alkyl, haloalkyl, or $G^2$.

Still other compounds that are intended include those wherein $R^2$ and $R^3$, together with the carbon atoms to which they are attached and in embodiments herein above, form a monocyclic ring as generally described in the Summary, $R^1$ is optionally substituted phenyl or optionally substituted naphthyl; and $R^4$ is $C_{1-6}$ alkyl, haloalkyl, or $C_{3-6}$ cycloalkyl.

Still other compounds that are intended include those wherein $R^2$ and $R^3$, together with the carbon atoms to which they are attached, form a monocyclic ring as generally described in the Summary and in embodiments herein above, $R^1$ is optionally substituted cycloalkyl, and $R^4$ is $C_{1-6}$ alkyl, haloalkyl, or $C_{3-6}$ cycloalkyl.

Still other compounds that are intended include those wherein $R^2$ and $R^3$, together with the carbon atoms to which they are attached, form a monocyclic ring as generally described in the Summary and in embodiments herein above, L is C(O), $R^1$ is $G^1$, and $R^4$ is alkyl, haloalkyl, or $G^2$.

Still other compounds that are intended include those wherein $R^2$ and $R^3$, together with the carbon atoms to which they are attached, form a monocyclic ring as generally described in the Summary and in embodiments herein above, L is C(O), $R^1$ is optionally substituted phenyl or optionally substituted naphthyl, and $R^4$ is alkyl, haloalkyl, or $G^2$.

Still other compounds that are intended include those wherein $R^2$ and $R^3$, together with the carbon atoms to which they are attached, form a monocyclic ring as generally described in the Summary and in embodiments herein above, L is C(O), $R^1$ is optionally substituted cycloalkyl, and $R^4$ is alkyl, haloalkyl, or $G^2$.

Exemplary compounds of the invention include, but are not limited to,

N-[(5Z)-4-butyl-2-tert-butylisothiazol-5(2H)-ylidene]-5-chloro-2-methoxybenzamide;

N-[(5Z)-4-butyl-2-(1,1-dimethylpropyl)isothiazol-5(2H)-ylidene]-5-chloro-2-methoxybenzamide;

N-[(5Z)-4-butyl-2-cyclobutylisothiazol-5(2H)-ylidene]-5-chloro-2-methoxybenzamide;

N-[(5Z)-4-butyl-2,3-dimethylisothiazol-5(2H)-ylidene] hexahydro-2,5-methanopentalene-3a(1H)-carboxamide;

N-[(5Z)-4-butyl-2-(1-methylcyclobutyl)isothiazol-5(2H)-ylidene]-5-chloro-2-methoxybenzamide;

N-[(5Z)-4-allyl-2-tert-butylisothiazol-5(2H)-ylidene]-5-chloro-2-methoxybenzamide;

N-[(5Z)-2-tert-butyl-4-[(3-methyl-4,5-dihydroisoxazol-5-yl)methyl]isothiazol-5(2H)-ylidene]-5-chloro-2-methoxybenzamide;

N-[(5Z)-2-tert-butyl-4-(cyclopropylmethyl)isothiazol-5(2H)-ylidene]-5-chloro-2-methoxybenzamide;

N-[(3Z)-1-tert-butyl-5-propyl-4,5,6,7-tetrahydro-2,1-benzisothiazol-3(1H)-ylidene]-5-chloro-2-methoxybenzamide;

N-[(3Z)-1-tert-butyl-1,4,6,7-tetrahydro-3H-spiro[2,1-benzisothiazole-5,2'-[1,3]dioxolan]-3-ylidene]-5-chloro-2-methoxybenzamide;
N-[(5Z)-2-tert-butyl-4-(2-hydroxyethyl)isothiazol-5(2H)-ylidene]-5-chloro-2-methoxybenzamide;
N-[(5Z)-2-tert-butyl-4-(2-methoxyethyl)isothiazol-5(2H)-ylidene]-5-chloro-2-methoxybenzamide;
N-[(5Z)-2-tert-butyl-4-(2-morpholin-4-ylethyl)isothiazol-5(2H)-ylidene]-5-chloro-2-methoxybenzamide;
N-[(5Z)-2-tert-butyl-4-[2-(5,5-dimethyl-1,3-dioxan-2-yl)ethyl]isothiazol-5(2H)-ylidene]-5-chloro-2-methoxybenzamide;
N-[(5Z)-4-(2-azidoethyl)-2-tert-butylisothiazol-5(2H)-ylidene]-5-chloro-2-methoxybenzamide;
N-[(5Z)-2-tert-butyl-4-[(3E)-3-(methoxyimino)propyl]isothiazol-5(2H)-ylidene]-5-chloro-2-methoxybenzamide;
N-[(5Z)-4-(2-aminoethyl)-2-tert-butylisothiazol-5(2H)-ylidene]-5-chloro-2-methoxybenzamide;
N-[(5Z)-2-tert-butyl-4-[2-(dimethylamino)ethyl]isothiazol-5(2H)-ylidene]-5-chloro-2-methoxybenzamide;
N-[(5Z)-2-tert-butyl-4-methylisothiazol-5(2H)-ylidene]-5-chloro-2-methoxybenzamide;
N-[(5Z)-2-tert-butyl-4-(3-hydroxybutyl)isothiazol-5(2H)-ylidene]-5-chloro-2-methoxybenzamide;
N-[(5Z)-2-tert-butyl-4-(2-cyanoethyl)isothiazol-5(2H)-ylidene]-5-chloro-2-methoxybenzamide;
N-[(5Z)-2-tert-butyl-4-(2,3-dihydroxypropyl)isothiazol-5(2H)-ylidene]-5-chloro-2-methoxybenzamide;
N-[(5Z)-2-tert-butyl-4-[(E)-(methoxyimino)methyl]isothiazol-5(2H)-ylidene]-5-chloro-2-methoxybenzamide;
N-[(5Z)-2-tert-butyl-4-(1,3-dioxolan-2-ylmethyl)isothiazol-5(2H)-ylidene]-5-chloro-2-methoxybenzamide;
N-[(5Z)-2-tert-butyl-4-(1-hydroxy-2-methylpropyl)isothiazol-5(2H)-ylidene]-5-chloro-2-methoxybenzamide;
N-[(5Z)-2-tert-butyl-4-(cyanomethyl)isothiazol-5(2H)-ylidene]-5-chloro-2-methoxybenzamide;
N-[(5Z)-4-[(1Z)-but-1-enyl]-2-tert-butylisothiazol-5(2H)-ylidene]-5-chloro-2-methoxybenzamide;
N-[(5Z)-4-butyl-2-tert-butylisothiazol-5(2H)-ylidene]-5-cyano-2-methoxybenzamide;
N-[(5Z)-2-tert-butyl-4-(2-ethylcyclopropyl)isothiazol-5(2H)-ylidene]-5-chloro-2-methoxybenzamide;
N-[(5Z)-2-tert-butyl-4-(hydroxymethyl)isothiazol-5(2H)-ylidene]-5-chloro-2-methoxybenzamide;
N-[(5Z)-2-tert-butyl-4-(methoxymethyl)isothiazol-5(2H)-ylidene]-5-chloro-2-methoxybenzamide;
N-[(5Z)-2-tert-butyl-4-(ethoxymethyl)isothiazol-5(2H)-ylidene]-5-chloro-2-methoxybenzamide;
N-[(5Z)-2-tert-butyl-4-(3-cyanopropyl)isothiazol-5(2H)-ylidene]-5-chloro-2-methoxybenzamide;
N-[(5Z)-2-tert-butyl-4-[hydroxy(phenyl)methyl]isothiazol-5(2H)-ylidene]-5-chloro-2-methoxybenzamide;
N-[(5Z)-4-(azidomethyl)-2-tert-butylisothiazol-5(2H)-ylidene]-5-chloro-2-methoxybenzamide;
N-[(5Z)-2-tert-butyl-4-(2-cyclobutyl-1-hydroxyethyl)isothiazol-5(2H)-ylidene]-5-chloro-2-methoxybenzamide;
N-[(5Z)-2-tert-butyl-4-[cyclobutyl(hydroxy)methyl]isothiazol-5(2H)-ylidene]-5-chloro-2-methoxybenzamide;
N-[(5Z)-4-benzyl-2-tert-butylisothiazol-5(2H)-ylidene]-5-chloro-2-methoxybenzamide;
N-[(5Z)-2-tert-butyl-4-(2-cyclobutylethyl)isothiazol-5(2H)-ylidene]-5-chloro-2-methoxybenzamide;
N-[(5Z)-2-tert-butyl-4-isobutylisothiazol-5(2H)-ylidene]-5-chloro-2-methoxybenzamide;
N-[(5Z)-2-tert-butyl-4-(cyclobutylmethyl)isothiazol-5(2H)-ylidene]-5-chloro-2-methoxybenzamide;
N-[(5Z)-2-tert-butyl-4-tetrahydro-2H-pyran-4-ylisothiazol-5(2H)-ylidene]-5-chloro-2-methoxybenzamide;
N-[(5Z)-2-tert-butyl-4-[hydroxy(1,3-thiazol-2-yl)methyl]isothiazol-5(2H)-ylidene]-5-chloro-2-methoxybenzamide;
N-[(5Z)-4-butyl-2-tert-butylisothiazol-5(2H)-ylidene]-2,5-dimethoxybenzamide;
N-[(5Z)-4-butyl-2-tert-butylisothiazol-5(2H)-ylidene]-5-fluoro-2-methoxybenzamide;
N-[(5Z)-4-butyl-2-tert-butylisothiazol-5(2H)-ylidene]-2-methoxy-5-methylbenzamide;
N-[(5Z)-2-tert-butyl-4-[hydroxy(thien-2-yl)methyl]isothiazol-5(2H)-ylidene]-5-chloro-2-methoxybenzamide;
methyl 4-{(5Z)-2-tert-butyl-5-[(5-chloro-2-methoxybenzoyl)imino]-2,5-dihydroisothiazol-4-yl}butanoate;
methyl 4-{(5Z)-2-tert-butyl-5-[(5-cyano-2-methoxybenzoyl)imino]-2,5-dihydroisothiazol-4-yl}butanoate;
N-[(5Z)-4-butyl-2-tert-butylisothiazol-5(2H)-ylidene]-5-chloro-2-fluorobenzamide;
N-[(5Z)-4-butyl-2-tert-butylisothiazol-5(2H)-ylidene]-5-chloro-2-(2,2,2-trifluoroethoxy)benzamide;
N-[(5Z)-4-butyl-2-tert-butylisothiazol-5(2H)-ylidene]-2-methoxy-5-(methylsulfonyl)benzamide;
N-[(5Z)-2-tert-butyl-4-[hydroxy(1,3-thiazol-4-yl)methyl]isothiazol-5(2H)-ylidene]-5-chloro-2-methoxybenzamide;
N-[(5Z)-2-tert-butyl-4-(2-furylmethyl)isothiazol-5(2H)-ylidene]-5-chloro-2-methoxybenzamide;
N-[(5Z)-2-tert-butyl-4-(2-furylmethyl)isothiazol-5(2H)-ylidene]-5-cyano-2-methoxybenzamide;
N-[(5Z)-2-tert-butyl-4-(1,3-thiazol-4-ylmethyl)isothiazol-5(2H)-ylidene]-5-chloro-2-methoxybenzamide;
N-[(5Z)-2-tert-butyl-4-(thien-2-ylmethyl)isothiazol-5(2H)-ylidene]-5-cyano-2-methoxybenzamide;
N-[(5Z)-2-tert-butyl-4-(thien-2-ylmethyl)isothiazol-5(2H)-ylidene]-5-chloro-2-methoxybenzamide;
5-amino-N-[(5Z)-4-butyl-2-tert-butylisothiazol-5(2H)-ylidene]-2-methoxybenzamide;
N-[(5Z)-4-butyl-2-tert-butylisothiazol-5(2H)-ylidene]-5-formyl-2-methoxybenzamide;
N-[(5Z)-4-butyl-2-tert-butylisothiazol-5(2H)-ylidene]-2-methoxy-5-[(E)-(methoxyimino)methyl]benzamide;
N-[(5Z)-4-butyl-2-tert-butylisothiazol-5(2H)-ylidene]-5-(formylamino)-2-methoxybenzamide;
N-[(5Z)-4-butyl-2-tert-butylisothiazol-5(2H)-ylidene]-5-[(E)-(hydroxyimino)methyl]-2-methoxybenzamide;
3-({[(5Z)-4-butyl-2-tert-butylisothiazol-5(2H)-ylidene]amino}carbonyl)-4-methoxybenzoic acid;
N-[(5Z)-4-butyl-2-tert-butylisothiazol-5(2H)-ylidene]-5-iodo-2-methoxybenzamide;
N-[(5Z)-4-butyl-2-tert-butylisothiazol-5(2H)-ylidene]-5-ethynyl-2-methoxybenzamide;
N-[(5Z)-4-butyl-2-tert-butylisothiazol-5(2H)-ylidene]-2-methoxy-5-(trifluoromethoxy)benzamide;
5-acetyl-N-[(5Z)-4-butyl-2-tert-butylisothiazol-5(2H)-ylidene]-2-methoxybenzamide;
N-[(5Z)-4-butyl-2-tert-butylisothiazol-5(2H)-ylidene]-5-(difluoromethyl)-2-methoxybenzamide;
N-[(5Z)-4-butyl-2-tert-butylisothiazol-5(2H)-ylidene]-5-(fluoromethyl)-2-methoxybenzamide;
N-[(5Z)-2-tert-butyl-4-(tetrahydrofuran-2-ylmethyl)isothiazol-5(2H)-ylidene]-5-chloro-2-methoxybenzamide;
N-[(5Z)-4-butyl-2-tert-butylisothiazol-5(2H)-ylidene]-5-[(1Z)—N-hydroxyethanimidoyl]-2-methoxybenzamide;

N-[(5Z)-4-butyl-2-tert-butylisothiazol-5(2H)-ylidene]-5-(1,1-difluoro ethyl)-2-methoxybenzamide;
N-[(5Z)-2-tert-butyl-4-(2-furylmethyl)isothiazol-5(2H)-ylidene]-2-fluoro-3-(trifluoromethyl)benzamide;
N-[(5Z)-2-tert-butyl-4-(2-furylmethyl)isothiazol-5(2H)-ylidene]-2-methoxy-5-(trifluoromethyl)benzamide;
N-[(5Z)-2-tert-butyl-4-(isopropoxymethyl)isothiazol-5(2H)-ylidene]-5-chloro-2-methoxybenzamide;
N-[(5Z)-4-butyl-2-tert-butylisothiazol-5(2H)-ylidene]-2-fluoro-3-(trifluoromethyl)benzamide;
methyl 3-({[(5Z)-4-butyl-2-tert-butylisothiazol-5(2H)-ylidene]amino}carbonyl)-4-methoxybenzoate;
N-[(5Z)-2-tert-butyl-4-(4-oxopentyl)isothiazol-5(2H)-ylidene]-5-chloro-2-methoxybenzamide;
N-[(5Z)-2-tert-butyl-4-(4-oxopentyl)isothiazol-5(2H)-ylidene]-2-methoxy-5-(trifluoromethyl)benzamide;
N-[(5Z)-2-tert-butyl-4-(4-oxopentyl)isothiazol-5(2H)-ylidene]-2-fluoro-3-(trifluoromethyl)benzamide;
$N^3$-[(5Z)-4-butyl-2-tert-butylisothiazol-5(2H)-ylidene]-4-methoxyisophthalamide;
N-[(5Z)-2-tert-butyl-4-(4-hydroxy-4-methylpentyl)isothiazol-5(2H)-ylidene]-2-fluoro-3-(trifluoromethyl)benzamide;
N-[(5Z)-2-tert-butyl-4-(4-hydroxy-4-methylpentyl)isothiazol-5(2H)-ylidene]-5-chloro-2-methoxybenzamide;
N-[(5Z)-2-tert-butyl-4-(4-hydroxy-4-methylpentyl)isothiazol-5(2H)-ylidene]-2-methoxy-5-(trifluoromethyl)benzamide;
N-[(5Z)-4-butyl-2-tert-butylisothiazol-5(2H)-ylidene]-5-isopropyl-2-methoxybenzamide;
N-[(5Z)-2-tert-butyl-4-(4-fluoro-4-methylpentyl)isothiazol-5(2H)-ylidene]-5-chloro-2-methoxybenzamide;
N-[(5Z)-2-tert-butyl-4-(3-oxobutyl)isothiazol-5(2H)-ylidene]-5-chloro-2-methoxybenzamide;
N-[(5Z)-2-tert-butyl-4-[(2,2,2-trifluoroethoxy)methyl]isothiazol-5(2H)-ylidene]-5-chloro-2-methoxybenzamide;
N-[(5Z)-2-tert-butyl-4-(4,4-difluoropentyl)isothiazol-5(2H)-ylidene]-5-chloro-2-methoxybenzamide;
N-[(5Z)-2-tert-butyl-4-(3-fluoro-3-methylbutyl)isothiazol-5(2H)-ylidene]-5-chloro-2-methoxybenzamide;
N-[(5Z)-2-tert-butyl-4-(4-fluoro-4-methylpentyl)isothiazol-5(2H)-ylidene]-2-methoxy-5-(trifluoromethyl)benzamide;
N-[(5Z)-2-tert-butyl-4-{[(2R)-tetrahydrofuran-2-ylmethoxy]methyl}isothiazol-5(2H)-ylidene]-5-chloro-2-methoxybenzamide;
N-[(5Z)-2-tert-butyl-4-[(2-fluoroethoxy)methyl]isothiazol-5(2H)-ylidene]-5-chloro-2-methoxybenzamide;
N-[(5Z)-2-tert-butyl-4-[(2,2-difluoroethoxy)methyl]isothiazol-5(2H)-ylidene]-5-chloro-2-methoxybenzamide;
methyl 3-({[(5Z)-4-butyl-2-tert-butylisothiazol-5(2H)-ylidene]amino}carbonyl)-2,2,3-trimethylcyclopentanecarboxylate;
methyl 3-({[(5Z)-4-butyl-2-tert-butylisothiazol-5(2H)-ylidene]amino}carbonyl)-1,2,2-trimethylcyclopentanecarboxylate;
N-[(5Z)-4-butyl-2-tert-butylisothiazol-5(2H)-ylidene]-1-phenylcyclohexanecarboxamide;
N-[(5Z)-4-butyl-2-tert-butylisothiazol-5(2H)-ylidene]-1-(2-chloro-4-fluorophenyl)cyclohexanecarboxamide;
3-({[(5Z)-4-butyl-2-tert-butylisothiazol-5(2H)-ylidene]amino}carbonyl)-2,2,3-trimethylcyclopentanecarboxylic acid;
N-[(5Z)-4-butyl-2-tert-butylisothiazol-5(2H)-ylidene]-3-oxocyclopentanecarboxamide;
N-[(5Z)-4-butyl-2-tert-butylisothiazol-5(2H)-ylidene]-1-phenylcyclopentanecarboxamide;
$N^1$-[(5Z)-4-butyl-2-tert-butylisothiazol-5(2H)-ylidene]-$N^3$,$N^3$,1,2,2-pentamethylcyclopentane-1,3-dicarboxamide;
$N^1$-[(5Z)-4-butyl-2-tert-butylisothiazol-5(2H)-ylidene]-$N^3$,1,2,2-tetramethylcyclopentane-1,3-dicarboxamide;
N-[(5Z)-4-butyl-2-tert-butylisothiazol-5(2H)-ylidene]-3-[(3,3-difluoro azetidin-1-yl)carbonyl]-1,2,2-trimethylcyclopentanecarboxamide;
(1S,4R)-N-[(5Z)-4-butyl-2-tert-butylisothiazol-5(2H)-ylidene]-4,7,7-trimethyl-3-oxo-2-oxabicyclo[2.2.1]heptane-1-carboxamide;
(1R,4S)-N-[(5Z)-4-butyl-2-tert-butylisothiazol-5(2H)-ylidene]-4,7,7-trimethyl-3-oxo-2-oxabicyclo[2.2.1]heptane-1-carboxamide;
ethyl 3-({[(5Z)-4-butyl-2-tert-butylisothiazol-5(2H)-ylidene]amino}carbonyl)pyrrolidine-1-carboxylate;
3-({[(5Z)-4-butyl-2-tert-butylisothiazol-5(2H)-ylidene]amino}carbonyl)-1,2,2-trimethylcyclopentanecarboxylic acid;
tert-butyl 3-({[(5Z)-4-butyl-2-tert-butylisothiazol-5(2H)-ylidene]amino}carbonyl)pyrrolidine-1-carboxylate;
N-[(5Z)-4-butyl-2-tert-butylisothiazol-5(2H)-ylidene]-1-(3-cyanopyridin-2-yl)pyrrolidine-3-carboxamide;
methyl 4-({[(5Z)-4-butyl-2-tert-butylisothiazol-5(2H)-ylidene]amino}carbonyl)bicyclo[2.2.2]octane-1-carboxylate;
N-[(5Z)-4-butyl-2-tert-butylisothiazol-5(2H)-ylidene]-5-oxo-1-phenylpyrrolidine-3-carboxamide;
N-[(5Z)-4-butyl-2-tert-butylisothiazol-5(2H)-ylidene]-5-chloro-N'-cyano-2-methoxybenzenecarboximidamide;
N-[(5Z)-4-butyl-2-tert-butylisothiazol-5(2H)-ylidene]-5-chloro-2-methoxybenzenecarbothioamide;
N-[(3Z)-1-tert-butyl-5-(trifluoromethyl)-4,5,6,7-tetrahydro-2,1-benzisothiazol-3(1H)-ylidene]-5-chloro-2-methoxybenzamide;
tert-butyl (3Z)-1-tert-butyl-3-[(5-chloro-2-methoxybenzoyl)imino]-1,4,6,7-tetrahydroisothiazolo[4,3-c]pyridine-5(3H)-carboxylate;
N-[(3Z)-1-tert-butyl-4,5,6,7-tetrahydroisothiazolo[4,3-c]pyridin-3(1H)-ylidene]-5-chloro-2-methoxybenzamide;
N-[(5Z)-4-butyl-2-tert-butylisothiazol-5(2H)-ylidene]-5-chloro-2-methoxybenzenesulfonamide;
N-[(5Z)-4-butyl-2-tert-butylisothiazol-5(2H)-ylidene]naphthalene-1-sulfonamide;
N-[(5Z)-4-butyl-2-tert-butylisothiazol-5(2H)-ylidene]-5-(dimethylamino)naphthalene-1-sulfonamide;
N-[(5Z)-4-butyl-2-tert-butylisothiazol-5(2H)-ylidene]cyclohexanesulfonamide;
N-[(5Z)-4-butyl-2-tert-butylisothiazol-5(2H)-ylidene]benzenesulfonamide;
N-[(5Z)-4-butyl-2-tert-butylisothiazol-5(2H)-ylidene]quinoline-8-sulfonamide;
N-[(5Z)-4-butyl-2-tert-butylisothiazol-5(2H)-ylidene]-2,2,3,3-tetramethylcyclopropanecarboxamide;
N-[(5Z)-4-butyl-2-tert-butylisothiazol-5(2H)-ylidene]-2,3-dichlorobenzenesulfonamide;
N-[(5Z)-4-butyl-2-tert-butylisothiazol-5(2H)-ylidene]adamantane-1-carboxamide;
N-[(5Z)-4-butyl-2-tert-butylisothiazol-5(2H)-ylidene]-N'-cyano-2-methoxy-5-(trifluoromethyl)benzenecarboximidamide;
N-[(5Z)-4-butyl-2-tert-butylisothiazol-5(2H)-ylidene]-2,2-dimethyl-4-oxo-3,4-dihydro-2H-pyran-6-carboxamide;
N-[(5Z)-4-butyl-2-tert-butylisothiazol-5(2H)-ylidene]-N'-cyano-2-ethoxy-5-(trifluoromethyl)benzenecarboximidamide;

N-[(5Z)-4-butyl-2-tert-butylisothiazol-5(2H)-ylidene]-2-methoxy-5-(trifluoromethyl)benzamide;
N-[(5Z)-2-tert-butyl-4-(3-cyanopropyl)isothiazol-5(2H)-ylidene]-5-chloro-N'-cyano-2-methoxybenzenecarboximidamide;
N-[(5Z)-4-butyl-2-tert-butylisothiazol-5(2H)-ylidene]-5-cyano-2-hydroxybenzamide;
N-[(5Z)-4-butyl-2-tert-butylisothiazol-5(2H)-ylidene]-5-cyano-2-(2,2,2-trifluoroethoxy)benzamide;
N-[(5Z)-2-tert-butyl-4-(3-cyanopropyl)isothiazol-5(2H)-ylidene]-5-cyano-2-(2,2,2-trifluoroethoxy)benzamide;
N-[(5Z)-2-tert-butyl-4-(3-cyanopropyl)isothiazol-5(2H)-ylidene]-5-cyano-2-hydroxybenzamide;
N-[(5Z)-2-tert-butyl-4-(3-cyanopropyl)isothiazol-5(2H)-ylidene]-5-chloro-2-(2,2,2-trifluoroethoxy)benzamide;
N-[(5Z)-2-tert-butyl-4-(3-cyanopropyl)isothiazol-5(2H)-ylidene]-2-methoxy-5-(trifluoromethyl)benzamide;
N-[(5Z)-4-butyl-2-tert-butylisothiazol-5(2H)-ylidene]-5-chloro-2-hydroxybenzamide;
N-[(5Z)-2-tert-butyl-4-(cyclopentylmethyl)isothiazol-5(2H)-ylidene]-5-chloro-2-methoxybenzamide;
N-[(5Z)-2-tert-butyl-4-(3-cyano-3-methylbutyl)isothiazol-5(2H)-ylidene]-5-chloro-2-methoxybenzamide;
N-[(5Z)-2-tert-butyl-4-(4-cyanobutyl)isothiazol-5(2H)-ylidene]-5-chloro-2-methoxybenzamide;
N-[(5Z)-4-butyl-2-tert-butylisothiazol-5(2H)-ylidene]-5-chloro-2-(2-fluoroethoxy)benzamide;
2-(2-amino-2-oxoethoxy)-N-[(5Z)-4-butyl-2-tert-butylisothiazol-5(2H)-ylidene]-5-chlorobenzamide;
2-(2-amino-2-oxoethoxy)-N-[(5Z)-2-tert-butyl-4-(3-cyanopropyl)isothiazol-5(2H)-ylidene]-5-chlorobenzamide;
N-[(5Z)-2-tert-butyl-4-(4,4,4-trifluorobutyl)isothiazol-5(2H)-ylidene]-5-chloro-2-methoxybenzamide;
N-[(5Z)-2-tert-butyl-4-isobutylisothiazol-5(2H)-ylidene]-2-methoxy-5-(trifluoromethyl)benzamide;
N-[(5Z)-2-tert-butyl-4-isobutylisothiazol-5(2H)-ylidene]-5-chloro-2-(2-fluoroethoxy)benzamide;
N-[(5Z)-2-tert-butyl-4-isobutylisothiazol-5(2H)-ylidene]-5-cyano-2-methoxybenzamide;
N-[(5Z)-2-tert-butyl-4-isobutylisothiazol-5(2H)-ylidene]-2-ethoxy-5-(trifluoromethyl)benzamide;
N-[(5Z)-2-tert-butyl-4-pentylisothiazol-5(2H)-ylidene]-5-chloro-2-methoxybenzamide;
N-[(5Z)-2-tert-butyl-4-(4-fluorobutyl)isothiazol-5(2H)-ylidene]-5-chloro-2-methoxybenzamide;
N-[(5Z)-2-tert-butyl-4-(4-fluorobutyl)isothiazol-5(2H)-ylidene]-2-methoxy-5-(trifluoromethyl)benzamide;
N-[(5Z)-4-butyl-2-tert-butylisothiazol-5(2H)-ylidene]-5-chloro-2-[2-(dimethylamino)-2-oxoethoxy]benzamide;
N-[(5Z)-4-butyl-2-(2,2,2-trifluoro-1,1-dimethylethyl)isothiazol-5(2H)-ylidene]-5-chloro-2-methoxybenzamide;
N-[(5Z)-4-butyl-2-(2-fluoro-1,1-dimethylethyl)isothiazol-5(2H)-ylidene]-2-methoxy-5-(trifluoromethyl)benzamide;
N-[(5Z)-4-butyl-2-tert-butylisothiazol-5(2H)-ylidene]-5-chloro-2-(cyanomethoxy)benzamide;
N-[(5Z)-4-butyl-2-(2-fluoro-1,1-dimethylethyl)isothiazol-5(2H)-ylidene]-5-chloro-2-methoxybenzamide;
N-[(5Z)-4-(benzyloxy)-2-tert-butylisothiazol-5(2H)-ylidene]-5-chloro-2-methoxybenzamide;
N-[(5Z)-2-tert-butyl-4-hydroxyisothiazol-5(2H)-ylidene]-5-chloro-2-methoxybenzamide;
N-[(5Z)-2-tert-butyl-4-(1-methylethoxy)isothiazol-5(2H)-ylidene]-5-chloro-2-methoxybenzamide;
N-[(5Z)-2-tert-butyl-4-(1-methylpropoxy)isothiazol-5(2H)-ylidene]-5-chloro-2-methoxybenzamide;
N-[(5Z)-2-tert-butyl-4-(4-fluorobutoxy)isothiazol-5(2H)-ylidene]-5-chloro-2-methoxybenzamide;
N-[(5Z)-2-tert-butyl-4-(cyanomethoxy)isothiazol-5(2H)-ylidene]-5-chloro-2-methoxybenzamide;
N-[(5Z)-2-tert-butyl-4-{[(2S)-5-oxopyrrolidin-2-yl]methoxy}isothiazol-5(2H)-ylidene]-5-chloro-2-methoxybenzamide;
N-[(5Z)-2-tert-butyl-4-{[(2R)-5-oxopyrrolidin-2-yl]methoxy}isothiazol-5(2H)-ylidene]-5-chloro-2-methoxybenzamide; and
tert-butyl[(5Z)-2-tert-butyl-5-{[(5-chloro-2-methoxyphenyl)carbonyl]imino}-3-methyl-2,5-dihydroisothiazol-4-yl]carbamate.

Other embodiments of the present application include a pharmaceutical composition comprising a therapeutically effective amount of one or more of the compounds of Formula (I) as described above, or a pharmaceutically acceptable salt thereof in combination with a pharmaceutically acceptable carrier.

Other embodiments of the present application include a method of treating neuropathic pain, nociceptive pain, and inflammatory pain in a mammal in need of such treatment comprising administering to the mammal a therapeutically effective amount of any of the compounds of Formula (I) described above, or a pharmaceutically acceptable salt thereof.

The present application also comprises a method of treating a disorder selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of any of the compounds of Formula (I) described above, or a pharmaceutically acceptable salt thereof.

Another embodiment included in the present application is a method of providing neuroprotection in a mammal in need of such treatment comprising administering to the mammal a therapeutically effective amount of any of the compounds of Formula (I) described above, or a pharmaceutically acceptable salt thereof.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the application were named by ACD/ChemSketch version 5.01 (developed by Advanced Chemistry Development, Inc., Toronto, ON, Canada) or were given names consistent with ACD nomenclature.

c. General Synthesis

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups L, m, q, r, u, $G^1$, $G^2$, $R^a$, $R^b$, $R^c$, $R^d$, $R^{Z1}$, $R^{Z3}$, $R^{Z2b}$, $R^{Za}$, $R^{21}$, $R^1$, $R^{1a}$, $R^{1g}$, $R^{1h}$, $R^2$, $R^{2a}$, $R^3$, $R^{3a}$, and $R^4$ have the meanings as set forth in the summary section unless otherwise noted, is exemplified in Schemes 1-9.

Abbreviations which have been used in the descriptions of the Schemes and the Examples that follow are: AIBN for azobisisobutyronitrile, DAST for (bis(methoxyethyl)amino sulfurtrifluoride; DMAP for 4-(dimethylamino)pyridine, DMF for N,N-dimethylformamide, DMSO for dimethyl sulfoxide, EDCI for 1-(3-dimethylaminopropyl)-3-ethylcarbodiimide hydrochloride, EtOH for ethanol, $Et_3N$ for triethylamine, $Et_2O$ for diethyl ether, $Et_2Zn$ for diethyl zinc, EtOAc for ethyl acetate, $CHCl_3$ for chloroform, $CH_2Cl_2$ for dichloromethane, HOBt for 1-hydroxybenzotriazole hydrate, KOtBu for potassium tert-butoxide, MeCN for acetonitrile, MeOH for methanol, NMP for N-methyl morpholine, $PdCl_2(PPh_3)_2$ for bis(triphenylphosphine)palladium(II) dichloride, $PdCl_2(dppf)$ for [1,1'-bis(diphenylphosphino)ferrocene] dichloropalladium(II), rt for room temperature, TBAF for is tetrabutyl ammonium fluoride, TMSI for iodotrimethylsilane, TFA for trifluoroacetic acid, and THF for tetrahydrofuran.

Compounds of general Formula (I) wherein L is C=O and $R^3$ is hydrogen can be prepared using general procedures as illustrated in Scheme 1.

Scheme 1

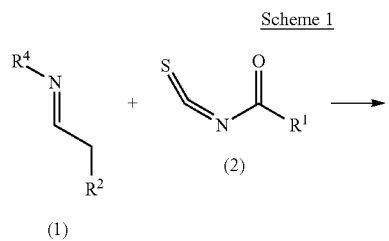

(1)  (2)

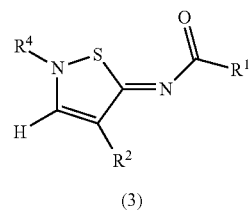

(3)

Isothiazolylidene compounds of structure (3) can be prepared by reacting a substituted imine of structure (1) with an isothiocyanate of structure (2) in a solvent such as but not limited to tetrahydrofuran, diethylether, acetonitrile, dichloromethane or chloroform, at a temperature from about 0° C. to about room temperature, for a period between about 1 and about 24 hours, followed by treatment with iodine or bromine, in a mixture of pyridine and methanol or ethanol, and subsequent treatment with sodium bicarbonate upon workup.

Isothiocyanates of structure (2) can be synthesized by treating acid halides of formula $R^1C(O)X^1$ wherein $X^1$ is halogen, with potassium thiocyanate in a solvent such as tetrahydrofuran, acetone, or mixture thereof, at ambient temperature. The acid halides can be obtained from the corresponding acids using general procedures known to one skilled in the art, for example, by treating with thionyl chloride in a suitable solvent such as toluene, at a temperature from about room temperature to about the reflux temperature of the solvent used.

Imines of structure (1) can be obtained from treatment of aldehydes of formula $R^2CH_2CHO$ with amines of formula $R^4NH_2$, optionally in the presence of an acid such as acetic acid, and optionally in the presence of a dehydrating agent such as magnesium sulfate, in a solvent such as dichloromethane. The reaction can be conducted at about room temperature to about 60° C.

Similarly, compounds of structure (5) wherein L is C=O, and X is absent, or selected from $CR^XR^Y$, O, S, NC(O)O (alkyl) or $N(R^X)$, and $R^X$ and $R^Y$ are each independently hydrogen, alkyl, or haloalkyl, can be prepared from imines of formula (4) (prepared from treating the corresponding ketones with amines of formula $R^4NH_2$ using general procedures described in Scheme 2 under conditions analogous to those in Scheme 1.

Scheme 2

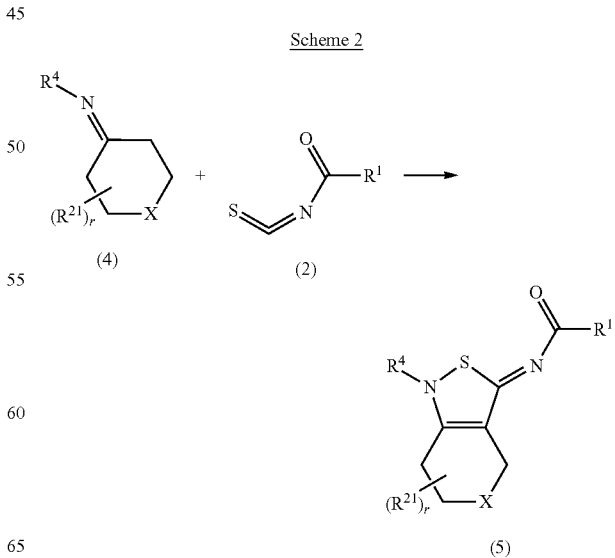

Compounds of general Formula (I) wherein L is C═O can be synthesized as shown in Scheme 3.

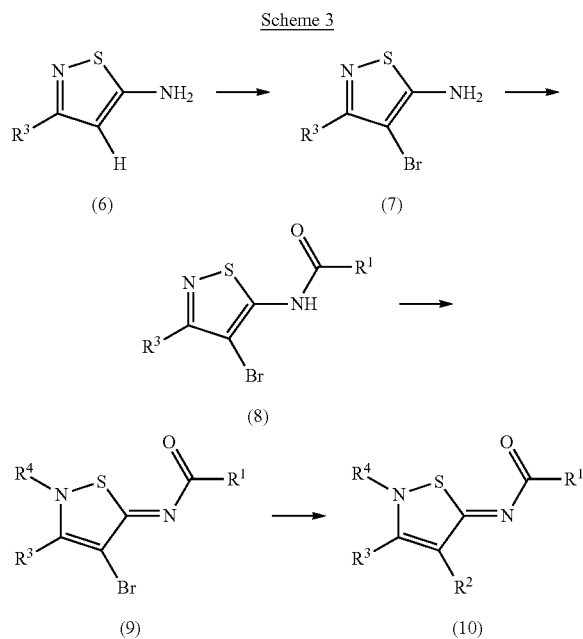

Aminoisothiazoles of structure (6) can be brominated with bromine in solvents such as benzene and/or acetic acid to provide compounds of formula (7). Acylation of compounds of structure (7) with acid halides of formula $R^1COX^1$, in the presence of a base such as triethylamine and in solvents such as tetrahydrofuran or dichloro methane afford compounds of structure (8). Alternatively, the transformation can be accomplished by treating compounds of structure (7) with acids of formula $R^1COOH$ in the presence of a coupling agent, a base and optionally a coupling auxiliary. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N', N'-tetramethyluronium hexafluorophosphate (HATU), and O-benzotriazol-1-yl-N,N,N',N'-tetramethyluronium tetrafluoroborate (TBTU). Examples of coupling auxiliarys include but are not limited to 1-hydroxy-7-azabenzotriazole (HOAT) and 1-hydroxybenzotriazole hydrate (HOBT). Examples of suitable bases include, but are not limited to, an organic base such as N-methyl morpholine or diisopropylethylamine, or an inorganic base such as sodium bicarbonate. The coupling reaction can be carried out in a solvent such as chloroform, dichloromethane, tetrahydrofuran, N,N-dimethylformamide, or mixtures thereof, at a temperature from about 0° C. to about 50° C.

Alkylation of (8) with compounds of formula $R^4X^2$ wherein $X^2$ is halogen, triflate or tosylate, in the presence of a base such as potassium carbonate, sodium hydride, potassium hydroxide or potassium tert-butoxide, and in a solvent such as N,N-dimethylformamide, acetonitrile, tetrahydrofuran or acetone, provides compounds of structure (9). Organometallic coupling of (9) with a zinc reagent of formula $R^2ZnX^3$ wherein $X^3$ is Br or Cl, in the presence of a palladium catalyst such as bis(tri-tert-butylphosphine)palladium(0) affords compounds of structure (10). The conversion can be performed in a solvent such as dimethylacetamide with heating at a temperature from about 50° C. to about 120° C.

Compounds of general Formula (I) wherein L is C═S can be prepared from compounds of Formula (I) wherein L is C═O by treating with Lawesson's reagent, in a solvent such as toluene, at a temperature of about room temperature to about 80° C.

Compounds of general Formula (I) wherein L is C═NCN can be prepared using general procedure as outlined in Scheme 4

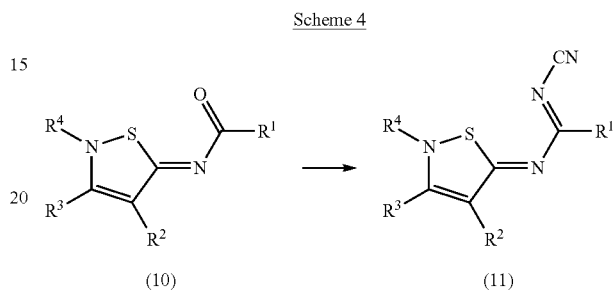

Compounds of structure (11) can be obtained from compounds of structure (10) by (a) treatment with Lawesson's reagent, in a solvent such as toluene, at a temperature of about room temperature to about 80° C., and (b) treatment of the product from step (a) with mercury (II) acetate and cyanamide.

Compounds of general formula (I) wherein $R^2$ is alkenyl or alkynyl can be functionalized to the corresponding cycloalkyl, heterocycle, heteroaryl, alcohols, acids and derivatives of acids, using procedures analogous to those known to one skilled in the art, for example, via [3+2] or [4+2] additions, ozonolysis, hydroboration, cyclopropanation, etc.

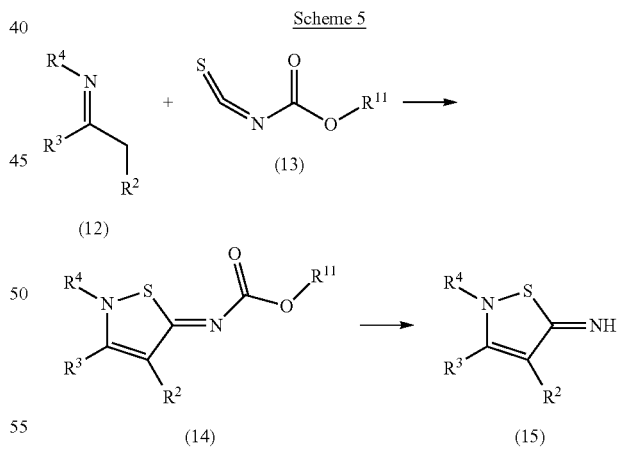

Compounds of formula (14) where $R^{11}$ is alkyl, allyl or benzyl can be prepared from compounds of formula (12) and (13) using the conditions described above in Scheme 1. Compounds of formula (14) where $R^{11}$ is alkyl, for example ethyl, can be converted to compounds of formula (15) by reaction with trimethylsilyliodide in a solvent such as dichloromethane or chloroform at temperatures from room temperature to about 70° C. Alternatively, compounds of formula (14) where $R^{11}$ is alkyl, for example ethyl, can be converted to compounds of formula (15) by hydrolysis with aqueous base such as sodium hydroxide or potassium hydroxide. When $R^{11}$ is tert-butyl, compounds of formula (14) can be converted to (15) by reaction with an acid such as trifluoroacetic acid or hydrochloric acid. When $R^{11}$ is benzyl, compounds of formula (14) can be converted to (15) by hydrogenation over a suitable transition metal catalyst like, for example, palladium on carbon.

room temperature to about 50° C. for 8-24 hours. The intermediate (20) can be treated with a boronic acid $(HO)_2B—R^1$ in the presence of copper carboxylates (like commercially available copper acetate or copper 2-thiophenecarboxylate), a trialkylphosphite (e.g., triethylphosphite) and tris(dibenzylideneacetone)dipalladium(0) or other selected Pd(0) catalysts in dimethoxyethane (or other aprotic solvents) at Scheme 6

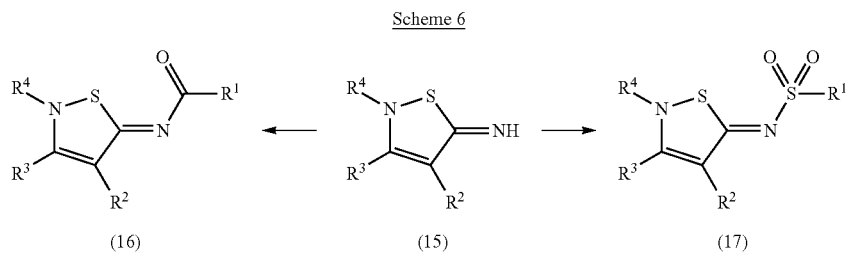

Compounds of formula (15) can be converted to compounds of formula (16) using the conditions described above for the conversion of compounds (7) to compounds (8). Compounds of formula (15) can be converted to compounds of formula (17) by reaction with a reagent $R^1SO_2Cl$ in the presence of a base such as, but not limited to, triethylamine or diethylisopropylamine and in a solvent such as, but not limited to, dichloromethane, tetrahydrofuran or dimethylformamide at room temperature to about 50° C.

80-100° C. for 12-24 hours to give compounds of formula (19).

Scheme 7

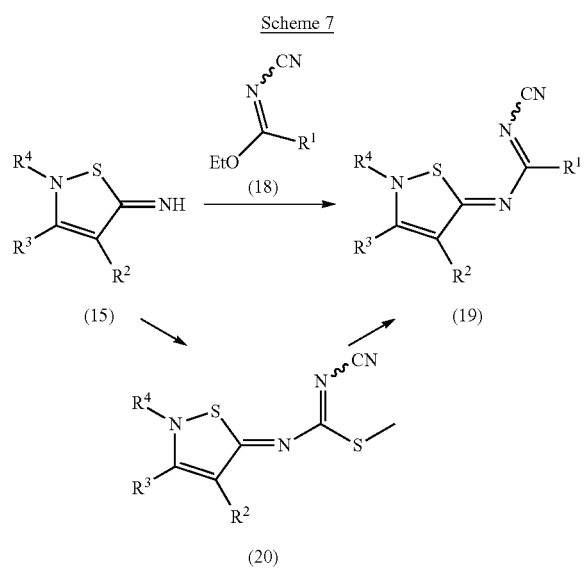

Scheme 8

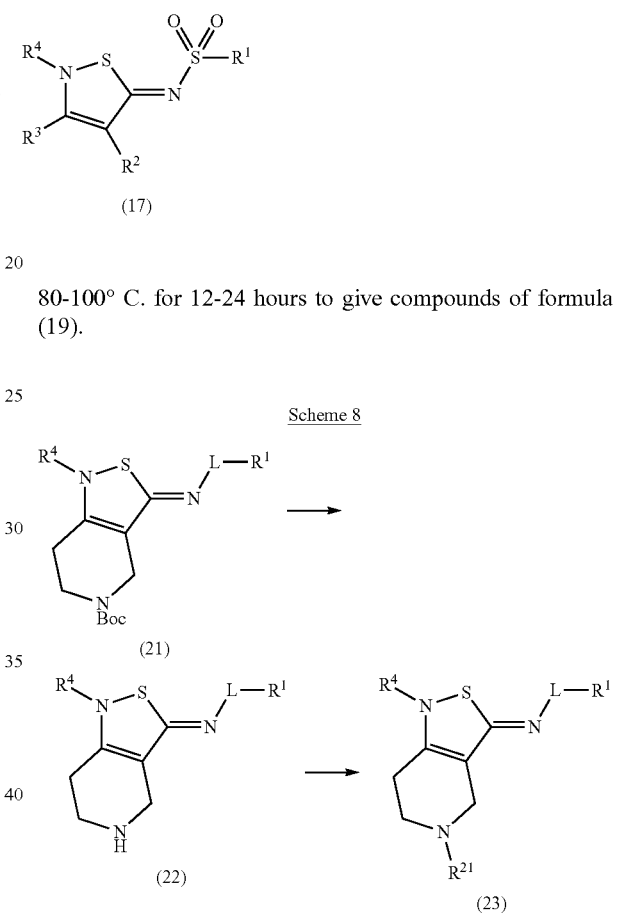

Compounds of formula (15) can be transformed to compounds of formula (19) by reaction with compounds of formula (18) in the presence of a base such as, but not limited to, triethylamine in solvents such as, but not limited to, ethanol, acetonitrile, tetrahydrofuran or toluene at temperatures from room temperature to about 100° C. Alternatively, compounds of formula (15) can be transformed to compounds of formula (19) through the intermediate compounds (20). Compounds of formula (15) can be converted to compounds of formula (20) by reaction with dimethylcyanocarbonimidodithioate in a solvent such as, but not limited to, THF, dioxane, acetonitrile, etc. in the presence of a base, like triethylamine, N-methylmorpholine, NaH, etc. at temperatures ranging from Compounds of formula (21) can be converted to compounds of formula (22) by reaction with an acid such as trifluoroacetic acid in a solvent such as dichloromethane or by reaction with hydrochloric acid. The compounds of formula (22) can be converted to compounds of formula (23) wherein $R^{21}$ is alkyl, alkenyl, alkynyl, $—C(O)(R^{1a})$, $—SO_2(R^{2a})$, $—C(O)N(R^{Z3})(R^{3a})$, $—S(O)_2N(R^{Z3})(R^{3a})$, $—(CR^{1g}R^{1h})_u$-$G^2$, $—(CR^{1g}R^{1h})_u—CN$, $—(CR^{1g}R^{1h})_u—O(R^{1a})$, and haloalkyl by a variety of transformations well known to those skilled in the art. For example, the substituent $R^{21}$ may be appended via the well-known reductive amination method by reaction with an appropriate aldehyde or ketone reagent in the presence of a reducing agent such as sodium cyanoborohydride. Another well-known method to transform (22) to (23) is by alkylation with a suitable halide, tosylate, mesylate or triflate reagent. The types of $R^{21}$ groups that can be appended in this manner are alkyl, alkenyl, alkynyl, $—(CR^{1g}R^{1h})_u$-$G^2$, $—(CR^{1g}R^{1h})_u—CN$, $—(CR^{1g}R^{1h})_u—O(R^{1a})$, and haloalkyl. Other $R^{21}$ groups such as $—C(O)(R^{1a})$, $—SO_2(R^{2a})$, $—C(O)N(R^{Z3})(R^{3a})$ and $—S(O)_2N(R^{Z3})(R^{3a})$ can be appended by reaction with appropriate acyl halides, sulfonyl halides, carbamoyl halides or isocyanates using conditions well-known to those skilled in the art.

Scheme 9

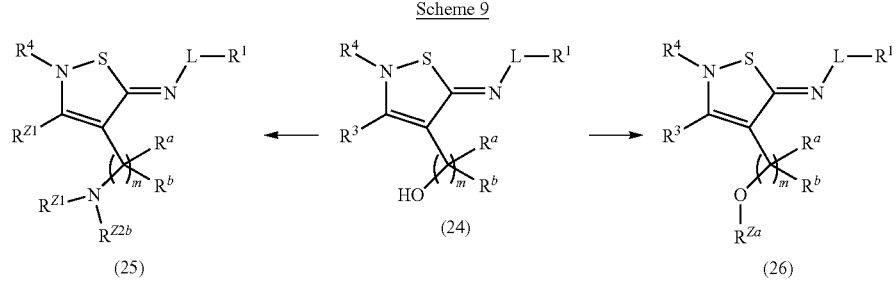

Compounds of formula (24) can be converted to compounds of formula (25) by standard synthetic transformations well known to those skilled in the art. For example, (24) can be converted to amines of formula (25) wherein $R^{Z2b}$ is hydrogen, alkyl, haloalkyl, $G^1$ or $—(CR^cR^d)_q$-$G^1$ by displacement of the corresponding halide, mesylate or tosylate derived from (24) with an appropriate amine $R^{Z1}R^{Z2b}$NH. Compounds (24) can be converted to primary amine compounds (25) ($R^{Z1}$ and $R^{Z2b}$ are each hydrogen) through displacement of the corresponding halide, mesylate or tosylate with an azide reagent and then reduction of the latter using methods well-known to those skilled in the art. Compounds (25) wherein $R^{Z1}$ and $R^{Z2b}$ are each hydrogen can be converted to compounds (25) wherein $R^{Z1}$ or $R^{Z2b}$ are other than hydrogen by standard synthetic transformations involving reaction with carbonyl compounds (ie, reductive amination), alkyl halides, acyl halides, sulfonyl halides, isocyanates and the like.

Compounds of formula (24) can be converted to compounds of formula (26) by standard etherification methods well-known to those skilled in the art. For example, compounds (24) can be reacted with alkylating agents $R^{Za}$—X (X=halo, OMs, OTs, etc). Alternatively, compounds (26) can be prepared by displacement of the corresponding halide, mesylate or tosylate derived from (24) with an appropriate alcohol $R^{Za}$—OH.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the convention manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

d. EXAMPLES

Example 1

N-[(5Z)-4-butyl-2-tert-butylisothiazol-5(2H)-ylidene]-5-chloro-2-methoxybenzamide Example 1A N-(tert-butyl)-N-hexylideneamine To t-butyl amine (5.25 mL, 50.0 mmol) and MgSO$_4$ (2 g) in CH$_2$Cl$_2$ (10 mL) at room temperature was added slowly hexanal (6.0 mL, 50 mmol) under N$_2$ at room temperature. The reaction became exothermic halfway through the addition so an ice bath was briefly used to control the reaction rate and avoid boiling off the solvent or amine. After the addition was complete, the reaction was stirred at room temperature for 2 h, filtered through celite under a stream of $N_2$ and washed with 20 mL dry $CH_2Cl_2$. The solvent was evaporated to give a pale yellow liquid. $^1$H NMR (300 MHz, $CDCl_3$) δ 0.87-0.91 (m, 3H), 1.17 (s, 9H), 1.25-1.35 (m, 4H), 1.45-1.55 (m, 2H), 2.23 (m, 2H), 7.59 (t, 1H).

Example 1B 5-chloro-2-methoxybenzoyl chloride

5-Chloro-2-methoxybenzoic acid (11.3 g, 60.56 mmol) and $SOCl_2$ (9 mL, 123.7 mmol) in toluene (20 mL) were heated gently while vigorous gas evolution occurred. After gas evolution had subsided, the reaction was heated to reflux for 1.5 h, cooled and stirred overnight at room temperature. The volatiles were evaporated in vacuo and the remaining material was treated with toluene and evaporated (2×) to remove excess $SOCl_2$ to provide a white solid that was taken directly on to the next step without purification. $^1$H NMR (300 MHz, $CDCl_3$) δ 3.92 (s, 3H), 6.95 (d, 1H), 7.53 (dd, 1H), 8.03 (d, 1H).

Example 1C 5-chloro-2-methoxybenzoyl isothiocyanate

The product of Example 1B (~60 mmol) and KSCN (5.83 g, 60 mmol) were mixed in anhydrous tetrahydrofuran (25 mL) and anhydrous acetone (40 mL) and stirred at room temperature for 2 hrs. The reaction was diluted with diethyl ether (100 mL), filtered through celite and solvents evaporated in vacuo to provide the title compound. $^1$H NMR (300 MHz, $CDCl_3$) δ 3.95 (s, 3H), 6.95 (d, 1H), 7.52 (dd, 1H), 7.84 (d, 1H).

Example 1D

N-[(5Z)-4-butyl-2-tert-butylisothiazol-5(2H)-ylidene]-5-chloro-2-methoxybenzamide To the product of Example 1A (1.90 g, 12.2 mmol) in tetrahydrofuran (10 mL) at room temperature under $N_2$ was added the product of Example 1C (2.30 g, 10.1 mmol). After 1 h at room temperature, the reaction was treated with $I_2$ (2.59 g, 10.2 mmol), methanol (30 mL) and pyridine (3 mL) and stirred for 1 hour. The reaction was then partitioned between saturated $NaHCO_3$/diethyl ether with continued stirring overnight. The reaction was diluted further with saturated $NaHCO_3$/diethyl ether, the layers separated and the aqueous phase extracted again with diethyl ether (2×). The organics were combined, dried ($MgSO_4$), filtered and solvent evaporated. Toluene/acetonitrile was added and evaporated 2× to remove excess pyridine and $H_2O$. The crude was flash chromatographed, eluting with diethyl ether:$CH_2Cl_2$:hexane (7:3:3) to provide 2.68 g of the desired product with impurities running above and below. This material was dissolved in a minimum of $CH_2Cl_2$, hexane added until slightly cloudy and allowed to sit for 4 hours. A white crystalline solid was collected and washed with cold 1:1 $CH_2Cl_2$:hexane to provide 962.78 mg of the title compound. The mother liquor was recrystallized from methanol to provide 555 mg additional title compound. The second mother liquor was concentrated to dryness, dissolved in a minimum of $CH_2Cl_2$ and flash chromatographed on silica gel, eluting with diethyl ether:$CH_2Cl_2$:hexane (7:1:3) to provide an additional 600 mg of the title compound. $^1$H NMR (300 MHz, $CDCl_3$) δ 0.98 (t, 3H), 1.37-1.49 (m, 2H), 1.65 (s, 9H), 1.67-1.77 (m, 2H), 2.83 (t, 2H), 3.92 (s, 3H), 6.91 (d, 1H), 7.34 (dd, 1H), 7.95 (s, 1H), 8.11 (d, 1H). MS (DCI/$NH_4^+$) m/z 381 (M+H)$^+$. Anal. calcd for $C_{19}H_{25}ClN_2O_2S$: C, 59.91; H, 6.61; N, 7.35. Found: C, 59.88; H, 6.67; N, 7.42.

Example 2

N-[(5Z)-4-butyl-2-(1,1-dimethylpropyl)isothiazol-5(2H)-ylidene]-5-chloro-2-methoxybenzamide Hexanal (0.123 mL, 1.0 mmol) was added dropwise to t-amylamine (0.117 mL, 1.0 mmol) in diethyl ether (1 mL) with $MgSO_4$ (240 mg) at 0° C. The reaction was allowed to warm to room temperature with stirring over 1 h, cooled again to 0° C., treated with Example 1C (230 mg, 1 mmol), stirred 1.5 h at 0° C., then treated with $I_2$ (250 mg) and pyridine (0.17 mL) and the reaction allowed to warm to room temperature with stirring overnight. The reaction was quenched in saturated $NaHCO_3$ and extracted with diethyl ether (3×). The organics were dried ($MgSO_4$), filtered and solvent evaporated. Flash chromatography over silica gel (2×) eluting with 33% ethyl acetate/hexane and then 45% ethyl acetate/hexane provided 22 mg of the title compound. $^1$H NMR (300 MHz, $CDCl_3$) δ 0.78 (t, 3H), 0.98 (t, 3H), 1.37-1.50 (m, 2H), 1.63 (s, 6H), 1.67-1.77 (m, 2H), 1.91 (q, 2H), 2.84 (t, 2H), 3.92 (s, 3H), 6.91 (d, 1H), 7.34 (dd, 1H), 7.90 (br s, 1H), 8.12 (d, 1H). MS (DCI/$NH_4^+$) m/z 395 (M+H)$^+$.

Example 3

N-[(5Z)-4-butyl-2-cyclobutylisothiazol-5(2H)-ylidene]-5-chloro-2-methoxybenzamide The title compound was prepared using the procedure as described in Example 2, substituting t-amylamine with cyclobutylamine. $^1$H NMR (300 MHz, $CDCl_3$) δ 0.94 (t, 3H), 1.34-1.46 (m, 2H), 1.59-1.69 (m, 2H), 1.87-1.97 (m, 2H), 2.30-2.44 (m, 2H), 2.60 (br m, 2H), 2.65 (dt, 2H), 3.91 (s, 3H), 5.38 (br t, 1H), 6.89 (s, 1H), 6.91 (d, 1H), 7.33 (dd, 1H), 7.97 (d, 1H). LC/MS (APCI$^+$) m/z 379 (M+H)$^+$.

Example 4

N-[(5Z)-4-butyl-2,3-dimethylisothiazol-5(2H)-ylidene]hexahydro-2,5-methanopentalene-3a(1H)-carboxamide Example 4A hexahydro-2,5-methanopentalene-3a(1H)-carbonyl chloride 3-Noradamantane carboxylic acid (4.99 g, 30.1 mmol) and $SOCl_2$ (5 mL, 69 mmol) in toluene (5 mL) were heated to 65° C. until vigorous evolution of gas commenced. The heating bath was removed for 5-10 minutes until gas evolution had moderated. Heating the reaction again at 65° C. was resumed for 2 hours. The reaction was cooled to room temperature, the volatiles removed in vacuo and toluene added and evaporated (2×) to remove excess $SOCl_2$. The crude acid chloride was used without further purification.

Example 4B

N-(4-bromo-3-methylisothiazol-5-yl)hexahydro-2,5-methanopentalene-3a(1H)-carboxamide To a solution of 4-bromo-3-methylisothiazol-5-amine (prepared as described in J. Chem. Soc. 1963, p 2032) (1.93 g, 10.1 mmol) in tetrahydrofuran (25 mL) with triethylamine (1.7 mL, 12.2 mmol) at 0° C. was added slowly a solution of Example 4A (1.9 g, 10.3 mmol) in tetrahydrofuran (15 mL). The reaction was allowed to warm to room temperature and stirred overnight. The reaction was evaporated to dryness, partitioned between $H_2O$/ethyl acetate and the aqueous extracted again (2×) with ethyl acetate. The organics were combined, dried ($MgSO_4$), filtered and solvent evaporated. Flash chromatography over silica gel eluting with 15% ethyl acetate/hexane provided 0.3 g of the title compound plus 1.8 g of diacylated compound. The latter was heated to reflux in methanol for 3 h, cooled, solvent evaporated and flash chromatographed over silica gel eluting with 20% ethyl acetate/hexane to provide an additional 0.99 g of the title compound. $^1$H NMR (300 MHz, $CDCl_3$) δ 1.63-1.76 (m, 4H), 1.87-1.98 (m, 4H), 2.10-2.15 (m, 2H), 2.45 (s, 3H), 2.81 (t, 1H), 8.23 (br s, 1H).

Example 4C

N-[(5Z)-4-bromo-2,3-dimethylisothiazol-5(2H)-ylidene]hexahydro-2,5-methanopentalene-3a(1H)-carboxamide The product of Example 4B (1.29 g, 3.79 mmol), $K_2CO_3$ (0.85 g) and iodomethane (1.2 mL, 5 equiv.) in a mixture of acetonitrile (10 mL), tetrahydrofuran (10 mL) and $CH_2Cl_2$ (3 mL) were stirred overnight at room temperature, treated with additional iodomethane (1.2 mL), heated to 65° C. for 3 h then stirred overnight at room temperature. The reaction was evaporated in vacuo, partitioned between $H_2O$/$CH_2Cl_2$ and the aqueous extracted again (2×) with $CH_2Cl_2$. The organics were dried ($MgSO_4$), filtered and solvent evaporated. Flash chromatography over silica gel eluting with 35-40% EtOAc/hexane, followed by 100% ethyl acetate provided 0.77 g of the title compound. $^1$H NMR (300 MHz, $CDCl_3$) δ 1.61-1.66 (m, 4H), 1.91 (m, 4H), 2.25-2.35 (m, 4H), 2.49 (s, 3H), 2.72 (t, 1H), 3.60 (s, 3H). MS (DCI/$NH_3$) m/z 355 (M+H)$^+$.

Example 4D

N-[(5Z)-4-butyl-2,3-dimethylisothiazol-5(2H)-ylidene]hexahydro-2,5-methanopentalene-3a(1H)-carboxamide A mixture of the product of Example 4C (44 mg, 0.12 mmol), bis(tri-tert-butylphosphine)palladium(0) (13 mg, 0.025 mmol) and 0.5 M n-butylzinc bromide/tetrahydrofuran (0.38 mL, 0.19 mmol) in dimethylacetamide (2 mL) was heated to 80-100° C. for 24 h, cooled, quenched in $H_2O$ and extracted with diethyl ether (3×). The organics were filtered through celite to breakup slight emulsion and solvents evaporated. The crude was flash chromatographed over silica gel eluting with 15% ethyl acetate/hexane to 25% ethyl acetate/hexane to provide the title compound. $^1$H NMR (300 MHz, $CDCl_3$) δ 0.94 (t, 3H), 1.28-1.40 (m, 2H), 1.51-1.64 (m, 6H), 1.82-1.92 (m, 4H), 2.28 (m, 4H), 2.32 (s, 3H), 2.67-2.77 (m, 3H), 3.53 (s, 3H). MS (DCI/$NH_4^+$) m/z 333 (M+H)$^+$.

Example 5

N-[(5Z)-4-butyl-2-(1-methylcyclobutyl)isothiazol-5(2H)-ylidene]-5-chloro-2-methoxybenzamide To a solution of 1-methylcyclobutylamine (454 mg, 5.33 mmol) in dry $CH_2Cl_2$ (1 mL) with $MgSO_4$ (250 mg) was added slowly hexanal (655 µL, 5.3 mmol). The reaction was stirred under $N_2$ for 1 h, filtered through a 0.45 µm PFTE filter, washed with 0.5 ml dry $CH_2Cl_2$, diluted with 2 mL tetrahydrofuran, and treated with Example 1C (703 mg, 3.09 mmol) with continued stirring. After 1 h, the reaction was treated with $I_2$ (750 mg), methanol (5 mL) and pyridine (1 mL) and continued stirring at room temperature for 1 h. The reaction was partitioned between saturated $NaHCO_3$/diethyl ether and stirred overnight. The layers were separated and the aqueous was extracted again with diethyl ether. The combined organic extracts were dried ($MgSO_4$), filtered and solvent evaporated. The crude was flash chromatographed on silica gel, eluting with diethyl ether:$CH_2Cl_2$:hexane (7:1:3) to provide 88.9 mg of the desired product with slight impurity. The product was chromatographed a second time using an Analogix® IT280™ instrument using an SF15-12g column, gradient eluting with ethyl acetate:hexane (0:100 to 50:50) over 20 minutes to provide 75 mg of the title compound. $^1$H NMR (300 MHz, $CDCl_3$) δ 0.98 (t, 3H), 1.39-1.49 (m, 2H), 1.70 (s, 3H), 1.71 (m, 2H), 1.95-2.06 (m, 2H), 2.29 (m, 2H), 2.69 (m, 2H), 2.83 (t, 2H), 3.91 (s, 3H), 6.91 (d, 1H), 7.33 (dd, 1H), 7.80 (s, 1H), 8.12 (d, 1H). MS (DCI/$NH_3$) m/z 393 (M+H)$^+$.

Example 6

N-[(5Z)-4-allyl-2-tert-butylisothiazol-5(2H)-ylidene]-5-chloro-2-methoxybenzamide

Example 6A 2-methyl-N-(pent-4-enylidene)propan-2-amine

To t-butylamine (5.28 mL, 50 mmol) in $CH_2Cl_2$ (10 mL) with $MgSO_4$ (2.1 g) was added slowly at 0° C. under $N_2$ 4-pentenal (4.94 mL, 50 mmol). After the addition was complete the reaction was stirred at 0° C. for 15 min then allowed to warm to room temperature and stirred for 2 hours. The reaction was filtered through celite, washed with 20 mL dry $CH_2Cl_2$ and the solvent evaporated at ambient temperature to provide a clear light yellow liquid. $^1$H NMR (300 MHz, $CDCl_3$) δ 1.17 (s, 9H), 2.2-2.4 (m, 4H), 4.95-5.1 (m, 2H), 5.83 (m, 1H), 7.61 (t, 1H).

Example 6B

N-[(5Z)-4-allyl-2-tert-butylisothiazol-5(2H)-ylidene]-5-chloro-2-methoxybenzamide The title compound was prepared using the procedure as described in Example 1D, substituting Example 6A for Example 1A. The product was purified by chromatography using an Analogix® IT280™ over a SF40-115 g column, gradient eluting with ethyl acetate:hexane (0:100 to 50:50 over 20 minutes, then 10 minutes at 50:50) to provide 1.1 g of material that contained some small impurities. The product was chromatographed a second time over silica gel, eluting with diethyl ether:$CH_2Cl_2$:hexane (7:2:3). The product obtained was crystallized from diethyl ether/hexane to provide the title compound. $^1$H NMR (300 MHz, $CDCl_3$) δ 1.65

(s, 9H), 3.62 (d, 2H), 3.92 (s, 3H), 5.16 (m, 2H), 6.0-6.15 (m, 1H) 6.92 (d, 1H), 7.34 (dd, 1H), 7.94 (s, 1H), 8.15 (d, 1H). MS (DCI/NH$_3$) m/z 365 (M+H)$^+$.

Example 7

N-[(5Z)-2-tert-butyl-4-[(3-methyl-4,5-dihydroisoxazol-5-yl)methyl]isothiazol-5(2H)-ylidene]-5-chloro-2-methoxybenzamide To a solution of acetaldoxime (95 µL, 2.43 mmol) in CHCl$_3$ (10 mL) under N$_2$ was added N-chlorosuccinimide (323 mg, 2.43 mmol) and pyridine (10 µL). After 2 hours at room temperature, Example 6B (150 mg) was added, followed by triethylamine (340 µL, 2.4 mmol) and the reaction continued to stir at room temperature for 21 hours. The reaction mixture was washed with water and partitioned. The aqueous layer was extracted again with CH$_2$Cl$_2$ and the combined organic extracts were dried (MgSO$_4$), filtered and solvent evaporated. The crude was chromatographed using the Analogix® IT280™ over a SF15-12 g column gradient eluting with ethyl acetate:hexane (0:100 to 100:0 over 25 minutes) to provide 128 mg of the title compound. $^1$H NMR (300 MHz, CDCl$_3$) δ 1.66 (s, 9H), 1.89 (s, 3H), 2.85 (m, 1H), 3.0-3.23 (m, 3H), 3.92 (s, 3H), 4.95 (m, 1H), 6.93 (d, 1H), 7.35 (dd, 1H), 8.09 (d, 1H), 8.20 (s, 1H). MS (DCI/NH$_3$) m/z 422 (M+H)$^+$.

Example 8

N-[(5Z)-2-tert-butyl-4-(cyclopropylmethyl)isothiazol-5(2H)-ylidene]-5-chloro-2-methoxybenzamide To a solution of dimethoxyethane (85 µL, 0.82 mmol) in dry CH$_2$Cl$_2$ (3 mL) under N$_2$ at –10° C. (EtOH/ice) was added dropwise a 1.0 M solution of Et$_2$Zn/heptane (0.82 mL). After the addition was complete, diiodomethane (0.13 mL, 1.6 mmol) was added dropwise and the reaction stirred 10 min at –10° C. The reaction was then treated with Example 6B (145 mg) in CH$_2$Cl$_2$ (1 mL) and allowed to warm to RT and stirred overnight (~16 h). The reaction was quenched in saturated NH$_4$Cl and extracted with a mix of EtOAc/Et$_2$O/CH$_2$Cl$_2$ and then again with Et$_2$O. The organics were dried (MgSO$_4$), filtered through celite and concentrated. The crude was chromatographed with the Analogix IT280™ gradient eluting with EtOAc:hexane (0:100 to 50:50) to provide 45 mg of the title compound. $^1$H NMR (300 MHz, CDCl$_3$) δ 0.28 (m, 2H), 0.57 (m, 2H), 1.25 (m, 1H), 1.67 (3, 9H), 2.75 (d, 2H), 3.91 (s, 3H), 6.91 (d, 1H), 7.33 (dd, 1H), 8.09 (s, 1H), 8.10 (d, 1H). MS (DCI/NH$_3$) m/z 379 (M+H)$^+$.

Example 9

N-[(3Z)-1-tert-butyl-5-propyl-4,5,6,7-tetrahydro-2,1-benzisothiazol-3(1H)-ylidene]-5-chloro-2-methoxybenzamide To a solution of tert-butylamine (366 mg, 5 mmol) in anhydrous hexane (20 mL) at 0° C. was added titanium(IV) chloride (133 mg, 0.5 mmol). After 5 min, the cooling bath was removed and 4-propylcyclohexanone (140 mg, 1 mmol) was added in one portion. The resulting mixture was stirred at ambient temperature for 2 h. Then, the precipitated solid was filtered and washed with anhydrous ethyl ether. The filtrate and washings were combined and concentrated under reduced pressure. The residue was dissolved in THF (20 mL) and treated with 5-chloro-2-methoxybenzoyl isothiocyanate (190 mg, 0.83 mmol) for 1 h at room temperature. Iodine (211 mg, 0.83 mmol) was added followed by addition of MeOH (10 mL) and pyridine (1 mL). The mixture was allowed to stir at room temperature for additional 2 h and then saturated sodium bicarbonate solution and ethyl ether were added. The mixture was stirred for 30 min, the ether layer was separated and the aqueous solution was extracted with ethyl ether. The ether extracts were combined, washed with brine, dried with anhydrous MgSO$_4$ and concentrated under reduced pressure. The residue was twice evaporated with toluene and acetonitrile and then purified by chromatography (hexane-EtOAc 1:1) to afford 70 mg of the title compound. $^1$H NMR (300 MHz, DMSO-d$_6$) δ ppm 0.85-1.02 (m, 3 H), 1.29-1.53 (m, 6 H), 1.68 (s, 9 H), 1.90-2.07 (m, 1 H), 2.19 (dd, J=15.9, 10.2 Hz, 1 H), 2.78-3.01 (m, 2 H), 3.09-3.26 (m, 1 H), 3.72-3.84 (m, 3 H), 7.11 (d, J=8.8 Hz, 1 H), 7.45 (dd, J=8.8, 3.1 Hz, 1 H), 7.68 (d, J=3.1 Hz, 1 H); MS (DCI/NH$_3$) m/z 421 (M+H)$^+$. Anal. calcd for C$_{22}$H$_{29}$ClN$_2$O$_2$S.0.1H$_2$O: C, 62.50; H, 6.96; N, 6.63. Found: C, 62.21; H, 6.99; N, 6.49.

Example 10

N-[(3Z)-1-tert-butyl-1,4,6,7-tetrahydro-3H-spiro[2,1-benzisothiazole-5,2'-[1,3]dioxolan]-3-ylidene]-5-chloro-2-methoxybenzamide The title compound was prepared according to the procedure of Example 9 by replacing 4-propylcyclohexanone with 1,4-dioxaspiro[4.5]decan-8-one. $^1$H NMR (300 MHz, DMSO-d$_6$) δ ppm 1.61-1.79 (m, 9 H), 1.94-2.08 (m, 2 H), 2.80-2.96 (m, 2 H), 3.13 (t, J=6.3 Hz, 2 H), 3.78 (s, 3 H), 3.90-4.06 (m, 4 H), 7.12 (d, J=9.1 Hz, 1 H), 7.46 (dd, J=8.7, 2.8 Hz, 1 H), 7.68-7.77 (m, 1 H); MS (DCI/NH$_3$) m/z 437 (M+H)$^+$.

Example 11

N-[(5Z)-2-tert-butyl-4-(2-methoxyethyl)isothiazol-5(2H)-ylidene]-5-chloro-2-methoxybenzamide

Example 11A 4-(tert-butyldimethylsilyloxy)butanal

To CH$_2$Cl$_2$ (150 mL) at –78° C. were added oxalyl chloride (6.83 g, 53.8 mmol) and dry DMSO (8.41 g, 108 mmol), dropwise. After 5 min, 4-(tert-butyldimethylsilyloxy)butan-1-ol (10 g, 48.9 mmol) in CH$_2$Cl$_2$ (5 mL) was added dropwise. The mixture was stirred for an additional 30 min at –78° C., and Et$_3$N (24.8 g, 245 mmol) was added. The mixture was then allowed to warm to room temperature over 30 min. After stirring for 3 hrs, 100 mL of water was added. The phases were separated, and the aqueous phase was extracted three times with 100 mL of diethyl ether. The combined organic phases were washed successively with 50 mL of aqueous 1% HCl, 50 mL of water, 50 mL of aqueous 5% NaHCO$_3$ and 50 mL of saturated aqueous NaCl. The organic layer was dried over MgSO$_4$, and the solvent was removed under reduced pressure, to provide the title compound.

Example 11B

N-(4-(tert-butyldimethylsilyloxy)butylidene)-2-methylpropan-2-amine

The title compound was prepared using the procedure as described in Example 1A substituting Example 11A for hexanal.

Example 11C

N-[(5Z)-2-tert-butyl-4-(2-{[tert-butyl(dimethyl)silyl] oxy}ethyl)isothiazol-5(2H)-ylidene]-5-chloro-2-methoxybenzamide The title compound was prepared using the procedure as described in Example 1D substituting Example 11B for 1A. MS (DCI/NH$_4^+$) m/z 483 (M+H)$^+$.

Example 11D

N-[(5Z)-2-tert-butyl-4-(2-hydroxyethyl)isothiazol-5 (2H)-ylidene]-5-chloro-2-methoxybenzamide The product from 11C (6.0 g, 12.4 mmol) in THF (10 mL) was treated with tetrabutylammonium fluoride (1M in THF) (14.9 mL, 14.9 mmol). The mixture was stirred at rt for 2 hrs. The reaction was diluted with H$_2$O, and the aqueous phase extracted with EtOAc (2x). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 2.5 g (55%) of the title compound. $^1$H NMR (500 MHz, CDCl$_3$) δ ppm 1.68 (s, 9 H) 3.04 (t, J=5.19 Hz, 2 H) 3.93 (s, 3 H) 3.95 (t, J=4.88 Hz, 2 H) 6.92 (d, J=8.85 Hz, 1 H) 7.35 (dd, J=8.85, 2.75 Hz, 1 H) 7.97 (s, 1 H) 8.00 (d, J=2.75 Hz, 1 H); MS (DCI/NH$_4^+$) m/z 369 (M+H)$^+$.

Example 11E

N-[(5Z)-2-tert-butyl-4-(2-methoxyethyl)isothiazol-5 (2H)-ylidene]-5-chloro-2-methoxybenzamide The product from 11D (70 mg, 0.19 mmol) in THF (5 mL) was treated with NaH (60%) (12 mg, 0.29 mmol) at rt. The mixture was stirred for 10 min, then to the mixture was added iodomethane (32.3 mg, 0.23 mmol). The reaction was stirred for an additional 30 min, quenched with H$_2$O, and extracted with EtOAc (2x). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 59 mg (81%) of the title compound. $^1$H NMR (500 MHz, CDCl$_3$) δ ppm 1.66 (s, 9 H) 3.10 (t, J=6.10 Hz, 2 H) 3.39 (s, 3 H) 3.72 (t, J=6.10 Hz, 2 H) 3.92 (s, 3 H) 6.92 (d, J=8.85 Hz, 1 H) 7.34 (dd, J=8.85, 2.75 Hz, 1 H) 8.09 (s, 1 H) 8.12 (d, J=2.75 Hz, 1 H); MS (DCI/NH$_4^+$) m/z 383 (M+H)$^+$.

Example 12

N-[(5Z)-2-tert-butyl-4-(2-morpholin-4-ylethyl) isothiazol-5(2H)-ylidene]-5-chloro-2-methoxybenzamide The product from 11D (100 mg, 0.27 mmol) in CH$_2$Cl$_2$ (10 mL) containing triethylamine (82 mg, 0.81 mmol) was treated with methanesulfonyl chloride (47 mg, 0.41 mmol) at 0° C. The mixture was stirred for 15 min at 0° C. and solvent removed. The residue was dissolved in THF (10 mL), treated with morpholine (118 mg, 1.36 mmol) and potassium carbonate (75 mg, 0.54 mmol) and refluxed for 12 hrs. Purification by reverse phase preparative HPLC on a Waters Symmetry C8 column (25 mm×100 mm, 7 Ξm particle size) using a gradient of 10% to 100% acetonitrile:0.1% aqueous trifluoroacetic acid over 8 minutes (10 minutes run time) at a flow rate of 40 mL/minutes afforded 62 mg (52%) of the title compound. $^1$H NMR (500 MHz, CDCl$_3$) δ ppm 1.66 (s, 9 H) 2.61-2.66 (m, 4 H) 2.75-2.80 (m, 2 H) 3.04 (t, J=7.93, 7.32 Hz, 2 H) 3.77 (t, J=4.58 Hz, 4 H) 3.92 (s, 3 H) 6.92 (d, J=8.85 Hz, 1 H) 7.35 (dd, J=8.85, 2.75 Hz, 1 H) 8.13 (s, 1 H) 8.15 (d, J=2.75 Hz, 1 H); MS (DCI/NH$_4^+$) m/z 438 (M+H)$^+$.

Example 13

N-[(5Z)-2-tert-butyl-4-[2-(5,5-dimethyl-1,3-dioxan-2-yl)ethyl]isothiazol-5(2H)-ylidene]-5-chloro-2-methoxybenzamide

Example 13A

N-(4-(5,5-dimethyl-1,3-dioxan-2-yl)butylidene)-2-methylpropan-2-amine

The title compound was prepared using the procedure as described in Example 1A substituting 4-(5,5-dimethyl-1,3-dioxan-2-yl)butanal for hexanal.

Example 13B

N-[(5Z)-2-tert-butyl-4-[2-(5,5-dimethyl-1,3-dioxan-2-yl)ethyl]isothiazol-5(2H)-ylidene]-5-chloro-2-methoxybenzamide The title compound was prepared using the procedure as described in Example 1 D substituting Example 13A for 1A. $^1$H NMR (500 MHz, CDCl$_3$) δ ppm 0.73 (s, 3 H) 1.21 (s, 3 H) 1.64 (s, 9 H) 2.07-2.13 (m, 2 H) 2.95 (t, J=7.93 Hz, 2 H) 3.53 (dd, J=99.47, 11.29 Hz, 4 H) 3.92 (s, 3 H) 4.50 (t, J=5.19 Hz, 1 H) 6.91 (d, J=8.85 Hz, 1 H) 7.33 (dd, J=8.85, 2.75 Hz, 1 H) 7.98 (s, 1 H) 8.13 (d, J=2.75 Hz, 1 H); MS (DCI/NH$_4^+$) m/z 467 (M+H)$^+$.

Example 14

N-[(5Z)-4-(2-azidoethyl)-2-tert-butylisothiazol-5 (2H)-ylidene]-5-chloro-2-methoxybenzamide The product from 11D (209 mg, 0.57 mmol) in CH$_2$Cl$_2$ (20 mL) containing triethylamine (172 mg, 1.7 mmol) was treated with methanesulfonyl chloride (97 mg, 0.85 mmol) at 0° C. The mixture was stirred for 20 min at 0° C., solvent removed, the residue dissolved in DMF (10 mL) and treated with sodium azide (184 mg, 2.83 mmol). The mixture was heated at 80° C. for 2 hrs, diluted with H$_2$O and extracted with EtOAc (2x). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 120 mg (54%) of the title compound. $^1$H NMR (500 MHz, CDCl$_3$) δ ppm 1.67 (s, 9 H) 3.10 (t, J=6.71 Hz, 2 H) 3.71 (t, J=6.41 Hz, 2 H) 3.93 (s, 3 H) 6.93 (d, J=8.85 Hz, 1 H) 7.36 (dd, J=8.85, 2.75 Hz, 1 H) 8.05 (s, 1 H) 8.11 (d, J=2.75 Hz, 1 H); MS (DCI/NH$_4^+$) m/z 394 (M+H)$^+$.

Example 15

N-[(5Z)-2-tert-butyl-4-[(3E)-3-(methoxyimino)propyl]isothiazol-5(2H)-ylidene]-5-chloro-2-methoxybenzamide

Example 15A (Z)-N-(2-tert-butyl-4-(3-oxopropyl)isothiazol-5(2H)-ylidene)-5-chloro-2-methoxybenzamide Example 13B (620 mg, 1.33 mmol) in THF (2 mL) was treated with 2N HCl (10 mL, 20 mmol). The mixture was heated at 60° C. for 12 hrs, cooled to room temperature and extracted with isopropanol/CH$_2$Cl$_2$ (1:3)(2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 304 mg (60%) of the title compound. $^1$H NMR (500 MHz, CDCl$_3$) δ ppm 1.66 (s, 9 H) 3.02 (t, J=6.41 Hz, 2 H) 3.12 (t, J=6.71 Hz, 2 H) 3.92 (s, 3 H) 6.92 (d, J=8.85 Hz, 1 H) 7.35 (dd, J=8.85, 2.75 Hz, 1 H) 8.06 (s, 1 H) 8.09 (d, J=2.75 Hz, 1 H); MS (DCI/NH$_4$$^+$) m/z 381 (M+H)$^+$.

Example 15B

N-[(5Z)-2-tert-butyl-4-[(3E)-3-(methoxyimino)propyl]isothiazol-5(2H)-ylidene]-5-chloro-2-methoxybenzamide The product from 15A (26 mg, 0.07 mmol) in EtOH (2 mL) was treated with O-methylhydroxylamine hydrochloride (12 mg, 0.14 mmol) and sodium acetate (6 mg, 0.07 mmol). The mixture was stirred at rt for 1 hr, solvent removed and purified by column chromatography using an Analogix® Intelliflash280™ (SiO$_2$, 0-50% Hexane in ethyl acetate) to afford 5.5 mg (19%) of the title compound. $^1$H NMR (500 MHz, CDCl$_3$) δ ppm 1.66 (s, 9 H) 2.64-2.71 (m, 2 H) 2.99-3.06 (m, 2 H) 3.82 (s, 3 H) 3.92 (s, 3 H) 6.93 (s, 1 H) 7.35 (dd, J=8.85, 2.75 Hz, 1 H) 7.46 (t, J=5.80 Hz, 1 H) 8.02 (s, 1 H) 8.10 (d, J=2.75 Hz, 1 H); MS (DCI/NH$_4$$^+$) m/z 410 (M+H)$^+$.

Example 16

N-[(5Z)-2-tert-butyl-4-[2-(dimethylamino)ethyl]isothiazol-5(2H)-ylidene]-5-chloro-2-methoxybenzamide Example 16A N-[(5Z)-4-(2-aminoethyl)-2-tert-butylisothiazol-5(2H)-ylidene]-5-chloro-2-methoxybenzamide The product from Example 14 (70 mg, 0.18 mmol) in EtOH (10 mL) was treated with Pd/C (10 mg) under a hydrogen balloon for 3 hrs. The Pd/C was filtered off and washed with EtOH. The filtrate was concentrated to afford 60 mg (91%) of the title compound. $^1$H NMR (500 MHz, CDCl$_3$) δ ppm 1.68 (s, 9 H) 3.08 (dd, J=5.80, 4.88 Hz, 2 H) 3.27 (dd, J=5.19 Hz, 2 H) 3.92 (s, 3 H) 6.94 (d, J=8.85 Hz, 1 H) 7.37 (dd, J=8.85, 2.75 Hz, 1 H) 7.97 (d, J=2.75 Hz, 1 H) 8.03 (s, 1 H); MS (DCI/NH$_4$$^+$) m/z 368 (M+H)$^+$.

Example 16B N-[(5Z)-2-tert-butyl-4-[2-(dimethylamino)ethyl]isothiazol-5(2H)-ylidene]-5-chloro-2-methoxybenzamide The product from Example 16A (60 mg, 0.16 mmol) in CH$_2$Cl$_2$ (10 mL) was treated with paraformaldehyde (60 mg) and sodium boroneacetate (44 mg, 0.16 mmol). The mixture was stirred at rt for 12 hrs. Diluted with H$_2$O, the mixture was extracted with CH$_2$Cl$_2$ (1×). The organics were combined, dried (MgSO$_4$), filtered and solvent evaporated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes to afford 13 mg (20%) of the title compound. $^1$H NMR (500 MHz, CDCl$_3$) δ ppm 1.66 (s, 9 H) 2.59 (s, 6 H) 3.03-3.10 (m, 2 H) 3.12-3.19 (m, 2 H) 3.93 (s, 3 H) 6.93 (d, J=8.85 Hz, 1 H) 7.36 (dd, J=8.85, 3.05 Hz, 1 H) 8.13 (d, J=2.75 Hz, 1 H) 8.17 (s, 1 H); MS (DCI/NH$_4$$^+$) m/z 396 (M+H)$^+$.

Example 17

N-[(5Z)-2-tert-butyl-4-methylisothiazol-5(2H)-ylidene]-5-chloro-2-methoxybenzamide Example 17A 2-methyl-N-propylidenepropan-2-amine The title compound was prepared using the procedure as described in Example 1A substituting propionaldehyde for hexanal.

Example 17B

N-[(5Z)-2-tert-butyl-4-methylisothiazol-5(2H)-ylidene]-5-chloro-2-methoxybenzamide The title compound was prepared using the procedure as described in Example 1D substituting Example 17A for Example 1A. $^1$H NMR (500 MHz, CDCl$_3$) δ ppm 2.39 (s, 3 H) 3.92 (s, 3 H) 6.92 (d, J=8.85 Hz, 1 H) 7.33 (dd, J=8.85, 2.75 Hz, 1 H) 7.97 (s, 1 H) 8.13 (d, J=2.75 Hz, 1 H); MS (DCI/NH$_4$$^+$) m/z 339 (M+H)$^+$.

Example 18

N-[(5Z)-2-tert-butyl-4-(3-hydroxybutyl)isothiazol-5(2H)-ylidene]-5-chloro-2-methoxybenzamide The product from Example 15A (125 mg, 0.33 mmol) in THF (20 mL) was treated with methylmagnesium bromide (3N) (220 μl, 0.66 mmol) at −40° C. The reaction mixture was allowed to warm to −15° C. for 2 hrs and quenched with NH$_4$Cl. The mixture was extracted with CH$_2$Cl$_2$ (2×). The organics were combined, dried (MgSO$_4$), filtered and solvent evaporated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes to afford 29 mg (22%) of the title compound. $^1$H NMR (500 MHz, CDCl$_3$) δ ppm 1.14 (d, J=6.41 Hz, 3 H) 1.52-1.61 (m, 1 H) 1.67 (s, 9 H) 1.70-1.81 (m, 1 H) 2.72 (dt, J=14.34, 4.27 Hz, 1 H) 3.22-3.31 (m, 1 H) 3.53-3.62 (m, 1 H) 3.94 (s, 3 H) 6.92 (d, J=8.85 Hz, 1 H) 7.34 (dd, J=8.85, 2.75 Hz, 1 H) 7.99 (s, 1 H) 8.03 (d, J=2.75 Hz, 1 H); MS (DCI/NH$_4$$^+$) m/z 397 (M+H)$^+$.

Example 19

N-[(5Z)-2-tert-butyl-4-(2-cyanoethyl)isothiazol-5(2H)-ylidene]-5-chloro-2-methoxybenzamide The product from Example 15A (50 mg, 0.13 mmol) in NMP (1 mL) was treated with hydroxylamine hydrochloride (18 mg, 0.26 mmol). The mixture was heated at 100° C. in a microwave reactor (300W, CEM Explorer®) for 15 min. The crude mixture was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford the title compound. $^1$H NMR (500 MHz, CDCl$_3$) δ ppm 1.68 (s, 9 H) 2.93 (t, J=6.71 Hz, 2 H) 3.14 (t, J=7.02 Hz, 2 H) 3.93 (s, 3 H) 6.94 (d, J=8.85 Hz, 1 H) 7.37 (dd, J=8.85, 3.05 Hz, 1 H) 8.07 (d, J=2.75 Hz, 1 H) 8.11 (s, 1 H); MS (DCI/NH$_4$$^+$) m/z 378 (M+H)$^+$.

Example 20

N-[(5Z)-2-tert-butyl-4-(2,3-dihydroxypropyl)isothiazol-5(2H)-ylidene]-5-chloro-2-methoxybenzamide The product from Example 6B (160 mg, 0.44 mmol) in acetone (3 mL) and water (0.5 mL) was treated with 4-methymorpholine N-oxide (154 mg, 1.32 mmol) and osmium tetroxide (6 mg, 0.02 mmol). The mixture was stirred at rt for 12 hrs, quenched with saturated aqueous Na$_2$S$_2$O$_3$ and extracted twice with isopropanol/CH$_2$Cl$_2$ (1:3). The organics were combined, dried (MgSO$_4$), filtered and solvent evaporated. The residue was purified by reverse phase preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 minutes run time) at a flow rate of 40 mL/minute to afford 67 mg (38%) of the title compound. $^1$H NMR (400 MHz, CDCl$_3$) δ ppm 1.68 (s, 9 H) 3.02-3.07 (m, 2 H) 3.53 (dd, J=4.60, 0.92 Hz, 2 H) 3.90-3.93 (m, 2 H) 3.93 (s, 3 H) 6.93 (d, J=8.90 Hz, 1 H) 7.37 (dd, J=8.90, 2.76 Hz, 1 H) 7.99 (d, J=2.76 Hz, 1 H) 8.00 (s, 1 H); MS (DCI/NH$_4$$^+$) m/z 399 (M+H)$^+$.

Example 21

N-[(5Z)-2-tert-butyl-4-[(E)-(methoxyimino)methyl]isothiazol-5(2H)-ylidene]-5-chloro-2-methoxybenzamide Example 21A N-[(5Z)-2-tert-butyl-4-formylisothiazol-5(2H)-ylidene]-5-chloro-2-methoxybenzamide The product from Example 6B (200 mg, 0.55 mmol) in acetone (6 mL) and water (3 mL) was treated with osmium tetroxide (5 mg, 0.02 mmol). The mixture was stirred at rt for 10 min, then to the mixture was added sodium periodate (258 mg, 1.2 mmol) in portions. The reaction was stirred at rt for 12 hrs, quenched with saturated aqueous Na$_2$S$_2$O$_3$ and extracted twice with isopropanol/CH$_2$Cl$_2$ (1:3). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 78 mg (40%) of the title compound. $^1$H NMR (500 MHz, CDCl$_3$) δ ppm 1.69 (s, 9 H) 3.96 (s, 3 H) 6.97 (d, J=8.85 Hz, 1 H) 7.43 (dd, J=8.85, 2.75 Hz, 1 H) 8.30 (d, J=2.75 Hz, 1 H) 8.67 (s, 1 H) 10.46 (s, 1 H); MS (DCI/NH$_4$$^+$) m/z 353 (M+H)$^+$.

Example 21B

N-[(5Z)-2-tert-butyl-4-[(E)-(methoxyimino)methyl]isothiazol-5(2H)-ylidene]-5-chloro-2-methoxybenzamide The title compound was prepared using the procedure as described in Example 15B substituting Example 21A for Example 15A. $^1$H NMR (500 MHz, CDCl$_3$) δ ppm 1.70 (s, 9 H) 3.94 (s, 3 H) 3.95 (s, 3 H) 6.94 (d, J=8.85 Hz, 1 H) 7.38 (dd, J=8.85, 2.75 Hz, 1 H) 8.23 (d, J=2.75 Hz, 1 H) 8.57 (s, 1 H) 8.62 (s, 1 H); MS (DCI/NH$_4$$^+$) m/z 382 (M+H)$^+$.

Example 22

N-[(5Z)-2-tert-butyl-4-(1,3-dioxolan-2-ylmethyl)isothiazol-5(2H)-ylidene]-5-chloro-2-methoxybenzamide Example 22A 3-(1,3-dioxolan-2-yl)propanal To the solution of 2-(2-bromoethyl)-1,3-dioxolane (10 g, 55.2 mmol) in THF (50 mL) was added magnesium (1.6 g, 66.3 mmol) and trace amount of I$_2$ as initiator. The reaction mixture was stirred at rt for 2 hrs. After cooling to −78° C., the mixture was quenched with dry DMF (1.39 g, 66.3 mmol) and kept at −78° C. for 2 hrs. After dilution with H$_2$O the reaction mixture was extracted with CH$_2$Cl$_2$ (2×), followed by distillation (45-55° C. @ 8 mmHg) to afford 2 g (28%) of the title compound. MS (DCI/NH$_4$$^+$) m/z 131 (M+H)$^+$.

Example 22B

N-(3-(1,3-dioxolan-2-yl)propylidene)-2-methylpropan-2-amine

The title compound was prepared using the procedure as described in Example 1A substituting Example 22A for hexanal.

Example 22C

N-[(5Z)-2-tert-butyl-4-(1,3-dioxolan-2-ylmethyl)isothiazol-5(2H)-ylidene]-5-chloro-2-methoxybenzamide The title compound was prepared using the procedure as described in Example 1D substituting Example 22B for Example 1A. $^1$H NMR (400 MHz, CDCl$_3$) δ ppm 1.66 (s, 9 H) 3.23 (d, J=4.60 Hz, 2 H) 3.87-4.05 (m, 4 H) 3.92 (s, 3 H) 5.21 (t, J=4.91 Hz, 1 H) 6.91 (d, J=8.90 Hz, 1 H) 7.34 (dd, J=8.90, 2.76 Hz, 1 H) 8.15 (d, J=3.07 Hz, 1 H) 8.16 (s, 1 H); MS (DCI/NH$_4$$^+$) m/z 411 (M+H)$^+$.

Example 23

N-[(5Z)-2-tert-butyl-4-(1-hydroxy-2-methylpropyl)isothiazol-5(2H)-ylidene]-5-chloro-2-methoxybenzamide The product from Example 21A (50 mg, 0.14 mmol) in THF (5 mL) was cooled to −40° C. To the solution was dropwise added isopropylmagnesium bromide (3 M) (94 μL, 0.28 mmol). The reaction was kept at −40° C. for 30 min, quenched with saturated aqueous NH$_4$Cl, and the mixture was extracted with EtOAc (2×). The organics were combined, dried (MgSO$_4$), filtered and solvent evaporated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford 7.8 mg (14%) of the title compound. $^1$H NMR (400 MHz, CDCl$_3$) δ ppm 0.99 (d, J=6.75 Hz, 6 H) 1.67 (s, 9 H) 2.11-2.26 (m, 1 H) 3.96 (s, 3 H) 4.59 (d, J=6.44 Hz, 1 H) 6.93 (d, J=8.90 Hz, 1 H) 7.39 (dd, J=8.90, 2.76 Hz, 1 H) 7.94 (s, 1 H) 8.10 (d, J=2.76 Hz, 1 H); MS (DCI/NH$_4^+$) m/z 397 (M+H)$^+$.

Example 24

N-[(5Z)-2-tert-butyl-4-(cyanomethyl)isothiazol-5 (2H)-ylidene]-5-chloro-2-methoxybenzamide

Example 24A 4-oxobutanenitrile 4,4-Diethoxybutanenitrile (10 g, 63.6 mmol) in water (100 mL) was treated with 4-methylbenzenesulfonic acid (200 mg, 1.2 mmol) and refluxed for 2 hrs. The pH was adjusted to 7 and the mixture was extracted with CH$_2$Cl$_2$ (6×). The organics were combined, dried (MgSO$_4$), filtered and solvent evaporated to afford the crude product.

Example 24B 4-(tert-butylimino)butanenitrile

The title compound was prepared using the procedure as described in Example 1A substituting Example 24A for hexanal.

Example 24C

N-[(5Z)-2-tert-butyl-4-(cyanomethyl)isothiazol-5 (2H)-ylidene]-5-chloro-2-methoxybenzamide The title compound was prepared using the procedure as described in Example 1D substituting Example 24B for Example 1A. $^1$H NMR (500 MHz, CDCl$_3$) δ ppm 1.69 (s, 9 H) 3.93 (s, 3 H) 3.97 (s, 2 H) 6.94 (d, J=8.85 Hz, 1 H) 7.38 (dd, J=8.85, 2.75 Hz, 1 H) 8.16 (d, J=2.75 Hz, 1 H) 8.21 (s, 1 H); MS (DCI/NH$_4^+$) m/z 364 (M+H)$^+$.

Example 25

N-[(5Z)-4-[(1Z)-but-1-enyl]-2-tert-butylisothiazol-5 (2H)-ylidene]-5-chloro-2-methoxybenzamide

Example 25A

N-((Z)-hex-3-enylidene)-2-methylpropan-2-amine

The title compound was prepared using the procedure as described in Example 1A substituting (Z)-hex-3-enal for hexanal.

Example 25B

N-[(5Z)-4-[(1Z)-but-1-enyl]-2-tert-butylisothiazol-5 (2H)-ylidene]-5-chloro-2-methoxybenzamide The title compound was prepared using the procedure as described in Example 1D substituting Example 25A for Example 1A. $^1$H NMR (400 MHz, CDCl$_3$) δ ppm 1.12 (t, J=7.67 Hz, 3 H) 1.69 (s, 9 H) 2.24-2.35 (m, 2 H) 3.92 (s, 3 H) 5.70 (dt, J=11.66, 7.06 Hz, 1 H) 6.71 (dt, J=11.66, 1.53 Hz, 1 H) 6.91 (d, J=8.90 Hz, 1 H) 7.34 (dd, J=8.90, 2.76 Hz, 1 H) 8.16 (s, 1 H) 8.18 (d, J=3.07 Hz, 1 H); MS (DCI/NH$_4^+$) m/z 379 (M+H)$^+$.

Example 26

N-[(5Z)-4-butyl-2-tert-butylisothiazol-5(2H)-ylidene]-5-cyano-2-methoxybenzamide

Example 26A methyl 5-cyano-2-methoxybenzoate

3-Bromo-4-methoxybenzonitrile (10 g, 47 mmol) in MeOH (100 mL) was treated with triethyamine (9.1 g, 12.5 mL, 90 mmol) and PdCl$_2$(dppf)CH$_2$Cl$_2$ (1.0 g). The mixture was heated at 100° C. under CO at 60 psi for 4 hrs, then filtered and the filtrate concentrated. The residue was purified by column chromatography using an Analogix® Intelliflash280™ (SiO$_2$, 0-50% Hexane in ethyl acetate) to afford 8.2 g (93%) of the title compound. $^1$H NMR (500 MHz, CDCl$_3$) δ ppm 3.92 (s, 3 H) 3.98 (s, 3 H) 7.06 (d, J=8.54 Hz, 1 H) 7.76 (dd, J=8.54, 2.14 Hz, 1 H) 8.10 (d, J=2.14 Hz, 1 H).

Example 26B 5-cyano-2-methoxybenzoic acid

A mixture of the product from Example 26A (6.1 g, 31.9 mmol) and lithium hydroxide monohydrate (5.36 g, 128 mmol) in THF (100 mL) and H$_2$O (50 mL) was stirred at rt for 3 hrs. The reaction pH was adjusted to 3 with 3N HCl, and the mixture was extracted twice with isopropanol/CH$_2$Cl$_2$ (1:3). The organics were combined, dried (MgSO$_4$), filtered and concentrated to afford 5.6 g (99%) of the title compound. $^1$H NMR (500 MHz, CDCl$_3$) δ ppm 4.15 (s, 3 H) 7.17 (d, J=8.85 Hz, 1 H) 7.86 (dd, J=8.85, 2.44 Hz, 1 H) 8.47 (d, J=2.14 Hz, 1 H).

Example 26C 5-cyano-2-methoxybenzoyl chloride

The title compound was prepared using the procedure as described in Example 1B substituting Example 26B for 5-chloro-2-methoxybenzoic acid.

Example 26D 5-cyano-2-methoxybenzoyl isothiocyanate

The title compound was prepared using the procedure as described in Example 1C substituting Example 26C for Example 1B.

Example 26E

N-[(5Z)-4-butyl-2-tert-butylisothiazol-5(2H)-ylidene]-5-cyano-2-methoxybenzamide The title compound was prepared using the procedure as described in Example 1D substituting Example 26D for Example 1C. $^1$H NMR (400 MHz, CDCl$_3$) δ ppm 0.99 (t, J=7.36 Hz, 3 H) 1.39-1.49 (m, 2 H) 1.66 (s, 9 H) 1.68-1.76 (m, 2 H) 2.83 (dd, J=7.67 Hz, 2 H) 3.99 (s, 3 H) 7.04 (d, J=8.90

Hz, 1 H) 7.68 (dd, J=8.59, 2.15 Hz, 1 H) 7.97 (s, 1 H) 8.46 (d, J=2.15 Hz, 1 H); MS (DCI/NH$_4^+$) m/z 372 (M+H)$^+$.

Example 27

N-[(5Z)-2-tert-butyl-4-(2-ethylcyclopropyl)isothiazol-5(2H)-ylidene]-5-chloro-2-methoxybenzamide To a solution of CH$_2$Cl$_2$ (10 mL) and 1,2-dimethoxyethane (95 mg, 1.06 mmol) at −10° C. was added diethylzinc (130 mg, 1.06 mmol). To this solution was added dropwise diiodomethane (565 mg, 2.1 mmol). After the addition was complete, the resulting clear solution was stirred for 10 min at −10° C. A solution of Example 25B (200 mg, 0.53 mmol) was added to the reaction mixture, which was allowed to warm to room temperature and stir overnight. The reaction was quenched with NH$_4$Cl then acetone and extracted with EtOAc (2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 159 mg (77%) of the title compound. $^1$H NMR (400 MHz, CDCl$_3$) δ ppm 0.59 (q, J=5.52 Hz, 1 H) 0.92 (t, J=7.36, 6.44 Hz, 3 H) 0.94-1.14 (m, 2 H) 1.16-1.29 (m, 2 H) 1.65 (s, 9 H) 2.11-2.33 (m, 1 H) 3.91 (s, 3 H) 6.91 (d, J=8.90 Hz, 1 H) 7.33 (dd, J=8.90, 2.76 Hz, 1 H) 7.81 (s, 1 H) 8.08 (d, J=2.76 Hz, 1 H); MS (DCI/NH$_4^+$) m/z 393 (M+H)$^+$.

Example 28

N-[(5Z)-2-tert-butyl-4-(methoxymethyl)isothiazol-5(2H)-ylidene]-5-chloro-2-methoxybenzamide Example 28A N-[(5Z)-2-tert-butyl-4-(hydroxymethyl)isothiazol-5(2H)-ylidene]-5-chloro-2-methoxybenzamide The product from Example 21A (50 mg, 0.14 mmol) in THF (10 mL) was treated with sodium borohydride (21 mg, 0.57 mmol) at −40° C. for 1 hr, quenched with saturated NH$_4$Cl, extracted with EtOAc (2×), dried over MgSO$_4$, filtered and concentrated to afford 50 mg of the title compound. $^1$H NMR (500 MHz, CDCl$_3$) δ ppm 1.67 (s, 9 H) 3.93 (s, 3 H) 4.88 (s, 2 H) 6.94 (d, J=8.85 Hz, 1 H) 7.37 (dd, J=8.85, 3.05 Hz, 1 H) 8.05 (s, 1 H) 8.08 (d, J=2.75 Hz, 1 H); MS (DCI/NH$_4^+$) m/z 355 (M+H)$^+$.

Example 28B

N-[(5Z)-2-tert-butyl-4-(methoxymethyl)isothiazol-5(2H)-ylidene]-5-chloro-2-methoxybenzamide The title compound was prepared using the procedure as described in Example 11E substituting Example 28A for Example 11D. $^1$H NMR (500 MHz, CDCl$_3$) δ ppm 1.67 (s, 3 H) 3.51 (s, 3 H) 3.93 (s, 3 H) 4.73 (s, 2 H) 6.92 (d, J=8.85 Hz, 1 H) 7.35 (dd, J=8.85, 2.75 Hz, 1 H) 8.15 (d, J=2.75 Hz, 1 H) 8.18 (s, 1 H); MS (DCI/NH$_4^+$) m/z 369 (M+H)$^+$.

Example 29

N-[(5Z)-2-tert-butyl-4-(ethoxymethyl)isothiazol-5(2H)-ylidene]-5-chloro-2-methoxybenzamide The title compound was prepared using the procedure as described in Example 11E substituting Example 28A for Example 11D and iodoethane for iodomethane. $^1$H NMR (500 MHz, CDCl$_3$) δ ppm 1.30 (t, J=7.02 Hz, 3 H) 1.67 (s, 9 H) 3.69 (q, J=7.02 Hz, 2 H) 3.92 (s, 3 H) 4.77 (s, 2 H) 6.92 (d, J=8.85 Hz, 1 H) 7.35 (dd, J=8.85, 2.75 Hz, 1 H) 8.14 (d, J=3.05 Hz, 1 H) 8.19 (s, 1 H); MS (DCI/NH$_4^+$) m/z 383 (M+H)$^+$.

Example 30

N-[(5Z)-2-tert-butyl-4-(3-cyanopropyl)isothiazol-5(2H)-ylidene]-5-chloro-2-methoxybenzamide Example 30A 6-oxohexanenitrile The title compound was prepared using the procedure as described in Example 21A substituting hept-6-enenitrile for Example 6B.

Example 30B 6-(tert-butylimino)hexanenitrile

The title compound was prepared using the procedure as described in Example 1A substituting Example 30A for hexanal.

Example 30C

N-[(5Z)-2-tert-butyl-4-(3-cyanopropyl)isothiazol-5(2H)-ylidene]-5-chloro-2-methoxybenzamide The title compound was prepared using the procedure as described in Example 1D substituting Example 30B for Example 1A. $^1$H NMR (400 MHz, CDCl$_3$) δ ppm 1.67 (s, 9 H) 2.13-2.24 (m, 2 H) 2.42 (t, J=7.06 Hz, 2 H) 2.98 (t, J=7.36 Hz, 2 H) 3.92 (s, 3 H) 6.92 (d, J=8.59 Hz, 1 H) 7.35 (dd, J=8.90, 2.76 Hz, 1 H) 8.01 (s, 1 H) 8.08 (d, J=2.76 Hz, 1 H); MS (DCI/NH$_4^+$) m/z 392 (M+H)$^+$.

Example 31

N-[(5Z)-2-tert-butyl-4-[hydroxy(phenyl)methyl]isothiazol-5(2H)-ylidene]-5-chloro-2-methoxybenzamide The title compound was prepared using the procedure as described in Example 23 substituting phenylmagnesium bromide for isopropylmagnesium bromide. $^1$H NMR (400 MHz, CDCl$_3$) δ ppm 1.57 (s, 9 H) 3.95 (s, 3 H) 6.25 (s, 1 H) 6.96 (t, J=9.21 Hz, 1 H) 7.30-7.46 (m, 4 H) 7.50-7.56 (m, 2 H) 8.18 (d, J=2.76 Hz, 1 H) 9.51 (s, 1 H); MS (DCI/NH$_4^+$) m/z 431 (M+H)$^+$.

Example 32

N-[(5Z)-4-(azidomethyl)-2-tert-butylisothiazol-5(2H)-ylidene]-5-chloro-2-methoxybenzamide The title compound was prepared using the procedure as described in Example 14 substituting Example 28A for Example 11D. $^1$H NMR (500 MHz, CDCl$_3$) δ ppm 1.67 (s, 9 H) 3.93 (s, 3 H) 4.65 (s, 2 H) 6.93 (d, J=8.85 Hz, 1 H) 7.37 (dd, J=8.85, 2.75 Hz, 1 H) 8.12 (m, 1 H) 8.20 (d, J=2.75 Hz, 1 H); MS (DCI/NH$_4^+$) m/z 380 (M+H)$^+$.

Example 33

N-[(5Z)-2-tert-butyl-4-(2-cyclobutyl-1-hydroxy-ethyl)isothiazol-5(2H)-ylidene]-5-chloro-2-methoxybenzamide To (bromomethyl)cyclobutane (211 mg, 1.42 mmol) in THF (20 mL) was added magnesium (41.3 mg, 1.7 mmol), and initiator iodine (10 mg). The mixture was stirred at rt for 2 hrs, then cooled to −40° C. and added to a solution of Example 21A (100 mg, 0.28 mmol) in THF (20 mL). The mixture was allowed to warm to room temperature, quenched with saturated aqueous $NH_4Cl$, and extracted with EtOAc (2×). The organics were combined, dried ($MgSO_4$), filtered and solvent evaporated. The residue was purified by column chromatography using an Analogix® Intelliflash280™ ($SiO_2$, 0-50% Hexane in ethyl acetate) to afford 63 mg (53%) of the title compound. $^1$H NMR (400 MHz, $CDCl_3$) δ ppm 1.62-1.78 (m, 2 H) 1.65 (s, 9 H) 1.76-1.94 (m, 2 H) 1.97-2.18 (m, 4 H) 2.47-2.59 (m, 1 H) 3.92 (s, 3 H) 4.88 (dd, J=8.29, 6.14 Hz, 1 H) 6.93 (d, J=8.90 Hz, 1 H) 7.37 (dd, J=8.90, 3.07 Hz, 1 H) 7.95 (s, 1 H) 8.05 (d, J=2.76 Hz, 1 H); MS (DCI/$NH_4^+$) m/z 423 $(M+H)^+$.

Example 34

N-[(5Z)-2-tert-butyl-4-[cyclobutyl(hydroxy)methyl]isothiazol-5(2H)-ylidene]-5-chloro-2-methoxybenzamide The title compound was prepared using the procedure as described in Example 33 substituting bromocyclobutane for (bromomethyl)cyclobutane. $^1$H NMR (400 MHz, $CDCl_3$) δ ppm 1.65 (s, 9 H) 1.82-2.01 (m, 4 H) 2.08-2.20 (m, 2 H) 2.80-2.92 (m, 1 H) 3.94 (s, 3 H) 4.85 (d, J=7.67 Hz, 1 H) 6.93 (d, J=8.90 Hz, 1 H) 7.37 (dd, J=8.59, 2.76 Hz, 1 H) 7.91 (s, 1 H) 8.03 (d, J=2.76 Hz, 1 H); MS (DCI/$NH_4^+$) m/z 409 $(M+H)^+$.

Example 35

N-[(5Z)-4-benzyl-2-tert-butylisothiazol-5(2H)-ylidene]-5-chloro-2-methoxybenzamide The product from Example 31 (20 mg, 0.05 mmol) in TFA (0.5 mL) was treated with triethylsilane (54 mg, 0.5 mmol). The mixture was heated at 60° C. for 12 hrs, solvent evaporated and the residue purified by reverse phase preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 minutes run time) at a flow rate of 40 mL/minute to afford 4.8 mg (25%) of the title compound. $^1$H NMR (400 MHz, $CDCl_3$) δ ppm 1.61 (s, 9 H) 3.93 (s, 3 H) 4.18 (s, 2 H) 6.92 (d, J=8.90 Hz, 1 H) 7.20-7.28 (m, 1 H) 7.29-7.39 (m, 5 H) 7.78 (s, 1 H) 8.14 (d, J=2.76 Hz, 1 H); MS (DCI/$NH_4^+$) m/z 415 $(M+H)^+$.

Example 36

N-[(5Z)-2-tert-butyl-4-(2-cyclobutylethyl)isothiazol-5(2H)-ylidene]-5-chloro-2-methoxybenzamide

Example 36A

O-{1-[(5Z)-2-tert-butyl-5-{[(5-chloro-2-methoxyphenyl)carbonyl]imino}-2,5-dihydroisothiazol-4-yl]-2-cyclobutylethyl}O-phenyl thiocarbonate The product from Example 33 (32 mg, 0.07 mmol) in $CH_2Cl_2$ (5 mL) containing pyridine (17 mg, 0.2 mmol) was treated dropwise with O-phenyl carbonochloridothioate (18 mg, 0.11 mmol). The mixture was stirred at room temperature for 1 hr, solvent removed and the residue purified by column chromatography using an Analogix® Intelliflash280™ ($SiO_2$, 0-50% Hexane in ethyl acetate) to afford 32 mg (81%) of the title compound. MS (DCI/$NH_4^+$) m/z 559 $(M+H)^+$.

Example 36B

N-[(5Z)-2-tert-butyl-4-(2-cyclobutylethyl)isothiazol-5(2H)-ylidene]-5-chloro-2-methoxybenzamide The product from Example 36A (32 mg, 0.06 mmol) was immediately treated with 2 mL (0.03 mmol) of a stock solution of AIBN (12 mg (0.073 mmol in 5 mL of anhydrous toluene)) and tributylstannane (33.3 mg, 0.114 mmol), and the resulting mixture was heated to 85-90° C. After 30 min, additional tributylstannane (33.3 mg, 0.114 mmol) and AIBN stock solution (1 mL) were added. The reaction was refluxed for an additional 30 min, concentrated in vacuo and the residue purified by reverse phase preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 minutes run time) at a flow rate of 40 mL/minute to afford 13.2 mg (57%) of the title compound. $^1$H NMR (400 MHz, $CDCl_3$) δ ppm 1.61-1.75 (m, 2 H) 1.65 (s, 9 H) 1.77-1.94 (m, 4 H) 2.04-2.16 (m, 2 H) 2.30-2.41 (m, 1 H) 2.73 (dd, J=7.67 Hz, 2 H) 3.92 (s, 3 H) 6.91 (d, J=8.59 Hz, 1 H) 7.34 (dd, J=8.90, 3.07 Hz, 1 H) 7.93 (s, 1 H) 8.14 (d, J=2.76 Hz, 1 H); MS (DCI/$NH_4^+$) m/z 407 $(M+H)^+$.

Example 37

N-[(5Z)-2-tert-butyl-4-isobutylisothiazol-5(2H)-ylidene]-5-chloro-2-methoxybenzamide

Example 37A

O-{1-[(5Z)-2-tert-butyl-5-{[(5-chloro-2-methoxyphenyl)carbonyl]imino}-2,5-dihydroisothiazol-4-yl]-2-methylpropyl}O-phenyl thiocarbonate The title compound was prepared using the procedure as described in Example 36A substituting Example 23 for Example 33. MS (DCI/$NH_4^+$) m/z 533 $(M+H)^+$.

Example 37B

N-[(5Z)-2-tert-butyl-4-isobutylisothiazol-5(2H)-ylidene]-5-chloro-2-methoxybenzamide The title compound was prepared using the procedure as described in Example 36B substituting Example 37A for Example 36A. $^1$H NMR (400 MHz, $CDCl_3$) δ ppm 0.97 (d, J=6.44 Hz, 6 H) 1.66 (s, 9 H) 2.05-2.19 (m, 1 H) 2.70 (d, J=7.06 Hz, 2 H) 3.91 (s, 3 H) 6.91 (d, J=8.59 Hz, 1 H) 7.33 (dd, J=8.90, 2.76 Hz, 1 H) 7.91 (s, 1 H); MS (DCI/$NH_4^+$) m/z 381 $(M+H)^+$.

Example 38

N-[(5Z)-2-tert-butyl-4-(cyclobutylmethyl)isothiazol-5(2H)-ylidene]-5-chloro-2-methoxybenzamide

Example 38A

O-{[(5Z)-2-tert-butyl-5-{[(5-chloro-2-methoxyphenyl)carbonyl]imino}-2,5-dihydroisothiazol-4-yl](cyclobutyl)methyl}O-phenyl thiocarbonate The title compound was prepared using the procedure as described in Example 36A substituting Example 34 for Example 33. MS (DCI/NH$_4^+$) m/z 545 (M+H)$^+$.

Example 38B

N-[(5Z)-2-tert-butyl-4-(cyclobutylmethyl)isothiazol-5(2H)-ylidene]-5-chloro-2-methoxybenzamide The title compound was prepared using the procedure as described in Example 36B substituting Example 38A for Example 36A. $^1$H NMR (400 MHz, CDCl$_3$) δ ppm 1.65 (s, 9 H) 1.73-1.84 (m, 2 H) 1.84-1.95 (m, 2 H) 2.04-2.16 (m, 2 H) 2.69-2.79 (m, 1 H) 2.92 (d, J=7.67 Hz, 2 H) 3.92 (s, 3 H) 6.91 (d, J=8.59 Hz, 1 H) 7.33 (dd, J=8.90, 2.76 Hz, 1 H) 7.89 (s, 1 H) 8.09 (d, J=2.76 Hz, 1 H); MS (DCI/NH$_4^+$) m/z 393 (M+H)$^+$.

Example 39

N-[(5Z)-2-tert-butyl-4-tetrahydro-2H-pyran-4-yl-isothiazol-5(2H)-ylidene]-5-chloro-2-methoxybenzamide

Example 39A

2-methyl-N-(2-(tetrahydro-2H-pyran-4-yl)ethylidene)propan-2-amine

The title compound was prepared using the procedure as described in Example 1A substituting 2-(tetrahydro-2H-pyran-4-yl)acetaldehyde for hexanal.

Example 39B

N-[(5Z)-2-tert-butyl-4-tetrahydro-2H-pyran-4-yl-isothiazol-5(2H)-ylidene]-5-chloro-2-methoxybenzamide The title compound was prepared using the procedure as described in Example 1D substituting Example 39A for Example 1A. $^1$H NMR (500 MHz, CDCl$_3$) δ ppm 1.64-1.68 (s, 9 H) 1.77 (qd, J=13.12, 12.21, 4.27 Hz, 2 H) 2.06 (dt, J=12.82, 1.83 Hz, 2 H) 3.36-3.45 (m, 1 H) 3.65 (td, J=11.90, 1.83 Hz, 2 H) 3.92 (s, 3 H) 4.08 (dd, J=11.29, 3.97 Hz, 2 H) 6.92 (d, J=8.85 Hz, 1 H) 7.35 (dd, J=8.85, 2.75 Hz, 1 H) 7.93 (s, 1 H) 8.08 (d, J=3.05 Hz, 1 H); MS (DCI/NH$_4^+$) m/z 409 (M+H)$^+$.

Example 40

N-[(5Z)-2-tert-butyl-4-[hydroxy(1,3-thiazol-2-yl)methyl]isothiazol-5(2H)-ylidene]-5-chloro-2-methoxybenzamide The title compound was prepared using the procedure as described in Example 23 substituting thiazol-2-yllithium for isopropylmagnesium bromide. $^1$H NMR (500 MHz, CDCl$_3$) δ ppm 1.82 (s, 9 H) 4.19 (s, 3 H) 6.83 (s, 1 H) 7.09 (d, J=8.85 Hz, 1 H) 7.40 (d, J=3.36 Hz, 1 H) 7.62 (dd, J=8.85, 2.75 Hz, 1 H) 7.79-7.82 (m, 1 H) 8.16 (d, J=2.75 Hz, 1 H) 8.94 (s, 1 H); MS (DCI/NH$_4^+$) m/z 438 (M+H)$^+$.

Example 41

N-[(5Z)-4-butyl-2-tert-butylisothiazol-5(2H)-ylidene]-2,5-dimethoxybenzamide A mixture of the product from Example 110B (400 mg), 2,5-dimethoxybenzoic acid (86 mg, 0.47 mmol), EDCI (181 mg, 0.94 mmol), HOBt (145 mg, 0.94 mmol) and DMAP (12 mg, 0.1 mmol) in pyridine (10 mL) was stirred at rt for 1 hr. The solvent was removed in vacuo, the mixture diluted with water, and extracted with EtOAc. The organic extract was dried (Na$_2$SO$_4$), filtered and concentrated. The residue was washed with a small amount of EtOAc and filtered to afford 36 mg of the title compound. $^1$H NMR (400 MHz, CDCl$_3$) δ ppm 0.97 (t, J=7.36 Hz, 3 H) 1.38-1.48 (m, 2 H) 1.65 (s, 9 H) 1.68-1.78 (m, 2 H) 2.83 (dd, J=7.67 Hz, 2 H) 3.83 (s, 3 H) 3.89 (s, 3 H) 6.93-6.94 (m, 1 H) 6.95 (d, J=3.07 Hz, 1 H) 7.73 (d, J=2.76 Hz, 1 H) 7.93 (s, 1 H); MS (ESI) m/z 377 (M+H)$^+$.

Example 42

N-[(5Z)-4-butyl-2-tert-butylisothiazol-5(2H)-ylidene]-5-fluoro-2-methoxybenzamide The title compound was prepared using the procedure as described in Example 41 substituting 5-fluoro-2-methoxybenzoic acid for 2,5-dimethoxybenzoic acid. $^1$H NMR (400 MHz, CDCl$_3$) δ ppm 0.98 (t, J=7.36 Hz, 3 H) 1.37-1.48 (m, 2 H) 1.62-1.67 (s, 9 H) 1.67-1.77 (m, 2 H) 2.82 (dd, J=7.67 Hz, 2 H) 3.92 (s, 3 H) 6.92 (dd, J=8.90, 4.30 Hz, 1 H) 7.05-7.11 (m, 1 H) 7.88 (dd, J=9.51, 3.38 Hz, 1 H) 7.94 (s, 1 H); MS (DCI/NH$_4^+$) m/z 365 (M+H)$^+$.

Example 43

N-[(5Z)-4-butyl-2-tert-butylisothiazol-5(2H)-ylidene]-2-methoxy-5-methylbenzamide The title compound was prepared using the procedure as described in Example 41 substituting 2-methoxy-5-methylbenzoic acid for 2,5-dimethoxybenzoic acid. $^1$H NMR (400 MHz, CDCl$_3$) δ ppm 0.98 (t, J=7.36 Hz, 3 H) 1.38-1.50 (m, 2 H) 1.65 (s, 9 H) 1.67-1.79 (m, 2 H) 2.34 (s, 3 H) 2.84 (dd, J=7.98, 7.36 Hz, 2 H) 3.90 (s, 3 H) 6.88 (d, J=8.59 Hz, 1 H) 7.18 (dd, J=9.21, 2.46 Hz, 1 H) 7.92 (s, 1 H) 7.93 (d, J=2.45 Hz, 1 H); MS (DCI/NH$_4^+$) m/z 361 (M+H)$^+$.

Example 44

N-[(5Z)-2-tert-butyl-4-[hydroxy(thien-2-yl)methyl]isothiazol-5(2H)-ylidene]-5-chloro-2-methoxybenzamide To 2-bromothiophene (444 mg, 2.72 mmol) in THF (10 mL) was added dropwise n-butyllithium (2.5M) (1.09 mL, 2.72 mmol) at −78° C. The reaction was stirred at −78° C. for 15 min and treated with Example 21A (240 mg, 0.68 mmol) in THF (1 mL). The reaction was stirred at −78° C. for 1 hr, quenched with saturated aqueous NH$_4$Cl and extracted with EtOAc (2×). The organics were combined, dried (MgSO$_4$), filtered and solvent evaporated. The residue was purified by column chromatography using an Analogix® Intelliflash280™ (SiO$_2$, 0-75% Hexane in ethyl acetate) to afford 93 mg (31%) of the title compound. $^1$H NMR (400 MHz, CDCl$_3$) δ ppm 1.62 (s, 9 H) 3.94 (s, 3 H) 6.36 (s, 1 H) 6.94 (d, J=8.90 Hz, 1 H) 7.01 (dd, J=4.91, 3.38 Hz, 1 H) 7.09 (d, J=3.38 Hz, 1 H) 7.30 (dd, J=4.91, 1.23 Hz, 1 H) 7.38 (dd, J=8.90, 2.45 Hz, 1 H) 7.78 (s, 1 H) 8.07 (d, J=2.76 Hz, 1 H); MS (DCI/NH$_4$$^+$) m/z 437 (M+H)$^+$.

Example 45 methyl 4-{(5Z)-2-tert-butyl-5-[(5-chloro-2-methoxybenzoyl)imino]-2,5-dihydroisothiazol-4-yl}butanoate Example 45A methyl 6-(tert-butylimino)hexanoate The title compound was prepared using the procedure as described in Example 1A substituting methyl 6-oxohexanoate for hexanal.

Example 45B methyl 4-{(5Z)-2-tert-butyl-5-[(5-chloro-2-methoxybenzoyl)imino]-2,5-dihydroisothiazol-4-yl}butanoate The title compound was prepared using the procedure as described in Example 1D substituting Example 45A for Example 1A. $^1$H NMR (400 MHz, CDCl$_3$) δ ppm 1.66 (s, 9 H) 2.01-2.15 (m, 2 H) 2.43 (t, J=7.36 Hz, 2 H) 2.87 (t, J=7.98, 7.36 Hz, 2 H) 3.68 (s, 3 H) 3.92 (s, 3 H) 6.92 (d, J=8.90 Hz, 1 H) 7.34 (dd, J=8.90, 2.76 Hz, 1 H) 7.98 (s, 1 H); MS (DCI/NH$_4$$^+$) m/z 425 (M+H)$^+$.

Example 46 methyl 4-{(5Z)-2-tert-butyl-5-[(5-cyano-2-methoxybenzoyl)imino]-2,5-dihydroisothiazol-4-yl}butanoate The title compound was prepared using the procedure as described in Example 1D substituting Example 45A for Example 1A, and Example 26D for Example 1C. $^1$H NMR (400 MHz, CDCl$_3$) δ ppm 1.67 (s, 9 H) 2.04-2.14 (m, 2 H) 2.43 (t, J=7.36 Hz, 2 H) 2.87 (dd, J=7.36 Hz, 2 H) 3.69 (s, 3 H) 3.99 (s, 3 H) 7.04 (d, J=8.59 Hz, 1 H) 7.68 (dd, J=8.90, 2.45 Hz, 1 H) 8.01 (s, 1 H) 8.47 (d, J=2.46 Hz, 1 H); MS (DCI/NH$_4$$^+$) m/z 416 (M+H)$^+$.

Example 47

N-[(5Z)-4-butyl-2-tert-butylisothiazol-5(2H)-ylidene]-5-chloro-2-(2,2,2-trifluoroethoxy)benzamide Example 47A N-[(5Z)-4-butyl-2-tert-butylisothiazol-5(2H)-ylidene]-5-chloro-2-fluorobenzamide The title compound was prepared using the procedure as described in Example 41 substituting 5-chloro-2-fluorobenzoic acid for 2,5-dimethoxybenzoic acid. MS (DCI/NH$_4$$^+$) m/z 369 (M+H)$^+$.

Example 47B

N-[(5Z)-4-butyl-2-tert-butylisothiazol-5(2H)-ylidene]-5-chloro-2-(2,2,2-trifluoroethoxy)benzamide A mixture of the product from Example 47A (101 mg, 0.27 mmol), trifluoroethanol (33 mg, 0.32 mmol) and potassium tert-butoxide (2 M) (340 µL, 0.68 mmol) in THF (10 mL) was stirred at rt for 12 hrs. The mixture was diluted with water, and extracted with EtOAc. The organic extract was dried (Na$_2$SO$_4$), filtered and concentrated. The residue was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minute to afford 34 mg (28%) of the title compound. $^1$H NMR (400 MHz, CDCl$_3$) δ ppm 0.97 (t, J=7.36 Hz, 3 H) 1.37-1.48 (m, 2 H) 1.65-1.75 (m, 2 H) 1.68 (s, 9 H) 4.50 (q, J=8.59 Hz, 2 H) 7.05 (d, J=8.59 Hz, 1 H) 7.34 (dd, J=8.90, 2.76 Hz, 1 H) 7.97 (s, 1 H) 8.11 (d, J=2.76 Hz, 1 H); MS (DCI/NH$_4$$^+$) m/z 449 (M+H)$^+$.

Example 48

N-[(5Z)-4-butyl-2-tert-butylisothiazol-5(2H)-ylidene]-2-methoxy-5-(methylsulfonyl)benzamide The title compound was prepared using the procedure as described in Example 41 substituting 2-methoxy-5-(methylsulfonyl)benzoic acid for 2,5-dimethoxybenzoic acid. $^1$H NMR (400 MHz, CDCl$_3$) δ ppm 0.98 (t, J=7.36 Hz, 3 H) 1.37-1.49 (m, 2 H) 1.67 (s, 9 H) 1.68-1.77 (m, 2 H) 2.83 (dd, J=7.67 Hz, 2 H) 3.06 (s, 3 H) 4.01 (s, 3 H) 7.10 (d, J=8.59 Hz, 1 H) 7.97 (dd, J=8.59, 2.46 Hz, 1 H) 7.96 (s, 1 H) 8.65 (d, J=2.46 Hz, 1 H); MS (DCI/NH$_4$$^+$) m/z 425 (M+H)$^+$.

Example 49

N-[(5Z)-2-tert-butyl-4-[hydroxy(1,3-thiazol-4-yl)methyl]isothiazol-5(2H)-ylidene]-5-chloro-2-methoxybenzamide The title compound was prepared using the procedure as described in Example 44 substituting 4-bromothiazole for 2-bromothiophene. $^1$H NMR (500 MHz, CDCl$_3$) δ ppm 1.66 (s, 9 H) 3.98 (s, 3 H) 6.38 (s, 1 H) 6.96 (d, J=8.85 Hz, 1 H) 7.34 (d, J=3.36 Hz, 1 H) 7.40 (dd, J=8.85, 2.75 Hz, 1 H) 7.77 (d, J=3.05 Hz, 1 H) 8.08 (d, J=2.75 Hz, 1 H) 8.28 (s, 1 H); MS (DCI/NH$_4$$^+$) m/z 438 (M+H)$^+$.

Example 50

N-[(5Z)-2-tert-butyl-4-(2-furylmethyl)isothiazol-5(2H)-ylidene]-5-chloro-2-methoxybenzamide Example 50A 3-(furan-2-yl)propan-1-ol To 3-(furan-2-yl)propanoic acid (1.4 g, 10 mmol) in THF (50 mL) was added dropwise borane (1M) (20 mL, 20 mmol). The mixture was stirred at rt for 12 hrs, quenched with MeOH, and the mixture was concentrated. The resulting residue was purified by column chromatography using an Analogix® Intelliflash280™ (SiO$_2$, 0-50% Hexane in ethyl acetate) to afford 1.0 g (79%) of the title compound. $^1$H NMR (500 MHz, CDCl$_3$) δ ppm 1.87-1.94 (m, 2 H) 2.74 (t, J=7.32 Hz, 2 H) 3.69 (t, J=6.10 Hz, 2 H) 6.28 (dd, J=3.05, 1.83 Hz, 1 H) 7.30 (d, J=0.92 Hz, 1 H).

Example 50B 3-(furan-2-yl)propanal

The product from Example 50A (2.0 g, 15.9 mmol) in CH$_2$Cl$_2$ (50 mL) was treated with Dess-Martin periodinane (8.1 g, 19.2 mmol) in portions. The mixture was stirred at rt for 2 hrs, quenched with saturated NaS$_2$O$_3$, and the mixture was extracted with CH$_2$Cl$_2$. The CH$_2$Cl$_2$ layer was washed with saturated NaHCO$_3$, dried over MgSO$_4$, filtered and concentrated. The resulting residue was purified by column chromatography using an Analogix® Intelliflash280™ (SiO$_2$, 0-50% Hexane in ethyl acetate) to afford 1.44 g (73%) of the title compound. $^1$H NMR (500 MHz, CDCl$_3$) δ ppm 2.80 (t, J=8.24, 6.41 Hz, 2 H) 2.98 (t, J=7.32 Hz, 2 H) 6.02 (d, J=3.97 Hz, 1 H) 6.19-6.36 (m, 1 H) 7.28-7.33 (m, 1 H) 9.82 (s, 1 H).

Example 50C

N-(3-(furan-2-yl)propylidene)-2-methylpropan-2-amine

The title compound was prepared using the procedure as described in Example 1A substituting Example 50B for hexanal.

Example 50D ethyl [(5Z)-2-tert-butyl-4-(furan-2-ylmethyl)isothiazol-5(2H)-ylidene]carbamate The title compound was prepared using the procedure as described in Example 1D substituting Example 50C for Example 1A and o-ethyl carbonisothiocyanatidate for Example 1C. $^1$H NMR (400 MHz, CDCl$_3$) δ ppm 1.37 (t, J=7.36 Hz, 3 H) 1.58 (s, 9 H) 4.04 (s, 2 H) 4.29 (q, J=7.06 Hz, 2 H) 6.11 (d, J=3.38 Hz, 1 H) 6.31 (dd, J=3.07, 1.84 Hz, 1 H) 7.34 (d, J=1.84 Hz, 1 H) 7.76 (s, 1 H); MS (DCI/NH$_4^+$) m/z 309 (M+H)$^+$.

Example 50E 2-tert-butyl-4-(furan-2-ylmethyl)isothiazol-5(2H)-imine

The product from Example 50D (300 mg, 0.97 mmol) in chloroform (20 mL) was treated with TMSI (389 mg, 1.95 mmol). The reaction mixture was stirred at 65° C. for 12 hrs, diluted with CH$_2$Cl$_2$, the organic was washed with H$_2$O, dried over MgSO$_4$, filtered and concentrated to afford the title compound. MS (DCI/NH$_4^+$) m/z 237 (M+H)$^+$.

Example 50F

N-[(5Z)-2-tert-butyl-4-(2-furylmethyl)isothiazol-5(2H)-ylidene]-5-chloro-2-methoxybenzamide The title compound was prepared using the procedure as described in Example 41 substituting Example 51E for Example 110B and 5-chloro-2-methoxybenzoic acid for 2,5-dimethoxybenzoic acid. $^1$H NMR (400 MHz, CDCl$_3$) δ ppm 1.64 (s, 9 H) 3.92 (s, 3 H) 4.21 (s, 2 H) 6.17 (d, J=2.45 Hz, 1 H) 6.34 (dd, J=3.07, 1.84 Hz, 1 H) 6.92 (d, J=8.90 Hz, 1 H) 7.34 (dd, J=8.90, 2.76 Hz, 1 H) 7.36 (d, J=1.84 Hz, 1 H) 7.95 (s, 1 H) 8.14 (d, J=2.76 Hz, 1 H); MS (DCI/NH$_4^+$) m/z 405 (M+H)$^+$.

Example 51

N-[(5Z)-2-tert-butyl-4-(2-furylmethyl)isothiazol-5(2H)-ylidene]-5-cyano-2-methoxybenzamide The title compound was prepared using the procedure as described in Example 41 substituting Example 51E for Example 110B and Example 26B for 2,5-dimethoxybenzoic acid. $^1$H NMR (400 MHz, CDCl$_3$) δ ppm 1.65 (s, 9 H) 3.99 (s, 3 H) 4.21 (s, 2 H) 6.17 (d, J=3.07 Hz, 1 H) 6.35 (dd, J=3.07, 1.84 Hz, 1 H) 7.04 (d, J=8.59 Hz, 1 H) 7.37 (d, J=1.84 Hz, 1 H) 7.68 (dd, J=8.59, 2.15 Hz, 1 H) 7.98 (s, 1 H) 8.48 (d, J=2.15 Hz, 1 H); MS (DCI/NH$_4^+$) m/z 396 (M+H)$^+$.

Example 52

N-[(5Z)-2-tert-butyl-4-(1,3-thiazol-4-ylmethyl)isothiazol-5(2H)-ylidene]-5-chloro-2-methoxybenzamide

Example 52A

O-{[(5Z)-2-tert-butyl-5-{[(5-chloro-2-methoxyphenyl)carbonyl]imino}-2,5-dihydroisothiazol-4-yl](1,3-thiazol-4-yl)methyl}O-phenyl thiocarbonate The title compound was prepared using the procedure as described in Example 36A substituting Example 49 for Example 33. MS (DCI/NH$_4^+$) m/z 574 (M+H)$^+$.

Example 52B

N-[(5Z)-2-tert-butyl-4-(1,3-thiazol-4-ylmethyl)isothiazol-5(2H)-ylidene]-5-chloro-2-methoxybenzamide The title compound was prepared using the procedure as described in Example 36B substituting Example 52A for Example 36A. $^1$H NMR (500 MHz, CDCl$_3$) δ ppm 1.65 (s, 9 H) 3.93 (s, 3 H) 4.58 (s, 2 H) 6.93 (d, J=8.85 Hz, 1 H) 7.24 (d, J=3.36 Hz, 1 H) 7.36 (dd, J=8.85, 3.05 Hz, 1 H) 7.71 (d, J=3.36 Hz, 1 H) 8.19 (s, 1 H) 8.23 (d, J=2.75 Hz, 1 H); MS (DCI/NH$_4^+$) m/z 422 (M+H)$^+$.

Example 53

N-[(5Z)-2-tert-butyl-4-(thien-2-ylmethyl)isothiazol-5(2H)-ylidene]-5-cyano-2-methoxybenzamide

Example 53A 3-(thiophen-2-yl)propan-1-ol

The title compound was prepared using the procedure as described in Example 50A substituting 3-(thiophen-2-yl)propanoic acid for 3-(furan-2-yl)propanoic acid. MS (DCI/NH$_4^+$) m/z 143 (M+H)$^+$.

Example 53B 3-(thiophen-2-yl)propanal

The title compound was prepared using the procedure as described in Example 50B substituting Example 53A for Example 50A.

Example 53C 2-methyl-N-(3-(thiophen-2-yl)propylidene)propan-2-amine

The title compound was prepared using the procedure as described in Example 1A substituting Example 53B for hexanal.

Example 53D ethyl [(5Z)-2-tert-butyl-4-(thiophen-2-ylmethyl)isothiazol-5(2H)-ylidene]carbamate The title compound was prepared using the procedure as described in Example 1D substituting Example 53C for Example 1A and o-ethyl carbonisothiocyanatidate for Example 1C.MS (DCI/NH$_4^+$) m/z 325 (M+H)$^+$.

Example 53E 2-tert-butyl-4-(thiophen-2-ylmethyl)isothiazol-5(2H)-imine

The title compound was prepared using the procedure as described in Example 50E substituting Example 53D for Example 50D. MS (DCI/NH$_4^+$) m/z 253 (M+H)$^+$.

Example 53F

N-[(5Z)-2-tert-butyl-4-(thien-2-ylmethyl)isothiazol-5(2H)-ylidene]-5-cyano-2-methoxybenzamide The title compound was prepared using the procedure as described in Example 41 substituting Example 53D for Example 110B and Example 26B for 2,5-dimethoxybenzoic acid. $^1$H NMR (500 MHz, CDCl$_3$) δ ppm 1.64 (s, 9 H) 4.00 (s, 3 H) 4.39 (s, 2 H) 6.95-6.99 (m, 2 H) 7.05 (d, J=8.85 Hz, 1 H) 7.18 (dd, J=4.58, 2.14 Hz, 1 H) 7.69 (dd, J=8.54, 2.14 Hz, 1 H) 7.95 (s, 1 H) 8.52 (d, J=2.14 Hz, 1 H); MS (DCI/NH$_4^+$) m/z 412 (M+H)$^+$.

Example 54

N-[(5Z)-2-tert-butyl-4-(thien-2-ylmethyl)isothiazol-5(2H)-ylidene]-5-chloro-2-methoxybenzamide The title compound was prepared using the procedure as described in Example 41 substituting Example 53E for Example 110B and 5-chloro-2-methoxybenzoic acid for 2,5-dimethoxybenzoic acid. $^1$H NMR (400 MHz, CDCl$_3$) δ ppm 1.62 (s, 9 H) 3.93 (s, 3 H) 4.39 (brs, 2 H) 6.90-6.98 (m, 3 H) 7.17 (dd, J=4.60, 2.15 Hz, 1 H) 7.35 (dd, J=8.90, 2.76 Hz, 1 H) 7.91 (s, 1 H) 8.18 (d, J=2.76 Hz, 1 H); MS (DCI/NH$_4^+$) m/z 421 (M+H)$^+$.

Example 55

5-amino-N-[(5Z)-4-butyl-2-tert-butylisothiazol-5(2H)-ylidene]-2-methoxybenzamide

Example 55A tert-butyl (3-{[(5Z)-4-butyl-2-tert-butylisothiazol-5(2H)-ylidene]carbamoyl}-4-methoxyphenyl)carbamate The title compound was prepared from Example 110B using the procedure as described in Example 41 substituting 5-(tert-butoxycarbonylamino)-2-methoxybenzoic acid for 2,5-dimethoxybenzoic acid. MS (DCI/NH$_4^+$) m/z 462 (M+H)$^+$.

Example 55B 5-amino-N-[(5Z)-4-butyl-2-tert-butylisothiazol-5(2H)-ylidene]-2-methoxybenzamide The product from Example 55A (71 mg, 0.15 mmol) was treated with TFA (1 mL) at rt for 10 min, solvent removed and the mixture treated with saturated aqueous NaHCO$_3$, and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 51 mg (92%) of the title compound. $^1$H NMR (500 MHz, CDCl$_3$) δ ppm 0.97 (t, J=7.32 Hz, 3 H) 1.36-1.47 (m, 2 H) 1.64 (s, 9 H) 1.67-1.77 (m, 2 H) 2.83 (dd, J=7.93 Hz, 2 H) 3.49 (brs, 2 H) 3.87 (s, 3 H) 6.76 (dd, J=8.54, 3.05 Hz, 1 H) 6.83 (d, J=8.54 Hz, 1 H) 7.54 (d, J=2.75 Hz, 1 H) 7.90 (s, 1 H); MS (DCI/NH$_4^+$) m/z 362 (M+H)$^+$.

Example 56

N-[(5Z)-4-butyl-2-tert-butylisothiazol-5(2H)-ylidene]-5-formyl-2-methoxybenzamide

Example 56A

N-[(5Z)-4-butyl-2-tert-butylisothiazol-5(2H)-ylidene]-5-formyl-2-hydroxybenzamide The title compound was prepared from Example 110B using the procedure as described in Example 41 substituting 5-formyl-2-hydroxybenzoic acid for 2,5-dimethoxybenzoic acid. MS (DCI/NH$_4^+$) m/z 361 (M+H)$^+$.

Example 56B

N-[(5Z)-4-butyl-2-tert-butylisothiazol-5(2H)-ylidene]-5-formyl-2-methoxybenzamide A mixture of Example 56A (350 mg, 0.97 mmol) and cesium carbonate (375 mg, 1.94 mmol) in DMF (20 mL) was treated with iodomethane (165 mg, 1.17 mmol). The mixture was stirred at rt for 2 hrs, diluted with H$_2$O and extracted with EtOAc (2×). The organic layer was dried over MgSO$_4$, filtered and concentrated. The residue was purified by column chromatography using an Analogix® Intelliflash280™

(SiO$_2$, 0-50% Hexane in ethyl acetate) to afford 246 mg (68%) of the title compound. $^1$H NMR (400 MHz, CDCl$_3$) δ ppm 0.99 (t, J=7.36 Hz, 3 H) 1.36-1.51 (m, 2 H) 1.67 (s, 9 H) 1.68-1.78 (m, 2 H) 2.85 (dd, J=7.67 Hz, 2 H) 4.02 (s, 3 H) 7.11 (d, J=8.59 Hz, 1 H) 7.97 (dd, J=8.59, 2.15 Hz, 1 H) 7.96 (s, 1 H) 8.64 (d, J=2.15 Hz, 1 H) 9.96 (s, 1 H); MS (DCI/NH$_4$$^+$) m/z 375 (M+H)$^+$.

Example 57

N-[(5Z)-4-butyl-2-tert-butylisothiazol-5(2H)-ylidene]-2-methoxy-5-[(E)-(methoxyimino)methyl]benzamide The title compound was prepared using the procedure as described in Example 15B substituting Example 56B for Example 15A. $^1$H NMR (500 MHz, CDCl$_3$) δ ppm 0.99 (t, J=7.63 Hz, 3 H) 1.39-1.49 (m, 2 H) 1.66 (s, 9 H) 1.68-1.79 (m, 2 H) 2.83 (dd, J=7.63 Hz, 2 H) 3.95 (s, 3 H) 3.96 (s, 3 H) 6.99 (d, J=8.85 Hz, 1 H) 7.72 (dd, J=8.54, 2.14 Hz, 1 H) 7.94 (s, 1 H) 8.07 (s, 1 H) 8.27 (d, J=2.14 Hz, 1 H); MS (DCI/NH$_4$$^+$) m/z 404 (M+H)$^+$.

Example 58

N-[(5Z)-4-butyl-2-tert-butylisothiazol-5(2H)-ylidene]-5-(formylamino)-2-methoxybenzamide The title compound was prepared using the procedure as described in Example 41 substituting Example 55B for Example 110B and formic acid for 2,5-dimethoxybenzoic acid. $^1$H NMR (400 MHz, CDCl$_3$) δ ppm 0.90-1.04 (m, 6 H) 1.34-1.47 (m, 4 H) 1.60-1.68 (m, 18 H) 1.65-1.77 (m, 4 H) 2.82 (t, J=7.98 Hz, 4 H) 3.89-3.96 (m, 6 H) 6.91-7.02 (m, 2 H) 7.09-7.16 (m, 1 H) 7.20-7.33 (m, 1 H) 7.86-8.01 (m, 4 H) 8.31-8.38 (m, 1 H) 8.52-8.60 (m, 1 H); MS (DCI/NH$_4$$^+$) m/z 390 (M+H)$^+$.

Example 59

N-[(5Z)-4-butyl-2-tert-butylisothiazol-5(2H)-ylidene]-5-[(E)-(hydroxyimino)methyl]-2-methoxybenzamide The title compound was prepared using the procedure as described in Example 15B substituting Example 56B for Example 15A and hydroxylamine hydrochloride for O-methylhydroxylamine hydrochloride. $^1$H NMR (400 MHz, CDCl$_3$) δ ppm 0.98 (t, J=7.36 Hz, 3 H) 1.38-1.48 (m, 2 H) 1.65 (s, 9 H) 1.67-1.77 (m, 2 H) 2.83 (dd, J=7.98 Hz, 2 H) 3.96 (s, 3 H) 7.00 (d, J=8.90 Hz, 1 H) 7.15 (s, 1 H) 7.69 (dd, J=8.59, 2.15 Hz, 1 H) 7.93 (s, 1 H) 8.14 (s, 1 H) 8.29 (d, J=2.15 Hz, 1 H); MS (DCI/NH$_4$$^+$) m/z 390 (M+H)$^+$.

Example 60

3-({[(5Z)-4-butyl-2-tert-butylisothiazol-5(2H)-ylidene]amino}carbonyl)-4-methoxybenzoic acid Aqueous sodium hydroxide (6M) (85 μL) was added dropwise to a stirred solution of urea hydrogen peroxide (223 mg, 2.4 mmol) and Example 56B (100 mg, 0.267 mmol) in MeOH (5 mL) at rt. The mixture was then heated at 65° C. for 2 hrs, acidified with HCl, and extracted with CH$_2$Cl$_2$/isopropanol (3:1). The organic layer was dried over MgSO$_4$, filtered and concentrated. The resulting residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford 26 mg (25%) of the title compound. $^1$H NMR (400 MHz, CDCl$_3$) δ ppm 0.98 (t, J=7.06 Hz, 3 H) 1.40-1.51 (m, 2 H) 1.63-1.75 (m, 2 H) 1.82 (s, 9 H) 2.90 (dd, J=8.29, 7.36 Hz, 2 H) 4.17 (s, 3 H) 7.16 (d, J=8.90 Hz, 1 H) 8.29 (dd, J=9.21, 2.15 Hz, 1 H) 8.69 (d, J=2.15 Hz, 3 H) 8.71 (s, 1 H); MS (DCI/NH$_4$$^+$) m/z 391 (M+H)$^+$.

Example 61

N-[(5Z)-4-butyl-2-tert-butylisothiazol-5(2H)-ylidene]-5-iodo-2-methoxybenzamide

The title compound was prepared from Example 110B using the procedure as described in Example 41 substituting 5-iodo-2-methoxybenzoic acid for 2,5-dimethoxybenzoic acid. $^1$H NMR (400 MHz, CDCl$_3$) δ ppm 0.99 (t, J=7.06 Hz, 3 H) 1.38-1.50 (m, 2 H) 1.65 (s, 9 H) 1.67-1.77 (m, 2 H) 2.83 (dd, J=7.67 Hz, 2 H) 3.90 (s, 3 H) 6.75 (d, J=8.59 Hz, 1 H) 7.65 (dd, J=8.59, 2.15 Hz, 1 H) 7.94 (s, 1 H) 8.40 (d, J=2.45 Hz, 1 H); MS (DCI/NH$_4$$^+$) m/z 473 (M+H)$^+$.

Example 62

N-[(5Z)-4-butyl-2-tert-butylisothiazol-5(2H)-ylidene]-5-ethynyl-2-methoxybenzamide Example 62A N-[(5Z)-4-butyl-2-tert-butylisothiazol-5(2H)-ylidene]-2-methoxy-5-[(trimethylsilyl)ethynyl]benzamide A mixture of the product from Example 61 (330 mg, 0.7 mmol), ethynyltrimethylsilane (206 mg, 2.1 mmol), PdCl$_2$(PPh$_3$)$_2$ (49 mg, 0.07 mmol), triethylamine (201 mg, 2.1 mmol) and CuI (33 mg, 0.18 mmol) in DMF (5 mL) was heated at 50° C. for 16 hrs, diluted with H$_2$O and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 300 mg (97%) of the title compound. MS (DCI/NH$_4$$^+$) m/z 443 (M+H)$^+$.

Example 62B

N-[(5Z)-4-butyl-2-tert-butylisothiazol-5(2H)-ylidene]-5-ethynyl-2-methoxybenzamide The product from Example 62A (300 mg, 0.68 mmol) in THF (10 mL) was treated with TBAF (1M) (1.7 mL, 1.7 mmol), stirred at rt for 1 hr, diluted with H$_2$O and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 183 mg (73%) of the title compound. $^1$H NMR (400 MHz, CDCl$_3$) δ ppm 0.98 (t, J=7.36 Hz, 3 H) 1.36-1.50 (m, 2 H) 1.65 (s, 9 H) 1.67-1.77 (m, 2 H) 2.83 (dd, J=7.98 Hz, 2 H) 2.99 (s, 1 H) 3.94 (s, 3 H) 6.93 (d, J=8.59 Hz, 1 H) 7.52 (dd, J=8.59, 2.15 Hz, 1 H) 7.93 (s, 1 H) 8.28 (d, J=2.15 Hz, 1 H); MS (DCI/NH$_4$$^+$) m/z 371 (M+H)$^+$.

Example 63

N-[(5Z)-4-butyl-2-tert-butylisothiazol-5(2H)-ylidene]-2-methoxy-5-(trifluoromethoxy)benzamide The title compound was prepared from Example 110B using the procedure as described in Example 41 substituting 2-methoxy-5-(trifluoromethoxy)benzoic acid for 2,5-dimethoxybenzoic acid. $^1$H NMR (400 MHz, CDCl$_3$) δ ppm 0.98 (t, J=7.67 Hz, 3 H) 1.37-1.48 (m, 2 H) 1.65 (s, 9 H) 1.67-1.78 (m, 2 H) 2.82 (t, J=7.67 Hz, 2 H) 3.93 (s, 3 H) 6.96 (d, J=9.21 Hz, 1 H) 7.23 (d, J=3.38 Hz, 1 H) 7.94 (s, 1 H) 8.03 (d, J=3.07 Hz, 1 H); MS (DCI/NH$_4^+$) m/z 431 (M+H)$^+$.

Example 64

5-acetyl-N-[(5Z)-4-butyl-2-tert-butylisothiazol-5 (2H)-ylidene]-2-methoxybenzamide

Example 64A 5-acetyl-N-[(5Z)-4-butyl-2-tert-butylisothiazol-5 (2H)-ylidene]-2-hydroxybenzamide The title compound was prepared from Example 110B using the procedure as described in Example 41 substituting 5-acetyl-2-hydroxybenzoic acid for 2,5-dimethoxybenzoic acid. MS (DCI/NH$_4^+$) m/z 375 (M+H)$^+$.

Example 64B 5-acetyl-N-[(5Z)-4-butyl-2-tert-butylisothiazol-5 (2H)-ylidene]-2-methoxybenzamide The title compound was prepared using the procedure as described in Example 56B substituting Example 64A for Example 56A. $^1$H NMR (500 MHz, CDCl$_3$) δ ppm 0.99 (t, J=7.32 Hz, 3 H) 1.40-1.49 (m, 2 H) 1.66 (s, 9 H) 1.70-1.80 (m, 2 H) 2.61 (s, 3 H) 2.85 (t, J=7.63 Hz, 2 H) 4.00 (s, 3 H) 7.04 (d, J=8.85 Hz, 1 H) 7.96 (s, 1 H) 8.07 (dd, J=8.54, 2.44 Hz, 1 H) 8.75 (d, J=2.44 Hz, 1 H); MS (DCI/NH$_4^+$) m/z 389 (M+H)$^+$.

Example 65

N-[(5Z)-4-butyl-2-tert-butylisothiazol-5(2H)-ylidene]-5-(difluoromethyl)-2-methoxybenzamide The product from Example 56B (140 mg, 0.37 mmol) was dissolved in CH$_2$Cl$_2$ (4 mL), treated with DAST (121 mg, 0.75 mmol) and a drop of MeOH to catalyze the reaction. The mixture was stirred at rt for 12 hrs, quenched with saturated aqueous NaHCO$_3$ and extracted with CH$_2$Cl$_2$ (2×). The combined organic layers were dried over MgSO$_4$, filtered and concentrated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford the title compound. $^1$H NMR (500 MHz, CDCl$_3$) δ ppm 0.98 (t, J=7.63 Hz, 3 H) 1.44 (m, 2 H) 1.66 (s, 9 H) 1.73 (m, 2 H) 2.84 (t, J=7.63 Hz, 2 H) 3.96 (s, 3 H) 6.66 (t, J=56.76 Hz, 1 H) 7.05 (d, J=8.54 Hz, 1 H) 7.57 (d, J=9.76 Hz, 1 H) 7.96 (s, 1 H) 8.29 (s, 1 H); MS (DCI/NH$_4^+$) m/z 397 (M+H)$^+$.

Example 66

N-[(5Z)-4-butyl-2-tert-butylisothiazol-5(2H)-ylidene]-5-(fluoromethyl)-2-methoxybenzamide

Example 66A

N-[(5Z)-4-butyl-2-tert-butylisothiazol-5(2H)-ylidene]-5-(hydroxymethyl)-2-methoxybenzamide The title compound was prepared using the procedure as described in Example 28A substituting Example 56B for Example 21A. MS (DCI/NH$_4^+$) m/z 377 (M+H)$^+$.

Example 66B

N-[(5Z)-4-butyl-2-tert-butylisothiazol-5(2H)-ylidene]-5-(fluoromethyl)-2-methoxybenzamide The product from Example 66A (120 mg, 0.32 mmol) in CH$_2$Cl$_2$ (10 mL) at −78° C. was treated with bis(methoxyethyl)amino sulfurtrifluoride (106 mg, 0.48 mmol). The reaction was kept at −78° C. for 1 hr, quenched with saturated aqueous NaHCO$_3$ and extracted with CH$_2$Cl$_2$ (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 56 mg (46%) of the title compound. $^1$H NMR (500 MHz, CDCl$_3$) δ ppm 0.99 (t, J=7.32 Hz, 3 H) 1.38-1.48 (m, 2 H) 1.65 (s, 9 H) 1.68-1.76 (m, 2 H) 2.84 (dd, J=7.93 Hz, 2 H) 3.95 (s, 3 H) 5.31 (s, 1 H) 5.41 (s, 1 H) 7.01 (d, J=8.54 Hz, 1 H) 7.45 (dt, J=8.54, 2.14 Hz, 1 H) 7.93 (s, 1 H) 8.18 (t, J=2.14 Hz, 1 H); MS (DCI/NH$_4^+$) m/z 379 (M+H)$^+$.

Example 67

N-[(5Z)-2-tert-butyl-4-(tetrahydrofuran-2-ylmethyl) isothiazol-5(2H)-ylidene]-5-chloro-2-methoxybenzamide

Example 67A 3-(tetrahydrofuran-2-yl)propanoic acid (E)-3-(Furan-2-yl)acrylic acid (10 g, 72.4 mmol) was treated with Pd/C (1 g) in MeOH (100 mL). The mixture was heated at 60° C. at 60 psi under H$_2$ for 12 hrs. After filtering off the catalyst, the filtrate was concentrated to afford 9.8 g (93%) of the title compound. $^1$H NMR (500 MHz, CDCl$_3$) δ ppm 1.42-1.56 (m, 1 H) 1.77-1.96 (m, 4 H) 1.93-2.07 (m, 1 H) 2.41-2.56 (m, 2 H) 3.71-3.79 (m, 1 H) 3.82-3.94 (m, 2 H); MS (DCI/NH$_4^+$) m/z 145 (M+H)$^+$.

Example 67B 3-(tetrahydrofuran-2-yl)propan-1-ol

The title compound was prepared using the procedure as described in Example 50A substituting Example 67A for 3-(furan-2-yl)propanoic acid. $^1$H NMR (500 MHz, CDCl$_3$) δ ppm 1.41-1.52 (m, 1 H) 1.64-1.73 (m, 4 H) 1.83-1.93 (m, 2 H)

1.95-2.03 (m, 1 H) 3.37-3.44 (m, 1 H) 3.61-3.71 (m, 2 H) 3.71-3.78 (m, 1 H) 3.80-3.86 (m, 1 H) 3.85-3.94 (m, 1 H).

Example 67C 3-(tetrahydrofuran-2-yl)propanal

The title compound was prepared using the procedure as described in Example 50B substituting Example 67B for Example 50A.

Example 67D 2-methyl-N-(3-(tetrahydrofuran-2-yl)propylidene)propan-2-amine

The title compound was prepared using the procedure as described in Example 1A substituting Example 67C for hexanal.

Example 67E

N-[(5Z)-2-tert-butyl-4-(tetrahydrofuran-2-ylmethyl)isothiazol-5(2H)-ylidene]-5-chloro-2-methoxybenzamide The title compound was prepared using the procedure as described in Example 1D substituting Example 67D for Example 1A. $^1$H NMR (400 MHz, CDCl$_3$) δ ppm 1.46-1.59 (m, 1 H) 1.81 (s, 9 H) 1.79-1.88 (m, 1 H) 1.88-2.02 (m, 1 H) 2.06-2.23 (m, 1 H) 2.98-3.15 (m, 1 H) 3.26-3.47 (m, 1 H) 3.68-3.85 (m, 2 H) 4.10 (s, 3 H) 4.13-4.20 (m, 1 H) 7.08 (d, J=8.90 Hz, 1 H) 7.62 (dd, J=8.90, 2.45 Hz, 1 H) 8.15 (d, J=2.76 Hz, 1 H) 9.17-9.29 (m, 1 H); MS (DCI/NH$_4^+$) m/z 409 (M+H)$^+$.

Example 68

N-[(5Z)-4-butyl-2-tert-butylisothiazol-5(2H)-ylidene]-5-[(1Z)—N-hydroxyethanimidoyl]-2-methoxybenzamide The title compound was prepared using the procedure as described in Example 15B substituting Example 64B for Example 15A and hydroxylamine hydrochloride for O-methylhydroxylamine hydrochloride. $^1$H NMR (400 MHz, CDCl$_3$) δ ppm 0.98 (t, J=7.36 Hz, 3 H) 1.37-1.50 (m, 2 H) 1.65 (s, 9 H) 1.68-1.80 (m, 2 H) 2.29 (s, 3 H) 2.84 (dd, J=7.67 Hz, 2 H) 3.95 (s, 3 H) 6.98 (d, J=8.59 Hz, 1 H) 7.75 (dd, J=8.90, 2.45 Hz, 1 H) 7.93 (s, 1 H) 8.39 (d, J=2.45 Hz, 1 H); MS (DCI/NH$_4^+$) m/z 404 (M+H)$^+$.

Example 69

N-[(5Z)-4-butyl-2-tert-butylisothiazol-5(2H)-ylidene]-5-(1,1-difluoroethyl)-2-methoxybenzamide The product from Example 64B (50 mg, 0.13 mmol) was treated with bis(methoxyethyl)amino sulfurtrifluoride (57 mg, 0.26 mmol). The reaction was heated at 85° C. for 16 hrs, quenched with saturated aqueous NaHCO$_3$ and extracted with CH$_2$Cl$_2$ (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 12.1 mg (23%) of the title compound. $^1$H NMR (400 MHz, CDCl$_3$) δ ppm 0.98 (t, J=7.06 Hz, 3 H) 1.39-1.51 (m, 2 H) 1.65-1.75 (m, 2 H) 1.80 (s, 9 H) 1.95 (t, J=18.10 Hz, 3 H) 2.92 (dd, J=7.98 Hz, 2 H) 4.14 (s, 3 H) 7.17 (d, J=8.90 Hz, 1 H) 7.80 (dd, J=8.90, 2.45 Hz, 1 H) 8.22 (d, J=2.45 Hz, 1 H) 8.79-8.83 (m, 1 H); MS (DCI/NH$_4^+$) m/z 389 (M+H)$^+$.

Example 70

N-[(5Z)-2-tert-butyl-4-(2-furylmethyl)isothiazol-5(2H)-ylidene]-2-fluoro-3-(trifluoromethyl)benzamide The title compound was prepared using the procedure as described in Example 41 substituting Example 50E for Example 110B and 2-fluoro-3-(trifluoromethyl)benzoic acid for 2,5-dimethoxybenzoic acid. $^1$H NMR (400 MHz, CDCl$_3$) δ ppm 1.65 (s, 9 H) 4.22 (s, 2 H) 6.17 (d, J=3.38 Hz, 1 H) 6.31-6.35 (m, 1 H) 7.25 (s, 1 H) 7.30 (t, J=7.67 Hz, 1 H) 7.69 (td, J=6.14, 1.23 Hz, 1 H) 8.00 (s, 1 H) 8.44 (td, J=7.98, 1.53 Hz, 1 H); MS (DCI/NH$_4^+$) m/z 427 (M+H)$^+$.

Example 71

N-[(5Z)-2-tert-butyl-4-(2-furylmethyl)isothiazol-5(2H)-ylidene]-2-methoxy-5-(trifluoromethyl)benzamide The title compound was prepared using the procedure as described in Example 41 substituting Example 50E for Example 110B and 2-methoxy-5-(trifluoromethyl)benzoic acid for 2,5-dimethoxybenzoic acid. $^1$H NMR (400 MHz, CDCl$_3$) δ ppm 1.64 (s, 9 H) 3.98 (s, 3 H) 4.21 (s, 2 H) 6.18 (dd, J=3.07, 0.92 Hz, 1 H) 6.34 (dd, J=3.07, 1.84 Hz, 1 H) 7.06 (d, J=8.59 Hz, 1 H) 7.35-7.37 (m, 1 H) 7.65 (dd, J=8.90, 2.46 Hz, 1 H) 7.96 (s, 1 H) 8.43 (d, J=2.15 Hz, 1 H); MS (DCI/NH$_4^+$) m/z 439 (M+H)$^+$.

Example 72

N-[(5Z)-2-tert-butyl-4-(isopropoxymethyl)isothiazol-5(2H)-ylidene]-5-chloro-2-methoxybenzamide The product from Example 28A (50 mg, 0.14 mmol) in dioxane (5 mL) was treated with NaH (60%) (7 mg, 0.17 mmol) stirred at rt for 10 min and treated with isopropyl methanesulfonate (78 mg, 0.56 mmol). The reaction was heated at 85° C. for 12 hrs, quenched with H$_2$O, the mixture was extracted with EtOAc (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 5.2 mg (9%) of the title compound. $^1$H NMR (400 MHz, CDCl$_3$) δ ppm 1.22 (d, J=6.14 Hz, 6 H) 1.81 (s, 9 H) 3.75-3.83 (m, 1 H) 4.12 (s, 3 H) 4.92 (s, 2 H) 7.10 (d, J=9.21 Hz, 1 H) 7.63 (dd, J=9.21, 2.76 Hz, 1 H) 8.18 (d, J=2.45 Hz, 1 H) 9.28 (s, 1 H); MS (DCI/NH$_4^+$) m/z 397 (M+H)$^+$.

Example 73

N-[(5Z)-4-butyl-2-tert-butylisothiazol-5(2H)-ylidene]-2-fluoro-3-(trifluoromethyl)benzamide The title compound was prepared using the procedure as described in Example 41 substituting 2-fluoro-3-(trifluoromethyl)benzoic acid for 2,5-dimethoxybenzoic acid. $^1$H NMR (500 MHz, CDCl$_3$) δ ppm 0.98 (t, J=7.32 Hz, 3 H) 1.38-1.47 (m, 2 H) 1.67 (s, 9 H) 1.68-1.76 (m, 2 H) 2.84 (dd, J=7.63 Hz, 2 H) 7.30 (t, J=7.63 Hz, 1 H) 7.69 (td, J=7.63, 1.53 Hz, 1 H) 7.99 (s, 1 H) 8.43 (td, J=8.24, 1.53 Hz, 1 H); MS (DCI/NH$_4^+$) m/z 403 (M+H)$^+$.

Example 74 methyl 3-({[(5Z)-4-butyl-2-tert-butylisothiazol-5 (2H)-ylidene]amino}carbonyl)-4-methoxybenzoate The product from Example 61 (199 mg, 0.42 mmol) in MeOH (5 mL) was added to PdCl$_2$(dppf)CH$_2$Cl$_2$ (Heraeus) (15.4 mg, 0.02 mmol) and Et$_3$N (117 µL, 0.84 mmol) in a 20 mL pressure bottle. The mixture was pressurized with CO (60 psi), and stirred 16 hr at 100° C. The solvent was removed and the resulting residue was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minute to afford 15 mg (9%) of the title compound. $^1$H NMR (500 MHz, CDCl$_3$) δ ppm 1.00 (t, J=7.32 Hz, 3 H) 1.40-1.49 (m, 2 H) 1.66 (s, 9 H) 1.70-1.79 (m, 2 H) 2.85 (t, J=7.63 Hz, 2 H) 3.89 (s, 3 H) 3.99 (s, 3 H) 7.01 (d, J=8.85 Hz, 1 H) 7.95 (s, 1 H) 8.09 (dd, J=8.54, 2.14 Hz, 1 H) 8.80 (d, J=2.14 Hz, 1 H); MS (DCI/NH$_4^+$) m/z 405 (M+H)$^+$.

Example 75

N-[(5Z)-2-tert-butyl-4-(4-oxopentyl)isothiazol-5 (2H)-ylidene]-5-chloro-2-methoxybenzamide

Example 75A 6-oxoheptanal

The title compound was prepared using the procedure as described in Example 21A substituting 1-methylcyclohex-1-ene for Example 6B.

Example 75B 7-(tert-butylimino)heptan-2-one

The title compound was prepared using the procedure as described in Example 1A substituting Example 75A for hexanal.

Example 75C ethyl [(5Z)-2-tert-butyl-4-(4-oxopentyl)isothiazol-5 (2H)-ylidene]carbamate The title compound was prepared using the procedure as described in Example 1D substituting Example 75B for Example 1A and o-ethyl carbonisothiocyanatidate for Example 1C. MS (DCI/NH$_4^+$) m/z 313 (M+H)$^+$.

Example 75D 5-(2-tert-butyl-5-imino-2,5-dihydroisothiazol-4-yl) pentan-2-one The title compound was prepared using the procedure as described in Example 110B substituting Example 75C for Example 110A. MS (DCI/NH$_4^+$) m/z 241 (M+H)$^+$.

Example 75E

N-[(5Z)-2-tert-butyl-4-(4-oxopentyl)isothiazol-5 (2H)-ylidene]-5-chloro-2-methoxybenzamide The title compound was prepared using the procedure as described in Example 41 substituting Example 75D for Example 110B. $^1$H NMR (400 MHz, CDCl$_3$) δ ppm 1.65 (s, 9 H) 1.98-2.07 (m, 2 H) 2.14 (s, 3 H) 2.56 (t, J=7.06 Hz, 2 H) 2.83 (t, J=7.98, 7.36 Hz, 2 H) 3.91 (s, 3 H) 6.92 (d, J=8.90 Hz, 1 H) 7.34 (dd, J=8.90, 2.76 Hz, 1 H) 7.97 (s, 1 H) 8.11 (d, J=2.76 Hz, 1 H); MS (DCI/NH$_4^+$) m/z 409 (M+H)$^+$.

Example 76

N-[(5Z)-2-tert-butyl-4-(4-oxopentyl)isothiazol-5 (2H)-ylidene]-2-methoxy-5-(trifluoromethyl)benzamide The title compound was prepared using the procedure as described in Example 41 substituting Example 75D for Example 110B and 2-methoxy-5-(trifluoromethyl)benzoic acid for 5-chloro-2-methoxybenzoic acid. $^1$H NMR (400 MHz, CDCl$_3$) δ ppm 1.67 (s, 9 H) 1.99-2.08 (m, 2 H) 2.14 (s, 3 H) 2.56 (t, J=7.36 Hz, 2 H) 2.84 (t, J=7.67 Hz, 2 H) 3.98 (s, 3 H) 7.06 (d, J=8.90 Hz, 1 H) 7.65 (dd, J=8.90, 2.45 Hz, 1 H) 7.99 (s, 1 H) 8.40 (d, J=2.45 Hz, 1 H) MS (DCI/NH$_4^+$) m/z 443 (M+H)$^+$.

Example 77

N-[(5Z)-2-tert-butyl-4-(4-oxopentyl)isothiazol-5 (2H)-ylidene]-2-fluoro-3-(trifluoromethyl)benzamide The title compound was prepared using the procedure as described in Example 41 substituting Example 75D for Example 110B and 2-fluoro-3-(trifluoromethyl)benzoic acid for 5-chloro-2-methoxybenzoic acid. $^1$H NMR (400 MHz, CDCl$_3$) δ ppm 1.67 (s, 9 H) 1.99-2.08 (m, 2 H) 2.13 (s, 3 H) 2.56 (t, J=7.06 Hz, 2 H) 2.85 (t, J=7.36 Hz, 2 H) 7.30 (t, J=7.67 Hz, 1 H) 7.69 (td, J=7.67, 1.84, 1.23 Hz, 1 H) 8.02 (s, 1 H) 8.40 (td, J=7.67, 1.53 Hz, 1 H); MS (DCI/NH$_4^+$) m/z 431 (M+H)$^+$.

Example 78

N$^3$-[(5Z)-4-butyl-2-tert-butylisothiazol-5(2H)-ylidene]-4-methoxyisophthalamide The product from Example 26E (110 mg, 0.3 mmol) was treated with concentrated sulfuric acid (1 mL). The mixture was heated at 40° C. for 1 hr, diluted with H$_2$O, neutralized with saturated Na$_2$CO$_3$, and extracted with EtOAc (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 107 mg (93%) of the title compound. $^1$H NMR (500 MHz, CDCl$_3$) δ ppm 0.99 (t, J=7.32 Hz, 3 H) 1.40-1.48 (m, 2 H) 1.66 (s, 9 H) 1.69-1.76 (m, 2 H) 2.84 (dd, J=7.63 Hz, 2 H) 3.99 (s, 3 H) 7.06 (d, J=8.54 Hz, 1 H) 7.96 (s, 1 H) 8.02 (dd, J=8.85, 2.44 Hz, 1 H) 8.51 (d, J=2.44 Hz, 1 H); MS (DCI/NH$_4^+$) m/z 390 (M+H)$^+$.

Example 79

N-[(5Z)-2-tert-butyl-4-(4-hydroxy-4-methylpentyl) isothiazol-5(2H)-ylidene]-2-fluoro-3-(trifluoromethyl)benzamide To the suspension of cerium(III) chloride (86 mg, 0.35 mmol) in THF (3 mL) was added the product from Example 77 (100 mg, 0.23 mmol) in THF (0.5 mL). The mixture was stirred at rt for 1 hr. The above mixture was cooled to −40° C. and methylmagnesium bromide (41.6 mg, 0.348 mmol) was added dropwise. The reaction was stirred for 40 min at −40° C., quenched with saturated aqueous $NH_4Cl$ and extracted with $CH_2Cl_2$ (2×). The combined organic layers were dried over $MgSO_4$, filtered and concentrated. The residue was purified by column chromatography using an Analogix® Intelliflash280™ ($SiO_2$, 0-50% Hexane in ethyl acetate) to afford 57 mg (55%) of the title compound. $^1H$ NMR (500 MHz, $CDCl_3$) δ ppm 1.23 (s, 6 H) 1.57-1.61 (m, 2 H) 1.68 (s, 9 H) 1.74 (s, 1 H) 1.81-1.89 (m, 2 H) 2.88 (t, J=7.63 Hz, 2 H) 7.30 (t, J=7.93 Hz, 1 H) 7.69 (t, J=6.41 Hz, 1 H) 8.01-8.04 (m, 1 H) 8.39 (td, J=7.93, 1.53 Hz, 1 H); MS ($DCI/NH_4^+$) m/z 447 $(M+H)^+$.

Example 80

N-[(5Z)-2-tert-butyl-4-(4-hydroxy-4-methylpentyl) isothiazol-5(2H)-ylidene]-5-chloro-2-methoxybenzamide The title compound was prepared using the procedure as described in Example 79 substituting Example 75E for Example 77. $^1H$ NMR (400 MHz, $CDCl_3$) δ ppm 1.24 (s, 6 H) 1.55-1.62 (m, 2 H) 1.65 (s, 9 H) 1.79-1.90 (m, 2 H) 2.87 (t, J=7.67 Hz, 2 H) 3.91 (s, 3 H) 6.91 (d, J=8.90 Hz, 1 H) 7.33 (dd, J=8.90, 2.76 Hz, 1 H) 7.97 (s, 1 H) 8.09 (d, J=2.76 Hz, 1 H); MS ($DCI/NH_4^+$) m/z 425 $(M+H)^+$.

Example 81

N-[(5Z)-2-tert-butyl-4-(4-hydroxy-4-methylpentyl) isothiazol-5(2H)-ylidene]-2-methoxy-5-(trifluoromethyl)benzamide The title compound was prepared using the procedure as described in Example 79 substituting Example 76 for Example 77. $^1H$ NMR (500 MHz, $CDCl_3$) δ ppm 1.23 (s, 6 H) 1.56-1.71 (m, 2 H) 1.67 (s, 9 H) 1.80-1.90 (m, 2 H) 2.87 (t, J=7.63 Hz, 2 H) 3.97 (s, 3 H) 7.05 (d, J=8.85 Hz, 1 H) 7.64 (dd, J=8.54, 2.14 Hz, 1 H) 7.99 (s, 1 H) 8.37 (d, J=2.44 Hz, 1 H); MS ($DCI/NH_4^+$) m/z 459 $(M+H)^+$.

Example 82

N-[(5Z)-4-butyl-2-tert-butylisothiazol-5(2H)-ylidene]-5-isopropyl-2-methoxybenzamide

Example 82A 5-isopropyl-2-methoxybenzoic acid

5-Isopropyl-2-methoxybenzaldehyde (2.8 g, 15.7 mmol) was dissolved in acetone (40 mL). To this solution was added sulfamic acid (2.29 g, 23.57 mmol) and sodium chlorite (1.71 g, 18.85 mmol) in water (40 mL). The mixture was stirred at rt in an open flask for 12 hrs. The acetone was removed and the mixture was extracted with $Et_2O$. The organic layer was dried over $MgSO_4$, filtered and concentrated to afford the title compound. MS ($DCI/NH_4^+$) m/z 212 $(M+NH4)^+$.

Example 82B

N-[(5Z)-4-butyl-2-tert-butylisothiazol-5(2H)-ylidene]-5-isopropyl-2-methoxybenzamide The title compound was prepared using the procedure as described in Example 41 substituting Example 82A for 2,5-dimethoxybenzoic acid. $^1H$ NMR (300 MHz, $CDCl_3$) δ ppm 0.98 (t, J=7.14 Hz, 3 H) 1.26 (d, J=7.14 Hz, 6 H) 1.37-1.50 (m, 2 H) 1.65 (s, 9 H) 1.68-1.80 (m, 2 H) 2.84 (dd, J=7.54 Hz, 2 H) 2.86-2.98 (m, 1 H) 3.91 (s, 3 H) 6.91 (d, J=8.72 Hz, 1 H) 7.25 (dd, J=9.91, 2.78 Hz, 1 H) 7.92 (s, 1 H) 7.99 (d, J=2.78 Hz, 1 H); MS ($DCI/NH_4^+$) m/z 389 $(M+H)^+$.

Example 83

N-[(5Z)-2-tert-butyl-4-(4-fluoro-4-methylpentyl) isothiazol-5(2H)-ylidene]-5-chloro-2-methoxybenzamide The product from Example 80 (50 mg, 0.12 mmol) in $CH_2Cl_2$ (4 mL) was treated with DAST (38 mg, 0.24 mmol) at −78° C. The mixture was stirred at −78° C. for 1.5 hrs, quenched with saturated aqueous $NaHCO_3$ and extracted with $CH_2Cl_2$ (2×). The combined organic layers were dried over $MgSO_4$, filtered and concentrated. The residue was purified by column chromatography using an Analogix® Intelliflash280™ ($SiO_2$, 0-50% Hexane in ethyl acetate) to afford 29 mg (58%) of the title compound. $^1H$ NMR (400 MHz, $CDCl_3$) δ ppm 1.38 (d, J=21.48 Hz, 6 H) 1.65 (s, 9 H) 1.68-1.80 (m, 2 H) 1.81-1.93 (m, 2 H) 2.84 (t, J=7.67 Hz, 2 H) 3.91 (s, 3 H) 6.91 (d, J=8.90 Hz, 1 H) 7.33 (dd, J=8.59, 2.76 Hz, 1 H) 7.97 (s, 1 H) 8.11 (d, J=2.76 Hz, 1 H); MS ($DCI/NH_4^+$) m/z 427 $(M+H)^+$.

Example 84

N-[(5Z)-2-tert-butyl-4-(3-oxobutyl)isothiazol-5(2H)-ylidene]-5-chloro-2-methoxybenzamide

Example 84A 5-oxohexanal

The title compound was prepared using the procedure as described in Example 21A substituting 1-methylcyclopent-1-ene for Example 6B.

Example 84B 6-(tert-butylimino)hexan-2-one

The title compound was prepared using the procedure as described in Example 1A substituting Example 84A for hexanal.

Example 84C ethyl [(5Z)-2-tert-butyl-4-(3-oxobutyl)isothiazol-5 (2H)-ylidene]carbamate The title compound was prepared using the procedure as described in Example 1D substituting Example 84B for Example 1A and o-ethyl carbonisothiocyanatidate for Example 1C. ¹H NMR (300 MHz, CDCl₃) δ ppm 1.37 (t, J=7.14 Hz, 3 H) 1.60 (s, 9 H) 2.09 (s, 3 H) 2.88 (t, J=4.36, 3.17 Hz, 4 H) 4.29 (q, J=7.14 Hz, 2 H) 7.94 (s, 1 H); MS (DCI/NH₄⁺) m/z 299 (M+H)⁺.

Example 84D 4-(2-tert-butyl-5-imino-2,5-dihydroisothiazol-4-yl)butan-2-one

The title compound was prepared using the procedure as described in Example 110B substituting Example 84C for Example 110A. MS (DCI/NH₄⁺) m/z 227 (M+H)⁺.

Example 84E

N-[(5Z)-2-tert-butyl-4-(3-oxobutyl)isothiazol-5(2H)-ylidene]-5-chloro-2-methoxybenzamide The title compound was prepared using the procedure as described in Example 41 substituting Example 84D for Example 110B. ¹H NMR (400 MHz, CDCl₃) δ ppm 1.64 (s, 9 H) 2.14 (s, 3 H) 2.95-3.08 (m, 4 H) 3.92 (s, 3 H) 6.92 (d, J=8.90 Hz, 1 H) 7.35 (dd, J=8.59, 2.76 Hz, 1 H) 8.07 (s, 1 H) 8.09 (d, J=2.76 Hz, 1 H); MS (DCI/NH₄⁺) m/z 395 (M+H)⁺.

Example 85

N-[(5Z)-2-tert-butyl-4-[(2,2,2-trifluoroethoxy)methyl]isothiazol-5(2H)-ylidene]-5-chloro-2-methoxybenzamide

Example 85A

[(5Z)-2-tert-butyl-5-{[(5-chloro-2-methoxyphenyl)carbonyl]imino}-2,5-dihydroisothiazol-4-yl]methyl methanesulfonate The product from Example 28A (300 mg, 0.85 mmol) in CH₂Cl₂ (10 mL) containing triethylamine (257 mg, 2.54 mmol) was treated with methanesulfonyl chloride (145 mg, 1.27 mmol) at 0° C. The mixture was stirred for 30 min at 0° C., diluted with water and extracted with CH₂Cl₂ (2×). The combined organic layers were dried over MgSO₄, filtered and concentrated to afford the title compound.

Example 85B

N-[(5Z)-2-tert-butyl-4-[(2,2,2-trifluoroethoxy)methyl]isothiazol-5(2H)-ylidene]-5-chloro-2-methoxybenzamide 2,2,2-Trifluoroethanol (48 mg, 0.48 mmol) in DMF (2 mL) and THF (2.0 mL) was treated for sodium hydride (23 mg, 0.58 mmol). The reaction was stirred at rt for 10 min, treated with Example 85A (80 mg, 0.19 mmol) in THF (0.5 mL), heated at 85° C. for 1.5 hrs, diluted with H₂O and extracted with EtOAc (2×). The combined organic layers were dried over MgSO₄, filtered and concentrated. The residue was purified by column chromatography using an Analogix® Intelliflash280™ (SiO₂, 0-50% Hexane in ethyl acetate) to afford 24 mg (29%) of the title compound. ¹H NMR (500 MHz, CDCl₃) δ ppm 1.68 (s, 9 H) 3.93 (s, 3 H) 4.05 (q, J=8.85 Hz, 2 H) 4.94 (s, 2 H) 6.93 (d, J=8.85 Hz, 1 H) 7.37 (dd, J=8.85, 2.75 Hz, 1 H) 8.12 (d, J=2.75 Hz, 1 H) 8.19 (s, 1 H); MS (DCI/NH₄⁺) m/z 437 (M+H)⁺.

Example 86

N-[(5Z)-2-tert-butyl-4-(4,4-difluoropentyl)isothiazol-5(2H)-ylidene]-5-chloro-2-methoxybenzamide The title compound was prepared using the procedure as described in Example 69 substituting Example 75E for Example 64B. ¹H NMR (400 MHz, CDCl₃) δ ppm 1.63 (t, J=18.41 Hz, 3 H) 1.65 (s, 9 H) 1.91-2.01 (m, 4 H) 2.87 (t, J=7.36 Hz, 2 H) 3.92 (s, 3 H) 6.92 (d, J=8.90 Hz, 1 H) 7.34 (dd, J=8.90, 2.76 Hz, 1 H) 7.96 (s, 1 H) 8.10 (d, J=2.76 Hz, 1 H); MS (DCI/NH₄⁺) m/z 431 (M+H)⁺.

Example 87

N-[(5Z)-2-tert-butyl-4-(3-fluoro-3-methylbutyl)isothiazol-5(2H)-ylidene]-5-chloro-2-methoxybenzamide

Example 87A

N-[(5Z)-2-tert-butyl-4-(3-hydroxy-3-methylbutyl)isothiazol-5(2H)-ylidene]-5-chloro-2-methoxybenzamide The title compound was prepared using the procedure as described in Example 79 substituting Example 84E for Example 75E. MS (DCI/NH₄⁺) m/z 411 (M+H)⁺.

Example 87B

N-[(5Z)-2-tert-butyl-4-(3-fluoro-3-methylbutyl)isothiazol-5(2H)-ylidene]-5-chloro-2-methoxybenzamide The title compound was prepared using the procedure as described in Example 83 substituting Example 87A for Example 80. ¹H NMR (400 MHz, CDCl₃) δ ppm 1.47 (d, J=21.48 Hz, 6 H) 1.65 (s, 9 H) 2.02-2.14 (m, 2 H) 2.90-2.97 (m, 2 H) 3.92 (s, 3 H) 6.92 (d, J=8.90 Hz, 1 H) 7.34 (dd, J=8.90, 2.76 Hz, 1 H) 7.98 (s, 1 H) 8.16 (d, J=2.76 Hz, 1 H); MS (DCI/NH₄⁺) m/z 413 (M+H)⁺.

Example 88

N-[(5Z)-2-tert-butyl-4-(4-fluoro-4-methylpentyl)isothiazol-5(2H)-ylidene]-2-methoxy-5-(trifluoromethyl)benzamide The title compound was prepared using the procedure as described in Example 83 substituting Example 81 for Example 80. ¹H NMR (400 MHz, CDCl₃) δ ppm 1.37 (d, J=21.48 Hz, 6 H) 1.66 (s, 9 H) 1.67-1.78 (m, 2 H) 1.83-1.94 (m, 2 H) 2.84 (t, J=7.98, 7.36 Hz, 2 H) 3.97 (s, 3 H) 7.05 (d, J=8.29 Hz, 1 H) 7.64 (dd, J=7.98, 2.45 Hz, 1 H) 7.96-7.99 (m, 1 H) 8.40 (d, J=2.45 Hz, 1 H); MS (DCI/NH₄⁺) m/z 461 (M+H)⁺.

Example 89

N-[(5Z)-2-tert-butyl-4-{[(2R)-tetrahydrofuran-2-ylmethoxy]methyl}isothiazol-5(2H)-ylidene]-5-chloro-2-methoxybenzamide The title compounds was obtained from Example 85A using the procedure as described in Example 85B substituting (R)-(tetrahydrofuran-2-yl)methanol for 2,2,2-trifluoroethanol. $^1$H NMR (400 MHz, CDCl$_3$) δ ppm 1.59-1.69 (m, 1 H) 1.66 (s, 9 H) 1.86-2.04 (m, 3 H) 3.58-3.70 (m, 2 H) 3.76-3.84 (m, 1 H) 3.86-3.94 (m, 1 H) 3.92 (s, 3 H) 4.10-4.19 (m, 1 H) 4.84 (s, 2 H) 6.92 (d, J=8.90 Hz, 1 H) 7.34 (dd, J=8.90, 2.76 Hz, 1 H) 8.13 (d, J=2.76 Hz, 1 H) 8.24 (s, 1 H); MS (DCI/NH$_4^+$) m/z 439 (M+H)$^+$.

Example 90

N-[(5Z)-2-tert-butyl-4-[(2-fluoroethoxy)methyl]isothiazol-5(2H)-ylidene]-5-chloro-2-methoxybenzamide The title compounds was obtained from Example 85A using the procedure as described in Example 85B substituting 2-fluoroethanol for 2,2,2-trifluoroethanol. $^1$H NMR (400 MHz, CDCl$_3$) δ ppm 1.67 (s, 9 H) 3.82-3.95 (m, 2 H) 3.92 (s, 3 H) 4.62 (dt, J=47.56, 3.99 Hz, 2 H) 4.86 (s, 2 H) 6.92 (d, J=8.90 Hz, 1 H) 7.35 (dd, J=8.29, 2.76 Hz, 1 H) 8.13 (d, J=2.76 Hz, 1 H) 8.21 (s, 1 H); MS (DCI/NH$_4^+$) m/z 401 (M+H)$^+$.

Example 91

N-[(5Z)-2-tert-butyl-4-[(2,2-difluoroethoxy)methyl]isothiazol-5(2H)-ylidene]-5-chloro-2-methoxybenzamide The title compounds was obtained from Example 85A using the procedure as described in Example 85B substituting 2,2-difluoroethanol for 2,2,2-trifluoroethanol. $^1$H NMR (400 MHz, CDCl$_3$) δ ppm 3.86 (td, J=14.12, 3.99 Hz, 2 H) 3.92 (s, 3 H) 4.88 (s, 2 H) 5.95 (tt, J=55.24, 4.30 Hz, 1 H) 6.93 (d, J=8.90 Hz, 1 H) 7.36 (dd, J=8.90, 2.76 Hz, 1 H) 8.12 (d, J=2.76 Hz, 1 H) 8.18 (s, 1 H); MS (DCI/NH$_4^+$) m/z 419 (M+H)$^+$.

Example 92 methyl 3-({[(5Z)-4-butyl-2-tert-butylisothiazol-5(2H)-ylidene]amino}carbonyl)-2,2,3-trimethylcyclopentanecarboxylate

Example 92A ethyl [(5Z)-4-butyl-2-tert-butylisothiazol-5(2H)-ylidene]carbamate To a solution of hexanal (Aldrich, 20.0 g, 200 mmol) in acetonitrile (20 mL) in a 100-mL, round-bottomed flask containing molecular sieves (10 g) was added neat t-butylamine (Aldrich, 16.1 g, 220 mmol). The mixture was stirred at room temperature overnight. The solids were removed by vacuum filtration through a glass frit and the liquor was concentrated by rotary evaporator to give the crude imine as a pale yellow oil. The crude imine was dissolved in anhydrous tetrahydrofuran (200 mL) containing pyridine (Aldrich, 15.8 g, 200 mmol) and O-ethyl carbonisothiocyanatidate (Aldrich, 15.7 g, 120 mmol) was added dropwise. The resulting yellow mixture was stirred at room temperature for 1 hour. Anhydrous methanol (100 mL) and iodine (Aldrich, 30.5 g, 120 mmol) were added to form a brown slurry. The mixture was stirred at room temperature for 2 hours. The excess iodine was quenched by addition of solid sodium metabisulfite until the mixture changed to yellow. Saturated aqueous sodium bicarbonate solution was added and the mixture was stirred at room temperature for 15 minutes. The mixture was extracted with dichloromethane (3×75 mL). The combined organic extracts were dried (MgSO$_4$), filtered, and concentrated by rotary evaporator to give a brown oil. The product was purified by flash chromatography (silica gel: 25-95% ethyl acetate in hexanes) to afford 31.6 g (56%) of the title compound. $^1$H NMR (DMSO-d$_6$) δ 0.90 (t, J=7.3 Hz, 3H), 1.22 (t, J=7.1 Hz, 3H), 1.23-1.36 (m, 2H), 1.50-1.60 (m, 2H), 1.55 (s, 9H), 2.51 (t, J=7.5 Hz, 2H), 4.10 (q, J=7.1 Hz, 2H), 8.45 (s, 1H); MS (ESI+) m/z 285 (M+H)$^+$.

Example 92B 2-tert-butyl-4-butylisothiazol-5(2H)-imine

To a 250-mL, round-bottomed flask containing a magnetic stir bar were added the product from Example 92A (7.11 g, 25.0 mmol) and chloroform (100 mL). Neat iodotrimethylsilane (Aldrich, 6.25 g, 31.1 mmol) was added. A reflux condenser with nitrogen inlet was attached and a heating mantle was applied. The yellow reaction mixture was heated to 60° C. and stirred overnight. After cooling to room temperature, saturated aqueous sodium bicarbonate solution was added. The organic layer was separated and the aqueous layer was extracted with dichloromethane (2×50 mL). The combined organic layers were dried (MgSO$_4$), filtered, and concentrated by rotary evaporator to give a yellow semi-solid. The product was purified by flash chromatography (silica get: 30-90% ethyl acetate in hexanes) to afford the title compound. LC-MS (ESI+) m/z 213 (M+H)$^+$

Example 92C methyl 3-({[(5Z)-4-butyl-2-tert-butylisothiazol-5(2H)-ylidene]amino}carbonyl)-2,2,3-trimethylcyclopentanecarboxylate To a 20-mL scintillation vial containing a magnetic stir bar were added the product from Example 92B (637 mg, 3.00 mmol), racemic 3-(methoxycarbonyl)-1,2,2-trimethylcyclopentanecarboxylic acid (Maybridge, 771 mg, 3.60 mmol), and 2-(1H-benzo[d][1,2,3]triazol-1-yl)-1,1,3,3-tetramethylisouronium tetrafluoroborate (TBTU, Bachem, 1.16 g, 3.60 mmol). Anhydrous acetontirile (8 mL) was added to form a white slurry. Neat triethylamine (Aldrich, 1.09 g, 10.8 mm01) was added via syringe to form a tan solution. The reaction flask was heated to 60° C. in a shaker block and mixed for 2 hours. The volatiles were removed by rotary evaporator to give a brown oil. The product was purified by flash chromatography (silica gel: 2-20% ethyl acetate in hexanes) to afford the title compound. $^1$H NMR (DMSO-d$_6$) δ 0.50 (s, 3H), 0.90 (t, J=7.5 Hz, 3H), 1.21 (s, 3H), 1.24-1.36 (m, 2H), 1.30 (s, 3H), 1.41-1.51 (m, 1H), 1.57 (s, 9H), 1.57-1.67 (m, 2H), 1.73-1.87 (m, 1H), 2.01-2.11 (m, 1H), 2.62-2.67 (m, 2H), 2.70-2.81 (m, 1H), 2.85-2.91 (m, 1H), 3.60 (s, 3H), 8.50 (s, 1H). MS (ESI+) m/z 409 (M+H)$^+$. Anal. calcd. for C$_{22}$H$_{36}$N$_2$O$_3$S: C, 64.67; H, 8.88; N, 6.86. Found: C, 64.20; H, 8.71; N, 6.59.

Example 93 methyl 3-({[(5Z)-4-butyl-2-tert-butylisothiazol-5(2H)-ylidene]amino}carbonyl)-1,2,2-trimethylcyclopentanecarboxylate The product from Example 92B and racemic 3-(methoxycarbonyl)-2,2,3-trimethylcyclopentanecarboxylic (Maybridge) were processed using the method described in Example 92C to afford the title compound. $^1$H NMR (DMSO-$d_6$) δ 0.53 (s, 3H), 0.90 (t, J=7.3 Hz, 3H), 1.20 (s, 3H), 1.23 (s, 3H), 1.23-1.40 (m, 2H), 1.41-1.50 (m, 1H), 1.57 (s, 9H), 1.57-1.67 (m, 2H), 1.71-1.84 (m, 1H), 2.24-2.36 (m, 1H), 2.41-2.48 (m, 1H), 2.61-2.67 (m, 2H), 3.00-3.06 (m, 1H), 3.59 (s, 3H), 8.51 (s, 1H). MS (ESI+) m/z 409 (M+H)$^+$. Anal. calcd. for $C_{22}H_{36}N_2O_3S$: C, 64.67; H, 8.88; N, 6.86. Found: C, 64.37; H, 8.67; N, 6.50.

Example 94

N-[(5Z)-4-butyl-2-tert-butylisothiazol-5(2H)-ylidene]-1-phenylcyclohexanecarboxamide The product from Example 92B and 1-phenylcyclohexanecarboxylic acid (Aldrich) were processed using the method described in Example 92C to afford the title compound. $^1$H NMR (DMSO-$d_6$) δ 0.90 (t, J=7.3 Hz, 3H), 1.20-1.77 (m, 21H), 2.61-2.69 (m, 4H), 7.10-7.15 (m, 1H), 7.21-7.27 (m, 2H), 7.35-7.39 (m, 2H), 8.51 (s, 1H). MS (ESI+) m/z 399 (M+H)$^+$. Anal. calcd. for $C_{24}H_{34}N_2OS$: C, 72.32; H, 8.60; N, 7.03. Found: C, 72.24; H, 8.59; N, 7.10.

Example 95

N-[(5Z)-4-butyl-2-tert-butylisothiazol-5(2H)-ylidene]-1-(2-chloro-4-fluorophenyl)cyclohexanecarboxamide The product from Example 92B and (2-chloro-4-fluorophenyl)cyclohexanecarboxylic acid (Acros) were processed using the method described in Example 92C to afford the title compound. $^1$H NMR (DMSO-$d_6$) δ 0.76 (t, J=7.3 Hz, 3H), 1.06-1.18 (m, 2H), 1.33-1.53 (m, 8H), 1.56 (s, 9H), 1.71-1.81 (m, 2H), 1.92-2.00 (m, 2H), 2.34-2.42 (m, 2H), 7.14-7.22 (m, 2H), 7.57 (dd, J=8.6, 6.3 Hz, 1H), 8.46 (s, 1H). MS (ESI+) m/z 451 (M+H)$^+$. Anal. calcd. for $C_{24}H_{32}ClFN_2OS$: C, 63.91; H, 7.15; N, 6.21. Found: C, 64.04; H, 7.08; N, 6.10.

Example 96

3-({[(5Z)-4-butyl-2-tert-butylisothiazol-5(2H)-ylidene]amino}carbonyl)-2,2,3-trimethylcyclopentanecarboxylic acid To a 20-mL scintillation vial containing a magnetic stir bar were added the product from Example 92C (102 mg, 0.250 mmol) and potassium hydroxide (84 mg, 1.50 mmol). Ethanol (1 mL) and water (0.25 mL) were added. The vial was heated to 60° C. and the reaction mixed for 24 hours. After cooling to room temperature, the pH was adjusted to ~1 by addition of 1N hydrochloric acid. The mixture was extracted with dichloromethane (3×10 mL). The combined organic extracts were dried (MgSO$_4$), filtered, and concentrated by rotary evaporator to afford a tan solid. The product was recrystallized from ethyl acetate/hexanes to afford 74 mg (75%) of the title compound. $^1$H NMR (DMSO-$d_6$) δ 0.63 (br s, 3H), 0.91 (t, J=7.3 Hz, 3H), 1.23-1.38 (m, 8H), 1.57-1.68 (m, 12H), 1.76-1.87 (m, 1H), 2.00-2.11 (m, 1H), 2.65-2.84 (m, 4H), 8.7 (br s, 1H), 11.7 (br s, 1H). MS (ESI+) m/z 395 (M+H)$^+$.

Example 97

N-[(5Z)-4-butyl-2-tert-butylisothiazol-5(2H)-ylidene]-3-oxocyclopentanecarboxamide The product from Example 92B and 3-oxocyclopentanecarboxylic acid (Aldrich) were processed using the method described in Example 92C to afford the title compound. $^1$H NMR (DMSO-$d_6$) δ 0.91 (t, J=7.5 Hz, 3H), 1.25-1.36 (m, 2H), 1.57 (s, 9H), 1.55-1.84 (m, 2H), 1.98-2.06 (m, 1H), 2.13-2.28 (m, 3H), 2.39-2.42 (m, 2H), 2.61-2.66 (m, 2H), 3.27-3.34 (m, 1H), 8.55 (s, 1H). MS (ESI+) m/z 323 (M+H)$^+$. Anal. calcd. for $C_{17}H_{26}N_2O_2S$: C, 63.32; H, 8.13; N, 8.69. Found: C, 63.19; H, 8.07; N, 8.66.

Example 98

N-[(5Z)-4-butyl-2-tert-butylisothiazol-5(2H)-ylidene]-1-phenylcyclopentanecarboxamide The product from Example 92B and 1-phenylcyclopentanecarboxylic acid (Aldrich) were processed using the method described in Example 92C to afford the title compound. $^1$H NMR (DMSO-$d_6$) δ 0.90 (t, J=7.3 Hz, 3H), 1.23-1.35 (m, 2H), 1.54 (s, 9H), 1.54-1.69 (m, 6H), 1.78-1.87 (m, 2H), 2.61-2.66 (m, 2H), 2.86-2.93 (m, 2H), 7.10-7.16 (m, 1H), 7.21-7.26 (m, 2H), 7.31-7.38 (m, 2H), 8.50 (s, 1H). MS (ESI+) m/z 385 (M+H)$^+$. Anal. calcd. for $C_{23}H_{32}N_2OS$: C, 71.83; H, 8.39; N, 7.28. Found: C, 71.58; H, 8.21; N, 7.05.

Example 99

$N^1$-[(5Z)-4-butyl-2-tert-butylisothiazol-5(2H)-ylidene]-$N^3$,$N^3$,1,2,2-pentamethylcyclopentane-1,3-dicarboxamide To a 20-mL scintillation vial were added the product from Example 96 (118 mg, 0.300 mmol), dimethylamine hydrochloride (Aldrich, 36.7 mg, 0.450 mmol), and 2-(1H-benzo[d][1,2,3]tria-zol-1-yl)-1,1,3,3-tetramethylisouronium tetrafluoroborate (TBTU, Bachem, 144 mg, 0.450 mmol) Anhydrous acetonitrile (3 mL) was added to form a yellow slurry. Neat triethylamine (Aldrich, 182 mg, 1.80 mmol) was added to form a tan solution. The reaction was stirred at 25° C. in a shaker block for 24 hr. The volatiles removed by rotary evaporator to give a brown oil. The product was purified by flash chromatography (silica gel: 10-45% ethyl acetate in hexanes). The product was recrystallized from hexanes to afford 67.0 mg (53%) of the title compound. $^1$H NMR (DMSO-$d_6$) δ 0.49 (s, 3H), 0.90 (t, J=7.3 Hz, 3H), 1.25 (s, 3H), 1.26 (s, 3H), 1.28-1.33 (m, 2H), 1.37-1.46 (m, 1H), 1.57 (s, 9H), 1.57-1.70 (m, 3H), 2.01-2.10 (m, 1H), 2.62-2.67 (m, 2H), 2.74-2.83 (m, 1H), 2.83 (s, 3H), 3.05 (s, 3H), 3.33-3.39 (m, 1H), 8.49 (s, 1H). MS (ESI+) m/z 422 (M+H)$^+$. Anal. calcd. for $C_{23}H_{39}N_3O_2S$: C, 65.52; H, 9.32; N, 9.97. Found: C, 65.13; H, 9.22; N, 9.55.

Example 100

$N^1$-[(5Z)-4-butyl-2-tert-butylisothiazol-5(2H)-ylidene]-$N^3$,1,2,2-tetramethylcyclopentane-1,3-dicarboxamide The product from Example 96 and methylamine hydrochloride (Aldrich) were processed using the method described in Example 99 to afford the title compound. $^1$H NMR (DMSO-$d_6$) δ 0.47 (s, 3H), 0.90 (t, J=7.3 Hz, 3H), 1.19 (s, 3H), 1.22 (s, 3H), 1.26-1.33 (m, 2H), 1.36-1.45 (m, 1H), 1.57 (s, 9H), 1.57-1.68 (m, 3H), 1.95-2.07 (m, 1H), 2.57 (d, J=4.7 Hz, 3H), 2.60-2.67 (m, 3H), 2.72-2.83 (m, 1H), 4.78 (q, J=4.5 Hz, 1H), 8.49 (s, 1H). MS (ESI+) m/z 408 (M+H)$^+$. Anal. calcd. for $C_{22}H_{37}N_3O_2S$: C, 64.83; H, 9.15; N, 10.31. Found: C, 64.55; H, 9.02; N, 10.29.

Example 101

N-[(5Z)-4-butyl-2-tert-butylisothiazol-5(2H)-ylidene]-3-[(3,3-difluoroazetidin-1-yl)carbonyl]-1,2,2-trimethylcyclopentanecarboxamide The product from Example 96 and 3,3-difluoroazetidine hydrochloride (Oakwood)) were processed using the method described in Example 99 to afford the title compound. $^1$H NMR (DMSO-d$_6$) δ 0.51 (s, 3H), 0.90 (t, J=7.3 Hz, 3H), 1.22 (s, 3H), 1.25 (s, 3H), 1.26-1.36 (m, 2H), 1.39-1.48 (m, 1H), 1.57 (s, 9H), 1.57-1.78 (m, 3H), 1.93-2.07 (m, 1H), 2.62-2.67 (m, 2H), 2.72-2.83 (m, 1H), 2.88-2.94 (m, 1H), 4.14-4.37 (m, 2H), 4.41-4.52 (m, 1H), 4.73-4.86 (m, 1H), 8.50 (s, 1H). MS (ESI+) m/z 470 (M+H)$^+$. Anal. calcd. for C$_{24}$H$_{37}$F$_2$N$_3$O$_2$S: C, 61.38; H, 7.94; N, 8.95. Found: C, 61.35; H, 7.84; N, 8.96.

Example 102

(1S,4R)-N-[(5Z)-4-butyl-2-tert-butylisothiazol-5(2H)-ylidene]-4,7,7-trimethyl-3-oxo-2-oxabicyclo[2.2.1]heptane-1-carboxamide To a 20-mL scintillation vial containing a magnetic stir bar were added the product from Example 92B (327 mg, 1.75 mmol) and (1S)-(−)-camphanic acid chloride (Aldrich, 474 mg, 2.19 mmol) and anhydrous tetrahydrofuran (12 mL). Triethylamine (797 mg, 7.88 mmol) was added via syringe and the resulting yellow slurry was stirred at room temperature for 24 h. The volatiles removed by rotary evaporator to give a brown oil. The product was purified by flash chromatography (silica gel: 20-80% ethyl acetate in hexanes) to afford 527 mg (77%) of the title compound. $^1$H NMR (DMSO-d$_6$) δ 0.79 (s, 3H), 0.90 (t, J=7.3 Hz, 3H), 1.01 (s, 3H), 1.07 (s, 3H), 1.22-1.39 (m, 2H), 1.60 (s, 9H), 1.50-1.67 (m, 3H), 1.61-2.02 (m, 2H), 2.45-2.54 (m, 1H), 2.65-2.70 (m, 2H), 8.66 (s, 1H). MS (ESI+) m/z 393 (M+H)$^+$. Anal. calcd. for C$_{21}$H$_{32}$N$_2$O$_3$S: C, 64.25; H, 8.22; N, 7.14. Found: C, 64.04; H, 8.22; N, 7.01.

Example 103

(1R,4S)-N-[(5Z)-4-butyl-2-tert-butylisothiazol-5(2H)-ylidene]-4,7,7-trimethyl-3-oxo-2-oxabicyclo[2.2.1]heptane-1-carboxamide The product from Example 92B and (1R)-(+)-camphanic acid chloride (Fluka) were processed using the method described in Example 102 to afford the title compound. $^1$H NMR (DMSO-d$_6$) δ 0.79 (s, 3H), 0.90 (t, J=7.3 Hz, 3H), 1.01 (s, 3H), 1.06 (s, 3H), 1.25-1.37 (m, 2H), 1.60 (s, 9H), 1.50-1.67 (m, 3H), 1.61-2.02 (m, 2H), 2.45-2.54 (m, 1H), 2.65-2.70 (m, 2H), 8.66 (s, 1H). MS (ESI+) m/z 393 (M+H)$^+$. Anal. calcd. for C$_{21}$H$_{32}$N$_2$O$_3$S: C, 64.25; H, 8.22; N, 7.14. Found: C, 64.16; H, 8.05; N, 7.03.

Example 104 ethyl 3-({[(5Z)-4-butyl-2-tert-butylisothiazol-5(2H)-ylidene]amino}carbonyl)pyrrolidine-1-carboxylate

Example 104A tert-butyl 3-{[(5Z)-4-butyl-2-tert-butylisothiazol-5(2H)-ylidene]carbamoyl}pyrrolidine-1-carboxylate The product from Example 92B and 1-(tert-butoxycarbonyl)pyrrolidine-3-carboxylic acid (Aldrich) were processed using the method described in Example 92C to afford the title compound. MS (ESI+) m/z 410 (M+H)$^+$.

Example 104B

N-[(5Z)-4-butyl-2-tert-butylisothiazol-5(2H)-ylidene]pyrrolidine-3-carboxamide

To a 20-mL scintillation vial containing a magnetic stir bar were added the product from Example 104A (143 mg, 0.350 mmol), anhydrous dichloromethane (5 mL), and trifluoroacetic acid (200 mg, 1.75 mmol). The pale yellow solution was stirred at room temperature for 4 hours. The pH of the reaction mixture was adjusted to ~9 by addition of saturated aqueous sodium bicarbonate solution. The mixture was extracted with dichloromethane (3×10 mL). The combined organic extracts were dried (MgSO$_4$), filtered, and concentrated by rotary evaporator to afford the title compound. The crude product was used without purification for the next step. MS (ESI+) m/z 310 (M+H)$^+$.

Example 104C ethyl 3-({[(5Z)-4-butyl-2-tert-butylisothiazol-5(2H)-ylidene]amino}carbonyl)pyrrolidine-1-carboxylate The product from Example 104B and ethylchloroformate (Aldrich) were processed using the method described in Example 102 to afford the title compound. $^1$H NMR (DMSO-d$_6$) δ 0.91 (t, J=7.3 Hz, 3H), 1.18 (t, J=6.9 Hz, 3H), 1.24-1.37 (m, 3H), 1.51-1.64 (m, 3H), 1.58 (s, 9H), 2.05-2.14 (m, 2H), 2.61-2.66 (m, 2H), 3.21-3.28 (m, 1H), 3.49-3.64 (m, 2H), 4.02 (q, J=7.1 Hz, 2H), 8.57 (s, 1H). (ESI+) m/z 410 (M+H)$^+$.

Example 105

3-({[(5Z)-4-butyl-2-tert-butylisothiazol-5(2H)-ylidene]amino}carbonyl)-1,2,2-trimethylcyclopentanecarboxylic acid The product from Example 93 was processed using the method described in Example 96 to afford the title compound. $^1$H NMR (DMSO-d$_6$) δ 0.75 (s, 3H), 0.92 (t, J=7.3 Hz, 3H), 1.19 (s, 3H), 1.23 (s, 3H), 1.30-1.42 (m, 2H), 1.45-1.66 (m, 4H), 1.69 (br s, 9H), 1.84-1.96 (m, 1H), 2.00-2.13 (m, 1H), 2.78-2.92 (m, 3H), 9.1 (br s, 1H), 13.1 (br s, 1H). MS (ESI+) m/z 395 (M+H)$^+$.

Example 106 tert-butyl 3-({[(5Z)-4-butyl-2-tert-butylisothiazol-5(2H)-ylidene]amino}carbonyl)pyrrolidine-1-carboxylate The product from Example 92B and 1-(tert-butoxycarbonyl)pyrrolidine-3-carboxylic acid (Aldrich) were processed using the method described in Example 92C to afford the title compound. $^1$H NMR (DMSO-d$_6$) δ 0.91 (t, J=7.3 Hz, 3H), 1.27-1.35 (m, 2H), 1.39 (s, 9H), 1.55-1.65 (m, 12H), 2.06-2.11 (m, 2H), 2.62-2.67 (m, 2H), 3.19-3.30 (m, 2H), 3.45-3.54 (m, 2H), 8.56 (s, 1H). MS (ESI+) m/z 410 (M+H)$^+$.

Example 107

N-[(5Z)-4-butyl-2-tert-butylisothiazol-5(2H)-ylidene]-1-(3-cyanopyridin-2-yl)pyrrolidine-3-carboxamide To a 20-mL scintillation vial were added the product from Example 104B (54.2 mg, 0.175 mmol), the 2-fluoronicotinonitrile (Aldrich, 32.1 mg, 0.263 mmol), and anhydrous acetonitrile (2 mL). Neat triethylamine (53.1 mg, 0.525 mmol) was added. The reaction mixture was heated to 60° C. in a heated shaker block and mixed for 24 hours. After cooling to room temperature, the volatiles were removed by rotary evaporator. The product was purified by flash chromatography (silica gel: 20-65% ethyl acetate in hexanes) to give 54.6 mg (76%) of the title compound. $^1$H NMR (DMSO-$d_6$) δ 0.88 (t, J=7.3 Hz, 3H), 1.21-1.34 (m, 3H), 1.52-1.62 (m, 1H), 1.57 (s, 9H), 2.20-2.27 (m, 2H), 2.59-2.64 (m, 2H), 3.35-3.43 (m, 1H), 3.69-3.78 (m, 2H), 3.88-3.95 (m, 1H), 4.04-4.09 (m, 1H), 6.69 (dd, J=7.5, 4.8 Hz, 1H), 7.93 (dd, J=7.9, 2.0 Hz, 1H), 8.31 (dd, J=4.8, 2.0 Hz, 1H), 8.57 (s, 1H). MS (ESI+) m/z 412 (M+H)$^+$.

Example 108 methyl 4-({[(5Z)-4-butyl-2-tert-butylisothiazol-5 (2H)-ylidene]amino}carbonyl)bicyclo[2.2.2]octane-1-carboxylate The product from Example 92B and 4-(methoxycarbonyl) bicyclo[2.2.2]octane-1-carboxylic acid (Oakwood) were processed using the method described in Example 92C to afford the title compound. $^1$H NMR (DMSO-$d_6$) δ 0.91 (t, J=7.3 Hz, 3H), 1.23-1.36 (m, 2H), 1.58 (s, 9H), 1.58-1.66 (m, 2H), 1.70-1.83 (m, 12 H), 2.61-2.66 (m, 2H), 3.58 (s, 3H), 8.49 (s, 1H). (ESI+) m/z 407 (M+H)$^+$. Anal. calcd. for $C_{22}H_{34}N_2O_3S$: C, 64.99; H, 8.43; N, 6.89. Found: C, 64.65; H, 8.24; N, 6.72.

Example 109

N-[(5Z)-4-butyl-2-tert-butylisothiazol-5(2H)-ylidene]-5-oxo-1-phenylpyrrolidine-3-carboxamide The product from Example 92B and 5-oxo-1-phenylpyrrolidine-3-carboxylic acid (Princeton Bio) were processed using the method described in Example 92C to afford the title compound. $^1$H NMR (DMSO-$d_6$) δ 0.91 (t, J=7.3 Hz, 3H), 1.26-1.38 (m, 2H), 1.58-1.66 (m, 2H), 1.61 (s, 9H), 2.64-2.69 (m, 2H), 2.85-2.89 (m, 2H), 3.49-3.58 (m, 1H), 4.12 (s, 1H), 4.14 (d, J=1.7 Hz, 1H), 7.08-7.14 (m, 1H), 7.31-7.38 (m, 2H), 7.62-7.68 (m, 2H), 8.48 (s, 1H). (ESI+) m/z 400 (M+H)$^+$.

Example 110

N-[(5Z)-4-butyl-2-tert-butylisothiazol-5(2H)-ylidene]-5-chloro-N'-cyano-2-methoxybenzenecarboximidamide Example 110A ethyl [(5Z)-4-butyl-2-tert-butylisothiazol-5(2H)-ylidene]carbamate To a solution of Example 1A (4.2 g, 27 mmol) in THF (100 mL) at room temperature under $N_2$ was added O-ethyl carbonisothiocyanatidate (3.55 g, 27 mmol). The reaction mixture was stirred for 1 hour and iodine (6.8 g, 27 mmol), MeOH (100 mL) and pyridine (10 mL) were added. The reaction mixture was stirred for 2 hours. The reaction mixture was poured into saturated NaHCO$_3$/Et$_2$O and stirred for 30 minutes. Additional saturated NaHCO$_3$ and Et$_2$O were added and the organic layer was separated. The aqueous layer was extracted with Et$_2$O (2×) and combined organics were dried (MgSO$_4$) and concentrated in vacuo. Toluene and acetonitrile were added and evaporated to remove water and pyridine. The crude compound was purified by flash chromatography using 0-100% EtOAc in hexane as eluent to give 5.2 g of the title compound as yellow solid. $^1$H NMR (300 MHz, CDCl$_3$) δ ppm 0.93 (t, J=7.3 Hz, 3 H), 1.27-1.47 (m, 5 H), 1.54-1.73 (m, 11 H), 2.59-2.74 (m, 2 H), 4.28 (q, J=7.1 Hz, 2 H), 7.78 (s, 1 H). MS (DCI/NH$_3$) m/z 285 (M+H)$^+$.

Example 110B 2-tert-butyl-4-butylisothiazol-5(2H)-imine

A solution of Example 110A (3.95 g, 13.89 mmol) in chloroform (35 mL) was treated with TMSI (2.65 mL, 19.5 mmol). The reaction mixture was stirred at 65° C. for 8 hours, cooled to room temperature, quenched with water and extracted between CH$_2$Cl$_2$ and saturated NaHCO$_3$, dried (MgSO$_4$) and concentrated to give the title compound (2.45 g, 83% yield). $^1$H NMR (300 MHz, CDCl$_3$) δ ppm 0.84-1.02 (m, 3 H), 1.30-1.51 (m, 2 H), 1.56-1.68 (m, 11 H), 2.73 (t, J=7.6 Hz, 2 H), 7.82 (s, 1 H), 11.68 (d, J=6.1 Hz, 1 H). MS (DCI/NH$_3$) m/z 213 (M+H)$^+$.

Example 110C methyl N-[(5Z)-4-butyl-2-tert-butylisothiazol-5(2H)-ylidene]-N-cyanoimidothiocarbamate A mixture of Example 110B (2.06 g, 9.71 mmol) and dimethyl cyanocarbonimidodithioate (1.36 g, 9.3 mmol) in THF (35 mL) was treated with Et$_3$N (0.98 g, 9.71 mmol) and stirred at 45° C. for 12 h. The mixture was concentrated under reduced pressure and the residue was purified by chromatography (hexane-EtOAc 1:1) to afford 1.65 g, (55% yield) of the title compound. $^1$H NMR (300 MHz-DMSO-$d_6$) δ 1.31 (s, 9H), 1.60 (m, 1H), 1.82 (quintet, J=7 Hz, 2H), 1.95 (m, 1H), 2.53 (s, 3H), 3.65 (m, 1H), 3.75 (m, 1H), 4.26 (m, 3H), 7.43 (s, 1H); MS (DCI/NH$_3$) m/z 339 (M+H)$^+$.

Example 110D

N-[(5Z)-4-butyl-2-tert-butylisothiazol-5(2H)-ylidene]-5-chloro-N'-cyano-2-methoxybenzenecarboximidamide To a mixture of Example 110C (0.67 g, 2.15 mol), 2-methoxy-5-chlorophenylboronic acid (1.046 g, 5.6 mmol), copper (I) acetate (0.794 g, 6.47 mmol) in dimethoxyethane (35 mL) were added tris(dibenzylideneacetone)dipalladium(0) 0.289 g, 0.315 mmol) and triethyl phosphite (0.170 mg, 1.0 mmol) and the mixture was refluxed for 16 h. The mixture was then concentrated under reduced pressure and the residue was chromatographed (hexane-EtOAc 1:1) to afford 550 mg (62% yield) of the title compound. $^1$H NMR (300 MHz, CDCl$_3$) δ ppm 0.96 (t, J=7.3 Hz, 3 H), 1.29-1.50 (m, 2 H), 1.60-1.75 (m, 11 H), 2.75-2.93 (m, 2 H), 3.92 (s, 3 H), 6.94 (d, J=8.8 Hz, 1 H), 7.37 (dd, J=8.8, 2.7 Hz, 1 H), 7.47 (d, J=2.7 Hz, 1 H), 8.06 (s, 1 H). MS (DCI/NH$_3$) m/z 405 (M+H)$^+$. Anal. calculated for $C_{20}H_{25}ClN_4OS$: C, 59.32; H, 6.22; N, 13.84. Found: C, 59.10; H, 5.85; N, 13.27

Example 111

N-[(5Z)-4-butyl-2-tert-butylisothiazol-5(2H)-ylidene]-5-chloro-2-methoxybenzenecarbothioamide To a solution of Example 1D (380 mg, 1 mmol) in toluene (25 mL) was added P$_2$S$_5$ (220 mg, 1 mmol) and the reaction mixture was heated at 82° C. for 75 minutes, concentrated under reduced pressure and purified via column chromatography (SiO$_2$, 0-25% EtOAc in hexanes) to provide the title compound (0.14 g, 34% yield). $^1$H NMR (300 MHz, CDCl$_3$) δ ppm 0.95 (t, J=7.3 Hz, 3 H), 1.40 (dd, J=15.1, 7.5 Hz, 2 H), 1.61-1.78 (m, 11 H), 2.84-3.00 (m, 2 H), 3.84 (s, 3 H), 6.90 (d, J=8.7 Hz, 1 H), 7.27-7.35 (m, 1 H), 7.66 (d, J=2.8 Hz, 1 H), 8.13 (s, 1 H). MS (DCI/NH$_3$) m/z 398 (M+H)$^+$.

Example 112

N-[(3Z)-1-tert-butyl-5-(trifluoromethyl)-4,5,6,7-tetrahydro-2,1-benzisothiazol-3(1H)-ylidene]-5-chloro-2-methoxybenzamide The title compound was prepared using the procedure as described in Example 9, substituting 4-(trifluoromethyl)cyclohexanone for 4-propylcyclohexanone. $^1$H NMR (300 MHz, CDCl$_3$) δ ppm 1.74 (s, 9 H), 1.78-2.03 (m, 1 H), 2.33 (dd, J=7.8, 2.4 Hz, 1 H), 2.40-2.63 (m, 1 H), 2.74-2.99 (m, 2 H), 3.16-3.47 (m, 2 H), 3.84-3.97 (m, 3 H), 6.84-7.04 (m, 1 H), 7.34 (dd, J=8.8, 2.7 Hz, 1 H), 8.07 (d, J=2.7 Hz, 1 H). MS (DCI/NH$_3$) m/z 447 (M+H)$^+$. Anal. calculated for C$_{20}$H$_{22}$ClF$_3$N$_2$O$_2$S: C, 53.75; H, 4.96; N, 6.27. Found: C, 53.71; H, 4.81; N, 6.25.

Example 113 tert-butyl (3Z)-1-tert-butyl-3-[(5-chloro-2-methoxybenzoyl)imino]-1,4,6,7-tetrahydroisothiazolo[4,3-c]pyridine-5(3H)-carboxylate The title compound was prepared using the procedure as described in Example 9, substituting commercially available tert-butyl 4-oxopiperidine-1-carboxylate for 4-propylcyclohexanone. $^1$H NMR (300 MHz, CDCl$_3$) δ ppm 1.45-1.60 (m, 9 H), 1.73 (s, 9 H), 3.03 (t, J=5.6 Hz, 2 H), 3.76 (t, J=5.8 Hz, 2 H), 3.91 (s, 3 H), 4.72 (s, 2 H), 6.91 (d, J=8.8 Hz, 1 H), 7.34 (dd, J=8.8, 2.7 Hz, 1 H), 8.09 (s, 1 H). MS (DCI/NH$_3$) m/z 481 (M+H)$^+$. Anal. calculated for C$_{23}$H$_{30}$ClN$_3$O$_4$S: C, 57.55; H, 6.30; N, 8.75. Found: C, 57.41; H, 6.37; N, 8.64

Example 114

N-[(3Z)-1-tert-butyl-4,5,6,7-tetrahydroisothiazolo[4,3-c]pyridin-3(1H)-ylidene]-5-chloro-2-methoxybenzamide Example 113 (800 mg, 1.66 mmol) in CH$_2$Cl$_2$ (10 mL) was treated with TFA (1.5 mL) and the reaction mixture was stirred at room temperature for 24 hours. The reaction mixture was concentrated under reduced pressure and the residue was partitioned between saturated NaHCO$_3$/EtOAc, organics were dried (MgSO$_4$), filtered and solvent evaporated. The crude was flash chromatographed on silica gel, eluting with 0-20% methanol in CH$_2$Cl$_2$ to provide 600 mg of the title compound. $^1$H NMR (300 MHz, DMSO-d$_6$) δ ppm 1.69 (s, 9 H), 2.34-2.51 (m, 2 H), 2.97 (s, 2 H), 3.78 (s, 3 H), 3.85 (s, 2 H), 7.11 (d, J=9.2 Hz, 1 H), 7.45 (dd, J=8.8, 2.7 Hz, 1 H), 7.69 (d, J=2.7 Hz, 1 H). MS (DCI/NH$_3$) m/z 380 (M+H)$^+$.

Example 115

N-[(5Z)-4-butyl-2-tert-butylisothiazol-5(2H)-ylidene]-5-chloro-2-methoxybenzenesulfonamide Example 110B (294 mg, 1.4 mmol) in CH$_2$Cl$_2$ (20 mL) was treated with triethylamine (0.193 mL, 1.4 mmol) and commercially available 5-chloro-2-methoxybenzene-1-sulfonyl chloride (334 mg, 1.4 mmol). The reaction mixture was stirred at room temperature for 18 hours, partitioned between CH$_2$Cl$_2$ and saturated NaHCO$_3$, dried (MgSO$_4$) and concentrated. The residue was purified by flash chromatography with 0-60% EtOAc in hexane to give the title compound (320 mg, 55%)$^{-1}$H NMR (300 MHz, DMSO-d$_6$) δ ppm 0.80 (t, J=7.3 Hz, 3 H), 1.11-1.29 (m, 2 H), 1.32-1.52 (m, 2 H), 1.57 (s, 9 H), 2.29-2.43 (m, 2 H), 3.65 (s, 3 H), 7.18 (d, J=8.8 Hz, 1 H), 7.58 (dd, J=8.8, 2.7 Hz, 1 H), 7.71 (d, J=2.7 Hz, 1 H), 8.46 (s, 1 H). MS (DCI/NH$_3$) m/z 417 (M+H)$^+$.

Example 116

N-[(5Z)-4-butyl-2-tert-butylisothiazol-5(2H)-ylidene]naphthalene-1-sulfonamide

The title compound was prepared using the procedure as described in Example 115, substituting 5-chloro-2-methoxybenzene-1-sulfonyl chloride with naphthalene-1-sulfonyl chloride. $^1$H NMR (300 MHz, CDCl$_3$) δ ppm 0.78 (t, J=7.3 Hz, 3 H), 1.12-1.32 (m, 2 H), 1.33-1.51 (m, 2 H), 1.56 (s, 9 H), 2.36-2.52 (m, 2 H), 7.39-7.71 (m, 4 H), 7.86 (d, J=8.7 Hz, 1 H), 7.96 (d, J=8.3 Hz, 1 H), 8.25 (d, J=7.5 Hz, 1 H), 8.90 (d, J=8.7 Hz, 1 H). MS (DCI/NH$_3$) m/z 403 (M+H)$^+$. Anal. calculated for C$_{21}$H$_{26}$N$_2$O$_2$S$_2$: C, 62.65; H, 6.51; N, 6.96. Found: C, 62.45, H, 6.44; N, 6.91.

Example 117

N-[(5Z)-4-butyl-2-tert-butylisothiazol-5(2H)-ylidene]-5-(dimethylamino)naphthalene-1-sulfonamide The title compound was prepared using the procedure as described in Example 115, substituting 5-chloro-2-methoxybenzene-1-sulfonyl chloride with 5-(dimethylamino)naphthalene-1-sulfonyl chloride. $^1$H NMR (300 MHz, CDCl$_3$) δ ppm 0.80 (t, J=7.1 Hz, 3 H), 1.15-1.33 (m, 2 H), 1.33-1.52 (m, 2 H), 1.52-1.64 (m, 9 H), 2.36-2.53 (m, 2 H), 2.85 (s, 6 H), 7.14 (d, J=7.8 Hz, 1 H), 7.38-7.58 (m, 2 H), 7.61 (s, 1 H), 8.25 (dd, J=7.1, 1.4 Hz, 1 H), 8.43 (d, J=8.5 Hz, 1 H), 8.57 (d, J=8.8 Hz, 1 H). MS (DCI/NH$_3$) m/z 446 (M+H)$^+$. Anal. calculated for C$_{23}$H$_{31}$N$_3$O$_2$S$_2$: C, 61.99; H, 7.01; N, 9.43. Found: C, 61.94; H, 7.04; N, 9.34

Example 118

N-[(5Z)-4-butyl-2-tert-butylisothiazol-5(2H)-ylidene]cyclohexanesulfonamide

The title compound was prepared using the procedure described in Example 115, substituting 5-chloro-2-methoxybenzene-1-sulfonyl chloride with cyclohexanesulfonyl chloride. $^1$H NMR (300 MHz, CDCl$_3$) δ ppm 0.82-1.00 (m, 3 H), 1.20-1.52 (m, 16 H), 1.66-1.82 (m, 1 H), 1.89-2.29 (m, 8 H), 6.94 (d, J=14.2 Hz, 1 H), 9.61 (s, 1 H). MS (DCI/NH$_3$) m/z 359 (M+H)$^+$. Anal. calculated for C$_{17}$H$_{30}$N$_2$O$_2$S$_2$: C, 56.94; H, 8.43; N, 7.81. Found: C, 56.55; H, 8.22; N, 7.49.

Example 119

N-[(5Z)-4-butyl-2-tert-butylisothiazol-5(2H)-ylidene]benzenesulfonamide

The title compound was prepared using the procedure as described in Example 115, substituting 5-chloro-2-methoxybenzene-1-sulfonyl chloride with benzenesulfonyl chloride.

¹H NMR (300 MHz, CDCl₃) δ ppm 0.87 (t, J=7.3 Hz, 3 H), 1.20-1.39 (m, 2 H), 1.43-1.63 (m, 11 H), 2.37-2.53 (m, 2 H), 7.37-7.54 (m, 4 H), 7.63 (s, 1 H), 7.93 (dd, J=8.1, 1.7 Hz, 1 H). MS (DCI/NH₃) m/z 353 (M+H)⁺. Anal. calculated for C₁₇H₂₄N₂O₂S₂: C, 57.92; H, 6.86; N, 7.95. Found: C, 57.61; H, 6.82; N, 8.0.

Example 120

N-[(5Z)-4-butyl-2-tert-butylisothiazol-5(2H)-ylidene]quinoline-8-sulfonamide The title compound was prepared using the procedure as described in Example 115, substituting 5-chloro-2-methoxybenzene-1-sulfonyl chloride with quinoline-8-sulfonyl chloride. ¹H NMR (300 MHz, CDCl₃) δ ppm 0.64-0.79 (m, 3 H), 1.09-1.30 (m, 2 H), 1.32-1.49 (m, 2 H), 1.59-1.69 (m, 9 H), 2.37-2.52 (m, 2 H), 7.40 (dd, J=8.5, 4.1 Hz, 1 H), 7.51-7.62 (m, 1 H), 7.65 (s, 1 H), 7.93 (dd, J=8.1, 1.4 Hz, 1 H), 8.16 (dd, J=8.3, 1.9 Hz, 1 H), 8.55 (dd, J=7.5, 1.4 Hz, 1 H), 8.88 (dd, J=4.2, 1.9 Hz, 1 H). MS (DCI/NH₃) m/z 404 (M+H)⁺. Anal. calculated for C₂₀H₂₅N₃O₂S₂: C, 59.52; H, 6.24; N, 10.41. Found: C, 59.59; H, 6.35; N, 10.08.

Example 121

N-[(5Z)-4-butyl-2-tert-butylisothiazol-5(2H)-ylidene]-2,2,3,3-tetramethylcyclopropanecarboxamide The title compound was prepared using the procedure as described in Example 115, substituting 5-chloro-2-methoxybenzene-1-sulfonyl chloride with 2,2,3,3-tetramethylcyclopropanecarbonyl chloride. ¹H NMR (300 MHz, CDCl₃) δ ppm 0.88-1.05 (m, 3 H), 1.19-1.28 (m, 6 H), 1.31-1.50 (m, 8 H), 1.54-1.72 (m, 12 H), 2.66-2.82 (m, 2 H), 7.82 (s, 1 H). MS (DCI/NH₃) m/z 337 (M+H)⁺. Anal. calculated for C₁₉H₃₂N₂OS: C, 67.81; H, 9.58; N, 8.32. Found: C, 67.73; H, 9.59; N, 8.45.

Example 122

N-[(5Z)-4-butyl-2-tert-butylisothiazol-5(2H)-ylidene]-2,3-dichlorobenzenesulfonamide The title compound was prepared using the procedure as described in Example 115, substituting 5-chloro-2-methoxybenzene-1-sulfonyl chloride with 2,3-dichlorobenzene-1-sulfonyl chloride. ¹H NMR (300 MHz, CDCl₃) δ ppm 0.88 (t, J=7.3 Hz, 3 H), 1.18-1.40 (m, 2 H), 1.46-1.57 (m, 2 H), 1.57-1.65 (m, 9 H), 2.41-2.56 (m, 2 H), 7.28-7.36 (m, 1 H), 7.58 (dd, J=8.3, 1.6 Hz, 1 H), 7.69 (s, 1 H), 8.16 (dd, J=7.9, 1.6 Hz, 1 H). MS (DCI/NH₃) m/z 422 (M+H)⁺. Anal. calculated for C₁₇H₂₂N₂Cl₂O₂S₂: C, 48.45; H, 5.26; N, 6.65. Found: C, 48.67; H, 5.35; N, 6.56.

Example 123

N-[(5Z)-4-butyl-2-tert-butylisothiazol-5(2H)-ylidene]adamantane-1-carboxamide The title compound was prepared using the procedure as described in Example 115, substituting 5-chloro-2-methoxybenzene-1-sulfonyl chloride with 1-adamantanecarbonyl chloride. ¹H NMR (300 MHz, CDCl₃) δ ppm 0.96 (t, J=7.3 Hz, 3 H), 1.29-1.48 (m, 2 H), 1.60 (s, 9 H), 1.62-1.72 (m, 2 H), 1.76 (s, 6 H), 2.04 (s, 9 H), 2.71-2.81 (m, 2 H), 7.85 (s, 1 H). MS (DCI/NH₃) m/z 375 (M+H)⁺. Anal. calculated for C₂₂H₃₄N₂OS: C, 70.54; H, 9.15; N, 7.48. Found: C, 70.51; H, 9.21; N, 8.06.

Example 124

N-[(5Z)-4-butyl-2-tert-butylisothiazol-5(2H)-ylidene]-N'-cyano-2-methoxy-5-(trifluoromethyl)benzenecarboximidamide The title compound was prepared using the procedure as described in Example 110D, substituting 2-methoxy-5-chlorophenylboronic acid with 2-methoxy-5-trifluoromethylphenylboronic acid. ¹H NMR (300 MHz, CDCl₃) δ ppm 0.96 (t, J=7.3 Hz, 3 H), 1.31-1.51 (m, 2 H), 1.58-1.76 (m, 11 H), 2.75-2.91 (m, 2 H), 3.99 (s, 3 H), 7.08 (d, J=8.8 Hz, 1 H), 7.68 (dd, J=8.8, 1.7 Hz, 1 H), 7.77 (d, J=2.4 Hz, 1 H), 8.07 (s, 1 H). MS (DCI/NH₃) m/z 439 (M+H)⁺. Anal. calculated for C₂₁H₂₅F₃N₄OS: C, 57.52; H, 5.75; N, 12.78. Found: C, 57.44; H, 5.22; N, 12.84.

Example 125

N-[(5Z)-4-butyl-2-tert-butylisothiazol-5(2H)-ylidene]-2,2-dimethyl-4-oxo-3,4-dihydro-2H-pyran-6-carboxamide The title compound was prepared using the procedure as described in Example 115, substituting 5-chloro-2-methoxybenzene-1-sulfonyl chloride with 2,2-dimethyl-4-oxo-3,4-dihydro-2H-pyran-6-carbonyl chloride. ¹H NMR (300 MHz, DMSO-d₆) δ ppm 0.88-0.98 (m, 3 H), 1.22-1.38 (m, 2 H), 1.38-1.46 (m, 6 H), 1.55-1.70 (m, 11 H), 2.57 (s, 2 H), 2.65-2.77 (m, 2 H), 6.24 (s, 1 H), 8.73 (s, 1 H). MS (DCI/NH₃) m/z 365 (M+H)⁺.

Example 126

N-[(5Z)-4-butyl-2-tert-butylisothiazol-5(2H)-ylidene]-N'-cyano-2-ethoxy-5-(trifluoromethyl)benzenecarboximidamide The title compound was prepared using the procedure as described in Example 110D, substituting 2-methoxy-5-chlorophenylboronic acid with 2-ethoxy-5-trifluoromethylphenylboronic acid. ¹H NMR (300 MHz, CDCl₃) δ ppm 0.96 (t, J=7.3 Hz, 3 H), 1.33-1.46 (m, 2 H), 1.46-1.55 (m, 3 H), 1.60-1.78 (m, 11 H), 2.74-2.92 (m, 2 H), 4.23 (q, J=7.0 Hz, 2 H), 7.05 (d, J=8.7 Hz, 1 H), 7.65 (dd, J=9.1, 2.0 Hz, 1 H), 7.77 (d, J=2.4 Hz, 1 H), 8.07 (s, 1 H). MS (DCI/NH₃) m/z 453 (M+H)⁺. Anal. calculated for C₂₂H₂₇F₃N₄OS: C, 58.39; H, 6.01; N, 12.38. Found: C, 58.04; H, 5.84; N, 12.26.

Example 127

N-[(5Z)-4-butyl-2-tert-butylisothiazol-5(2H)-ylidene]-2-methoxy-5-(trifluoromethyl)benzamide To a solution of Example 110B (1.0 g, 4.7 mmol) in THF (50 mL) were added 2-methoxy-5-(trifluoromethyl)benzoic acid (1.1 g, 5.2 mmol, JRD Fluorochemicals Ltd), N-(3-dimethylaminopropyl)-N-ethylcarbodimide hydrochloride (1.0 g, 5.2 mmol, Aldrich), 1-hydroxybenzotriazole (0.8 g, 5.2 mmol, Aldrich) and triethylamine (2.0 mL, 14.3 mmol, Aldrich). The mixture was stirred at 60° C. for 12 hr. The reaction mixture was then cooled to room temperature, diluted with 1 M aqueous NaHCO₃ (50 mL) and extracted with ethyl acetate (2×50 mL). The combined organic extracts were dried (Na$_2$SO$_4$), filtered and concentrated. The residue was purified by column chromatography using an Analogix® Intelliflash280™ (SiO$_2$, 0-50% ethyl acetate in hexanes) to afford 1.23 g (63%) of the title compound. $^1$H NMR (300 MHz, DMSO-d$_6$) δ ppm 0.93 (t, J=7.3 Hz, 3 H), 1.17-1.45 (m, 2 H), 1.62 (s, 9 H), 1.64-1.73 (m, 2 H), 2.64-2.80 (m, 2 H), 3.88 (s, 3 H), 7.30 (d, J=8.7 Hz, 1 H), 7.80 (dd, J=8.3, 2.8 Hz, 1 H), 8.08 (d, J=2.4 Hz, 1 H), 8.64 (s, 1 H); MS (ESI$^+$) m/z 415 (M+H)$^+$; Anal. Calculated C$_{20}$H$_{25}$F$_3$N$_2$O$_2$S: C, 57.95; H, 6.08; N, 6.76. Found: C, 57.82; H, 5.92; N, 7.07.

Example 128

N-[(5Z)-2-tert-butyl-4-(3-cyanopropyl)isothiazol-5 (2H)-ylidene]-5-chloro-N'-cyano-2-methoxybenzen-ecarboximidamide Example 128A ethyl [(5Z)-2-tert-butyl-4-(3-cyanopropyl)isothiazol-5(2H)-ylidene]carbamate Example 30A, 2-methylpropan-2-amine (Aldrich), O-ethyl carbonisothiocyanatidate (Aldrich) and iodine (EMD chemicals) were processed using the method described in Example 110A to afford the title compound. MS (ESL') m/z 296 (M+H)$^+$.

Example 128B 4-(2-tert-butyl-5-imino-2,5-dihydroisothiazol-4-yl) butanenitrile

Example 128A and iodotrimethylsilane (Aldrich) were processed using the method described in Example 110B to afford the title compound. MS (ESI+) m/z 224 (M+H)$^+$.

Example 128C

Ethyl 5-chloro-2-methoxybenzimidate hydrochloride

A cooled solution of 5-chloro-2-methoxybenzonitrile (9.3 g, 0.056 mol, Maybridge) and ethanol (16.2 mL, 0.28 mol) in CH$_2$Cl$_2$ (40 mL) was bubbled with HCl gas at 0° C. for 30 min. The reaction mixture was kept in refrigerator for 5 days. The reaction mixture was then concentrated and triturated with diethyl ether to remove unreacted starting material. The precipitate was dried under reduced pressure to obtain 7.1 g (51%) of the title compound. MS (ESI+) m/z 214 (M+H)$^+$.

Example 128D ethyl 5-chloro-N-cyano-2-methoxybenzimidate

A solution of ethyl 5-chloro-2-methoxybenzimidate (1.3 g, 6.2 mmol, obtained after aqueous bicarbonate wash of Example 128C) in MeCN (2 mL) was added to a solution of sodium phosphate monobasic monohydrate (3.4 g, 24.7 mmol), sodium phosphate dibasic heptahydrate (3.3 g, 12.4 mmol) and cyanamide (0.52 g, 12.4 mmol) in water (20 mL). The reaction mixture was stirred at room temperature overnight and then extracted with dichloromethane (3×15 mL). The combined organic extracts were dried (Na$_2$SO$_4$), filtered and concentrated. The residue contained about 30% of starting material. The residue was reprocessed with half the amounts of the reagents to drive the reaction to completion and that yielded 1.32 g (90%) of the title compound. MS (ESI+) m/z 239 (M+H)$^+$.

Example 128E

N-[(5Z)-2-tert-butyl-4-(3-cyanopropyl)isothiazol-5 (2H)-ylidene]-5-chloro-N'-cyano-2-methoxybenzen-ecarboximidamide A mixture of Example 128B (0.2 g, 0.9 mmol, crude), Example 128D (0.25 g, 1.0 mmol), and triethylamine (0.25 mL, 1.8 mmol) in ethanol (1 mL) was heated in a 20 mL scintillation vial at 80° C. for 2 hr. The reaction mixture was cooled to room temperature, concentrated and then diluted with saturated NaHCO$_3$ (10 mL). The aqueous layer was extracted with ethyl acetate (3×15 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 115 mg (15%) of the title compound. $^1$H NMR (300 MHz, DMSO-d$_6$) δ ppm 1.67 (s, 9 H), 1.83-2.07 (m, 2 H), 2.49-2.58 (m, 2 H), 2.77-2.90 (m, 2 H), 3.82 (s, 3 H), 7.22 (d, J=8.8 Hz, 1 H), 7.38 (d, J=2.7 Hz, 1 H), 7.54 (dd, J=8.8, 2.7 Hz, 1 H), 8.92 (s, 1 H); MS (ESI+) m/z 416 (M+H)$^+$; Anal. Calculated C$_{20}$H$_{22}$ClN$_5$OS: C, 57.75; H, 5.33; N, 16.84. Found: C, 57.59; H, 5.13; N, 16.38.

Example 129

N-[(5Z)-4-butyl-2-tert-butylisothiazol-5(2H)-ylidene]-5-cyano-2-hydroxybenzamide The title compound was obtained as a byproduct from Example 130B. $^1$H NMR (300 MHz, DMSO-d$_6$) δ ppm 0.83-1.11 (m, 3 H), 1.22-1.51 (m, 2 H), 1.56-1.74 (m, 2 H), 1.66 (s, 9 H), 2.63-2.79 (m, 2 H), 7.08 (d, J=8.8 Hz, 1 H), 7.82 (dd, J=8.6, 2.2 Hz, 1 H), 8.24 (d, J=2.4 Hz, 1 H), 8.87 (s, 1 H), 14.99 (s, 1 H); MS (ESI$^+$) m/z 358 (M+H)$^+$.

Example 130

N-[(5Z)-4-butyl-2-tert-butylisothiazol-5(2H)-ylidene]-5-cyano-2-(2,2,2-trifluoroethoxy)benzamide Example 130A 5-cyano-2-(2,2,2-trifluoroethoxy)benzoic acid To a refluxing mixture of acetone (20 mL), methyl 5-cyano-2-hydroxybenzoate (2.0 g, 11.3 mmol, Astatech) and potassium carbonate (3.1 g, 22.6 mmol) in a 40 mL sealed vial was added dropwise 2,2,2-trifluoroethyl trifluoromethane-sulfonate (3.9 g, 16.9 mmol, TCI). The mixture was stirred at reflux overnight and then concentrated under reduced pressure. The residue was dissolved in water (50 mL) and dichloromethane (50 mL). The layers were separated and the aqueous layer was extracted with dichloromethane (3×50 mL). The combined organic extracts were dried (Na$_2$SO$_4$), filtered and concentrated to afford 1.8 g of crude methyl 5-cyano-2-(2,2,2-trifluoroethoxy)benzoate that was suspended in methanol/water (1:1, 100 mL) and treated with an aqueous solution of 5N sodium hydroxide (2.8 mL, 13.9 mmol). After stirring at 40° C. for 16 h, the reaction mixture was concentrated and then washed with methylene chloride. The aqueous layer was acidified to pH-2 with aqueous 2N HCl solution to precipitate the product. The precipitate was filtered and dried under reduced pressure to afford 1.1 g of a product mixture of the title compound with unreacted 5-cyano-2-hydroxybenzoic acid (5:2 ratio). MS (ESI+) m/z 263 (M+NH$_4$)+.

Example 130B

N-[(5Z)-4-butyl-2-tert-butylisothiazol-5(2H)-ylidene]-5-cyano-2-(2,2,2-trifluoroethoxy)benzamide Example 130A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.91 (t, 3 H), 1.20-1.47 (m, 2 H), 1.53-1.72 (m, 2 H), 1.63 (s, 9 H), 2.57-2.85 (m, 2 H), 4.94 (q, J=8.9 Hz, 2 H), 7.40 (d, J=8.7 Hz, 1 H), 7.97 (dd, J=8.7, 2.4 Hz, 1 H), 8.17 (d, J=2.0 Hz, 1 H), 8.67 (s, 1 H); MS (ESI+) m/z 440 (M+H)+.

Example 131

N-[(5Z)-2-tert-butyl-4-(3-cyanopropyl)isothiazol-5(2H)-ylidene]-5-cyano-2-(2,2,2-trifluoroethoxy)benzamide Example 128B, Example 130A, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.90-2.04 (m, 2 H), 2.52-2.57 (m, 2 H), 2.76-2.87 (m, 2 H), 4.94 (q, J=8.8 Hz, 2 H), 7.40 (d, J=8.8 Hz, 1 H), 7.97 (dd, J=8.6, 2.2 Hz, 1 H), 8.21 (d, J=2.0 Hz, 1 H), 8.71 (s, 1 H); MS (ESI+) m/z 451 (M+H)+; Anal. Calculated C$_{21}$H$_{21}$F$_3$N$_4$O$_2$S: C, 55.99; H, 4.70; N, 12.44. Found: C, 56.15; H, 4.83; N, 12.25.

Example 132

N-[(5Z)-2-tert-butyl-4-(3-cyanopropyl)isothiazol-5(2H)-ylidene]-5-cyano-2-hydroxybenzamide The title compound was obtained as byproduct for Example 131. $^1$H NMR (300 MHz, DMSO-d$_6$) δ ppm 1.67 (s, 9 H), 1.92-2.12 (m, 2 H), 2.58 (t, J=7.1 Hz, 2 H), 2.77-2.91 (m, 2 H), 7.09 (d, J=8.8 Hz, 1 H), 7.82 (dd, J=8.6, 2.2 Hz, 1 H), 8.26 (d, J=2.0 Hz, 1 H), 8.88 (s, 1 H), 14.75 (s, 1 H); MS (ESI+) m/z 369 (M+H)+; Anal. Calculated C$_{19}$H$_{20}$N$_4$O$_2$S: C, 61.94; H, 5.47; N, 15.21. Found: C, 61.49; H, 5.40; N, 14.87.

Example 133

N-[(5Z)-2-tert-butyl-4-(3-cyanopropyl)isothiazol-5(2H)-ylidene]-5-chloro-2-(2,2,2-trifluoroethoxy)benzamide Example 133A 5-chloro-2-(2,2,2-trifluoroethoxy)benzoic acid Commercially available, methyl 5-chloro-2-hydroxybenzoate (Maybridge), potassium carbonate, 2,2,2-trifluoroethyl trifluoromethanesulfonate (TCI) and sodium hydroxide were processed according to the method of Example 130A to obtain the title compound. MS (ESI+) m/z 253 (M–H)'.

Example 133B

N-[(5Z)-2-tert-butyl-4-(3-cyanopropyl)isothiazol-5(2H)-ylidene]-5-chloro-2-(2,2,2-trifluoroethoxy)benzamide Example 128B, Example 133A, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.90-2.14 (m, 2 H), 2.50-2.61 (m, 2 H), 2.76-2.91 (m, 2 H), 4.79 (q, J=9.0 Hz, 2 H), 7.25 (d, J=8.8 Hz, 1 H), 7.53 (dd, J=9.0, 2.9 Hz, 1 H), 7.85 (s, 1 H), 8.70 (s, 1 H); MS (ESI+) m/z 460 (M+H)+; Anal. Calculated C$_{20}$H$_{21}$ClF$_3$N$_3$O$_2$S: C, 52.23; H, 4.60; N, 9.14. Found: C, 51.97; H, 4.32; N, 8.74.

Example 134

N-[(5Z)-2-tert-butyl-4-(3-cyanopropyl)isothiazol-5(2H)-ylidene]-2-methoxy-5-(trifluoromethyl)benzamide Example 128B, 2-methoxy-5-(trifluoromethyl)benzoic acid (JRD fluorochemicals), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.92-2.07 (m, 2 H), 2.55 (t, J=7.1 Hz, 2 H), 2.77-2.89 (m, 2 H), 3.79-3.95 (m, 3 H), 7.30 (d, J=8.5 Hz, 1 H), 7.80 (dd, J=9.0, 2.9 Hz, 1 H), 8.07 (d, J=2.0 Hz, 1 H), 8.69 (s, 1 H); MS (ESI+) m/z 426 (M+H)+; Anal. Calculated C$_{20}$H$_{22}$F$_3$N$_3$O$_2$S: C, 56.46; H, 5.21; N, 9.88. Found: C, 56.26; H, 5.15; N, 9.78.

Example 135

N-[(5Z)-4-butyl-2-tert-butylisothiazol-5(2H)-ylidene]-5-chloro-2-hydroxybenzamide Example 110B, 5-chloro-2-hydroxybenzoic acid (Aldrich), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.85-1.02 (m, 3 H), 1.26-1.49 (m, 2 H), 1.57-1.71 (m, 2 H), 1.65 (s, 9 H), 2.64-2.81 (m, 2 H), 6.96 (d, J=8.8 Hz, 1 H), 7.42 (dd, J=8.8, 2.7 Hz, 1 H), 7.84 (d, J=3.1 Hz, 1 H), 8.83 (s, 1 H), 13.92 (s, 1 H); LCMS (ESI+) m/z 367 (M+H)+.

Example 136

N-[(5Z)-2-tert-butyl-4-(cyclopentylmethyl)isothiazol-5(2H)-ylidene]-5-chloro-2-methoxybenzamide Example 136A 3-cyclopentylpropanal To CH$_2$Cl$_2$ (100 mL) at –78° C. were added oxalyl chloride (4.1 mL, 46.8 mmol, Aldrich) and dry DMSO (5.5 mL, 78.0 mmol, Aldrich), dropwise. After 5 min, 3-cyclopentylpropan-1-ol (5.0 g, 39.0 mmol, Aldrich) in 5 mL of CH$_2$Cl$_2$ was added. The mixture was stirred for an additional 0.5 hr at –78°

C., and triethylamine (27.2 mL, 195.0 mmol) was added. The mixture was then allowed to warm to room temperature over 0.5 hr. After stirring for 3 hr, 100 mL of water was added. The phases were separated, and the aqueous phase was extracted with diethyl ether (3×100 mL). The combined organic extracts were washed successively with 50 mL of aqueous 1% HCl, 50 mL of water, 50 mL of aqueous 5% NaHCO$_3$ and 50 mL of saturated aqueous NaCl. The organic layer was dried (MgSO$_4$), filtered and concentrated to provide 4.1 g (83%) of the title compound. MS (ESI$^+$) m/z 144 (M+NH$_4$)$^+$.

Example 136B

N-[(5Z)-2-tert-butyl-4-(cyclopentylmethyl)isothiazol-5(2H)-ylidene]-5-chloro-2-methoxybenzamide Example 136A, 2-methylpropan-2-amine (Aldrich), Example 1C and iodine were processed using the method described in Example 110A to afford the title compound. $^1$H NMR (300 MHz, DMSO-d$_6$) δ ppm 1.13-1.36 (m, 2 H), 1.43-1.57 (m, 2 H), 1.53-1.71 (m, 2 H), 1.62 (s, 9 H), 2.17-2.38 (m, 1 H), 2.69 (d, J=7.5 Hz, 2 H), 3.79 (s, 3 H), 7.13 (d, J=8.7 Hz, 1 H), 7.47 (dd, J=8.9, 3.0 Hz, 1 H), 7.72 (d, J=2.8 Hz, 1 H), 8.64 (s, 1 H); MS (ESI$^+$) m/z 407 (M+H)$^+$; Anal. Calculated C$_{21}$H$_{27}$ClN$_2$O$_2$S: C, 61.98; H, 6.69; N, 6.88. Found: C, 61.55; H, 6.46; N, 6.88.

Example 137

N-[(5Z)-2-tert-butyl-4-(3-cyano-3-methylbutyl)isothiazol-5(2H)-ylidene]-5-chloro-2-methoxybenzamide Example 137A 2,2-dimethyl-6-oxohexanenitrile To a suspension of trimethylamine oxide (1.5 g, 19.6 mmol, Aldrich) in DMSO (10 mL) was added 6-bromo-2,2-dimethylhexanenitrile (0.84 mL, 4.9 mmol, Aldrich). After stirring at room temperature overnight, the reaction mixture was quenched with water (10 mL) and extracted with hexanes (4×10 mL). The combined organic extracts were washed with brine (20 mL), dried (NaSO$_4$), filtered and concentrated to afford 0.65 g (80% pure) of the title compound. MS (ESI+) m/z 157 (M+NH$_4$)$^+$.

Example 137B

N-[(5Z)-2-tert-butyl-4-(3-cyano-3-methylbutyl)isothiazol-5(2H)-ylidene]-5-chloro-2-methoxybenzamide Example 137A, 2-methylpropan-2-amine (Aldrich), Example 1C and iodine were processed using the method described in Example 110A to afford the title compound. $^1$H NMR (300 MHz, DMSO-d$_6$) δ ppm 1.39 (s, 6 H), 1.62 (s, 9 H), 1.88-2.06 (m, 2 H), 2.80-2.91 (m, 2 H), 3.81 (s, 3 H), 7.14 (d, J=8.9 Hz, 1 H), 7.47 (dd, J=8.9, 2.8 Hz, 1 H), 7.84 (d, J=2.8 Hz, 1 H), 8.71 (s, 1 H); MS (ESI$^+$) m/z 420 (M+H)$^+$.

Example 138

N-[(5Z)-2-tert-butyl-4-(4-cyanobutyl)isothiazol-5(2H)-ylidene]-5-chloro-2-methoxybenzamide Example 138A 7-oxoheptanenitrile 7-bromoheptanenitrile and trimethylamine oxide were processed using the method described in Example 137A to afford the title compound. MS (ESI$^+$) m/z 143 (M+NH$_4$)$^+$.

Example 138B

N-[(5Z)-2-tert-butyl-4-(4-cyanobutyl)isothiazol-5(2H)-ylidene]-5-chloro-2-methoxybenzamide Example 138A, 2-methylpropan-2-amine (Aldrich), Example 1C and iodine were processed using the method described in Example 110A to afford the title compound. $^1$H NMR (300 MHz, DMSO-d$_6$) δ ppm 1.52-1.61 (m, 2 H), 1.62 (s, 9 H), 1.71-1.89 (m, 2 H), 2.55 (t, J=7.1 Hz, 2 H), 2.74 (t, J=7.4 Hz, 2 H), 3.80 (s, 3 H), 7.13 (d, J=8.9 Hz, 1 H), 7.47 (dd, J=8.9, 2.8 Hz, 1 H), 7.74 (d, J=2.8 Hz, 1 H), 8.65 (s, 1 H); MS (ESI$^+$) m/z 406 (M+H)$^+$.

Example 139

N-[(5Z)-4-butyl-2-tert-butylisothiazol-5(2H)-ylidene]-5-chloro-2-(2-fluoroethoxy)benzamide Example 139A 5-chloro-2-(2-fluoroethoxy)benzoic acid The title compound was obtained from 5-chloro-2-hydroxybenzoic acid (Aldrich) using the method described in Journal of Labelled Compounds & Radiopharmaceuticals (2001), 44(2), 127-139. MS (ESI$^+$) m/z 236 (M+NH$_4$)$^+$.

Example 139B

N-[(5Z)-4-butyl-2-tert-butylisothiazol-5(2H)-ylidene]-5-chloro-2-(2-fluoroethoxy)benzamide Example 139A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.80-1.00 (m, 3 H), 1.16-1.43 (m, 2 H), 1.52-1.72 (m, 2 H), 1.62 (s, 9 H), 2.62-2.84 (m, 2 H), 4.20-4.29 (m, 1 H), 4.30-4.41 (m, 1 H), 4.60-4.67 (m, 1 H), 4.75-4.83 (m, 1 H), 7.16 (d, J=8.7 Hz, 1 H), 7.47 (dd, J=8.7, 2.8 Hz, 1 H), 7.76 (d, J=2.8 Hz, 1 H), 8.63 (s, 1 H); MS (ESI$^+$) m/z 413 (M+H)$^+$; Anal. Calculated C$_{20}$H$_{26}$ClFN$_2$O$_2$S: C, 58.17; H, 6.35; N, 6.78. Found: C, 58.10; H, 6.24; N, 6.75.

Example 140

2-(2-amino-2-oxoethoxy)-N-[(5Z)-4-butyl-2-tert-butylisothiazol-5(2H)-ylidene]-5-chlorobenzamide Example 140A 2-(2-amino-2-oxoethoxy)-5-chlorobenzoic acid Commercially available, methyl 5-chloro-2-hydroxybenzoate (Maybridge), potassium carbonate, 2-chloroacetoni-

Example 140B 2-(2-amino-2-oxoethoxy)-N-[(5Z)-4-butyl-2-tert-butylisothiazol-5(2H)-ylidene]-5-chlorobenzamide Example 140A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 0.80-1.02 (m, 3 H), 1.21-1.44 (m, 2 H), 1.54-1.74 (m, 2 H), 1.63 (s, 9 H), 2.62-2.80 (m, 2 H), 4.59 (s, 2 H), 7.22 (d, J=8.8 Hz, 1 H), 7.50 (dd, J=8.8, 2.7 Hz, 1 H), 7.59 (s, 1 H), 7.88 (d, J=2.7 Hz, 1 H), 8.22 (s, 1 H), 8.68 (s, 1 H); MS (ESI$^+$) m/z 424 (M+H)$^+$.

Example 141

2-(2-amino-2-oxoethoxy)-N-[(5Z)-2-tert-butyl-4-(3-cyanopropyl)isothiazol-5(2H)-ylidene]-5-chlorobenzamide Example 140A, Example 128B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 1.63 (s, 9 H), 1.91-2.09 (m, 2 H), 2.54 (t, J=7.1 Hz, 2 H), 2.77-2.91 (m, 2 H), 4.59 (s, 2 H), 7.22 (d, J=8.8 Hz, 1 H), 7.51 (dd, J=9.0, 2.9 Hz, 1 H), 7.61 (s, 1 H), 7.90 (d, J=2.7 Hz, 1 H), 8.17 (s, 1 H), 8.73 (s, 1 H); LC/MS (ESI+) m/z 435 (M+H)$^+$.

Example 142

N-[(5Z)-2-tert-butyl-4-(4,4,4-trifluorobutyl)isothiazol-5(2H)-ylidene]-5-chloro-2-methoxybenzamide

Example 142A 6,6,6-trifluorohexanal

Commercially available 6-bromo-1,1,1-trifluorohexane (Oakwood) and trimethylamine oxide were processed using the method described in example 137A to afford the title compound. MS (ESI+) m/z 154 (M+NH$_4$—H$_2$O)$^+$.

Example 142B

N-[(5Z)-2-tert-butyl-4-(4,4,4-trifluorobutyl)isothiazol-5(2H)-ylidene]-5-chloro-2-methoxybenzamide Example 142A, 2-methylpropan-2-amine (Aldrich), Example 1C and iodine were processed using the method described in Example 110A to afford the title compound. $^1$H NMR (300 MHz, DMSO-$d_6$) δ ppm 1.62 (s, 9 H), 1.81-2.06 (m, 2 H), 2.19-2.43 (m, 2 H), 2.79 (t, J=7.5 Hz, 2 H), 3.79 (s, 3 H), 7.13 (d, J=9.1 Hz, 1 H), 7.47 (dd, J=8.7, 2.8 Hz, 1 H), 7.75 (d, J=2.8 Hz, 1 H), 8.67 (s, 1 H); MS (ESI$^+$) m/z 435 (M+H)$^+$; Anal. Calculated C$_{19}$H$_{22}$ClF$_3$N$_2$O$_2$S: C, 52.47; H, 5.10; N, 6.44. Found: C, 52.35; H, 5.02; N, 6.44.

Example 143

N-[(5Z)-2-tert-butyl-4-isobutylisothiazol-5(2H)-ylidene]-2-methoxy-5-(trifluoromethyl)benzamide

Example 143A 4-methylpentanal

Commercially available 4-methylpentan-1-ol, oxalyl chloride, DMSO, and triethylamine were processed using the method described in Example 136A to afford the title compound. MS (ESI+) m/z 100 (M+NH$_4$—H$_2$O)$^+$.

Example 143B ethyl [(5Z)-2-tert-butyl-4-(2-methylpropyl)isothiazol-5(2H)-ylidene]carbamate Example 143A, 2-methylpropan-2-amine (Aldrich), O-ethyl carbonisothiocyanatidate (Aldrich) and iodine (EMD chemicals) were processed using the method described in Example 110A to afford the title compound. MS (ESI+) m/z 285 (M+H)$^+$.

Example 143C 2-tert-butyl-4-isobutylisothiazol-5(2H)-imine

Example 143B and iodotrimethylsilane (Aldrich) were processed using the method described in Example 110B to afford the title compound. MS (ESI$^+$) m/z 213 (M+H)$^+$.

Example 143D

N-[(5Z)-2-tert-butyl-4-isobutylisothiazol-5(2H)-ylidene]-2-methoxy-5-(trifluoromethyl)benzamide Example 143C, 2-methoxy-5-(trifluoromethyl)benzoic acid (JRD fluorochemicals), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 0.89 (d, J=6.3 Hz, 6 H), 1.63 (s, 9 H), 1.94-2.16 (m, 1 H), 2.59 (d, J=7.1 Hz, 2 H), 3.88 (s, 3 H), 7.30 (d, J=8.7 Hz, 1 H), 7.79 (dd, J=9.1, 2.0 Hz, 1 H), 8.06 (d, J=2.4 Hz, 1 H), 8.63 (s, 1 H); MS (ESI+) m/z 415 (M+H)$^+$; Anal. Calculated C$_{20}$H$_{25}$F$_3$N$_2$O$_2$S: C, 57.95; H, 6.08; N, 6.76. Found: C, 58.04; H, 6.09; N, 6.79.

Example 144

N-[(5Z)-2-tert-butyl-4-isobutylisothiazol-5(2H)-ylidene]-5-chloro-2-(2-fluoroethoxy)benzamide Example 143C, Example 139A, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 0.89 (d, J=6.7 Hz, 6 H), 1.63 (s, 9 H), 1.81-2.17 (m, 1 H), 2.60 (d, J=7.1 Hz, 2 H), 4.16-4.29 (m, 1 H), 4.31-4.45 (m, 1 H), 4.59-4.69 (m, 1 H), 4.75-4.87 (m, 1 H), 7.16 (d, J=8.7

Hz, 1 H), 7.47 (dd, J=8.7, 2.8 Hz, 1 H), 7.75 (d, J=2.8 Hz, 1 H), 8.62 (s, 1 H); MS (ESI$^+$) m/z 413 (M+H)$^+$; Anal. Calculated C$_{20}$H$_{26}$ClFN$_2$O$_2$S: C, 58.17; H, 6.35; N, 6.78. Found: C, 58.21; H, 6.44; N, 6.80.

Example 145

N-[(5Z)-2-tert-butyl-4-isobutylisothiazol-5(2H)-ylidene]-5-cyano-2-methoxybenzamide Example 143C, Example 26B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.89 (d, J=6.3 Hz, 6 H), 1.63 (s, 9 H), 1.91-2.19 (m, 1 H), 2.59 (d, J=7.1 Hz, 2 H), 3.88 (s, 3 H), 7.29 (d, J=8.7 Hz, 1 H), 7.91 (dd, J=8.7, 2.4 Hz, 1 H), 8.08 (d, J=2.4 Hz, 1 H), 8.64 (s, 1 H); MS (ESI$^+$) m/z 372 (M+H)$^+$; Anal. Calculated C$_{20}$H$_{25}$N$_3$O$_2$S: C, 64.66; H, 6.78; N, 11.31. Found: C, 64.64; H, 6.62; N, 11.18.

Example 146

N-[(5Z)-2-tert-butyl-4-isobutylisothiazol-5(2H)-ylidene]-2-ethoxy-5-(trifluoromethyl)benzamide

Example 146A ethyl 2-fluoro-5-(trifluoromethyl)benzoate

To a solution of 2-fluoro-5-(trifluoromethyl)benzoyl chloride (5.0 g, 22.0 mmol) in THF (25 mL) was added Et$_3$N (3.1 mL, 22.0 mmol) followed by EtOH (1.3 mL, 22.0 mmol). This mixture was stirred at ambient temperature for 1 h and quenched with saturated, aqueous NH$_4$Cl (10 mL). The layers were separated and the aqueous layer was extracted with 3×10 mL EtOAc and the combined organics were dried over anhydrous Na$_2$SO$_4$, filtered and concentrated under reduced pressure. The crude material was purified by column chromatography (SiO$_2$, 60% hexanes in EtOAc) to give the title compound (4.8 g, 20.3 mmol, 92% yield). $^1$H NMR (300 MHz, CDCl$_3$) δ ppm 1.42 (t, J=7.1 Hz, 3 H), 4.43 (q, J=7.1 Hz, 2 H), 7.23-7.34 (m, 1 H), 7.74-7.82 (m, 1 H), 8.23 (dd, J=6.3, 2.4 Hz, 1 H).

Example 146B ethyl 2-ethoxy-5-(trifluoromethyl)benzoate

To EtOH (2.5 mL, 42.7 mmol) in 25 mL THF was added KOt-Bu (4.6 g, 40.6 mmol). The mixture stirred at ambient temperature for 20 min then Example 146A in 25 mL THF was added via cannula. The mixture stirred for 1 h at ambient temperature then was quenched with saturated, aqueous NH$_4$Cl. The layers were separated the aqueous layer was extracted with 3×10 mL EtOAc. The combined organics were dried over Na$_2$SO$_4$, filtered and concentrated under reduced pressure. Purification via column chromatography (SiO$_2$, 60% hexanes in EtOAc then 100% EtOAc) gave the title compound. MS (DCI/NH$_3$) m/z 263 (M+H)$^+$.

Example 146C 2-ethoxy-5-(trifluoromethyl)benzoic acid

To a solution of Example 146B (1.63 g, 6.2 mmol) in EtOH (50 mL) was added 40% aqueous KOH (5.81 g, 31.1 mmol). The mixture was allowed to stir for 1 h then was partially concentrated under reduced pressure. The material was diluted with 20 mL EtOAc and the solution was acidified with 10% aqueous HCl. The layers were separated and the aqueous layer was extracted with EtOAc (3×20 mL). The combined organics were dried over Na$_2$SO$_4$, filtered and concentrated under reduced pressure to give the title compound (1.39 g, 5.94 mmol, 95% yield). MS (DCI/NH$_3$) m/z 252 (M+NH$_4$)$^+$.

Example 146D

N-[(5Z)-2-tert-butyl-4-isobutylisothiazol-5(2H)-ylidene]-2-ethoxy-5-(trifluoromethyl)benzamide Example 143C, Example 146C, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.89 (d, J=6.3 Hz, 6 H), 1.35 (t, J=6.9 Hz, 3 H), 1.63 (s, 9 H), 1.94-2.19 (m, 1 H), 2.60 (d, J=7.1 Hz, 2 H), 4.18 (q, J=6.9 Hz, 2 H), 7.29 (d, J=8.7 Hz, 1 H), 7.76 (dd, J=9.1, 2.4 Hz, 1 H), 8.04 (d, J=2.4 Hz, 1 H), 8.63 (s, 1 H); MS (ESI$^+$) m/z 429 (M+H)$^+$; Anal. Calculated C$_{20}$H$_{27}$F$_3$N$_2$O$_2$S: C, 58.86; H, 6.35; N, 6.54. Found: C, 59.01; H, 6.38; N, 6.58.

Example 147

N-[(5Z)-2-tert-butyl-4-pentylisothiazol-5(2H)-ylidene]-5-chloro-2-methoxybenzamide Commercially available heptanal (Aldrich), 2-methylpropan-2-amine (Aldrich), Example 1C and iodine were processed using the method described in Example 110A to afford the title compound. $^1$H NMR (300 MHz, DMSO-d$_6$) δ ppm 0.80-0.98 (m, 3 H), 1.17-1.49 (m, 4 H), 1.62 (s, 9 H), 1.63-1.72 (m, 2 H), 2.62-2.89 (m, 2 H), 3.79 (s, 3 H), 7.13 (d, J=8.7 Hz, 1 H), 7.47 (dd, J=8.7, 2.8 Hz, 1 H), 7.75 (d, J=2.8 Hz, 1 H), 8.63 (s, 1 H); MS (ESI$^+$) m/z 395 (M+H)$^+$; Anal. Calculated C$_{20}$H$_{27}$ClN$_2$O$_2$S: C, 60.82; H, 6.89; N, 7.09. Found: C, 60.67; H, 6.96; N, 7.03.

Example 148

N-[(5Z)-2-tert-butyl-4-(4-fluorobutyl)isothiazol-5(2H)-ylidene]-5-chloro-2-methoxybenzamide

Example 148A 6-fluorohexanal

Commercially available, 1-bromo-6-fluorohexane (Narchem) and trimethylamine oxide were processed using the method described in example 137A to afford the title compound. MS (ESI+) m/z 136 (M+NH$_4$)$^+$.

Example 148B ethyl [(5Z)-2-tert-butyl-4-(4-fluorobutyl)isothiazol-5(2H)-ylidene]carbamate Example 148A, 2-methylpropan-2-amine (Aldrich), O-ethyl carbonisothiocyanatidate (Aldrich) and iodine were processed using the method described in Example 110A to afford the title compound. MS (ESI+) m/z 303 (M+H)$^+$.

Example 148C 2-tert-butyl-4-(4-fluorobutyl)isothiazol-5(2H)-imine

Example 148B and iodotrimethylsilane (Aldrich) were processed using the method described in Example 110B to afford the title compound. MS (ESI$^+$) m/z 231 (M+H)$^+$.

Example 148D

N-[(5Z)-2-tert-butyl-4-(4-fluorobutyl)isothiazol-5 (2H)-ylidene]-5-chloro-2-methoxybenzamide Example 148C, 5-chloro-2-methoxybenzoic acid (Aldrich), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.62 (s, 9 H), 1.68-1.86 (m, 4 H), 2.74 (t, J=7.3 Hz, 2 H), 3.79 (s, 3 H), 4.41 (t, J=5.9 Hz, 1 H), 4.50-4.64 (m, 1 H), 7.13 (d, J=9.1 Hz, 1 H), 7.47 (dd, J=8.7, 2.8 Hz, 1 H), 7.74 (d, J=2.8 Hz, 1 H), 8.65 (s, 1 H); MS (ESI+) m/z 399 (M+H)$^+$; Anal. Calculated C$_{19}$H$_{24}$ClFN$_2$O$_2$S: C, 57.20; H, 6.06; N, 7.02. Found: C, 57.12; H, 6.11; N, 7.06.

Example 149

N-[(5Z)-2-tert-butyl-4-(4-fluorobutyl)isothiazol-5 (2H)-ylidene]-2-methoxy-5-(trifluoromethyl)benzamide Example 148C, 2-methoxy-5-(trifluoromethyl)benzoic acid (JRD Fluorochemicals Ltd), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.66-1.87 (m, 4 H), 2.75 (t, J=7.3 Hz, 2 H), 3.88 (s, 3 H), 4.41 (t, J=5.9 Hz, 1 H), 4.51-4.67 (m, 1 H), 7.30 (d, J=8.5 Hz, 1 H), 7.79 (dd, J=8.5, 3.1 Hz, 1 H), 8.07 (d, J=2.0 Hz, 1 H), 8.67 (s, 1 H); MS (ESI$^+$) m/z 433 (M+H)$^+$; Anal. Calculated C$_{20}$H$_{24}$F$_4$N$_2$O$_2$S: C, 55.54; H, 5.59; N, 6.48. Found: C, 55.87; H, 5.61; N, 6.49.

Example 150

N-[(5Z)-4-butyl-2-tert-butylisothiazol-5(2H)-ylidene]-5-chloro-2-[2-(dimethylamino)-2-oxoethoxy]benzamide To a mixture of 3-pentanone (10 mL), potassium carbonate (0.28 g, 2.0 mmol) and Example 135 (0.25 g, 0.7 mmol) was added dropwise 2-chloro-N,N-dimethylacetamide (0.25 g, 2.0 mmol, Fluka). After refluxing for 36 hr, the reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 50 mg (16%) of the title compound. $^1$H NMR (300 MHz, DMSO-d$_6$) δ ppm 0.92 (t, J=7.3 Hz, 3 H), 1.33 (t, 2 H), 1.62 (s, 9 H), 1.63-1.71 (m, 2 H), 2.66-2.76 (m, 2 H), 2.83 (s, 3 H), 3.00 (s, 3 H), 4.87 (s, 2 H), 6.98 (d, J=9.2 Hz, 1 H), 7.42 (dd, J=9.0, 2.9 Hz, 1 H), 7.76 (d, J=3.1 Hz, 1 H), 8.62 (s, 1 H); MS (ESI$^+$) m/z 452 (M+H)$^+$; Anal. Calculated C$_{22}$H$_{30}$ClN$_3$O$_3$S: C, 58.46; H, 6.69; N, 9.30. Found: C, 58.41; H, 6.83; N, 9.26.

Example 151

N-[(5Z)-4-butyl-2-(2,2,2-trifluoro-1,1-dimethylethyl) isothiazol-5(2H)-ylidene]-5-chloro-2-methoxybenzamide

Example 151A ethyl [(5Z)-4-butyl-2-(2,2,2-trifluoro-1,1-dimethylethyl)isothiazol-5(2H)-ylidene]carbamate Commercially available hexanal (Aldrich), 1,1,1-trifluoro-2-methylpropan-2-amine (Chemcollect), O-ethyl carbonisothiocyanatidate (Aldrich) and iodine were processed using the method described in Example 110A to afford the title compound. MS (ESI$^+$) m/z 339 (M+H)$^+$.

Example 151B 4-butyl-2-(1,1,1-trifluoro-2-methylpropan-2-yl) isothiazol-5(2H)-imine Example 151A and iodotrimethylsilane (Aldrich) were processed using the method described in Example 110B to afford the title compound. MS (ESI$^+$) m/z 267 (M+H)$^+$.

Example 151C

N-[(5Z)-4-butyl-2-(2,2,2-trifluoro-1,1-dimethylethyl) isothiazol-5(2H)-ylidene]-5-chloro-2-methoxybenzamide Example 151B, 5-chloro-2-methoxybenzoic acid (Aldrich), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.76-1.03 (m, 3 H), 1.14-1.43 (m, 2 H), 1.57-1.76 (m, 2 H), 1.92 (s, 6 H), 2.65-2.85 (m, 2 H), 3.82 (s, 3 H), 7.16 (d, J=8.7 Hz, 1 H), 7.52 (dd, J=8.9, 3.0 Hz, 1 H), 7.84 (d, J=3.2 Hz, 1 H), 8.77 (s, 1 H); MS (ESI+) m/z 435 (M+H)$^+$; Anal. Calculated C$_{19}$H$_{22}$ClF$_3$N$_2$O$_2$S: C, 52.47; H, 5.10; N, 6.44. Found: C, 52.71; H, 5.18; N, 6.50.

Example 152

N-[(5Z)-4-butyl-2-(2-fluoro-1,1-dimethylethyl) isothiazol-5(2H)-ylidene]-2-methoxy-5-(trifluoromethyl)benzamide

Example 152A 1-fluoro-N-hexylidene-2-methylpropan-2-amine

To a suspension of 1-fluoro-2-methylpropan-2-amine hydrochloride (ABCR) (2 g, 15.7 mmol), anhydrous magnesium sulfate (3.77 g, 31.4 mmol) and potassium carbonate (2.17 g, 15.68 mmol) in dichloromethane (100 mL) was added drop wise hexanal (1.93 mL, 15.7 mmol) at 0° C. The reaction mixture was stirred for 10 h at room temperature, then filtered and concentrated to obtain the title compound as a pale yellow liquid.

Example 152B ethyl [(5Z)-4-butyl-2-(2-fluoro-1,1-dimethylethyl) isothiazol-5(2H)-ylidene]carbamate Example 152A, O-ethyl carbonisothiocyanatidate (Aldrich) and iodine were processed using the method described in Example 1D to afford the title compound. The product was purified by column chromatography using an Analogix® Intelliflash280™ (SiO$_2$, 0-50% ethyl acetate in Hexane) to provide the title compound. MS (ESI+) m/z 303 (M+H)$^+$.

Example 152C 4-butyl-2-(1-fluoro-2-methylpropan-2-yl)isothiazol-5(2H)-imine

Example 152B and iodotrimethylsilane (Aldrich) were processed using the method described in Example 110B to afford the title compound. MS (ESI+) m/z 231 (M+H)$^+$.

Example 152D

N-[(5Z)-4-butyl-2-(2-fluoro-1,1-dimethylethyl) isothiazol-5(2H)-ylidene]-2-methoxy-5-(trifluoromethyl)benzamide To a solution of Example 152C (0.46 g, 2.0 mmol) in THF (10 mL) were added 2-methoxy-5-(trifluoromethyl)benzoyl chloride (0.52 g, 2.2 mmol, JRD Fluorochemicals Ltd) and triethylamine (0.84 mL, 6.0 mmol). After stirring at 60° C. for 14 hr, the reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 75 mg of the title compound. $^1$H NMR (300 MHz, DMSO-d$_6$) δ ppm 0.93 (t, J=7.3 Hz, 3 H), 1.22-1.46 (m, 2 H), 1.65 (s, 2 H), 1.65 (s, 6 H), 2.63-2.83 (m, 2 H), 3.89 (s, 3 H), 4.60 (d, J=47.1 Hz, 2 H), 7.31 (d, J=8.8 Hz, 1 H), 7.80 (dd, J=8.6, 2.5 Hz, 1 H), 8.10 (d, J=2.4 Hz, 1 H), 8.63 (s, 1 H); MS (ESI$^+$) m/z 433 (M+H)$^+$; Anal. Calculated C$_{20}$H$_{24}$F$_4$N$_2$O$_2$S: C, 55.54; H, 5.59; N, 6.48. Found: C, 55.75; H, 5.23; N, 6.43.

Example 153

N-[(5Z)-4-butyl-2-tert-butylisothiazol-5(2H)-ylidene]-5-chloro-2-(cyanomethoxy)benzamide To a solution of Example 135 (300 mg, 0.82 mmol) in THF/DMF (1:1, 4 mL) were added sodium hydride (39.2 mg, 0.98 mmol) and 2-bromoacetonitrile (65 μL, 0.98 mmol). The reaction was stirred at 40° C. for 4 hrs and at 80° C. for overnight. The reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 15 mg of the title compound. $^1$H NMR (300 MHz, DMSO-d$_6$) δ ppm 0.93 (t, J=7.3 Hz, 3 H), 1.20-1.48 (m, 2 H), 1.53-1.77 (m, 2 H), 1.63 (s, 9 H), 2.62-2.82 (m, 2 H), 5.22 (s, 2 H), 7.29 (d, J=9.1 Hz, 1 H), 7.58 (dd, J=8.7, 2.8 Hz, 1 H), 7.86 (d, J=2.8 Hz, 1 H), 8.67 (s, 1 H); MS (ESI$^+$) m/z 406 (M+H)$^+$; Anal. Calculated C$_{20}$H$_{24}$ClN$_3$O$_2$S: C, 59.17; H, 5.96; N, 10.35. Found: C, 59.18; H, 5.78; N, 10.37.

Example 154

N-[(5Z)-4-butyl-2-(2-fluoro-1,1-dimethylethyl) isothiazol-5(2H)-ylidene]-5-chloro-2-methoxybenzamide The title compound was prepared using the procedure as described in Example 1D, substituting Example 152A for Example 1A. The product was purified by column chromatography using an Analogix® Intelliflash280™ (SiO$_2$, gradient 0-50% ethyl acetate in hexane) to provide the title compound. $^1$H NMR (400 MHz, CDCl$_3$) δ ppm 0.98 (t, J=7.4 Hz, 3 H), 1.36-1.48 (m, 2 H), 1.71 (s, 6 H), 1.70-1.78 (m, 2 H), 2.70-2.90 (m, 2 H), 3.92 (s, 3 H), 4.44 (d, J=47.3 Hz, 2 H), 6.92 (d, J=8.9 Hz, 1 H), 7.35 (dd, J=8.9, 3.1 Hz, 1 H), 8.00 (s, 1 H), 8.13 (d, J=3.1 Hz, 1 H). MS (ESI$^+$) m/z 399 (M+H)$^+$.

Example 155

N-[(5Z)-4-(benzyloxy)-2-tert-butylisothiazol-5(2H)-ylidene]-5-chloro-2-methoxybenzamide The title compound was prepared according to the procedure of Example 9 by replacing 4-propylcyclohexanone with 2-(benzyloxy)acetaldehyde. $^1$H NMR (300 MHz, DMSO-d$_6$) δ ppm 1.58 (s, 9 H), 3.80 (s, 3 H), 5.28 (s, 2 H), 7.14 (d, J=9.2 Hz, 1 H), 7.31-7.42 (m, 3 H), 7.44-7.54 (m, 3 H), 7.79 (d, J=2.7 Hz, 1 H), 8.73 (s, 1 H); MS (DCI/NH$_3$) m/z 431 (M+H)$^+$. Anal. calculated for C$_{22}$H$_{23}$ClN$_2$O$_3$S: C, 61.32; H, 5.38; N, 6.50. Found: C, 61.09; H, 5.43; N, 6.49.

Example 156

N-[(5Z)-2-tert-butyl-4-(1-methylethoxy)isothiazol-5 (2H)-ylidene]-5-chloro-2-methoxybenzamide

Example 156A

N-[(5Z)-2-tert-butyl-4-hydroxyisothiazol-5(2H)-ylidene]-5-chloro-2-methoxybenzamide A solution of Example 155 (500 mg, 1.16 mmol) in anhydrous CH$_2$Cl$_2$ (20 mL) was treated at 0° C. with triflic acid (1741 mg, 11.6 mmol) for 1 h. A saturated solution of sodium bicarbonate was added and the organic layer was separated, dried with anhydrous MgSO$_4$ and concentrated under reduced pressure to afford 400 mg of crude material, which was used directly without purification in the next reactions. $^1$H NMR (300 MHz, DMSO-d$_6$) δ ppm 1.55-1.71 (m, 9 H), 3.77-3.87 (m, 3 H), 7.18 (d, J=9.1 Hz, 1 H), 7.54 (dd, J=8.9, 2.2 Hz, 1 H), 7.81 (d, J=2.4 Hz, 1 H), 8.65 (s, 1 H); MS (DCI/NH$_3$) m/z 341 (M+H)$^+$.

Example 156B

N-[(5Z)-2-tert-butyl-4-(1-methylethoxy)isothiazol-5 (2H)-ylidene]-5-chloro-2-methoxybenzamide A mixture of product from Step 1 (70 mg, 0.2 mmol), 2-iodopropane (85 mg, 0.5 mmol) and potassium carbonate (42 mg, 0.3 mmol) in DMF (10 mL) was stirred at 50° C. for 12 h. The mixture was then poured into water and extracted with ethyl acetate. The acetate layer was washed with water, brine, dried with MgSO$_4$ and concentrated under reduced pressure. The residue was purified by chromatography (hexane EtOAc 1:1) to afford 49 mg of the title compound. $^1$H NMR (300 MHz, DMSO-d$_6$) δ ppm 1.27 (d, J=6.1 Hz, 6 H), 1.61 (s, 9 H), 3.80 (s, 3 H), 4.62-4.89 (m, 1 H), 7.13 (d, J=8.8 Hz, 1 H), 7.47 (dd, J=8.8, 2.7 Hz, 1 H), 7.75 (d, J=2.7 Hz, 1 H), 8.70 (s, 1 H); MS (DCI/NH$_3$) m/z 383 (M+H)$^+$. Anal. calculated for C$_{18}$H$_{23}$ClN$_2$O$_3$S: C, 56.46; H, 6.05; N, 7.32. Found: C, 57.13; H, 5.95; N, 6.93.

Example 157

N-[(5Z)-2-tert-butyl-4-(1-methylpropoxy)isothiazol-5(2H)-ylidene]-5-chloro-2-methoxybenzamide The title compound was prepared according to the procedure of Example 156B by replacing 2-iodopropane with 2-iodobutane. $^1$H NMR (300 MHz, DMSO-d$_6$) δ ppm 0.99 (t, J=7.5 Hz, 3 H), 1.21 (d, 3 H), 1.49-1.79 (m, 11 H), 3.80 (s, 3 H), 4.46-4.68 (m, J=5.9 Hz, 1 H), 7.13 (d, J=9.1 Hz, 1 H), 7.48 (dd, J=8.7, 2.8 Hz, 1 H), 7.80 (d, J=3.2 Hz, 1 H), 8.69 (s, 1 H); MS (DCI/NH$_3$) m/z 397 (M+H)$^+$.

Example 158

N-[(5Z)-2-tert-butyl-4-(4-fluorobutoxy)isothiazol-5(2H)-ylidene]-5-chloro-2-methoxybenzamide The title compound was prepared according to the procedure of Example 156B by replacing 2-iodopropane with 1-bromo-4-fluorobutane. $^1$H NMR (300 MHz, DMSO-d$_6$) δ ppm 1.53-1.63 (m, 9 H), 1.72-1.93 (m, 4 H), 3.79 (s, 3 H), 4.21 (t, J=6.3 Hz, 2 H), 4.46 (t, J=5.9 Hz, 1 H), 4.62 (t, J=5.9 Hz, 1 H), 7.13 (d, J=8.7 Hz, 1 H), 7.48 (dd, J=8.7, 2.8 Hz, 1 H), 7.76 (d, J=3.2 Hz, 1 H), 8.76 (s, 1 H); MS (DCI/NH$_3$) m/z 415 (M+H)$^+$.

Example 159

N-[(5Z)-2-tert-butyl-4-(cyanomethoxy)isothiazol-5(2H)-ylidene]-5-chloro-2-methoxybenzamide The title compound was prepared according to the procedure of Example 156B by replacing 2-iodopropane with 2-bromoacetonitrile. $^1$H NMR (300 MHz, DMSO-d$_6$) δ ppm 1.62 (s, 9 H), 3.82 (s, 3 H), 5.35 (s, 2 H), 7.15 (d, J=9.2 Hz, 1 H), 7.50 (dd, J=9.0, 2.9 Hz, 1 H), 7.86 (d, J=2.7 Hz, 1 H), 8.93 (s, 1 H); MS (DCI/NH$_3$) m/z 380 (M+H)$^+$.

Example 160

N-[(5Z)-2-tert-butyl-4-{[(2S)-5-oxopyrrolidin-2-yl]methoxy}isothiazol-5(2H)-ylidene]-5-chloro-2-methoxybenzamide The title compound was prepared according to the procedure of Example 156B by replacing 2-iodopropane with (S)-(5-oxopyrrolidin-2-yl)methyl 4-methylbenzenesulfonate. $^1$H NMR (300 MHz, DMSO-d$_6$) δ ppm 1.61 (s, 9 H), 1.83-1.98 (m, 1 H), 2.08-2.34 (m, 3 H), 3.80 (s, 3 H), 3.82-3.90 (m, 1 H), 3.96-4.08 (m, 1 H), 4.23 (dd, J=10.3, 4.8 Hz, 1 H), 7.14 (d, J=9.1 Hz, 1 H), 7.49 (dd, J=8.7, 2.8 Hz, 1 H), 7.78 (d, J=2.8 Hz, 1 H), 7.88 (s, 1 H), 8.81 (s, 1 H); MS (DCI/NH$_3$) m/z 438 (M+H)$^+$.

Example 161

N-[(5Z)-2-tert-butyl-4-{[(2R)-5-oxopyrrolidin-2-yl]methoxy}isothiazol-5(2H)-ylidene]-5-chloro-2-methoxybenzamide The title compound was prepared according to the procedure of Example 156B by replacing 2-iodopropane with (R)-(5-oxopyrrolidin-2-yl)methyl 4-methylbenzenesulfonate. $^1$H NMR (300 MHz, DMSO-d$_6$) δ ppm 1.54-1.65 (m, 9 H), 1.86-1.92 (m, 1 H), 2.06-2.32 (m, 3 H), 3.80 (s, 3 H), 3.82-3.86 (m, J=5.6, 5.6 Hz, 1 H), 3.95-4.07 (m, 1 H), 4.23 (dd, J=9.9, 4.8 Hz, 1 H), 7.14 (d, J=8.7 Hz, 1 H), 7.49 (dd, J=8.9, 3.0 Hz, 1 H), 7.78 (d, J=2.8 Hz, 1 H), 7.88 (s, 1 H), 8.81 (s, 1 H); MS (DCI/NH$_3$) m/z 438 (M+H)$^+$.

Example 162 tert-butyl [(5Z)-2-tert-butyl-5-{[(5-chloro-2-methoxyphenyl)carbonyl]imino}-3-methyl-2,5-dihydroisothiazol-4-yl]carbamate Example 162A ethyl (5Z)-2-tert-butyl-5-{[(5-chloro-2-methoxyphenyl)carbonyl]imino}-3-methyl-2,5-dihydroisothiazole-4-carboxylate To a solution of ethyl 3-oxobutanoate (1.3 g, 10 mmol) and 2-methylpropan-2-amine (0.73 g, 10 mmol) in toluene (15 mL) were added anhydrous magnesium sulfate (3.0 g, 25 mmol) and Montmorillonite K10 (3.0 g, 10 mmol). The resulting mixture was stirred at 45° C. for 14 h and then cooled to room temperature. The mixture was diluted with anhydrous ethyl ether, filtered and washed with ethyl ether. The filtrate and washings were combined and concentrated under reduced pressure. The residue was dissolved in THF (60 mL), 5-chloro-2-methoxybenzoyl isothiocyanate (2.16 g, 9.5 mmol) was added and the mixture was stirred at ambient temperature for 2 h. Iodine (2.4 g, 9.5 mmol) was added followed by addition of MeOH (100 mL) and pyridine (10 mL). The mixture was left overnight at room temperature and then treated with ethyl acetate and a saturated solution of sodium bicarbonate for additional 1 h. The layers were separated and the aqueous layer was extracted with ethyl acetate. The extracts were combined, washed with brine, dried with MgSO$_4$ and concentrated under reduced pressure. The solid was triturated with hexane-ethyl ether (1:1) to provide 2.8 g of the title compound. $^1$H NMR (300 MHz, DMSO-d$_6$) δ ppm 1.37 (t, 3 H), 1.74 (s, 9 H), 2.76 (s, 3 H), 3.82 (s, 3 H), 4.32 (q, J=6.9 Hz, 2 H), 7.16 (d, J=8.7 Hz, 1 H), 7.52 (dd, J=8.7, 2.8 Hz, 1 H), 8.01 (d, J=3.2 Hz, 1 H); MS (DCI/NH$_3$) m/z 411 (M+H)$^+$.

Example 162B (5Z)-2-tert-butyl-5-{[(5-chloro-2-methoxyphenyl)carbonyl]imino}-3-methyl-2,5-dihydroisothiazole-4-carboxylic acid To a solution of product from Example 162A (1.45 g, 3.5 mmol) in dioxane (7.5 mL) and ethanol (15 mL) was added 1N NaOH (5 mL, 5 mmol) and the mixture was stirred at room temperature for 16 h. Another portion of 1N NaOH (2.5 mL, 2.5 mmol) was added and reaction was continued for an additional 9 h. Water (15 mL) was added and organics were removed under reduced pressure. The solution was acidified to pH 4 and the solid was filtered, washed with water and dried under reduced pressure to provide 1.2 g of the title compound. $^1$H NMR (300 MHz, DMSO-$d_6$) δ ppm 1.74 (s, 9 H), 2.85 (s, 3 H), 3.85 (s, 3 H), 7.19 (d, J=8.7 Hz, 1 H), 7.54 (dd, J=9.1, 2.8 Hz, 1 H), 7.81 (d, J=2.8 Hz, 1 H); MS (DCI/NH$_3$) m/z 383 (M+H)$^+$.

Example 162C tert-butyl [(5Z)-2-tert-butyl-5-{[(5-chloro-2-methoxyphenyl)carbonyl]imino}-3-methyl-2,5-dihydroisothiazol-4-yl]carbamate A mixture of Example 162B (784 mg, 2 mmol), triethylamine (0.57 mL, 4.1 mmol) and diphenyl phosphorazidate (1.13 g, 4.1 mmol) in dioxane (10 mL) was refluxed at 80° C. for 3 h. tert-Butanol (30 mL) was added heating at 80° C. was continued for another 8 h. The mixture was cooled to room temperature and concentrated under reduced pressure. Water was added and the mixture was extracted with EtOAc. The acetate layer was washed with 10% NaHCO$_3$, brine and concentrated under reduced pressure. Chromatography (EtOAc-MeOH 9:1) afforded 10 mg of product. $^1$H NMR (300 MHz, DMSO-$d_6$) δ ppm 1.47 (s, 9 H), 1.68-1.76 (m, 9 H), 2.50-2.54 (m, 3 H), 3.79 (s, 3 H), 7.12 (d, J=8.7 Hz, 1 H), 7.47 (dd, J=8.9, 3.0 Hz, 1 H), 7.82 (d, J=2.8 Hz, 1 H), 8.45 (s, 1 H); MS (DCI/NH$_3$) m/z 454 (M+H)$^+$.

e. Biological Data (i) In Vitro Methods—CB$_2$ and CB$_1$ Radioligand Binding Assays:

The CB$_1$ and CB$_2$ radioligand binding assays described herein are utilized to determine the selectivity of compounds of the present invention for binding to CB$_2$ relative to CB$_1$ receptors.

HEK293 cells stably expressing human CB$_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 5 μg/well for human CB$_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat CB$_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 20 μg/well for rat CB$_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Compounds of the invention tested were found to bind to CB$_2$ receptors with K$_i$ of less than about 1,000 nM, preferably less than 400 nM, more preferably less than 200 nM, and most preferably lower than 100 nM.

HEK293 human CB$_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM MgCl$_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. The compounds of the present invention tested were found to bind to CB$_1$ receptors with K$_i$ of about 10 fold to about 1000 fold higher than that for CB$_2$ receptors. These results demonstrate that the compounds of the present invention tested preferably bind to CB$_2$ vs. CB$_1$ receptors, and therefore are selective ligands for the CB2 receptor.

ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441.

Certain compounds of the present invention tested showed a statistically significant change in paw withdrawal latency versus a saline vehicle at less than about 300 micromoles/kg in the incision model of postoperative pain. In a more preferred embodiment, compounds of the present invention tested showed efficacy at less than about 50 micromoles/kg in the incision model of postoperative pain.

Spinal Nerve Ligation Model of Neuropathic Pain:

A model of spinal nerve ligation-induced (SNL model) neuropathic pain was produced using the procedure originally described in Kim, S. H. and J. M. Chung, 1992, An experimental model for peripheral neuropathy produced by segmental spinal nerve ligation in the rat, Pain, 50, 355. The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and were acclimated to the test chambers for 20 minutes. The von Frey filaments were presented perpendicularly to the plantar surface of the selected hind paw, and were then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats.

Capsaicin-induced secondary mechanical hypersensitivity:

Rats were allowed to acclimate to the study room for 1 hour. They were then briefly restrained, and capsaicin was administered at 10 μL in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compound of the present invention showed a statistically significant change in paw withdrawal latency versus a saline vehicle at less than about 300 micromoles/kg. In a more preferred embodiment, compounds of the present invention showed efficacy of less than about 50 micromoles/kg.

f. Methods of Using the Compounds

One embodiment of the present invention provides a method for treating pain (for example, neuropathic pain or nociceptive pain) in a mammal (including human) in need of such treatment. The method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID).

Another embodiment of the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Yet another embodiment of the present invention relates to a method for providing neuroprotection in a mammal in need of such treatment. This method comprises administering to the mammal a therapeutically effective amount of any compounds described herein or a pharmaceutically acceptable salt thereof.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. —Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W.J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.1 mg/kg body weight to about 100 mg/kg body weight. More preferable doses can be in the range of from about 0.3 mg/kg body weight to about 30 mg/kg body weight. If desired, the effective daily dose can be divided into multiple doses for purposes of administration. Consequently, single dose compositions may contain such amounts or submultiples thereof to make up the daily dose.

g. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of the invention, or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

We claim:

1. A method for treating inflammatory disorders in a mammal in need of such treatment, comprising administering to the mammal a therapeutically effective amount of a compound having formula (I)

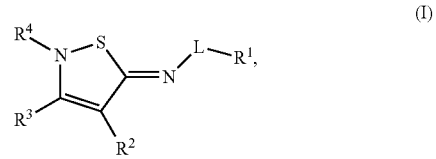

or pharmaceutically acceptable salts thereof, wherein
L is C=O, C=S, S(O)$_2$, or C=NCN;
R$^1$ is alkyl, alkenyl, alkynyl —(CR$^a$R$^b$)$_m$—OH, —(CR$^a$R$^b$)$_m$—O(alkyl), —(CR$^a$R$^b$)$_m$—CN, haloalkyl, or G$^1$;
R$^2$ is alkyl, alkenyl, alkynyl, G$^1$, —C(R$^{Zb}$)=NO(R$^{Z1}$), —O(R$^{Za}$), —N(R$^{Z1}$)(R$^{Z2b}$), —(CR$^a$R$^b$)$_m$—N$_3$, —(CR$^a$R$^b$)$_m$—CN, haloalkyl, —(CR$^a$R$^b$)$_m$—O(R$^{Za}$), —(CR$^a$R$^b$)$_m$—S(R$^{Zb}$), —(CR$^a$R$^b$)$_m$—C(O)O (R$^{Zb}$), —(CR$^a$R$^b$)$_m$—C(O)N(R$^{Z1}$)(R$^{Z2a}$), —(CR$^a$R$^b$)$_m$—SO$_2$N(R$^{Z1}$)(R$^{Z2a}$), —(CR$^a$R$^b$)$_m$—C(O)(R$^{Zb}$), —(CR$^a$R$^b$)$_m$—SO$_2$(R$^{Zd}$), —SO$_2$(R$^{Zd}$), —(CR$^a$R$^b$)$_m$—C(R$^{Zb}$)=NO(R$^{Z1}$), —(CR$^a$R$^b$)$_m$—N(R$^{Z1}$)(R$^{Z2b}$), or —(CR$^a$R$^b$)$_m$-G$^1$;
R$^3$ is hydrogen, alkyl, halogen, —CN, -G$^2$, haloalkyl, or —(CR$^a$R$^b$)$_m$-G$^2$;
R$^4$ is alkyl, alkenyl, alkynyl, —(CR$^a$R$^b$)$_n$—CN, —(CR$^a$R$^b$)$_n$—OH, —(CR$^a$R$^b$)$_n$—O(alkyl), haloalkyl, G$^2$, or —(CR$^a$R$^b$)$_m$ -G$^2$; or
R$^2$ and R$^3$ or R$^3$ and R$^4$, together with the atoms to which they are attached, form a five-, six-, or seven-membered monocyclic ring containing zero or one additional double bond, zero or one additional heteroatom selected from the group consisting of O, S, N, and N(H), each said ring is independently unsubstituted or substituted with 1, 2, 3, 4, or 5 substituents (R$^{21}$) selected from the group consisting of oxo, alkyl, alkenyl, alkyrtyl, halogen, —CN, —O($R^{1a}$), —C(O)OH, —C(O)O(alkyl), —C(O)($R^{1a}$), —N ($R^{Z3}$)($R^{3a}$), —N($R^{3a}$)C(O)$R^{1a}$, —N($R^{3a}$)C(O)O$R^{1a}$, —N($R^{3a}$)C(O)N($R^{Z3}$)($R^{3a}$), —N($R^{3a}$)S(O)$_2$($R^{2a}$), —N($R^{3a}$)S(O)$_2$N($R^{Z3}$)($R^{3a}$), —SO$_2$($R^{2a}$), —C(O)N($R^{Z3}$)($R^{3a}$), —S(O)$_2$N($R^{Z3}$)($R^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O($R^{1a}$), and haloalkyl, two adjacent or non-adjacent atoms of each of said ring ark, optionally linked by an alkylene bridge or one, two, three, or four carbon atoms; and two substituents ($R^{21}$) on the same carbon atom, together with said carbon atom, optionally form a 3-6 membered monocyclic ring containing 0, 1, or 2 heteroatoms selected from O, S, or N(H);

$R^{Za}$, at each occurrence, is independently hydrogen, alkyl, haloalkyl, —(CR$^c$R$^d$)$_p$—O(alkyl), G$^1$, —(CR$^c$R$^d$)$_q$—CN, or —(CR$^c$R$^d$)$_q$-G$^1$;

$R^{Zb}$, at each occurrence, is independently hydrogen, alkyl, haloalkyl, G$^1$, or —(CR$^c$R$^d$)$_q$-G$^1$;

$R^{Z1}$, at each occurrence, is independently hydrogen, alkyl or haloalkyl;

$R^{Z2a}$, at each occurrence, is independently hydrogen, alkyl, haloalkyl, G$^1$, or —(CR$^c$R$^d$)$_q$-G$^1$, or $R^{Z2b}$, at each occurrence, is independently hydrogen, alkyl, haloalkyl, G$^1$, —C(O)$R^{Zc}$, —C(O)O$R^{Zc}$, —C(O)N($R^{Z1}$)($R^{Zc}$), —S(O)$_2$$R^{Zd}$, —S(O)$_2$N($R^{Z1}$)($R^{Zc}$), or —(CR$^c$R$^d$)$_q$-G$^1$,$R^{Zc}$, at each occurrence, is independently hydrogen, alkyl, haloalkyl, G$^1$, or —(CR$^c$R$^f$)$_t$-G$^1$;

$R^{Zd}$, at each occurrence, is independently alkyl, haloalkyl, G$^1$, or —(CR$^c$ R$^f$)$_t$-G$^1$;

G$^1$, at each occurrence, is aryl, heteroaryl, cycloalkyl, cycloalkenyl, or heterocycle, wherein each G$^1$ is independently unsubstituted or substituted with 1, 2, 3, 4, or 5 substituents selected from the group consisting of alkyl, alkenyl, alkynyl, halogen, —CN, oxo, -G$^2$, —NO$_2$, —C($R^{Z3}$)=N—O($R^{1a}$), —OR$^{1a}$, —O—(CR$^{1g}$R$^{1h}$)$_u$—CN, —OC(O)$R^{1a}$, —OC(O)N($R^{Z3}$)($R^{3a}$), —O—(CR$^{1g}$R$^{1h}$)$_u$—CON($R^{Z3}$)($R^{3a}$), —O—(CR$^{1g}$R$^{1h}$)$_u$—SO$_2$N($R^{Z3}$)($R^{3a}$), —SR$^{1a}$, —S(O)$_2$R$^{2a}$, —S(O)$_2$N($R^{Z3}$)($R^{3a}$), —C(O)R$^{1a}$, —C(O)OR$^{1a}$, —C(O)N($R^{Z3}$)($R^{3a}$), —N($R^{Z3}$)($R^{3a}$), —N($R^{Z3}$)C(O)R$^{1a}$, —N($R^{Z3}$)S(O)$_2$R$^{2a}$, —N($R^{Z3}$)C(O)O($R^{1a}$), —N($R^{Z3}$)C(O)N($R^{Z3}$)($R^{3a}$), —(CR$^{1g}$R$^{1h}$)$_u$—NO$_2$, —(CR$^{1g}$R$^{1h}$)$_u$—OR$^{1a}$, —(CR$^{1g}$R$^{1h}$)$_u$—C(O)R$^{1a}$, —(CR$^{1g}$R$^{1h}$)$_u$—OC(O)N($R^{Z3}$)($R^{3a}$), —(CR$^{1g}$R$^{1h}$)$_u$—SR$^{1a}$, —(CR$^{1g}$R$^{1h}$)$_u$—S(O)$_2$R$^{2a}$, —(CR$^{1g}$R$^{1h}$)$_u$—S(O)$_2$ N($R^{Z3}$)($R^{3a}$), —(CR$^{1g}$R$^{1h}$)$_u$—C(O)R$^{1a}$, —(CR$^{1g}$R$^{1h}$)$_u$—C(O)OR$^{1a}$, —(CR$^{1g}$R$^{1h}$)$_u$—C(O)N($R^{Z3}$)($R^{3a}$), —(CR$^{1g}$R$^{1h}$)$_u$—N($R^{Z3}$)($R^{3a}$), —(CR$^{1g}$R$^{1h}$)$_u$—N($R^{Z3}$)C(O)R$^{1a}$, —(CR$^{1g}$R$^{1h}$)$_u$—N($R^{Z3}$)S(O)$_2$R$^{2a}$, —(CR$^{1g}$R$^{1h}$)$_u$—N($R^{Z3}$)C(O)O($R^{1a}$), —(CR$^{1g}$R$^{1h}$)$_u$—N($R^{Z3}$)C(O)N($R^{Z3}$)($R^{3a}$), —(CR$^{1g}$R$^{1h}$)$_u$-G$^2$, —(CR$^{1g}$R$^{1h}$)$_u$—CN, and haloalkyl;

$R^{1a}$ and $R^{3a}$, at each occurrence, is independently hydrogen, alkyl, haloalkyl, G$^2$, or —(CR$^k$R$^x$)$_v$-G$^2$;

$R^{2a}$, at each occurrence, is independently alkyl, haloalkyl, G$^2$, or —(CR$^k$R$^x$)$_v$-G$^2$;

G$^2$, at each occurrence, is aryl, heteroaryl, cycloalkyl, cycloalkenyl, or heterocycle, wherein each G$^2$ is independently unsubstituted or substituted with 1, 2, 3, 4, or 5 substituents selected from the group consisting of alkyd, alkenyl, alkynyl, halogen, —CN, oxo, —NO$_2$, —OR$^{1b}$, —OC(O)R$^{1b}$, —OC(O)N($R^{Z4}$)($R^{3b}$), —SR$^{1b}$, —S(O)$_2$R$^{2b}$, —S(O)$_2$N($R^{Z4}$)($R^{3b}$), —C(O)R$^{1b}$, —C(O)OR$^{1b}$, —C(O)N($R^{Z4}$)($R^{3b}$), —N($R^{Z4}$)($R^{3b}$), —N($R^{Z4}$)C(O)R$^{1b}$, —N($R^{Z4}$)C(O)O($R^{1b}$), —N($R^{Z4}$)C(O)N($R^{Z4}$)($R^3$), —(CR$^{2g}$R$^{2h}$)$_w$—NO$_2$, —(CR$^{2g}$R$^{2h}$)$_w$—OR$^{1b}$, —(CR$^{2g}$R$^{2h}$)$_w$—OC(O)R$^{1b}$, —(CR$^{2g}$R$^{2h}$)$_w$—OC(O)N($R^{Z4}$)($R^{3b}$), —(CR$^{2g}$R$^{2h}$)$_w$—SR$^{1b}$, —(CR$^{2g}$R$^{2h}$)$_w$—S(O)$_2$R$^{2b}$, —(CR$^{2g}$R$^{2h}$)$_w$—S(O)$_2$N($R^{Z4}$)($R^{3b}$), —(CR$^{2g}$R$^{2h}$)$_w$—C(O)R$^{1b}$, —(CR$^{2g}$R$^{2h}$)$_w$—C(O)OR$^{1b}$, —(CR$^{2g}$R$^{2h}$)$_w$—C(O)N($R^{Z4}$)($R^{3b}$), —(CR$^{2g}$R$^{2h}$)$_w$—N($R^{Z4}$)($R^{3b}$), —(CR$^{2g}$R$^{2h}$)$_w$—N($R^{Z4}$)C(O)R$^{1b}$, —(CR$^{2g}$R$^{2h}$)$_w$—N($R^{Z4}$)C(O)O($R^{1b}$), —(CR$^{2g}$R$^{2h}$)$_w$—N($R^{Z4}$)C(O)N($R^{Z4}$)($R^{3b}$), —(CR$^{2g}$R$^{2h}$)$_w$—CN, and haloalkyl;

m, q, t, u, v, and w, at each occurrence, are each independently 1, 2, 3, 4, or 5;

n and p, at each occurrence, are each independently 2, 3, 4, or 5;

$R^{1b}$ and $R^{3b}$, at each occurrence, is independently hydrogen, alkyl, or haloalkyl;

$R^{2b}$, at each occurrence, is independently alkyl or haloalkyl;

$R^a$, $R^c$, $R^d$, $R^e$, $R^f$, $R^{1g}$, $R^{1h}$, $R^{2g}$, $R^{2h}$, $R^k$, and $R^x$, at each occurrence, are each independently hydrogen, halogen, alkyl, or haloalkyl;

each occurrence of $R^{1p}$ is independently hydrogen, halogen, alkyl, haloalky, or OH; and $R^{Z3}$ and $R^{Z4}$, at each occurrence, are each independently hydrogen, alkyl, or haloalkyl;

with the proviso that the compound is other than
4-methyl-N-[(3Z)-1-phenyl-1,4,5,6-tetrahydro-3H-cyclopenta[c]isothiazol-3-ylidene]benzenesulfonamide;
N-[(3Z)-1-cyclohexyl-4,5,6,7-tetrahydro-2,1-benzisothiazol-3(1H)-ylidene]-4-methylbenzenesulfonamide; or
4-methyl-N-[(3Z)-1-phenyl-4,5,6,7-tetrahydo-2,1-benzisothiazol-3(1H)-ylidene]benzenesulfonamide.

2. The method of claim 1 wherein the compound is selected from the group consisting of
N-[(5Z)-4-butyl-2-tert-butylisothiazol-5(2H)-ylidene]-5-chloro-2-methoxybenzamide;
N-[(5Z)-4-butyl-2-(1,1-dimethylpropyl)isothiazol-5(2H)-ylidene]-5-chloro-2-methoxybenzamide;
N-[(5Z)-4-butyl-2-cyclobutylisothiazol-5(2H)-ylidene]-5-chloro-2-methoxybenzamide;
N-[(5Z)-4-butyl-2,3-dimethylisothiazol-5(2H)-ylidene] hexahydro-2,5-methanopentalene-3a(1H)-carboxamide:
N-[(5Z)-4-butyl-2-(1-methylcyclobutyl)isothiazol-5(2H)-ylidene]-5-chloro-2-methoxybenzamide;
N-[(5Z)-4-allyl-2-tert-butylisothiazol-5(2H)-ylidene]-5-chloro-2-methoxybenzamide;
N-[(5Z)-2-tert-butyl-4-[(3-methyl-4,5-dihydroisoxazol-5-yl)methyl]isothiazol-5(2H)-ylidene]-5-chloro-2-methoxybenzamide;
N-[(5Z)-2-tert-butyl-4-(cyclopropylmethyl)isothiazol-5 (2H)-ylidene]-5chloro-2-methoxybenzamide;
N-[(3Z)-1-tert-butyl-5-propyl-4,5,6,7-tetrahydro-2,1benzisothiazol-3(1H)-ylidene]-5-chloro-2methoxybenzamide;
N-[(3Z)-1-tert-butyl-1,4,6,7-tetrahydro-3H-spiro[2,1-benzisothiazole-5,2'-[1,3]dioxolan]-3-ylidene]-5-chloro-2-methoxybenzamide;
N-[(5Z)-2-tert-butyl-4-(2-hydroxyethyl)isothiazol-5(2H)-ylidene]-5-chloro-2-methoxybenzamide;
N-[(5Z)-2-tert-butyl-4-(2-methoxyethyl)isothiazol-5 (2H)-ylidene]-5-chloro 2-methoxybenzamide;
N-[(5Z)-2-tert-butyl-4-(2-morpholin-4-ylethyl)isothiazol-5(2H)-ylidene]-5-chloro-2-methoxybenzamide;
N-[(5Z)-2-tert-butyl-4-[2-(5,5-dimethyl-1,3-dioxan-2-yl) ethyl]isothiazol-5(2H)-ylidene]-5-chloro-2-methoxybenzamide;

N-[(5Z)-4-(2-azidoethyl)-2-tert-butylisothiazol-5(2H)-ylidene]-5-chloro-2-methoxybenzamide;
N-[(5Z)-2-tert-butyl-4-[(3E)-3-(methoxyimino)propy] isothiazol-5(2H)-ylidene]-5-chloro-2-methoxybenzamide;
N-[(5Z)-4-(2-aminoethyl)-2-tert-butylisothiazol-5(2H)-ylidene]-5-chloro-2-methoxybenzamide;
N-[(5Z)-2-tert-butyl-4-[2-(dimethylamino)ethyl]isothiazol-5 (2H)-ylidene]-chloro-2-methoxybenzamide;
N-[(5Z)-2-tert-butyl-4-methylisothiazol-5(2H)-ylidene]-5 -chloro-2-methoxybenzamide;
N-[(5Z)-2-tert-butyl-4-(3-hydroxybutyl)isothiazol-5(2H)-ylidene]-5-chloro-2-methoxybenzamide;
N-[(5Z)-2-tert-butyl-4-(2-cyanoethyl)isothiazol-5(2H)-ylidene]-5-chloro-2-methoxybenzamide;
N-[(5Z)-2-tert-butyl-4-(2,3-dihydroxypropyl)isothiazol-5 (2H)-ylidene]-5-chloro-2-methoxybenzamide;
N-[(5Z)-2-tert-butyl-4-[(E)-(methoxyimino)methyl] isothiazol-5(2H)-ylidene]-5chloro-2-methoxybenzamide;
N-[(5Z)-2-tert-butyl-4-(1,3-dioxolan-2-ylmethyl)isothiazol-5(2H)-ylidene]-5-chloro-2-methoxybenzamide;
N-[(5Z) 2-text-butyl-4-(1-hydroxy-2-methylpropyl) isothiazol-5(2H)-ylidene]-5-chloro-2-methoxybenzamide;
N-[(5Z)-2-tert-butyl-4-(cyanomethyl)isothiazol-5(2H)-ylidene]5-chloro-2-methoxybenzamide;
N-[(5Z)-4-[(1Z)-but-1enyl]-2-tert-butylisothiazol-5(2H)-yluidene]-5-chloro-2-methoxybenzamide;
N-[(5Z)-4-butyl-2-tert-butylisothiazol-5(2H)-ylidene]-5-cyano-2-methoxybenzarnide;
N-[(5Z)-2-tert-butyl-4-(2-ethylcyclopropyl)isothiazol-5 (2H)-ylidene]-5-chloro-2-methoxybenzamide;
N-[(5Z)-2-tert-butyl-4-(hydroxymethyl)isothiazol-5(2H)-ylidene]-5-chloro-2-methoxybenzaraide;
N-[(5Z)-2-tert-butyl-4-(methoxymethyl)isothiazol-5 (2H)-ylidene]-5-chloro-2-methoxybenzaimide;
N-[(5Z)-2-tert-butyl-4-(ethoxymethyl)isothiazol-5(2H)-ylidene]-5-chloro-2-methoxybenzamide;
N-[(5Z)-2-tert-butyl-4-(3-cyanopropyl)isothiazol-5(2H)-ylidene]-5-chloro-2-methoxybenzamide;
N-[(5Z)-2-tert-butyl-4-[hydroxy(phenyl)methyl]isothiazol-5(2H)-ylidene]-5-chloro-2-methoxybezamide;
N-[(5Z)-4-(azidomethyl)-2-tert-butylisothiazol-5(2H)-ylidene]-5-chloro-2-methoxybenzamide;
N-[(5Z)-2-tert-butyl-4-(2-cyclobutyl-1-hydroxyethyl) isothiazol-5(2H)-ylidene]-5-chloro-2-methoxybenzamide;
N-[(5Z)-2-tert-buty4-[cyclobutyl(hydroxy)methyl] isothiazol-5(2H)ylidene]-5-chloro-2-methoxybenzamide;
N-[(5Z)-4-benzyl-2-tert-butylisothiazol-5(2H)-ylidene]-5-chloro-2-methoxybenzamide;
N-[(5Z)-2-tert-butyl-4-(2-cyclobutylethyl)isothiazol-5(2 H)-ylidene]-5-chloro-2-methoxybenzamide;
N-[(5Z)-2-tert-butyl-4-isobutylisothiazol-5(2H)-ylidene]-5-chloro-2-methoxybenzamide;
N-[(5Z)-2-tert-butyl-4-(cyclobutylmethyl)isothiazol-5 (2H)-ylidene]-5-chloro-2-methoxybenzamide;
N-[(5Z)-2-tert-butyl-4-tetrahydro-2H-pyran-4-ylisothiazol-5(2H)-ylidene]-5-chloro-2-methoxybenzamide;
N-[(5Z)-2-tert-butyl-4-[hydroxy(1,3-thiazol-2-yl)methyl] isothiazol-5(2H)-ylidene]-5-chloro-2-methoxybenzamide;
N-[(5Z)-4-butyl-2-tert-butylisothiazol-5(2H)-ylidene]-2, 5-dimethoxybenzamide;
N-[(5Z)-4-butyl-2-tert-butylisothiazol-5(2H)-ylidene]-5-fluoro-2 -methoxybenzamide;
N-[(5Z)-4-butyl-2-tert-butylisothiazol-5(2H)-ylidene]-2-methoxy-5-methoxybenzamide;
N-[(5Z)-2-tert-butyl-4-[hydroxy(thien-2-yl)methyl] isothiazol-5(2H)-ylidene]-5-chloro-2-methoxybenzamide;
methyl 4-{(5Z)-2-tert-butyl-5-[(5-chloro-2-methoxybenzoyl)imino]-2,5-dihydroisothiazol-4-yl}butanoate;
methyl 4-{(5Z)-2-tert-butyl-5-[(5-cyano-2-methoxybenzoyl)imino]-2,5-dihydroisothiazol-4-yl}butanoate;
N-[(5Z)-4-butyl-2-tert-butylisothiazol-5(2H)-ylidene]-5-chloro-2-fluorobenzamide;
N-[(5Z)-4-butyl-2-tert-butylisothiazol-5(2H)-ylidene]-5-chloro-2-(2,2,2-trifluoroethoxy)benzamide;
N-[(5Z)-4-butyl-2-tert-butylisothiazol-5(2H)-ylidene]-2-methoxy-5-(methylsulfonyl)benzamide;
N-[(5Z)-2-test-butyl-4-[hydroxy(1,3-thiazol-4-yl)methyl] isothiazol-5(2H)-ylidene]-5-chloro-2-methoxybenzamide;
N-[(5Z)-2-tert-butyl-4-(2-furylmethyl)isothiazol-5(2H)-ylidene]-5-chloro-2-methoxybenzamide;
N-[(5Z)-2-tert-butyl-4-(2-furylmethyl)isothiazol-5(2H)-ylidene]-5-cyano-2-methoxybenzamide;
N-[(5Z)-2-tert-butyl-4-(1,3-thiazol-4-ylmethyl)isothiazol-5(2H)ylidene]-5-chloro-2-methoxybenzamide;
N-[(5Z)-2-tert-butyl-4-(thein-2-ylmethyl)isothiazol-5 (2H)-ylidene]-5-cyano-2-methoxybenzamide;
N-[(5Z)-2-tert-butyl-4-(thien-2-ylmethyl)isothiazol-5 (2H)-ylidene]-5-chloro-2-methoxybenzamide;
5-amino-N-[(5Z)-4-butyl-2-tert-butylisothiazol-5(2H) ylidene]-2-methoxybenzamide;
N-[(5Z)-4-butyl-2-tert-butylisothiazol-5(2H)-ylidene]-5-formyl-2-methoxybenzamide;
N-[(5Z)-4-butyl-2-tert-butylisothiazol-5(2H)-ylidene]-2-methoxy-5-[(E)-(methoxyimino)methyl]benzamide;
N-[(5Z)-4-butyl-2-tert-butylisothiazol-5(2H)-ylidene]-5-(formylamino)-2-methoxybenzarmide;
N-[(5Z)-4-butyl-2-tert-butylisothiazol-5(2H)-ylidene]-5-[(E)-(hydroxyimino)methyl]-2-methoxybenzamide;
3-({[(5Z)-4-butyl-2-tert-butylisothiazol-5(2H)-ylidene] amino}carbonyl)-4-methoxybenzoic acid;
N-[(5Z)-4-butyl-2-tert-butylisothiazol-5(2H)-ylidene]-5-iodo-2-methoxybenzamide;
N-[(5Z)-4-butyl-2-tert-butylisothiazol-5(2H)-ylidene]-5-ethynyl 2methoxybenzamide;
N-[(5Z)-4-butyl-2-tert-butylisothiazol-5(2H)-ylidene]-2-methoxy-5-(trifluoromethoxy)benzamide;
5-acetyl-N-[(5Z)-4-butyl-2-tert-butylisothiazol-5(2H)-ylidene]-2-methoxybenzamide;
N-[(5Z)-4-butyl-2-tert-butylisothiazol-5(2H)-ylidene]-5-(difluoromethyl)-2-methoxybenzamide;
N-[(5Z)-4-butyl-2-tert-butylisothiazol-5(2H)-ylidene]-5-(fluoromethyl)-2-methoxybenzamide;
N-[(5Z)-2-tert-butyl-4-(tetrahydro furan-2-ylmethyl) isothiazol-5 (2H)-ylidene]-5-chloro-2-methoxybenzamide;
N-[(5Z)-4-butyl-2-tert-butylisothiazol-5(2H)-ylidene]-5-[(1Z)-N-hydroxyethanimidoyl]-2-methoxybenzamide;
N-[(5Z)-4-butyl-2-tert-butylisothiazol-5(2H)-ylidene]-5-(1,1-difluoro ethyl)-2-methoxybenzamide;
N-[(5Z)-2-text-butyl-4-(2-furylmethyl)isothiazol-5(2H)-ylidene]-2fluoro-3-(trifluoromethyl)benzamide;
N-[(5Z)-2-tert-butyl-4-(2-furylmethyl)isothiazol-5(2H)-ylidene]-2-methoxy-5-(trifluoromethyl)benzamide;
N-[(5Z)-2-tert-butyl-4-(isopropoxymethyl)isothiazol-5 (2H)-ylidene]-5-chloro-2-methoxybenzamide;

N-[(5Z)-4-butyl-2-tert-butylisothiazol-5(2H)-ylidene]-2-fluoro-3-(trifluoromethyl)benzamide;
methyl 3-({[(5Z)-4-butyl-2-tert-butylisothiazol-5(2H)-ylidene]amino}carbonyl)-4-methoxybenzoate;
N-[(5Z)-2-tert-butyl-4-(4-oxopentyl)isothiazol-5(2H)-ylidene]-5-chloro-2-methoxybenzamide;
N-[(5Z)-2-tert-butyl-4-(4-oxopentyl)isothiazol-5(2H)-ylidene]-2-methoxy-5-(trifluoromethyl)benzamide;
N-[(5Z)-2-tert-butyl-4-(4-oxopentyl)isothiazol-5(2H)-ylidene]-2- fluoro-3-(trifluoromethyl)benzamide;
N$^3$-[(5Z)-4-butyl-2-tert-butylisothiazol-5(2H)-ylidene]-4-methoxyisophthalamide;
N-[(5Z)-2-tert-butyl-4-(4-hydroxy-4-methylpentyl)isothiazol-5(2H)-ylidene]-2-fluoro-3-(trifluoromethyl)benzamide;
N-[(5Z)-2-tert-butyl-4-(4-hydroxy-4-methylpentyl)isothiazol-5(2H)-ylidene]-5-chloro-2-methoxybenzamide;
N-[(5Z)-2-tert-butyl-4-(4-hydroxy-4-methylpentyl)isothiazol-5(2H)-ylidene]-2-methoxy-5-(trifluoromethyl)benzamide;
N-[(5Z)-4-butyl-2-tert-butylisothiazol-5(2H)-ylidene]-5-isopropyl-2-methoxybenzamide;
N-[(5Z)-2-tert-butyl-4-(4-fluoro-4-methylpentyl)isothiazol-5(2H)-ylidene]-5-chloro-2-methoxybenzamide;
N-[(5Z)-2-tert-butyl-4-(3-oxobutyl)isothiazol-5(2H)-ylidene]-5-chluoro-2 -methoxybenzamide;
N-[(5Z)-2-tert-butyl-4-[(2,2,2-trifluoroethoxy)methyl]isothiazol-5(2H)-ylidene]-5-chloro-2-methoxybenzamide;
N-[(5Z)-2-tert-butyl-4-(4,4-difluoropentyl)isothiazol-5(2H)-ylidene]-5-chloro-2-methoxybenzamide;
N-[(5Z)-2-tert-butyl-4-(3-fluoro-3-methylbutyl)isothiazol-5(2H)-ylidene]-5-chloro-2-methoxybenzamide;
N-[(5Z)-2-tert-butyl-4-(4-fluoro-4-methylpentyl)isothiazol-5(2 Z)-ylidene]-2-methoxy-5-(trifluoromethyl)benzamide;
N-[(5Z)-2-tert-butyl-4-{[(2R)-tetrahydrofuran-2-ylmethoxy]methyl}isothiazol-5(2H)-ylidene]-5-chloro-2-methoxybenzamide;
N-[(5Z)-2-tert-butyl-4-[(2-fluoroethoxy)methyl]isothiazol-5(2H)-ylidene]-5-chloro-2-methoxybenzamide;
N-[(5Z)-2-tert-butyl-4-[(2,2-difluoroethoxy)methyl]isothiazol-5(2H)-ylidene]-5-chloro-2-methoxybenzamide;
methyl 3-({[(5Z)-4-butyl-2-tert-butylisothiazol-5(2H)-ylidene]amino}carbonyl)-2,2,3-trimethylcyclopentanecarboxylate;
methyl 3-({[(5Z)-4-butyl-2-tert-butylisothiazol-5(2H)-ylidene]amino}catbonyl)-1,2,2-trimethylcyclopentanecarboxylate;
N-[(5Z)-4-butyl-2-tert-butylisothiazol-5(2H)-ylidene]-1-phenylcyclobexancarboxamide;
N-[(5Z)-4-butyl-2-tert-butylisothiazol-5(2H)-ylidene]-1 (2-chloro-4-fluorophenyl)cyclohexanecarboxamide;
3-({[(5Z)-4-butyl-2-tert-butylisothiazol-5-(2H)-ylidene]amino}carbonyl) 2,2,3-trimethylcyclopentanecarboxylic acid;
N-[(5Z)-4-butyl-2-tert-butylisothiazol-5(2H)-ylidene]-3-oxocyclopentanecarboxamide;
N-[(5Z)-4-butyl-2-tert-butylisothiazol-5(2H)-ylidene]-1-phenylcyclopentanecarboxamide;
N$^1$-[(5Z)-4-butyl-2-tert-butylisothiazol-5(2H)-ylidene]-N$^3$, N$^3$, 1,2,2-pentamethylcyclopentane-1,3-dicarboxamide;
N$^1$-[(5Z)-4-butyl-2-tert-butylisothiazol-5(2H)-ylidene]-N$^3$,1,2,2-tetramethylcyclopentane-1,3-dicarboxamide;
N-[(5Z)-4-butyl-2-tert-butylisothiazol-5(2H)-ylidene]-3-[3,3-difluoro azetidin-1-yl)carbonyl]-1,2,2-trimethylcyclopentanecarboxamide;
(1S,4R)-N-[(5Z)-4-butyl-2-tert-butylisothiazol-5(2H)-ylidene]-4,7,7-trimethyl-3-oxo-2-oxabicyclo[2.2.1]heptane-1-carboxamide;
(1R,4 S)-N-[(5Z)-4-butyl-2-tert-butylisothiazol-5(2H)-ylidene]-4,7,7-trimethyl-3-oxo-2-oxabicyclo[2.2.1]heptane-1-carboxamide;
ethyl 3-({[(5Z)-4-butyl-2-tert-butylisothiazol-5(2H)-ylidene]amino}carbonyl)pyrrolidine-1-carboxylate;
3-({[(5Z)-4-butyl-2-tert-butylisothizol-5(2H)-ylidene]amino}carbonyl)-1,2,2-trimethylcyclopentanecarboxylic acid;
tert-butyl 3({[(5Z)-4-butyl-2-tert-butylisothiazol-5(2H)-ylidene]amino}carbonyl)pyrrtolidine-1-carboxylate;
N-[(5Z)-4-butyl-2-tert-butylisothiazol-5(2H)-ylidene]-1-(3-cyanopyridin-2-yl)pyrrolidine-3-carboxamide;
methyl 4-({[(5Z)-4-butyl-2-tert-butylisothiazol-5(2H)-ylidene]amino}carbonyl)bicyclo[2,2,2]octane-1-carboxylate;
N-[(5Z)-4-butyl-2-tert-butylisothiazol-5(2H)-ylidene]-5-oxo-1-phenylpyrrolidine-3-carboxamide;
N-[(5Z)-4-butyl-2-tert-butylisothiazol-5(2H)-ylidene]-5-chloro-N'-cyano-2-methoxybenzenecarboximidamide;
N-[(5Z)-4-butyl-2-tert-butylisothiazol-5(2H)-ylidene]-5chloro-2-methoxybenzenecarbothioamide;
N-[(3Z)-1-tert-butyl-5-(trifluoromethyl)-4,5,6,7-tetrahydro-2,1-benzisothiazol-3(1H)-ylidene]-5-chloro-2-methoxybenzaniide;
tert-butyl (3Z)-1-tert-butyl-3-[(5-chloro-2-methoxybenzoyl)imino]-1,4,6,7-tetrahydroisothiazolo[4,3-c]pyridine-5(3H)-carboxylate;
N-[(3Z)-1-tert-butyl-4,5,6,7-tetrahydroisothiazolo[4,3-c]pyridin-3(1H)-ylidene]-5-chloro-2-methoxybenzamide;
N-[(5Z)-4-butyl-2-tert-butylisothiazol-5(2H)-ylidene]-5-chloro-2-methoxybenzenesulfonamide;
N-[(5Z)-4-butyl-2-tert-butylisothiazol-5(2H)-ylidene] naphthalene-1sulfonamide;
N-[(5Z)-4-butyl-2-tert-butylisothiazol-5(2H)-ylidene]-5-(dimethylamino)naphthalene-1-sulfonamide;
N-[(5Z)-4-butyl-2-tert-butylisothiazol-5(2H)-ylidene]cyclohexanesulfonamide;
N-[(5Z)-4-butyl-2-tert-butylisothiazol-5(2H)-ylidene] benzenesulfonamide;
N-[(5Z)-4-butyl 2-tert-butylisothiazol-5(2H)-ylidene] quinoline-8-sulfonamide;
N-[(5Z)-4-butyl-2-tert-butylisothiazol-5(2H)-ylidene]-2,2,3,3-tetramethylcyclopropanecarboxamide;
N-[(5Z)-4-butyl-2-tert-butylisothiazol-5(2H)-ylidene]-2,3-dichlorobenzenesulfonamide;
N-[(5Z)-4-butyl-2-tert-butylisothiazol-5(2H)-ylidene] adamantane-1-carboxamide;
N-[(5Z)-4-butyl-2-tert-butylisothiazol-5(2H)-ylidene]-N'-cyano-2-methoxy-5-(trifluoromethyl)benzenecarboximidamide;
N-[(5Z)-4-butyl-2-tert-butylisothiazol-5(2H)-ylidene]-2,2-dimethyl-4-oxo-3,4-dihydro-2H-pyran-6-carboxamide;
N-[(5Z)-4-butyl-2-tert-butylisothiazol-5(2H)-ylidene]-N'-cyano-2-ethoxy-5(trifluoromethyl)benzenecarboximidamide;
N-[(5Z)-4-butyl-2-tert-butylisothiazol-5(2H)-ylidene]-2-methoxy-5-(trifluoromethyl)benzarnide;

N-[(5Z)-2-tert-butyl-4-(3cyanopropyl)isothiazol-5(2H)-ylidene]-5-chloro-N'-cyano-2-methoxybenzenecarboximidamide;

N-[(5Z)-4-butyl-2-tert-butylisothiazol-5(2H)-ylidene]-5-cyano-2-hydroxybenzarnide;

N-[(5Z)-4-butyl-2-tert-butylisothiazol-5(2H)-ylidene]-5-cyano-2-(2,2,2-trifluoroethoxy)benzamide;

N-[(5Z)-2-tert-butyl-4-(3-cyanopropyl)isothiazol-5(2H)-ylidene]-5-cyano-2-(2,2,2-trifluoroethoxy)benzamide;

N-[(5Z)-2-tert-butyl-4-(3-cyanopropyl)isothiazol-5(2H)-ylidene]-5-cyano-2-hydroxybenzamide;

N-[(5Z)-2-tert-butyl-4-(3-cyanopropyl)isothiazol-5(2H)-ylidene]-5-chloro-2-(2,2,2-trifluoroethoxy)benzamide;

N-[(5Z)-2-tert-butyl-4-(3-cyanopropyl)isothiazol-5(2H)-ylidene]-2-methoxy-5-(trifluoromethyl)benzamide;

N-[(5Z)-4-butyl-2-tert-butylisothiazol-5(2H)-ylidene]-5-chloro-2-hydroxybenzamide;

N-[(5Z)-2-tert-butyl-4-(cyclopentylmethyl)isothiazol-5(2H)-ylidene]-5-chloro-2-methoxybenzamide;

N-[(5Z)-2-tert-butyl-4-(3-cyano-3-methylbutyl)isothiazol-5(2H)-yliden]-5-chloro-2-methoxybenzamide;

N-[(5Z)-2-tert-butyl-cyanobutypisothiazol-5(2H)-ylidene]-5-chloro-2-methoxybenzamide;

N-[(5Z)-4-butyl-2-tert-butylisothiazol-5(2H)-ylidene]5-chloro-2-(2-fluoroethoxy)benzamide;

2-(2-amino-2-oxoethoxy)-N-[(5Z)-4-butyl-2-tert-butylisothiazol-5(2H)-ylidene]-5-chlorobenzamide;

2-(2-amino-2-oxoethoxy)-N-[(5Z)-2-tert-butyl-4-(3-cyanopropyl)isothiazol-5(2H)-ylidene]-5-chlotobenzamide;

N-[(5Z)-2-tert-butyl-4-(4,4,4-trifluorobutyl)isothiazol-5(2H)-ylidene]-5-chloro-2-methoxybenazanide;

N-[(5Z)-2-tent-butyl-4-isobutylisothiazol-5(2H)-yliden]-2-methoxy-5-(trifluoromethyl)benzamide;

N-[(5Z)-test-butyl-4-isobutylisothiazol-5(2H)-ylidene]-5-chloro-2-(2-fluoroethoxy)benzamide;

N-[(5Z)-2-tert-butyl-4-isobutylisothiazol-5(2H)-ylidene]-5-cyano-2-methoxybenzamide;

N-[(5Z)-2-tert-butyl-4-isobutylisothiazol-5(2H)-ylidene]-2-ethoxy-5-(trifluoromethyl)benzamide;

N-[(5Z)-2-tert-butyl-4-pentylisothiazol-5(2H)-ylidene]-5-chloro-2-methoxybenzamide;

N-[(5Z)-2-tert-butyl-4-(4-fluorobutyl)isothiazol-5(2H)-ylidene]-chloro-2-methoxybenzamide;

N-[(5Z)-2-tert-butyl-4-(4-fluorobutyl)isothiazol-5(2H)-ylidene]-2-methoxy-5-(trifluoromethyl)benzamide;

N-[(5Z)-4-butyl-2-tert-butylisothiazol-5(2H)-ylidene]-5-chloro-2-[2-(dimethylamino)-2-oxoethoxy]benzamide;

N-[(5Z)-4-butyl-2-(2,2,2-trifluoro-1,1-dimethylethyl)isothiazol-5(2H)-ylidenel]-5-chloro-2-methoxybenzamide;

N-[(5Z)-4-butyl-2-(2-fluoro-1,1-dimethylethyl)isothiazol-5(2H)ylidene]-2-methoxy-5-(trifluoromethyl)benzamide;

N-[(5Z)-4-butyl-2-tert-butylisothiazol-5(2H)-ylidenel]-5-chloro-2-(cyanomethoxy)benzamide;

N-[(5Z)-4-butyl 2 (2-fluoro-1,1-dimethylethyl)isothiazol-5-(2H)-ylidene]-5-chloro-2-methoxybenzamide;

N-[(5Z)-4(benzyloxy)-2-tert butylsothiazol-5(2H)-ylidene]-5-chloro-2-methoxvbenzamide;

N-[(5Z)-2-tert-butyl-4-hydroxyisothiazol-5(2H)-ylidene]-5-chloro-2-methoxybenzamide;

N-[(5Z)-2-tert-butyl-4-(1-methylpropoxy)isothiazol-5(2H)-ylidene]-5-chloro-2-methoxybenzamide;

N-[(5Z)-2-tert-butyl-4-(1-methylpropoxy)isothiazol-5(2H)-ylidene]5-chloro-2-methoxybenzamide;

N-[(5Z)-2-tert-butyl-4-(4-fluorobutoxy)isothiazol-5(2H)-ylidene]-5-chloro-2-methoxybenzarnide;

N-[(5Z)-2-tert-butyl-4-(cyanomethoxy)isothiazol-5-(2H)-ylidene]-5-chloro-2-methoxybenzamide;

N-[(5Z)-2tert-butyl-4-{[(2S)-5-oxopyrrolidin-2-yl]methoxy}isothiazol-5(2H)-ylidene]-5-chloro-2-methoxybenzamide;

N-[(5Z)-2-tert-butyl-4-{[(2R)-5-oxopyrrolidin-2-yl]methoxy}isothiazol-5(2H)-ylidene]5-chloro-2-methoxybenzamide; and tert-butyl[(5Z)-2-tert-butyl-5-{[(5-chloro-2-methoxyphenyl)carbonyl]imino}-3-methyl-2,5-dihydroisothiazol-4-yl]carbamate, or a pharmaceutically acceptable salt thereof.

* * * * *